US012667543B2

(12) United States Patent
Smith et al.

(10) Patent No.: US 12,667,543 B2
(45) Date of Patent: Jun. 30, 2026

(54) METHODS OF PREPARING LIPID NANOPARTICLES

(71) Applicant: ModernaTX, Inc., Cambridge, MA (US)

(72) Inventors: Mike Smith, Cambridge, MA (US); Allen Horhota, Westford, MA (US); Jason Auer, Cambridge, MA (US); Brie Skinner, Cambridge, MA (US)

(73) Assignee: ModernaTX, Inc., Cambridge, MA (US)

( * ) Notice: Subject to any disclaimer, the term of this patent is extended or adjusted under 35 U.S.C. 154(b) by 888 days.

(21) Appl. No.: 17/424,780

(22) PCT Filed: Jan. 31, 2020

(86) PCT No.: PCT/US2020/016082

§ 371 (c)(1),
(2) Date: Jul. 21, 2021

(87) PCT Pub. No.: WO2020/160397

PCT Pub. Date: Aug. 6, 2020

(65) Prior Publication Data

US 2022/0062175 A1 Mar. 3, 2022

Related U.S. Application Data

(60) Provisional application No. 62/799,620, filed on Jan. 31, 2019.

(51) Int. Cl.
*A61K 9/1272* (2025.01)
*A61K 9/51* (2006.01)
*A61K 48/00* (2006.01)

(52) U.S. Cl.
CPC .......... *A61K 9/1272* (2013.01); *A61K 9/5123* (2013.01); *A61K 48/0025* (2013.01)

(58) Field of Classification Search
CPC . A61K 9/1272; A61K 9/5123; A61K 48/0025
See application file for complete search history.

(56) References Cited

U.S. PATENT DOCUMENTS 4,737,323 A 4/1988 Martin et al.
4,857,319 A 8/1989 Crowe et al.
4,946,683 A 8/1990 Forssen
5,013,497 A 5/1991 Yiournas et al.
5,049,392 A 9/1991 Weiner et al.
5,194,654 A 3/1993 Hostetler et al.
5,223,263 A 6/1993 Hostetler et al.
5,256,555 A 10/1993 Milburn et al.
5,750,114 A 5/1998 Burke et al.
6,303,378 B1 10/2001 Bridenbaugh et al.
6,696,038 B1 2/2004 Mahato et al.
7,094,423 B1 8/2006 Maurer et al.
7,371,404 B2 5/2008 Panzner et al.
8,058,069 B2 11/2011 Yaworski et al.
8,158,601 B2 4/2012 Chen et al.
8,420,123 B2 4/2013 Troiano et al.
8,460,696 B2 6/2013 Slobodkin et al.
8,466,122 B2 6/2013 Heyes et al.
8,563,041 B2 10/2013 Grayson et al.
8,569,256 B2 10/2013 Heyes et al.
8,603,499 B2 12/2013 Zale et al.
8,603,500 B2 12/2013 Zale et al.
8,603,501 B2 12/2013 Zale et al.
8,603,534 B2 12/2013 Zale et al.
8,603,535 B2 12/2013 Troiano et al.
8,613,951 B2 12/2013 Zale et al.
8,628,801 B2 1/2014 Garreta et al.
8,642,076 B2 2/2014 Manoharan et al.
8,663,599 B1 3/2014 Sung et al.
8,663,700 B2 3/2014 Troiano et al.
8,691,750 B2 4/2014 Constien et al.
8,691,966 B2 4/2014 Kariko et al.
8,697,098 B2 4/2014 Perumal et al.
8,709,483 B2 4/2014 Farokhzad et al.
8,710,200 B2 4/2014 Schrum et al.
8,734,853 B2 5/2014 Sood et al.
8,754,062 B2 6/2014 De Fougerolles et al.
8,822,663 B2 9/2014 Schrum et al.
8,980,864 B2 3/2015 Hoge et al.
8,999,380 B2 4/2015 Bancel et al.
9,221,891 B2 12/2015 Bancel et al.

(Continued)

FOREIGN PATENT DOCUMENTS

AU 652831 B2 9/1994
CN 101291653 A 10/2008

(Continued)

OTHER PUBLICATIONS

Kulkarni et al.; Lipid Nanoparticles Enabling Gene Therapies: From Concepts to Clinical Utility; Nucleic Acid Therapeutics vol. 28, No. 3, 2018; Mary Ann Liebert, Inc.; DOI: 10.1089/nat.2018.0721 (Year: 2018).*

Cullis et al.; Lipid Nanoparticle Systems for Enabling Gene Therapies; CrossMark; Molecular Therapy vol. 25 No. Jul. 7, 2017 The American Society of Gene and Cell Therapy. (Year: 2017).*

Q=V/RT; https://www.cs.montana.edu/webworks/projects/stevesbook/contents/chapters/chapter008/section002/blue/page003.html#:~:text=1.1)%20Flow%20Rate%20Q%20%3D%20V,time%20R%20is%2010%20minutes.; site accesed Jun. 2024 (Year: 2016).*

Patel et al.; Arginoplexes: an arginine-anchored nanoliposomal carrier for gene delivery; Springer Science + Business Media Dordrecht 2014; J Nanopart Res (2014) 16:2345 (Year: 2014).*

Lopes et al.; Lipid nanoparticles containing oryzalin for the treatment of leishmaniasis; Elsevier; European Journal of Pharmaceutical Sciences 45 (2012) 442-450 (Year: 2012).*

(Continued)

*Primary Examiner* — Robert A Wax
*Assistant Examiner* — John W Lippert, III
(74) *Attorney, Agent, or Firm* — Foley & Lardner LLP

(57) ABSTRACT

The present disclosure provides methods of producing lipid nanoparticle (LNP) formulations and the produced LNP formulations thereof. The present disclosure also provides therapeutic and diagnostic uses related to the produced LNP formulations.

18 Claims, 36 Drawing Sheets

Specification includes a Sequence Listing.

(56) References Cited

U.S. PATENT DOCUMENTS 9,283,287 B2 3/2016 Chakraborty et al.
9,303,079 B2 4/2016 Chakraborty et al.
9,364,433 B2 6/2016 Andersson et al.
9,464,124 B2 10/2016 Bancel et al.
9,512,456 B2 12/2016 Wang et al.
9,533,047 B2 1/2017 De Fougerolles et al.
9,572,896 B2 2/2017 Bancel et al.
9,597,380 B2 3/2017 Chakraborty et al.
9,693,958 B2 7/2017 Zhu
9,803,199 B2 10/2017 Koizumi et al.
9,868,691 B2 1/2018 Benenato
9,872,900 B2 1/2018 Ciaramella et al.
10,023,626 B2 7/2018 Bolen et al.
10,064,934 B2 9/2018 Ciaramella et al.
10,064,935 B2 9/2018 Ciaramella et al.
10,124,055 B2 11/2018 Ciaramella et al.
10,207,010 B2 2/2019 Besin et al.
10,232,055 B2 3/2019 Kariko et al.
10,273,269 B2 4/2019 Ciaramella
10,286,086 B2 5/2019 Roy et al.
10,323,076 B2 6/2019 Ellsworth et al.
10,385,088 B2 8/2019 Fraley et al.
10,449,244 B2 10/2019 Ciaramella et al.
10,465,190 B1 11/2019 Chen et al.
10,493,143 B2 12/2019 Ciaramella et al.
10,526,629 B2 1/2020 Rabideau et al.
10,653,712 B2 5/2020 Hoge et al.
10,653,767 B2 5/2020 Ciaramella et al.
10,695,419 B2 6/2020 Ciaramella et al.
10,857,105 B2 12/2020 Benenato et al.
10,925,958 B2 2/2021 Ciaramella
11,027,025 B2 6/2021 Hoge et al.
11,045,540 B2 6/2021 Ciaramella
11,103,578 B2 8/2021 Ciaramella et al.
11,351,242 B1 6/2022 Panther et al.
11,384,352 B2 7/2022 Miracco
11,406,703 B2 8/2022 Kramarczyk et al.
11,464,848 B2 10/2022 Ciaramella et al.
11,485,960 B2 11/2022 Dousis et al.
11,497,807 B2 11/2022 Ciaramella et al.
11,744,801 B2 9/2023 Schariter et al.
11,786,607 B2 10/2023 Hoge et al.
12,090,235 B2 9/2024 Horhota et al.
12,496,561 B2 12/2025 Kirby et al.
2003/0073619 A1 4/2003 Mahato et al.
2003/0092653 A1 5/2003 Kisich et al.
2003/0135040 A1 7/2003 Eritja et al.
2003/0165849 A1 9/2003 Zhang et al.
2004/0132683 A1 7/2004 Felgner et al.
2004/0142474 A1 7/2004 Mahato et al.
2005/0079212 A1 4/2005 Wheeler et al.
2005/0143336 A1 6/2005 Ramesh et al.
2005/0287540 A1 12/2005 Murphy et al.
2006/0008910 A1 1/2006 Maclachlan et al.
2006/0083780 A1 4/2006 Heyes et al.
2006/0083781 A1 4/2006 Shastri et al.
2007/0252295 A1 11/2007 Panzner et al.
2009/0042825 A1 2/2009 Matar et al.
2009/0042829 A1 2/2009 Matar et al.
2009/0098162 A1 4/2009 Friedman et al.
2010/0068226 A1 3/2010 Taylor et al.
2010/0112042 A1 5/2010 Polisky et al.
2010/0130588 A1 5/2010 Yaworski et al.
2010/0267806 A1 10/2010 Bumcrot et al.
2011/0200582 A1 8/2011 Baryza et al.
2011/0244026 A1 10/2011 Guild et al.
2011/0256175 A1 10/2011 Hope et al.
2012/0101148 A1 4/2012 Aking et al.
2012/0177724 A1 7/2012 Irvine et al.
2012/0178702 A1 7/2012 Huang et al.
2012/0201872 A1 8/2012 Huang et al.
2012/0276209 A1 11/2012 Cullis et al.
2012/0295832 A1 11/2012 Constien et al.
2013/0017223 A1 1/2013 Hope et al.
2013/0037977 A1 2/2013 Burke et al.
2013/0064894 A1 3/2013 Martin et al.
2013/0065942 A1 3/2013 Matar et al.
2013/0090372 A1 4/2013 Budzik et al.
2013/0102034 A1 4/2013 Schrum
2013/0115274 A1 5/2013 Knopov et al.
2013/0116307 A1 5/2013 Heyes et al.
2013/0122054 A1 5/2013 Harashima et al.
2013/0122104 A1 5/2013 Yaworski et al.
2013/0123338 A1 5/2013 Heyes et al.
2013/0129785 A1 5/2013 Manoharan et al.
2013/0150625 A1 6/2013 Budzik et al.
2013/0156845 A1 6/2013 Manoharan et al.
2013/0158021 A1 6/2013 Dong et al.
2013/0164400 A1 6/2013 Knopov et al.
2013/0172406 A1 7/2013 Zale et al.
2013/0178541 A1 7/2013 Stanton et al.
2013/0183244 A1 7/2013 Hanes et al.
2013/0183355 A1 7/2013 Jain et al.
2013/0189351 A1 7/2013 Geall
2013/0195759 A1 8/2013 Mirkin et al.
2013/0195968 A1 8/2013 Geall et al.
2013/0195969 A1 8/2013 Geall et al.
2013/0202684 A1 8/2013 Geall et al.
2013/0236500 A1 9/2013 Zale et al.
2013/0236533 A1 9/2013 Von Andrian et al.
2013/0236968 A1 9/2013 Manoharan et al.
2013/0236974 A1 9/2013 De Fougerolles
2013/0243848 A1 9/2013 Lobovkina et al.
2013/0245103 A1 9/2013 De Fougerolles et al.
2013/0245107 A1 9/2013 De Fougerolles et al.
2013/0251766 A1 9/2013 Zale et al.
2013/0251816 A1 9/2013 Zale et al.
2013/0251817 A1 9/2013 Zale et al.
2013/0259923 A1 10/2013 Bancel et al.
2013/0274504 A1 10/2013 Colletti et al.
2013/0274523 A1 10/2013 Bawiec, III et al.
2013/0302432 A1 11/2013 Zale et al.
2013/0330401 A1 12/2013 Payne et al.
2013/0338210 A1 12/2013 Manoharan et al.
2013/0344158 A1 12/2013 Zale et al.
2014/0037573 A1 2/2014 Eliasof et al.
2014/0037660 A1 2/2014 Fotin-Mleczek et al.
2014/0037714 A1 2/2014 Quay et al.
2014/0039032 A1 2/2014 Kuboyama et al.
2014/0044772 A1 2/2014 Maclachlan et al.
2014/0044791 A1 2/2014 Basilion et al.
2014/0045913 A1 2/2014 Kuboyama et al.
2014/0050775 A1 2/2014 Slobodkin et al.
2014/0065228 A1 3/2014 Yaworski et al.
2014/0079774 A1 3/2014 Brinker et al.
2014/0141070 A1 5/2014 Geall et al.
2014/0147432 A1 5/2014 Bancel et al.
2014/0148502 A1 5/2014 Bancel et al.
2014/0161830 A1 6/2014 Anderson et al.
2014/0193482 A1 7/2014 Bancel et al.
2014/0206752 A1 7/2014 Afeyan et al.
2014/0206753 A1 7/2014 Guild et al.
2014/0255472 A1 9/2014 Geall et al.
2014/0328825 A1 11/2014 Meis et al.
2014/0343139 A1 11/2014 Lippard et al.
2014/0348900 A1 11/2014 Zhu
2014/0378538 A1 12/2014 Bancel
2015/0030622 A1 1/2015 Marshall et al.
2015/0051268 A1 2/2015 Bancel et al.
2015/0056253 A1 2/2015 Bancel et al.
2015/0064242 A1 3/2015 Heyes et al.
2015/0079121 A1 3/2015 Weiner et al.
2015/0110857 A1 4/2015 DeRosa et al.
2015/0118183 A1 4/2015 Baumhof
2015/0124554 A1 5/2015 Haden et al.
2015/0141499 A1 5/2015 Bancel et al.
2015/0307542 A1 10/2015 Roy et al.
2015/0315541 A1 11/2015 Bancel et al.
2015/0374842 A1 12/2015 Brown et al.
2015/0376115 A1 12/2015 Ansell et al.
2016/0024140 A1 1/2016 Issa et al.
2016/0024141 A1 1/2016 Issa et al.
2016/0032273 A1 2/2016 Shahrokh et al.
2016/0038612 A1 2/2016 Hoge et al.

(56) References Cited

U.S. PATENT DOCUMENTS

| | | | |
|---|---|---|---|
| 2016/0151284 A1 | 6/2016 | Heyes et al. |
| 2016/0243221 A1 | 8/2016 | Hoge et al. |
| 2016/0367638 A1 | 12/2016 | Byers et al. |
| 2016/0376224 A1 | 12/2016 | Du et al. |
| 2017/0043037 A1 | 2/2017 | Kariko et al. |
| 2017/0130255 A1 | 5/2017 | Wang et al. |
| 2017/0202979 A1 | 7/2017 | Chakraborty et al. |
| 2017/0204152 A1 | 7/2017 | Nelson et al. |
| 2017/0210697 A1 | 7/2017 | Benenato et al. |
| 2017/0239371 A1 | 8/2017 | Guild et al. |
| 2018/0000953 A1 | 1/2018 | Almarsson et al. |
| 2018/0002393 A1 | 1/2018 | Bancel et al. |
| 2018/0214537 A1 | 8/2018 | Mutzke et al. |
| 2018/0221500 A1 | 8/2018 | Reshetnyak et al. |
| 2018/0237849 A1 | 8/2018 | Thompson |
| 2018/0243225 A1 | 8/2018 | Ciaramella |
| 2018/0243230 A1 | 8/2018 | Smith |
| 2018/0256628 A1 | 9/2018 | Hoge et al. |
| 2018/0271795 A1 | 9/2018 | Martini et al. |
| 2018/0271970 A1 | 9/2018 | Ciaramella et al. |
| 2018/0273977 A1 | 9/2018 | Mousavi et al. |
| 2018/0274009 A1 | 9/2018 | Marquardt et al. |
| 2018/0303929 A1 | 10/2018 | Ciaramella et al. |
| 2018/0311336 A1 | 11/2018 | Ciaramella et al. |
| 2018/0311343 A1 | 11/2018 | Huang et al. |
| 2018/0318409 A1 | 11/2018 | Valiante et al. |
| 2018/0369374 A1 | 12/2018 | Frederick et al. |
| 2018/0371047 A1 | 12/2018 | Ticho et al. |
| 2019/0002890 A1 | 1/2019 | Martini et al. |
| 2019/0008938 A1 | 1/2019 | Ciaramella et al. |
| 2019/0022004 A1 | 1/2019 | Kan et al. |
| 2019/0085368 A1 | 3/2019 | Bancel et al. |
| 2019/0175517 A1 | 6/2019 | Martini et al. |
| 2019/0175727 A1 | 6/2019 | Huang et al. |
| 2019/0192646 A1 | 6/2019 | Cohen et al. |
| 2019/0192653 A1 | 6/2019 | Hoge et al. |
| 2019/0216843 A1 | 7/2019 | DeRosa et al. |
| 2019/0241633 A1 | 8/2019 | Fotin-Mleczek et al. |
| 2019/0275170 A1 | 9/2019 | Benenato et al. |
| 2019/0298657 A1 | 10/2019 | Martini et al. |
| 2019/0298658 A1 | 10/2019 | Benenato et al. |
| 2019/0300906 A1 | 10/2019 | Martini et al. |
| 2019/0314292 A1 | 10/2019 | Benenato et al. |
| 2019/0336452 A1 | 11/2019 | Brader |
| 2019/0351040 A1 | 11/2019 | Valiante et al. |
| 2019/0351047 A1 | 11/2019 | Jasny et al. |
| 2019/0382774 A1 | 12/2019 | Hoge et al. |
| 2019/0390181 A1 | 12/2019 | Benenato et al. |
| 2020/0030432 A1 | 1/2020 | Ciaramella et al. |
| 2020/0032274 A1 | 1/2020 | Mauger et al. |
| 2020/0038499 A1 | 2/2020 | Narayanan et al. |
| 2020/0054737 A1 | 2/2020 | Ciaramella et al. |
| 2020/0069599 A1 | 3/2020 | Smith et al. |
| 2020/0069793 A1 | 3/2020 | Ciaramella |
| 2020/0069794 A1 | 3/2020 | Ciaramella et al. |
| 2020/0071689 A1 | 3/2020 | Miracco |
| 2020/0085916 A1 | 3/2020 | Martini et al. |
| 2020/0109420 A1 | 4/2020 | Brito et al. |
| 2020/0129608 A1 | 4/2020 | Ciaramella et al. |
| 2020/0129615 A1 | 4/2020 | Ciaramella et al. |
| 2020/0163878 A1 | 5/2020 | Baumhof et al. |
| 2020/0239869 A1 | 7/2020 | Issa et al. |
| 2020/0254086 A1 | 8/2020 | Hoge et al. |
| 2020/0282047 A1 | 9/2020 | Ciaramella et al. |
| 2020/0306191 A1 | 10/2020 | Schariter et al. |
| 2020/0368162 A1 | 11/2020 | Martini |
| 2021/0046173 A1 | 2/2021 | Ciaramella et al. |
| 2021/0087135 A1 | 3/2021 | Benenato et al. |
| 2021/0145982 A1 | 5/2021 | Hoge et al. |
| 2021/0163919 A1 | 6/2021 | Issa et al. |
| 2021/0187097 A1 | 6/2021 | Ciaramella et al. |
| 2021/0206818 A1 | 7/2021 | Huang et al. |
| 2021/0217484 A1 | 7/2021 | Giessel et al. |
| 2021/0228707 A1 | 7/2021 | Metkar et al. |
| 2021/0268086 A1 | 9/2021 | Zhong et al. |
| 2021/0309976 A1 | 10/2021 | Dousis et al. |
| 2021/0378980 A1 | 12/2021 | Horhota et al. |
| 2022/0031631 A1 | 2/2022 | Almarsson et al. |
| 2022/0047518 A1 | 2/2022 | Hennessy et al. |
| 2022/0054653 A1 | 2/2022 | Martini et al. |
| 2022/0125899 A1 | 4/2022 | Ashburn et al. |
| 2022/0145381 A1 | 5/2022 | Elich et al. |
| 2022/0236253 A1 | 7/2022 | Hopson |
| 2022/0241399 A1 | 8/2022 | Lusso et al. |
| 2022/0347292 A1 | 11/2022 | Panther et al. |
| 2022/0348900 A1 | 11/2022 | Shamashkin et al. |
| 2022/0349006 A1 | 11/2022 | Amato et al. |
| 2023/0000970 A1 | 1/2023 | Nachbagauer et al. |
| 2023/0277457 A1 | 9/2023 | Shepard et al. |
| 2023/0285297 A1 | 9/2023 | Smith et al. |
| 2024/0009131 A1 | 1/2024 | Schariter |
| 2024/0335393 A1 | 10/2024 | Smith et al. |
| 2024/0366522 A1 | 11/2024 | Smith et al. |

FOREIGN PATENT DOCUMENTS

| | | | |
|---|---|---|---|
| CN | 101939087 | A | 1/2011 |
| CN | 102068701 | A | 5/2011 |
| CN | 102204920 | A | 10/2011 |
| CN | 102813929 | A | 12/2012 |
| CN | 104644555 | A | 5/2015 |
| CN | 105555757 | A | 5/2016 |
| CN | 107020029 | A | 8/2017 |
| CN | 206549481 | U | 10/2017 |
| CN | 111315359 | A | 6/2020 |
| CN | 116133652 | A | 5/2023 |
| EP | 737750 | A2 | 10/1996 |
| EP | 1873180 | A1 | 1/2008 |
| EP | 2 123 349 | A2 | 11/2009 |
| EP | 2092064 | B1 | 9/2010 |
| EP | 2476430 | A1 | 7/2012 |
| EP | 2548960 | A1 | 1/2013 |
| EP | 2620161 | A1 | 7/2013 |
| EP | 2073848 | B1 | 8/2013 |
| EP | 1404860 | B1 | 11/2013 |
| EP | 2732825 | A1 | 5/2014 |
| EP | 3 020 701 | A1 | 5/2016 |
| EP | 3269395 | A1 | 1/2018 |
| EP | 3452101 | A2 | 3/2019 |
| JP | 2016540769 | A | 12/2016 |
| JP | 2019-167300 | A | 10/2019 |
| JP | 2019-533707 | A | 11/2019 |
| WO | WO-9303709 | A1 | 3/1993 |
| WO | WO-9314778 | A1 | 8/1993 |
| WO | WO-9617086 | A1 | 6/1996 |
| WO | WO-9730064 | A1 | 8/1997 |
| WO | WO-9914346 | A2 | 3/1999 |
| WO | WO-9952503 | A2 | 10/1999 |
| WO | WO-0105373 | A1 | 1/2001 |
| WO | WO-03086280 | A2 | 10/2003 |
| WO | WO-03097805 | A2 | 11/2003 |
| WO | WO-2005034979 | A2 | 4/2005 |
| WO | WO-2005118857 | A2 | 12/2005 |
| WO | WO-2005120152 | A2 | 12/2005 |
| WO | WO-2005121348 | A1 | 12/2005 |
| WO | WO-2006044456 | A1 | 4/2006 |
| WO | WO-2006044503 | A2 | 4/2006 |
| WO | WO-2006044505 | A2 | 4/2006 |
| WO | WO-2006044682 | A1 | 4/2006 |
| WO | WO-2006058088 | A2 | 6/2006 |
| WO | WO-2006063249 | A2 | 6/2006 |
| WO | WO-2006065479 | A2 | 6/2006 |
| WO | WO-2006065480 | A2 | 6/2006 |
| WO | WO-2007069068 | A2 | 6/2007 |
| WO | WO-2008014979 | A2 | 2/2008 |
| WO | WO-2008042973 | A2 | 4/2008 |
| WO | WO-2008068631 | A2 | 6/2008 |
| WO | WO-2008077592 | A1 | 7/2008 |
| WO | WO-2008/103276 | A2 | 8/2008 |
| WO | WO-2009024599 | A1 | 2/2009 |
| WO | WO-2009068649 | A2 | 6/2009 |
| WO | WO-2009095226 | A2 | 8/2009 |
| WO | WO-2009120247 | A2 | 10/2009 |
| WO | WO-2009127060 | A1 | 10/2009 |

(56) References Cited

FOREIGN PATENT DOCUMENTS

WO WO-2010033906 A2 3/2010
WO WO-2010042877 A1 4/2010
WO WO-2010045512 A2 4/2010
WO WO-2010053572 A2 5/2010
WO WO-2010054401 A1 5/2010
WO WO-2010054406 A1 5/2010
WO WO-2010088537 A3 9/2010
WO WO-2010111290 A1 9/2010
WO WO-2010129709 A1 11/2010
WO WO-2011026641 A1 3/2011
WO WO-2011062965 A2 5/2011
WO WO-2011068810 A1 6/2011
WO WO-2011071931 A2 6/2011
WO WO-2011119058 A2 9/2011
WO WO-2011120053 A1 9/2011
WO WO-2011127255 A1 10/2011
WO WO-2011140627 A1 11/2011
WO WO-2012006376 A2 1/2012
WO WO-2012006378 A1 1/2012
WO WO-2012030901 A1 3/2012
WO WO-2012031043 A1 3/2012
WO WO-2012031046 A2 3/2012
WO WO-2012045075 A1 4/2012
WO WO-2012094304 A1 7/2012
WO WO-2012099755 A1 7/2012
WO WO-2012112730 A2 8/2012
WO WO-2012129483 A1 9/2012
WO WO-2012135025 A2 10/2012
WO WO-2012149252 A2 11/2012
WO WO-2012149255 A2 11/2012
WO WO-2012149265 A2 11/2012
WO WO-2012149282 A2 11/2012
WO WO-2012149301 A2 11/2012
WO WO-2012149376 A2 11/2012
WO WO-2012149393 A2 11/2012
WO WO-2012152910 A1 11/2012
WO WO-2012153297 A1 11/2012
WO WO-2012153338 A2 11/2012
WO WO-2012159643 A1 11/2012
WO WO-2012166241 A1 12/2012
WO WO-2012168491 A1 12/2012
WO WO-2012170607 A2 12/2012
WO WO-2012170889 A1 12/2012
WO WO-2012170930 A1 12/2012
WO WO-2012170952 A2 12/2012
WO WO-2013006825 A1 1/2013
WO WO-2013006834 A1 1/2013
WO WO-2013006837 A1 1/2013
WO WO-2013006838 A1 1/2013
WO WO-2013006842 A2 1/2013
WO WO-2013012476 A2 1/2013
WO WO-2013032829 A1 3/2013
WO WO-2013033438 A2 3/2013
WO WO-2013033563 A1 3/2013
WO WO-2013033620 A1 3/2013
WO WO-2013049328 A1 4/2013
WO WO-2013052167 A2 4/2013
WO WO-2013056132 A2 4/2013
WO WO-2013057715 A1 4/2013
WO WO-2013059496 A1 4/2013
WO WO-2013059922 A1 5/2013
WO WO-2013063468 A1 5/2013
WO WO-2013064911 A2 5/2013
WO WO-2013066274 A1 5/2013
WO WO-2013066903 A1 5/2013
WO WO-2013067537 A1 5/2013
WO WO-2013070872 A1 5/2013
WO WO-2013072929 A2 5/2013
WO WO-2013082529 A1 6/2013
WO WO-2013086322 A1 6/2013
WO WO-2013086354 A1 6/2013
WO WO-2013086373 A1 * 6/2013 ........... A61K 31/713
WO WO-2013086526 A1 6/2013
WO WO-2013087083 A1 6/2013
WO WO-2013087791 A1 6/2013
WO WO-2013090601 A2 6/2013
WO WO-2013093648 A2 6/2013
WO WO-2013112778 A1 8/2013
WO WO-2013112780 A1 8/2013
WO WO-2013113501 A1 8/2013
WO WO-2013113736 A1 8/2013
WO WO-2013135359 A1 9/2013
WO WO-2013138343 A1 9/2013
WO WO-2013138346 A1 9/2013
WO WO-2013143555 A1 10/2013
WO WO-2013143683 A1 10/2013
WO WO-2013143699 A1 10/2013
WO WO-2013148186 A1 10/2013
WO WO-2013148541 A1 10/2013
WO WO-2013149141 A1 10/2013
WO WO-2013151650 A1 10/2013
WO WO-2013151666 A2 10/2013
WO WO-2013151736 A2 10/2013
WO WO-2013154774 A1 10/2013
WO WO-2013155487 A1 10/2013
WO WO-2013155493 A1 10/2013
WO WO-2013158127 A1 10/2013
WO WO-2013158579 A1 10/2013
WO WO-2013166498 A1 11/2013
WO WO-2013173693 A1 11/2013
WO WO-2013174409 A1 11/2013
WO WO-2013177421 A2 11/2013
WO WO-2013185069 A1 12/2013
WO WO-2014008334 A1 1/2014
WO WO-2014024193 A1 2/2014
WO WO-2014025795 A1 2/2014
WO WO-2014026284 A1 2/2014
WO WO-2014028487 A1 2/2014
WO WO-2014028763 A1 2/2014
WO WO-2014042920 A1 3/2014
WO WO-2014043618 A1 3/2014
WO WO-2014047649 A1 3/2014
WO WO-2014052634 A1 4/2014
WO WO-2014053622 A1 4/2014
WO WO-2014053624 A1 4/2014
WO WO-2014053628 A1 4/2014
WO WO-2014053629 A1 4/2014
WO WO-2014053879 A1 4/2014
WO WO-2014053880 A1 4/2014
WO WO-2014053881 A1 4/2014
WO WO-2014053882 A1 4/2014
WO WO-2014054026 A1 4/2014
WO WO-2014062697 A2 4/2014
WO WO-2014064258 A1 5/2014
WO WO-2014064687 A1 5/2014
WO WO-2014066811 A1 5/2014
WO WO-2014071072 A2 5/2014
WO WO-2014072468 A1 5/2014
WO WO-2014072997 A1 5/2014
WO WO-2014074218 A1 5/2014
WO WO-2014074289 A1 5/2014
WO WO-2014074299 A1 5/2014
WO WO-2014074823 A1 5/2014
WO WO-2014078399 A1 5/2014
WO WO-2014081299 A1 5/2014
WO WO-2014081300 A1 5/2014
WO WO-2014081303 A1 5/2014
WO WO-2014081849 A1 5/2014
WO WO-2014066898 A9 6/2014
WO WO-2014089239 A1 6/2014
WO WO-2014089486 A1 6/2014
WO WO-2014108515 A1 7/2014
WO WO-2014127917 A1 8/2014
WO WO-2014140211 A1 9/2014
WO WO-2014144196 A1 9/2014
WO WO-2014152200 A1 9/2014
WO WO-2014152966 A1 9/2014
WO WO-2014153163 A1 9/2014
WO WO-2014159813 A1 10/2014
WO WO-2014160243 A1 10/2014
WO WO-2014168874 A2 10/2014
WO WO-2014172045 A1 10/2014
WO WO-2014182661 A2 11/2014
WO WO-2014210356 A1 12/2014

(56) References Cited

FOREIGN PATENT DOCUMENTS

WO WO-2015023461 A2 2/2015
WO WO-2015061491 A1 4/2015
WO WO-2015082080 A1 6/2015
WO WO-2015095340 A1 6/2015
WO WO-2015095346 A1 6/2015
WO WO-2015095351 A1 6/2015
WO WO-2015110957 A2 7/2015
WO WO-2015130584 A2 9/2015
WO WO-2015134332 A2 9/2015
WO WO-2015135558 A1 9/2015
WO WO-2015199952 A1 12/2015
WO WO-2016/046060 A1 3/2016
WO WO-2016037053 A1 3/2016
WO WO-2016123864 A1 8/2016
WO WO-2016164762 A1 10/2016
WO WO-2016201377 A1 12/2016
WO WO-2017011773 A2 1/2017
WO WO-2017015457 A1 1/2017
WO WO-2017031232 A1 2/2017
WO WO-2017/049245 A2 3/2017
WO WO-2017034991 A1 3/2017
WO WO-2017/070618 A1 4/2017
WO WO-2017066789 A1 4/2017
WO WO-2017070601 A1 4/2017
WO WO-2017070622 A1 4/2017
WO WO-2017075038 A1 5/2017
WO WO-2017099823 A1 6/2017
WO WO-2017112865 A1 6/2017
WO WO-2017127750 A1 7/2017
WO WO-2017191274 A2 11/2017
WO WO-2017201328 A1 11/2017
WO WO-2017201333 A1 11/2017
WO WO-2017218704 A1 12/2017
WO WO-2017219033 A1 12/2017
WO WO-2018006052 A1 1/2018
WO WO-2018039131 A1 3/2018
WO WO-2018081480 A1 * 5/2018 ............. A61K 47/18
WO WO-2018089540 A1 5/2018
WO WO-2018089790 A1 5/2018
WO WO-2018089801 A1 * 5/2018 ............. A61P 43/00
WO WO-2018157009 A1 8/2018
WO WO-2018170245 A1 9/2018
WO WO-2018170306 A1 9/2018
WO WO-2018170336 A1 9/2018
WO WO-2018232120 A1 12/2018
WO WO-2018232355 A1 12/2018
WO WO-2018232357 A1 12/2018
WO WO-2019036683 A1 2/2019
WO WO-2019036685 A1 2/2019
WO WO-2019/046809 A1 3/2019
WO WO-2019089818 A1 5/2019
WO WO-2019/207060 A1 10/2019
WO WO-2019202035 A1 10/2019
WO WO-2019226925 A1 11/2019
WO WO-2020002540 A1 1/2020
WO WO-2020006242 A1 1/2020
WO WO-2020047061 A1 3/2020
WO WO-2020056370 A1 3/2020
WO WO-2020061284 A1 3/2020
WO WO-2020061295 A1 3/2020
WO WO-2020061367 A1 3/2020
WO WO-2020061457 A1 3/2020
WO WO-2020077007 A1 4/2020
WO WO-2020081933 A1 4/2020
WO WO-2020097291 A1 5/2020
WO WO-2020160397 A1 8/2020
WO WO-2020172239 A1 8/2020
WO WO-2020185811 A1 9/2020
WO WO-2020190750 A1 9/2020
WO WO-2020232276 A1 11/2020
WO WO-2020243561 A1 12/2020
WO WO-2021007278 A1 1/2021
WO WO-2021016430 A1 1/2021
WO WO-2021030533 A1 2/2021
WO WO-2021050864 A1 3/2021
WO WO-2021055811 A1 3/2021
WO WO-2021127641 A1 6/2021
WO WO-2021155243 A1 8/2021
WO WO-2021155274 A1 8/2021
WO WO-2021159040 A2 8/2021
WO WO-2021159130 A2 8/2021
WO WO-2021173840 A1 9/2021
WO WO-2021204175 A1 10/2021
WO WO-2021211343 A1 10/2021
WO WO-2021222304 A1 11/2021
WO WO-2021231901 A1 11/2021
WO WO-2021231929 A1 11/2021
WO WO-2021231963 A1 11/2021
WO WO-2021237084 A1 11/2021
WO WO-2021247817 A1 12/2021
WO WO-2022032087 A1 2/2022
WO WO-2022067010 A1 3/2022
WO WO-2022081544 A1 4/2022
WO WO-2022081548 A1 4/2022
WO WO-2022150717 A1 7/2022
WO WO-2022155524 A1 7/2022
WO WO-2022155530 A1 7/2022
WO WO-2022187698 A1 9/2022
WO WO-2022204491 A1 9/2022
WO WO-2022212191 A1 10/2022
WO WO-2022212442 A1 10/2022
WO WO-2022212711 A2 10/2022
WO WO-2022221335 A1 10/2022
WO WO-2022221336 A1 10/2022
WO WO-2022221359 A1 10/2022
WO WO-2022221440 A1 10/2022
WO WO-2022232585 A1 11/2022
WO WO-2022241103 A1 11/2022
WO WO-2022266010 A1 12/2022
WO WO-2022266012 A1 12/2022
WO WO-2022266389 A1 12/2022
WO WO-2023283642 A2 1/2023
WO WO-2023283645 A1 1/2023
WO WO-2023283651 A1 1/2023
WO WO-2023009421 A1 2/2023
WO WO-2023009422 A1 2/2023

OTHER PUBLICATIONS

SM-102 pKa; https://broadpharm.com/product/bp-25499; site accessed Jun. 2024 (Year: 2024).*

Golub et al., Science, vol. 286, Oct. 15, 1999, pp. 531-537.*

American Cancer Society "Can Pancreatic Neuroendocrine Tumor Be Prevented?" waybback machine date of Jun. 9, 2023.*

Abu Lila et al., Application of polyglycerol coating to plasmid DNA lipoplex for the evasion of the accelerated blood clearance phenomenon in nucleic acid delivery. J Pharm Sci. Feb. 2014;103(2):557-66. doi: 10.1002/jps.23823. Epub Dec. 17, 2013.

Abu Lila et al., Use of polyglycerol (PG), instead of polyethylene glycol (PEG), prevents induction of the accelerated blood clearance phenomenon against long-circulating liposomes upon repeated administration. Int J Pharm. Nov. 1, 2013;456(1):235-42. doi: 10.1016/j.ijpharm.2013.07.059. Epub Aug. 5, 2013.

Adamiak, et al. glycoprotein E [Human alphaherpesvirus 2]. GenBank: ABU45436.1. Pub. Nov. 29, 2007, 1 page.

Adney et al., Efficacy of an Adjuvanted Middle East Respiratory Syndrome Coronavirus Spike Protein Vaccine in Dromedary Camels and Alpacas. Viruses. Mar. 2, 2019;11(3). pii: E212. doi: 10.3390/vl 1030212.

Agadjanyan, M., Prototype Alzheimer's Disease Vaccine Using the Immunodominant B Cell Type from Beta-Amyloid and Promiscuous T Cell Epitope Pan HLA DR-Binding Peptide, J Immunol, 2005, vol. 174, No. 3, pp. 1580-1586.

Agrawal et al., Immunization with inactivated Middle East Respiratory Syndrome coronavirus vaccine leads to lung immunopathology on challenge with live virus. Hum Vaccin Immunother. Sep. 2016;12(9):2351-6. doi:10.1080/21645515.2016.1177688. Epub Jun. 7, 2016.

Akinc, A., et al., "Targeted Delivery of RNAi Therapeutics with Endogenous and Exogenous Ligand-Based Mechanisms," Molecu-

(56) References Cited

OTHER PUBLICATIONS lar Therapy : The Journal of the American Society of Gene Therapy 18(7):1357-1364, Academic Press, United States (2010).
Al Kahlout et al., Comparative Serological Study for the Prevalence of Anti-MERS Coronavirus Antibodies in High- and Low-Risk Groups in Qatar. J Immunol Res. Feb. 18, 2019;2019:1386740. doi: 10.1155/2019/1386740. eCollection 2019. 9 pages.
Aleku, M., et al., Atu027, a liposomal small interfering RNA formulation targeting protein kinase N3, inhibits cancer progression. Cancer Res. 2008; 68: 9788-9798.
Alexander et al., The long view: a selective review of 40 years of Newcastle disease research. Avian Pathol. 2012;41(4):329-35. doi: 10.1080/03079457.2012.697991.
Anderson, D.M. et al., Stability of mRNA/cationic lipid lipoplexes in human and rat cerebrospinal fluid: methods and evidence for nonviral mRNA gene delivery to the central nervous system. Hum Gene Ther. Feb. 10, 2003; 14(3):191-202.
Andreakos et al., Amphoteric liposomes enable systemic antigen-presenting cell-directed delivery of CD40 antisense and are therapeutically effective in experimental arthritis. Arthritis Rheum. Apr. 2009;60(4):994-1005. doi: 10.1002/art.24434.
Andrews-Pfannkoch, C. et al., Hydroxyapatite-mediated separation of double-stranded DNA, single-stranded DNA, and RNA genomes from natural viral assemblages. Appl Environ Microbiol. Aug. 2010;76(15):5039-45. Epub Jun. 11, 2010.
Andries, O., et al., Comparison of the gene transfer efficiency of mRNA/GL67 and pDNA/GL67 complexes in respiratory cells. Mol Pharmaceutics. 2012; 9: 2136-2145.
Ausar et al., High-throughput screening of stabilizers for respiratory syncytial virus: identification of stabilizers and their effects on the conformational thermostability of viral particles. Hum Vaccin. May-Jun. 2007;3(3):94-103. Epub May 15, 2007.
Awasthi et al., Immunization With a Vaccine Combining Herpes Simplex Virus 2 (HSV-2) Glycoprotein C (gC) and gD Subunits Improves the Protection of Dorsal Root Ganglia in Mice and Reduces the Frequency of Recurrent Vaginal Shedding of HSV-2 DNA in Guinea Pigs Compared to Immunization With gD Alone. J Viral. Oct. 2011;85(20):10472-86. doi: 10.1128/JVI.00849-11. Epub Aug. 3, 2011.
Baars, A. et al., A Phase II Study of Active Specific Immunotherapy and 5-FU/Leucovorin as Adjuvant Therapy for Stage III Colon Carcinoma, British Journal of Cancer, 2002, vol. 86, No. 8, pp. 1230-1234.
Badawi et al., Immune Modulating Peptide for the Treatment and Suppression of Multiple Sclerosis. Clin Immunol. Aug. 2012; 144(2):127-138. Author manuscript, 22 pages.
Bag, J., Recovery of normal protein synthesis in heat-shocked chicken myotubes by liposome-mediated transfer of mRNAs. Can. J. Biochem. Cell Biol. 1985; 63(3): 231-235.
Betker et al., Nonadditive Effects of Repetitive Administration of Lipoplexes in Immunocompetent Mice. J Pharm Sci. Mar. 2017;106(3):872-881. doi:10.1016/i.xphs.2016.11.013. Epub Nov. 22, 2016.
Bettinger, T. et al., Peptide-mediated RNA delivery: a novel approach for enhanced transfection of primary and post-mitotic cells. Nucleic Acids Res. Sep. 15, 2001;29(18):3882-91.
Blenke, Intracellular delivery of RNA therapeutics with lipid nanoparticles, publicly available on Jan. 25, 2017, Department of Pharmaceutics, Utrecht Institute for Pharmaceutical Sciences (UIPS), Faculty of Science, University of Utrecht, Netherlands, 164 pages.
Bolhassani A., et al. , Improvement of Different Vaccine Delivery Systems for Cancer Therapy, Molecular Cancer, Jan. 7, 2011;10:3. 20 pages, doi: 10.1186/1476-4598-10-3.
Bonehill, A., et al., Single-step antigen loading and activation of dendritic cells by mRNA electroporation for the purpose of therapeutic vaccination in melanoma patients. Clin Cancer Res. May 2009; 15(10): 3366-3375.
Bonham et al., An assessment of the antisense properties of RNase H-competent and steric-blocking oligomers. Nucleic Acids Res. Apr. 11, 1995; 23(7): 1197-1203.
Borghaei et al., Phase I Dose Escalation, Pharmacokinetic and Pharmacodynamic Study of Naptumomab Estafenatox Alone in Patients With Advanced Cancer and With Docetaxel in Patients With Advanced Non-Small-Cell Lung Cancer. J Clin Oneal. Sep. 1, 2009;27(25):4116-23. doi: 10.1200/JCO.2008.20.2515. Epub Jul. 27, 2009.
Bose et al., Influence of cationic lipid concentration on properties of lipid-polymer hybrid nanospheres for gene delivery. Int J Nanomedicine. Sep. 2, 2015;10:5367-82. doi: 10.2147/IJN.S87120. eCollection 2015.
Bouxsein, N.F., et al., Structure and gene silencing activities of monovalent and pentavalent cationic lipid vectors complexed with siRNA. Biochem. 2007; 46(16):4785-4792.
Boyer-Diponio et al., Biological function of mutant forms of Jaggedi proteins in Alagille syndrome: inhibitory effect on Notch signaling. Hum Mol Genet. Nov. 15, 2007;16(22):2683-92. Epub Aug. 24, 2007.
Brennan, Ribonucleoside triphosphate concentration-dependent termination of bacteriophage SP0I transcription in vitro by Bacillus subtilis RNA polymerase. Virology Jun. 1984;135(2):555-60. doi: 10.1016/0042-6822(84)90211-3.
Brito et al., A cationic nanoemulsion for the delivery of next-generation RNA vaccines. Mol Ther. Dec. 2014;22(12):I-12. doi: 10.1038/mt.2014.133. Epub Jul. 16, 2014.
Brito et al., "Self-amplifying mRNA vaccines," Advances in Genetics, 2014, vol. 89, pp. 179-233.
Brown, Genomes. 2002. 2nd Edition. Oxford:Wiley-Liss. pp 1-20.
Burke et al., Formulation, stability, and delivery of live attenuated vaccines for human use. Crit Rev Ther Drug Carrier Syst. 1999; 16(1):1-83.
Byoung-Shik et al., Intranasal immunization with plasmid DNA encoding spike protein of SARS-coronavirus/polyethylenimine nanoparticles elicits antigen-specific humoral and cellular immune responses. BMC Immunol. Dec. 31, 2010;11:65. 9 pages doi: 10.1186/1471-2172-11-65.
Cao et al. 'MDR3/ABCB4 mRNA Therapy for Treating Progressive Familial Intrahepatic Cholestasis 3 (PFIC3)', Abstract No. 768, Molecular Therapy Apr. 22, 2019, vol. 27, No. 4, Suppl 1 pp. 358-359.
Carnahan et al., Epratuzumab, a Humanized Monoclonal Antibody Targeting CD22 Characterization of in Vitro Properties Clin Cancer Res. Sep. 1, 2003;9(10 Pt 2):3982S-90S.
Chamberlain et al., Recurrent lymphomatous meningitis treated with intra-CSF rituximab and liposomal ara-C. J Neurooncol. Feb. 2009;91(3):271-7. doi:10.1007/s11060-008-9707-1. Epub Sep. 27, 2008.
Chattopadhya Y et al., A chimeric vesiculo/alphavirus is an effective alphavirus vaccine. J Viral. Jan. 2013;87(1):395-402. doi: 10.1128/JVI.01860-12. Epub Oct. 17, 2012.
Chen, D., et al., Rapid discovery of potent siRNA-containing lipid nanoparticles enabled by controlled microfluidic formulation. J Am Chem Soc. 2012; 134: 6948-6951.
Chen et al., Human monoclonal antibodies targeting the haemagglutinin glycoprotein can neutralize H7N9 influenza virus. Nat Commun. Mar. 30, 2015;6:6714. 10 pages doi:10.1038/ncomms7714.
Chen et al., "Influence of particle size on the in vivo potency of lipid nanoparticle formulations of siRNA," Journal of Controlled Release, Aug. 10, 2016, pp. 236-244, vol. 235.
Chen et al., Molecular evolution and epidemiology of four serotypes of dengue virus in Thailand from 1973 to 2007. Epidemiol Infect. Feb. 2013;141(2):419-24. doi:10.1017/S0950268812000908. Epub May 14, 2012.
Chudley et al., Harmonisation of short-term in vitro culture for the expansion of antigen-specific CDS(+) T cells with detection by Elispot and HLA-multimer staining. Cancer Immunol Immunother. 2014;63(11):1199-1211.
Corazzelli et al., Biweekly rituximab, cyclophosphamide, vincristine, non-pegylated liposome-encapsulated doxorubicin and prednisone (R-COMP-14) in elderly patients with poor-risk diffuse large B-cell lymphoma and moderate to high 'life threat' impact cardiopathy. Br J Haematol. Sep. 2011;154(5):579-89. doi: 10.1111/j.1365-2141.2011.08786.x. Epub Jun. 28, 2011.

(56) References Cited

OTHER PUBLICATIONS

Cribbs, David H., Adjuvant-dependent Modulation of Th1 and Th2 Responses to Immunization with beta-amyloid, International Immunology, 2003, vol. 15, No. 4, pp. 505-514.
Crommelin et al., Addressing the Cold Reality of mRNA Vaccine Stability, J Pharm Sci, 2021, 110(3), 997-1001, DOI: 10.1016/j.xphs.2020.12.006.
Cun, Dongmei, et al., Preparation and characterization of poly(DL-lactide-co-glycolide) nanoparticles for siRNA delivery. International Journal of Pharmaceutics 390 (2010) 70-75.
Cunnigham, The herpes zoster subunit vaccine. Expert Opin Biol Ther. 2016;16(2):265-71. doi: 10.1517/14712598.2016.1134481.
Dahlman et al., In vivo endothelial siRNA delivery using polymeric nanoparticles with low molecular weight. Nat Nanotechnol. 2014;9(8):1-8. doi:10.1038/nnano.2014.84. Epub May 11, 2014.
Danaei et al., "Impact of particle Size and Polydispersity Index on the Clinical Applications of Lipidic nanocarrier Systems", Pharmaceutics, 2018, pp. 1-17, vol. 10.
Davtyan, H. et al., Immunogenicity, Efficacy, Safety, and Mechanism of Action of Epitope Vaccine (Lu AF20513) for Alzheimer's Disease: Prelude to a Clinical Trial, The Journal of Neuroscience, Mar. 2013, vol. 33, No. 11, pp. 4923-4934.
Delehanty, James B., Peptides for specific intracellular delivery and targeting of nanoparticles: implications for developing nanoparticle-mediated drug delivery. Ther Deliv. Sep. 2010;1(3):411-433. doi: 10.4155/tde.10.27.
Depledge et al., Deep Sequencing of Distinct Preparations of the Live Attenuated Varicella-Zoster Virus Vaccine Reveals a Conserved Core of Attenuating Single-Nucleotide Polymorphisms. J Viral. Sep. 12, 2016;90(19):8698-704.
Deshayes, S. et al., "Cell-penetrating peptides: tools for intracellular delivery of therapeutics," Cell. Mol. Life Sci., Aug. 2005, 62(16):1839-1849.
Dharap, S.S., et al., Tumor-specific Targeting of an Anticancer Drug Delivery System by LHRH Peptide, PNAS, 2005, vol. 102, No. 36, pp. 12962-12967.
Dickman et al., Ion Pair Reverse-Phase Chromatography: A Versatile Platform for the Analysis of RNA. Chromatography Today. 2011; 22-26.
Diken et al., Current Developments in Actively Personalized Cancer Vaccination with a Focus on RNA as the Drug Format. Prog Tumor Res. 2015;42:44-54. doi: 10.1159/000437184. Epub Sep. 4, 2015. Review.
Dong, Y. et al., Poly(d, 1-laclide-co-glycolide)/montmorillonite nanoparticles for oral delivery of anticancer drugs. Biomaterials. Oct. 2005;26(30):6068-76.
Dropulic et al., The challenge of developing a herpes simplex virus 2 vaccine. Expert Rev Vaccines. Dec. 2012;11(12):1429-40. doi:10.1586/erv.12.129. Author's Manuscript, 21 pages.
Du et al., Recombinant adeno-associated virus expressing the receptor-binding domain of severe acute respiratory syndrome coronavirus S protein elicits neutralizing antibodies: Implication for developing SARS vaccines. Virology. Sep. 15, 2006;353(1):6-16. doi: 10.1016/j.virol.2006.03.049. Epub Jun. 21, 2006.
Du, L. et al., Arginine-rich cell-penetrating peptide dramatically enhances AMO-mediated ATM Aberrant Splicing Correction and Enables Delivery to Brain and Cerebellum, Human Molecular Genetics, 2011, vol. 20, No. 16, pp. 3151-3160.
Durbin et al., RNAs Containing Modified Nucleotides Fail to Trigger RIG-I Conformational Changes for Innate Immune Signaling. mBio. Sep. 20, 2016;7(5):e00833-16. 11 pages doi: 10.1128/mBio.00833-16.
Easton, Le. et al., Rapid, nondenaturing RNA purification using weak anion-exchange fast performance liquid chromatography. RNA. Mar. 2010;16(3):647-53. Epub Jan. 25, 2010.
El Ouahabi, A., et al., Double long-chain amidine liposome-mediated self replicating RNA transfection. FEBS Letters. Feb. 1996; 380(1-2): 108-112.
Espeseth et al., Modified mRNA/lipid nanoparticle-based vaccines expressing respiratory syncytial virus F protein variants are immunogenic and protective in rodent models of RSV infection. NPJ Vaccines. Feb. 14, 2020;5:16. 14 pages doi:10.1038/s41541-020-0163-z. eCollection 2020.
Ewert et al., Cationic liposome-nucleic acid complexes for gene delivery and silencing: pathways and mechanisms for plasmid DNA and siRNA. Top Curr Chem. 2010;296:191-226. Author's Manuscript, 40 pages.
Ezzat, Kariem et al. PepFect 14, a Novel Cell-penetrating Peptide for Oligonucleotide Deliver in Solution and as Solid Formulation, Nucleic Acids Research, 2011, vol. 39, No. 12, pp. 5284-5298.
Fang et al., A Novel Cell-Penetrating Peptide Derived from Human Eosinophil Cationic Protein, PLOS One, 2013, vol. 8, Issue 3, e57318 (pp. 1-13).
Felgner, Pl Cationic lipid/polynucleotide condensates for in vitro and in vivo polynucleotide delivery—the cytofectins. J. of Liposome Research. 1993; 3(1): 3-16.
Felgner P. L., et al., "Lipofection: A Highly Efficient, Lipid-Mediated DNA-Transfection Procedure," Proceedings of the National Academy of Sciences USA, vol. 84 (21), Nov. 1987, pp. 7413-7417.
Felgner, Pl Particulate systems and polymers for in vitro and in vivo delivery of polynucleotides. Adv. Drug Delivery Rev. 1990; 5(3): 163-187.
Fleeton et al., Self-replicative RNA vaccines elicit protection against influenza A virus, respiratory syncytial virus, and a tickborne encephalitis virus. J Infect Dis. May 1, 2001;183(9):1395-8. Epub Mar. 30, 2001.
Freer et al., Varicella-zoster virus infection: natural history, clinical manifestations, immunity and current and future vaccination strategies. New Microbial. Apr. 2018;41(2):95-105. Epub Mar. 2, 2018.
Furie, Richard et al., A Phase III, Randomized, Placebo-Controlled Study of Belimumab, a Monoclonal Antibody That Inhibits B Lymphocyte Stimulator, in Patients With Systemic Lupus Erythematosus, Arthritis & Rheumatism, 2011, vol. 63, No. 12, pp. 3918-3930.
Furuichi, Caps on Eukaryotic mRNAs. eLS. John Wiley & Sons. Jul. 2014. 12 pages.
Gao, X. et al., Nonviral gene delivery: what we know and what is next. AAPS J. Mar. 23, 2007;9(1):E92-104.
Garcia-Manyes., S et al., "Nanomechanics of Lipid Bilayers: Heads or Tails?" Journal of the American Chemical Society, vol. 132, 2010, pp. 12874-12886.
Geall et al., Nonviral delivery of self-amplifying RNA vaccines. Proc Natl Acad Sci U S A. Sep. 4, 2012;109(36):14604-9. doi:10.1073/pnas.1209367109. Epub Aug. 20, 2012.
Genbank Submission; NIH/NCBI, Accession No. ADG45118.1. Schmidt-Chanasit et al., Jun. 24, 2010. 2 pages.
Genbank Submission; NIH/NCBI, Accession No. NM_I 72138.2. Zakaria et al., Jan. 13, 2020. 4 pages.
Genbank Submission; NIH/NCBI, Accession No. YP 009137218.1. Davidson. May 16, 2016. 2 Pages.
Genini et al., Serum Antibody Response to the gH/gL/pUL128-131 Five-Protein Complex of Human Cytomegalovirus (HCMV) in Primary and Reactivated HCMV Infections. J Clin Viral. Oct. 2011;52(2): 113-8. doi: 10.1016/i.icv.2011.06.018. Eoub Aug. 4, 2011.
Georgopoulos et al., Use of high-performance liquid chromatographic fractionation of large RNA molecules in the assay of group I intron ribozyme activity. J Chromatogr A. Jan. 28, 2000;868(1):109-14.
Giblin, M. et al., Selective Targeting of *E.coli* Heat-stable Enterotoxin Analogs to Human Colon Cancer Cells, Anticancer Research, 2006, vol. 26, pp. 3243-3252.
Giljohann, Da, et al., Gene regulation with polyvalent siRNA-nanoparticle conjugates. J Am Chem Soc. Feb. 2009; 131 (6): 2072-2073.
Gilkeson, G.S. et al., Induction of cross-reactive anti-dsDNA antibodies in preautoimmune NZB/NZW mice by immunization with bacterial DNA. J Clin Invest. Mar. 1995;95(3):1398-402.
Gjetting et al., In vitro and in vivo effects of polyethylene glycol (PEG)-modified lipid in DOTAP/cholesterol-mediated gene transfection. Int J Nanomedicine. Aug. 9, 2010;5:371-83.

(56) References Cited

OTHER PUBLICATIONS

Gluzman et al., Esterification of stearic acid with polyethylene glycols. Zhurnal Prikladnoi Khimii, Maik Nauka: Rossiiskaya Akademiya Nauk. Jan. 1, 1968;41(1):167-170.
Grabbe et al., Translating nanoparticulate-personalized cancer vaccines into clinical applications: case study with RNA-lipoplexes for the treatment of melanoma. Nanomedicine (Lond). Oct. 2016;11(20):2723-2734.
Hadinoto et al., Lipid-polymer Hybrid Nanoparticles as a New Generation Therapeutic Delivery Platform: A Review. Eur J Pharm Biopharm. Nov. 2013;85(3 Pt A):427-43. doi: 10.1016/j.ejpb.2013.07.002. Epub Jul. 17, 2013.
Hartmaier et al., Genomic analysis of 63,220 tumors reveals insights into tumor uniqueness and targeted cancer immunotherapy strategies. Genome Med. Feb. 24, 2017; 9:16. 9 pages doi: 10.1186/s13073-017-0408-2.
Hartmann et al., Handbook of RNA Biochemistry, Second Edition, "Part I RNA Synthesis and Detection." 2014. pp. 1-27.
Hashimoto et al., Relationship between the concentration of anti-polyethylene glycol (PEG) immunoglobulin M (IgM) and the intensity of the accelerated blood clearance (ABC) phenomenon against PEGylated liposomes in mice. Biol Pharm Bull. 2015;38(3):417-24. doi: 10.1248/bpb.b14-00653.
Hassett et al., "Optimization of Lipid Nanoparticles for Intramuscular Administration of mRNA Vaccines", Molecular Therapy: Nucleic Acids, Apr. 2019, vol. 15, 11 pages.
He, K. et al., Synthesis and Separation of Diastereomers of Ribonucleoside 5'-(alpha-P-Borano)triphosphates. J Org Chem. Aug. 21, 1998 ;63(17):5769-5773.
Hecker, Nonviral, cationic lipid-mediated delivery of mRNA. Methods Mol Biol. 2013;969:73-88. doi: 10.1007/978-1-62703-260-5 5.
Hecker, J.G. et al., Non-Viral DNA and mRNA Gene Delivery to the CNS Pre-Operatively for Neuroprotection and Following Neurotrauma. Molecular Therapy. 2004; 9, S258-S258.
Heesch et al., Abstract CT020: Merit: introducing individualized cancer vaccines for the treatment of TNBC—a phase I trial,' [abstract]. In: Proceedings of the 107th Annual Meeting of the American Association for Cancer Research; Apr. 16-20, 2016; New Orleans, LA. Philadelphia (PA): AACR; Cancer Res 2016; 76 (14 Suppl) 5 pages.
Heyes, J. et al. (2005), "Cationic lipid saturation influences intracellular delivery of encapsulated nucleic acids," Journal of Controlled Release, 107:276-287.
Hoerr, I. et al., In vivo application of RNA leads to induction of specific cytotoxic T lymphocytes and antibodies. EurJ Immunol. Jan. 2000;30(1): 1-7.
Hope et al., "Production of large unilamellar vesicles by a rapid extrusion procedure: characterization of size distribution, trapped volume and ability to maintain a membrane potential", Biochim Biophys Acta, 1985, 812, 55-65.
Hsu et al., Cationic lipid nanoparticles for therapeutic delivery of siRNA and miRNA to murine liver tumor. Nanomedicine. Nov. 2013;9(8): 1169-80. doi: 10.1016/j.nano.2013.05.007. Epub May 30, 2013.
Huber et al., Analysis of nucleic acids by on-line liquid chromatography-Mass spectrometry (Mass Spectrometry Reviews 2001, 20, pp. 310-343).
Hussein et al., Synthesis, Quantum Chemical Calculations and Properties of Nonionic and Nonionic-Anionic Surfactants Based on Fatty Alkyl Succinate. Journal of Surfactants and Detergents vol. 17, pp. 615-627(2014).
Ivanovska, N. et al., Immunization with a DNA chimeric molecule encoding a hemagglutinin peptide and a scFv CD21-specific antibody fragment induces long-lasting IgM and CTL responses to influenza virus. Vaccine. Mar. 10, 2006;24(11 ):1830-7. Epub Nov. 2, 2005.
Jachertz, D. et al., Treatment of P815 mastocytoma in DBA/2 mice with RNA. J Immunogen. 1974; 1: 355-362.
Janeway, C. et al., Immunobiology: the immune system in health and disease. Garland Publishing, Inc, London. 1997; 13:12-13:21.
Jayaraman et al., "Maximizing the Potency of siRNA Lipid Nanoparticles for Hepatic Gene Silencing in Vivo," Angew. Chem. Int. Ed. 2012, 51, 8529-8533.
Jia et al., Kinetic mechanism of GTP binding and RNA synthesis during transcription initiation by bacteriophage T7 RNA polymerase. J Biol Chem. Nov. 28, 1997;272(48):30147-53. doi: 10.1074/jbc.272.48.30147.
John et al., Multi-antigenic human cytomegalovirus mRNA vaccines that elicit potent humoral and cell-mediated immunity. Vaccine. Mar. 14, 2018;36(12):1689-1699. doi:10.1016/j.vaccine.2018.01.029. Epub Feb. 15, 2018.
Juliano, R.L., et al., Cell-targeting and cell-penetrating peptides for delivery of therapeutic and imaging agents. Wiley Interdisciplinary Reviews: Nanomedicine and Nanobiotechnology. May/Jun. 2009; 1(3): 324-335.
Kalantari-Dehagi et al., Discovery of Potential Diagnostic and Vaccine Antigens in Herpes Simplex Virus 1 and 2 by Proteome-Wide Antibody Profiling. J Viral. Apr. 2012;86(8):4328-39. doi: 10.1128/JVI.05194-11. Epub Feb. 8, 2012.
Kallen et al., A development that may evolve into a revolution in medicine: mRNA as the basis for novel, nucleotide-based vaccines and drugs. Ther Adv Vaccines. Jan. 2014;2(1):10-31. doi: 10.1177/2051013613508729.
Kallen et al., A novel, disruptive vaccination technology: self-adjuvanted RNActive® vaccines. Hum Vaccin Immunother. Oct. 2013;9(10):2263-76. doi: 10.4161/hv.25181. Epub Jun. 4, 2013. Review.
Kang, Hyunmin, Inhibition of MDR1 Gene Expression by Chimeric HNA Antisense Oligonucleotides, Nucleic Acids Research, 2004, vol. 32, No. 14, pp. 4411-4419.
Kariko et al., Phosphate-enhanced transfection of cationic lipid-complexed mRNA and plasmid DNA. Biochimica et Biophysica Acta. 1998. 1369:320-34.
Kariko et al., "Generating the optimal mRNA for therapy: HPLC purification eliminates immune activation and improves translation of nucleoside-modified, protein-encoding mRNA", Nucleic Acids Res. Nov. 2011;39(21):e142 (pp. 1-10).
Kariko, K., et al., In vivo protein expression from mRNA delivered into adult rat brain. J. of Neuroscience Methods. Jan. 2001; 105(1): 77-86.
Kariko K. et al., "Incorporation of pseudouridine into mRNA yields superior nonimmunogenic vector with increased translational capacity and biological stability," Molecular Therapy, Nature Publishing Group, vol. 16 (11):1833-1840 (2008).
Kauffman et al., Efficacy and immunogenicity of unmodified and pseudouridine-modified mRNA delivered systemically with lipid nanoparticles in vivo. Biomaterials. Dec. 2016;109:78-87. doi: 10.1016/j.biomaterials.2016.09.006. Epub Sep. 25, 2016.
Keown, Wa, et al., [41] Methods for Introducing DNA into Mammalian Cells. Methods in Enzymology, 1990, 185:527-37.
Keshwara et al., Rabies-based vaccine induces potent immune responses against Nipah virus. NPJ Vaccines. Apr. 15, 2019;4:15. Erratum in: NPJ Vaccines. May 13, 2019;4:18, 10 pages.
Kingston, 'Preparation of poly (A)+ RNA', Current protocols in molecular biology. 1993;21(1):4.5.1-4.5.3.
Kirchdoerfer et al., "Stabilized coronavirus spikes are resistant to conformational changes induced by receptor recognition or proteolysis.," Scientific Reports, (2018);8(1):15701, 11 pages. doi: 10.1038/s41598-018-34171-7.
Kirpotin, D.B., et al., Antibody targeting of long-circulating lipidic nanoparticles does not increase tumor localization but does increase internalization in animal models. Cancer Res. 2006; 66: 6732-6740.
Klinman, D.M. et al., DNA vaccines: safety and efficacy issues. Springer Semin Immunopathol. 1997;19(2):245-56.
Knudsen et al., Antisense properties of duplex- and triplex-forming PNAs. Nucleic Acids Res. Feb. 1, 1996; 24(3): 494-500.
Koch, G., et al., Quantitative Studies on the Infectivity of ribonucleic acid from partially purified and highly purified poliovirus preparations. Virology. Mar. 1960;10(3): 329-343.
Kowalski et al., Delivering the Messenger: Advances in Technologies for Therapeutic mRNA Delivery. Molecular Therapy. Apr. 4, 2019;27(4):710-28.

(56) References Cited

OTHER PUBLICATIONS

Kozielski, Kristen L. et al., Bioreducible Cationic Polymer-Based Nanoparticles for Efficient and Environmentally Triggered Cytoplasmic siRNA Delivery to Primary Human Brain Cancer Cells, ACS Nano, 2014, vol. 8, No. 4, pp. 3232-3241.
Krause et al., Prevention of the hemodynamic effects of iopromide-carrying liposomes in rats and pigs. Invest Radiol. Aug. 2000;35(8):493-503.
Kumar et al., Shielding of Lipid Nanoparticles for siRNA Delivery: Impact on Physicochemical Properties, Cytokine Induction, and Efficacy. Mol Ther Nucleic Acids. Nov. 18, 2014;3(11):e210, 7 pages. doi: 10.1038/mtna.2014.61.
Kussie, P. H. et al. "A single engineered amino acid substitution changes antibody fine specificity," J Immunol. Jan. 1, 1994; 152(1): 146-52.
Kutchko et al., Transcending the Prediction Paradigm: Novel Applications of Shape to RNA Function and Evolution. Wiley Interdiscip Rev RNA. Jan. 2017;8(1):e1374, 12 pages. doi: 10.1002/wrna.1374. Epub Jul. 10, 2016.
Laakkonen et al., Homing Peptides as Targeted Delivery Vehicles, Interactive Biology, 2010, vol. 2, pp. 326-337.
Lai, S.K., et al., Mucus-penetrating nanoparticles for drug and gene delivery to mucosal tissues. Adv Drug Deliv Rev. Feb. 27, 2009; 61(2): 158-171.
Lai, S.K., et al., Rapid transport of large polymeric nanoparticles in fresh undiluted human mucus. PNAS. Jan. 30, 2007; 104(5): 1482-1487.
Leader B., et al., Protein therapeutics: a summary and pharmacological classification. Nat Rev Drug Discov. Jan. 2008; 7(1): 21-39.
Lee et al., Separation and determination of polyethylene glycol fatty acid esters in cosmetics by a reversed-phase HPLC/ELSD. Talanta. Feb. 15, 2008;74(5):1615-20. doi: 10.1016/i.talanta.2007.10.020. Epub Oct. 18, 2007.
Lee, Justin B. et al., Lipid Nanoparticle siRNA Systems for Silencing the Androgen Receptor in Human Prostate Cancer in Vivo, International Journal of Cancer, 2012, vol. 131, pp. 781-790.
Lehto, T., et al., Cell-penetrating peptides for the delivery of nucleic acids. Expert Opin. Drug Deliv. Jul. 2012; 9(7): 823-836.
Leung et al., Microfluidic Mixing: A General Method for Encapsulating Macromolecules in Lipid Nanoparticle Systems. J Phys Chem B. Jul. 16, 2015;119(28):8698-706. doi: 10.1021/acs.ipcb.5b02891. Epub Jul. 7, 2015.
Lewandowski, L.J. et al., Separation of the infectious ribonucleic acid of potato spindle tuber virus from double-stranded ribonucleic acid of plant tissue extracts. J Virol. Nov. 1971;8(5):809-12.
Lewis, David, Dynamic Polyconjugates (DPC) Technology: An elegant solution to the siRNA delivery problem. Arrowhead Research Corp (Nasdaq: ARWR). Nov. 2011. 6 pages.
Li et al., Alagille syndrome is caused by mutations in human Jagged1, which encodes a ligand for Notch1. Nat Genet. Jul. 1997;16(3):243-51.
Li et al., Lipid-based nanoparticles for nucleic acid delivery. Pharm Res. Mar. 2007;24(3):438-49. doi: 10.1007/s11095-006-9180-5.
Li, L. et al., Overcoming obstacles to develop effective and safe siRNA therapeutics. Expert Opin Biol Ther. May 2009; 9(5): 609-19.
Li, L. et al., Preparation and gene delivery of alkaline amino acids-based cationic liposomes. Arch Pharm Res. Jul. 2008;31(7):924-31. Epub Aug. 14, 2008.
Lian, T. et al., Trends and developments in liposome drug delivery systems. J Pharm Sci. Jun. 2001;90(6):667-80.
Liu et al., Nucleic Acid Chemistry in the Organic Phase: From Functionalized Oligonucleotides to DNA Side Chain Polymers, J Am Chem Soc, 2014, 136, 14255-14262.
Lo, Albert et al., Hepatocellular Carcinoma Cell-Specific Peptide Ligand for Targeted Drug Delivery, Molecular Cancer Therapeutics, 2008, vol. 7, No. 3, pp. 579-589.
Lopez-Berestein et al., Treatment of systemic fungal infections with liposomalamphotericin B. Arch Intern Med. Nov. 1989;149(11):2533-6.
Lu et al., Bat-to-human: spike features determining 'host jump' of coronaviruses SARS-CoV, MERS-CoV, and beyond. Trends Microbial. Aug. 2015;23(8):468-78. doi: 10.1016/i.tim.2015.06.003. Epub Jul. 21, 2015.
Lu et al., IFNL3 mRNA structure is remodeled by a functional non-coding polymorphism associated with hepatitis C virus clearance. Sci Rep. 2015;5:16037, 14 pages.
Lu, Ruei-Min et al., Targeted Drug Delivery Systems Mediated by a Novel Peptide in Breast Cancer Therapy and Imaging, PLOS One, 2013, vol. 8, Issue 6, e66128, 13 pages.
Luo and Saltzman, "Synthetic DNA delivery systems", Nature Biotechnol. 2000;18(1): 33-37.
M. Kanapathipillai, et al., Nanoparticle targeting of anti-cancer drugs that alter intracellular signaling or influence the tumor microenvironment, Adv. Drug Deliv. Rev. (2014), pp. 1-12.
Maclachlan, Lipid Nanoparticle-mediated delivery of messenger RNA. Presentation. 1st International mRNA Health Conference. Tubingen, Germany. Oct. 24, 2013. http://files.shareholder.com/downloads/ABEA-50QJTB/2628241206x0x699789/47543d12-db34-4e6e-88a9-f3ae5d97b1d2/MacLachlan_mRNA_Conf_2013.pdf. Last accessed Dec. 22, 2016. 32 pages.
Madden et al., Systemic delivery of mRNA therapeutics using lipid nanoparticles (LNP): improved potency for novel LNP and influence of route of administration on protein expression. 2nd International mRNA Health Conference. Nov. 12, 2014. https://acuitastx.com/wp-content/uploads/2015/01/Poster-Second-International-mRNA-Health-Conference.pdf. 1 page.
Magee, W.E. et al., Marked stimulation of lymphocyte-mediated attack on tumor cells by target-directed liposomes containing immune RNA, Cancer Res., 1978, 38(4):1173-6.
Maier, et al., Biodegradable lipids enabling rapidly eliminated lipid nanoparticles for systemic delivery of RNAi therapeutics, Molecular Therapy, Aug. 1, 2013, pp. 1570-1578, vol. 21, No. 8.
Malone, R.W. et al., Cationic liposome-mediated RNA transfection. Proc Natl Acad Sci U S A. Aug. 1989;86 (16):6077-81.
Mar et al., Nucleic acid vaccination strategies against infectious diseases. Expert Opin Drug Deliv. 2015;12(12):1851-65. doi:10.1517/17425247.2015.1077559. Epub Sep. 12, 2015.
Marina et al., Dose escalation and pharmacokinetics of pegylated liposomal doxorubicin (Doxil) in children with solid tumors: a pediatric oncology group study. Clin Cancer Res. Feb. 2002;8(2):413-8.
Mas et al., Engineering, Structure and Immunogenicity of the Human Metapneumovirus F Protein in the Postfusion Conformation. PLoS Pathog. Sep. 9, 2016;12(9):e1005859. doi:10.1371/journal.ooat.1005859. eCollection Sep. 2016. 21 pages.
Mateo et al., Vaccines inducing immunity to Lassa virus glycoprotein and nucleoprotein protect macaques after a single shot. Sci Transl Med. Oct. 2, 2019;11(512):eaaw3163, 18 pages. doi: 10.1126/scitranslmed.aaw3163.
Mccormack, M., et al., Activation of the T-cell oncogene LM02 after gene therapy for X-linked severe combined immunodeficiency. N Engl J Med. Feb. 2004; 350: 913-922.
MEGAscript Kit Product Manual, Ambion/Invitrogen website: http://lools.invitrogen.com/content/sfs/manuals/ cms_072987.pdf, Publication Date: Oct. 27, 2009 (last accessed Mar. 17, 2013)("Ambion"), Author Life Technologies., 29 pages.
Mellits, K.H. et al., Removal of double-stranded contaminants from RNA transcripts: synthesis of adenovirus VA RNAI from a T7 vector. Nucleic Acids Res. Sep. 25, 1990;18(18):5401-6.
Michel et al., Cationic Nanoliposomes Meet mRNA: Efficient Delivery of Modified mRNA Using Hemocompatible and Stable Vectors for Therapeutic Applications. Mol Ther Nucleic Acids. Sep. 1, 20175;8:459-468. doi: 10.1016/j.omtn.2017.07.013. Epub Jul. 25, 2017.
Middleton et al., Hendra virus vaccine, a one health approach to protecting horse, human, and environmental health. Emerg Infect Dis. Mar. 2014;20(3):372-9. doi:10.3201/eid2003.131159.
Midoux et al., Lipid-based mRNA vaccine delivery systems. Expert Rev Vaccines. Feb. 2015; 14(2):221-34. doi: 10.1586/14760584.2015.986104. Epub Dec. 26, 2014. Review .
Mishra, N.C. et al., Induction by RNA of inositol independence in Neurospora crassa. Proc. Natl Acad. Sci. U.S.A., 1975, 72(2):642-5.

(56) References Cited

OTHER PUBLICATIONS

Mishra, R.K. et al., Improved leishmanicidal effect of phosphorothioate antisense oligonucleotides by LDL-mediated delivery. Biochim Biophys Acta. Nov. 7, 1995;1264(2):229-37.
Morello et al., Immunization With Herpes Simplex Virus 2 (HSV-2) Genes Plus Inactivated HSV-2 Is Highly Protective Against Acute and Recurrent HSV-2 Disease. J Viral. Apr. 2011;85(7):3461-72. doi: 10.1128/JVI.02521-10. Epub Jan. 26, 2011.
Muller, M.R. et al., Transfection of dendritic cells with RNA induces CD4- and COB- mediated T cell immunity against breast carcinomas and reveals the immunodominance of presented T cell epitopes. J Immunol. Jun. 15, 2003;170(12):5892-6.
Nair, S. et al., Soluble proteins delivered to dendritic cells via pH-sensitive liposomes induce primary cytotoxic T lymphocyte responses in vitro. J Exp Med. Feb. 1, 1992;175(2):609-12.
Nakamura, K. et al., Antigen restricted hybridization between antigen primed macrophage and thymic RNA. Immunol Commun. 1981;10(4-5):367-82.
Nakano et al., The structural stability and catalytic activity of DNA and RNA oligonucleotides in the presence of organic solvents, Biophysical Reviews, 2016, 8, 11-23.
NCT02410733—Evaluation of the Safety and Tolerability of i.v. Administration of a Cancer Vaccine in Patients With Advanced Melanoma (Lipa-MERIT)', ClinicalTrials.gov, Jul. 17, 2019, (Online), Viewed online Jan. 2, 2020, URL: https://www.clinicaltrials.gov/ct2/show/record/NCT02410733?term=NCT02410733&draw=2&rank=1 . 9 pages.
Nielsen et al. Toward Personalized Lymphoma Immunotherapy: Identification of Common Driver Mutations Recognized by Patient CDS+ T Cells. Clin Cancer Res. 2016;22(9):2226-2236.
Niu, M.C., et al., Poly(A)-attached RNA as activator in embryonic differentiation. Proc Soc Exp Biol Med. Oct. 1974;147 (1):318-22.
[No Author Listed], NEB RNase H (https://www.neb.com/products/m0297-rnase-h) Downloaded Mar. 30, 2020. 6 pages.
[No Author Listed], Oligotex Handbook, Qiagen, Jun. 2012 [retrieved from internet on Sep. 22, 2020] 104 pages https://www.qiagen.corn/au/resources/resourcedetail?id=f9fa1d98-d54d-47e7-a20b-8b0cb8975009&1ang=en.
[No Author Listed] Programme of the 1st International mRNA Health Conference, Germany; Oct. 2013. 32 pages.
[No Author Listed], User Guide for mMessage mMachine T7 Kit from Ambion. 2012. p. 1-36.
Obeid et al., The impact of solvent selection on the characteristics of niosome nanoparticles prepared by microfluidic mixing, International Journal of Charmaceutics: X, 2023, 5, 100168, 9 pages.
Oda et al., Mutations in the human Jagged1 gene are responsible for Alagille syndrome. Nat Genet. Jul. 1997;16(3):235-42.
Oja et al., Doxorubicin entrapped within liposome-associated antigens results in a selective inhibition of the antibody response to the linked antigen. Biochim Biophys Acta. Sep. 29, 2000;1468(1-2):31-40.
Okumura, K., et al., Bax mRNA therapy using cationic liposomes for human malignant melanoma. J Gene Med. 2008; 10: 910-917.
Oster, C.G., et al. Comparative study of DNA encapsulation into PLGA microparticles using modified double emulsion methods and spray drying techniques. Journal of Microencapsulation, May 2005; 22(3): 235-244.
Pallesen et al., Immunogenicity and structures of a rationally designed prefusion MERS-CoV spike antigen. Proc Natl Acad Sci US A. Aug. 29, 2017;114(35):E7348-E7357. doi: 10.1073/pnas.1707304114. Epub Aug. 14, 2017.
Pangburn, Todd et al., Peptide-and Aptamer-Functionalized Nanovectors for Targeted Delivery of Therapeutics, Journal of Biomedical Engineering, 2009, vol. 131, 20 pages.
Pardi et al., Developing an influenza vaccine using lipid nanoparticle-encapsulated nucleoside-modified mRNA. Eur. J. Immunol. Aug. 2016; 46(S1):1232-1233. Abstract 1349.
Pardi et al., "Expression kinetics of nucleoside-modified mRNA delivered in lipid nanoparticles to mice by various routes," Journal of Controlled Release, 217, 2015, 345-351.
Pardi et al., "Nucleoside-modified mRNA vaccines induce potent T follicular helper and germinal center B cell responses," Journal of Experimental Medicine, May 8, 2018, pp. 1571-1588, vol. 215, No. 6.
Parker et al., Targeting of Polyelectrolyte RNA Complexes to Cell Surface Integrins as an Efficient, Cytoplasmic Transfection Mechanism, Journal of Bioactive and Compatible Polymers, Jul. 2002, 17(4), 10 pages.
Patel et al., Arginoplexes: an arginine-anchored nanoliposomal carrier for gene delivery, Journal of Nanoparticle Research, 2014, 16:2345, 10 pages.
Petro et al., Herpes simplex type 2 virus deleted in glycoprotein D protects against vaginal, skin and neural disease. Elife. Mar. 10, 2015;4:e06054. 18 pages, doi:10.7554/eLife.06054.
Petsch et al., Protective efficacy of in vitro synthesized, specific mRNA vaccines against influenza A virus infection. Nat Biotechnol. Dec. 2012;30(12):1210-6. doi:10.1038/nbt.2436. Epub Nov. 25, 2012.
Phelan et al., Intercellular Delivery of Functional p53 by the Herpesvirus Protein VP22. Nature Biotechnology, 1998;16: 440-443.
Pollard, C,, et al., Type I Ifn counteracts the induction of antigen-specific immune responses by lipid-based delivery of mRNA vaccines. Mol Ther. Jan. 2013; 21(1): 251-259.
Popov et al., Multivalent rituximab lipid nanoparticles as improved lymphoma therapies: indirect mechanisms of action and in vivo activity. nNanomedicine (Lond). Nov. 2011;6(9):1575-91. doi: 10.2217/nnm.11.50. Epub Oct. 20, 2011.
Porteous et al., Evidence for safety and efficacy of DOTAP cationic liposome mediated CFTR gene transfer to the nasal epithelium of patients with cystic fibrosis. Gene Ther. Mar. 1997;4(3):210-8.
Poveda et al., Establishing Preferred Product Characterization for the Evaluation of RNA Vaccine Antigens. Vaccines (Basel). Sep. 27, 2019; 7, 131, 14 pages. doi: 10.3390/vaccines7040131.
Pubchem, Ethyl lauroyl arginate, Aug. 9, 2005, 19 pages, retrieved from https://pubchem.ncbi.nlm.nih.gov/compound/188214.
Rajasagi et al., Systematic identification of personal tumor-specific neoantigens in chronic lymphocytic leukemia. Blood. 2014; 124(3):453-462.
Ramamoorth et al., Non viral vectors in gene therapy—an overview. J Clin Diagn Res. Jan. 2015; 9(1): GE01-GE06.
Rammensee et al., Cancer Vaccines: Some Basic Considerations. Genomic and Personalized Medicine. 2009;573-589.
Read, M.L., et al., A versatile reducible polycation-based system for efficient delivery of a broad range of nucleic acids. Nucleic Acids Res. 2005; 33(9): e86, 16 pages.
Regberg et al., Applications of Cell-Penetrating Peptides for Tumor Targeting and Future Cancer Therapies. Pharmaceuticals, 2012; 5:991-1007.
Reichmuth, et al., "mRNA Vaccine Delivery Using Lipid Nanoparticles," Therapeutic Delivery (2016), v. 7, No. 5, pp. 319-334.
Riccardi et al., "Dressing up" an Old Drug: An Aminoacyl Lipid for the Functionalization of Ru(III)-Based Anticancer Agents. ACS Biomater. Sci. Eng. 2018, 4, 1, 163-174.
Riley et al., Simple repeat evolution includes dramatic primary sequence changes that conserve folding potential. Biochem Biophys Res Commun. Apr. 13, 2007;355(3):619-25. Epub Feb. 15, 2007.
Rodriguez, Pl et al., Minimal "self" peptides that inhibit phagocytic clearance and enhance delivery of nanoparticles. Science. Feb. 22, 2013; 339(6122): 971-975.
Rohloff, C.M., et al., Du Ros Technology delivers peptides and proteins at consistent rate continuously for 3 to 12 months. J Diabetes Sci Technol. May 2008; 2(3): 461-467.
Romano et al., Inter- and intra-host viral diversity in a large seasonal DENV2 outbreak. PLoS One. Aug. 2, 2013;8(8):e70318, 10 pages. doi: 10.1371/journal.pone.0070318. Print 2013.
Sabnis et al., "A Novel Amino Lipid Series for mRNA Delivery: Improved Endosomal Escape and Sustained Pharmacology and Safety in Non-human Primates," Molecular Therapy, Jun. 2018, vol. 26, No. 6, pp. 1509-1519.

(56) References Cited

OTHER PUBLICATIONS

Sahin et all, Personalized RNA mutanome vaccines mobilize poly-specific therapeutic immunity against cancer. Nature. Jul. 13, 2017;547(7662):222-226. doi: 10.1038/nature23003. Epub Jul. 5, 2017.
Saito, R., et al., Distribution of liposomes into brain and rat brain tumor models by convection-enhanced delivery monitored with magnetic resonance imaging. Cancer Res. Apr. 2004; 64: 2572-2579.
Sakuma, S. et al., Mucoadhesion of polystyrene nanoparticles having surface hydrophilic polymeric chains in the gastrointestinal tract. Int J Pharm. Jan. 25, 1999;177(2):161-72.
Schirrmacher, V. et al., Intra-pinna anti-tumor vaccination with self-replicating infectious RNA or with DNA encoding a model tumor antigen and a cytokine. Gene Ther. Jul. 2000;7(13):1137-47.
Schleiss, Cyotmegalovirus vaccines under clinical development. J Virus Erad. Oct. 5, 2016;2(4):198-207.
Schmidt et al., Progress in the development of human parainfluenza virus vaccines. Expert Rev Respir Med. Aug. 2011;5(4):515-26. doi: 10.1586/ers.11.32. Author's Manuscript, 20 pages.
Schott, J.W., et al., Viral and non-viral approaches for transient delivery of mRNA and proteins. Current Gene Ther. 2011; 11 (5): 382-398.
Schwendener, Liposomes as vaccine delivery systems: a review of the recent advances. Ther Adv Vaccines. Nov. 2014;2(6):159-82. doi: 10.1177/2051013614541440.
Semple, S.C., et al., "Rational design of cationic lipids for siRNA delivery", Nature Biotechnology, 2010, vol. 28, No. 2, 172-176.
Shah et al., Shingrix for Herpes Zoster: A Review. Skin Therapy Lett. Jul. 2019;24(4):5-7.
Shea, R.G. et al., Synthesis, hybridization properties and antiviral activity of lipid-oligodeoxynucleotide conjugates. Nucleic Acids Res. Jul. 11, 1990;18(13):3777-83.
Shimizu et al., Transport of PEGylated liposomes from the splenic marginal zone to the follicle in the induction phase of the accelerated blood clearance phenomenon. Immunobiology. May 2013;218(5):725-32. doi: 10.1016/j.imbio.2012.08.274. Epub Aug. 23, 2012.
Shin et al., Recent Advances in RNA Therapeutics and RNA Delivery Systems Based on Nanoparticles. Adv. Therap., Nov. 2018;1(7):1800065. Review. 27 pages.
Shinu et al., Multi-antigenic Human Cytomegalovirus mRNA Vaccines That Elicit Potent Humoral and Cell-Mediated Immunity. Vaccine. Mar. 14, 2018;36(12):1689-1699. doi: 10.1016/j.vaccine.2018.01.029. Epub Feb. 15, 2018.
Sieber et al., The Definition of Open Reading Frame Revisited. Trends Genet. Mar. 2018;34(3):167-170. doi: 10.1016/j.tig.2017.12.009. Epub Jan. 30, 2018.
Slater, The purification of poly(a)-containing RNA by affinity chromatography. Methods Mol Biol. 1985;2:117-20. doi: 10.1385/0-89603-064-4:117.
Srivastava, Progressive Familial Intrahepatic Cholestasis. Journal of Clinical and Experimental Hepatology. Mar. 2014;4(1):25-36.
Stanlis et al., Single-strand DNA Aptamers as Probes for Protein Localization in Cells, Journal of Histochemistry & Cytochemistry, 2003, 51(6), 797-808.
Stiles, D.K., et al., Widespread suppression of huntingtin with convection-enhanced delivery of siRNA. Experimental Neurology. Jan. 2012; 233(1): 463-471.
Strobel, I. et al., Human dendritic cells transfected with either RNA or DNA encoding influenza matrix protein M1 differ in their ability to stimulate cytotoxic T lymphocytes. Gene Ther. Dec. 2000; 7(23): 2028-2035.
Svinarchuk, F.P. et al., Inhibition of HIV proliferation in MT-4 cells by antisense oligonucleotide conjugated to lipophilic groups. Biochimie. 1993;75(1-2):49-54.
Tadin-Strapps, M., et al., "Development of lipoprotein(a) siRNAs for mechanism of action studies in non-human primate models of atherosclerosis", J Cardiovasc Transl Res, 2015, 8(1):44-53.
Taguchi et al., Effect of Repeated Injections of Adenosine Diphosphate-Encapsulated Liposomes Coated with a Fibrinogen—Chain Dodecapeptide Developed as a Synthetic Platelet Substitute on Accelerated Blood Clearance in a Healthy and an Anticancer Drug-Induced Thrombocytopenia Rat Model. J Pharm Sci. Sep. 2015;104(9):3084-91. doi: 10.1002/jps.24418. Epub Mar. 9, 2015.
Taguchi et al., Hemoglobin vesicles, polyethylene glycol (PEG)ylated liposomes developed as a red blood cell substitute, do not induce the accelerated blood clearance phenomenon in mice. Drug Metab Dispos. Nov. 2009;37(11):2197-203. doi: 10.1124/dmd.109.028852. Epub Aug. 13, 2009.
Tanaka, M. et al., Inhibition of heart transplant injury and graft coronary artery disease after prolonged organ ischemia by selective protein kinase C regulators. J Thorac Cardiovasc Surg. May 2005;129(5):1160-7.
Tang, D.C. et al., Genetic immunization is a simple method for eliciting an immune response. Nature. Mar. 12, 1992;356(6365):152-4.
Tavernier, G. et al., "mRNA as gene therapeutic: How to control protein expression," Journal of Controlled Release, vol. 150 (3):238-247(2011).
Terada et al., Characterization of Lipid Nanoparticles Containing Ionizable Cationic Lipids Using Design-of-Experiments Approach. Langmuir. Jan. 26, 2021;37(3):1120-1128. doi: 10.1021/acs.langmuir.0c03039. Epub Jan. 13, 2021.
Thess et al., Sequence-engineered mRNA Without Chemical Nucleoside Modifications Enables an Effective Protein Therapy in Large Animals. Mol Ther. Sep. 2015;23(9):1456-64. doi: 10.1038/mt.2015.103. Epub Jun. 8, 2015.
Torrecilla et al., Lipid Nanoparticles as Carriers for RNAi Against Viral Infections: Current Status and Future Perspectives. Biomed Res Int. 2014; 2014:161794, 17 pages. doi: 10.1155/2014/161794. Epub Aug. 12, 2014.
Tracy, M., "Progress in the Development of LNP Delivery for siRNA Advancing LNPs to the Clinic," International Liposome Research Days Meeting, Vancouver, Canada. Aug. 2010, pp. 1-52.
Treat, J. et al., in Liposomes in the Therapy of Infectious Disease and Cancer, Lopez-Berestein and Fidler (eds.), Liss, New York, 1989. 353-65.
Tripathy et al., Long-term expression of erythropoietin in the systemic circulation of mice after intramuscular injection of a plasmid DNA vector, Proc. Natl. Acad. Sci. USA. Oct. 1996; 93:10876-10880.
Uniprot; NIH/NCBI, Accession No. P06475.1. Swain et al., Jan. 1, 2015. 3 pages.
Uniprot; NIH/NCBI, Accession No. P06764.1. Hodgman et al., Jan. 7, 2015. 1 page.
Uzgun, S., et al., PEGylation improves nanoparticle formation and transfection efficiency of messenger RNA. Pharm Res. Sep. 2011; 28(9); 2223-2232.
Van Tendeloo V., et al. "Highly efficient gene delivery by mRNA electroporation in human hematopoietic cells: superiority to lipofection and passive pulsing of mRNA and to electroporation of plasmid cDNA for tumor antigen loading of dendritic cells," Blood, vol. 98(1):49-56 (2001).
Viklund et al., Enzymatic synthesis of surfactants based on polyethylene glycol and stearic or 12-hydroxystearic acid. Journal of Molecular Catalysis B Enzymatic 27(2):51-53, Feb. 2004.
Wang et al., Chapter 3: Lipid Nanoparticles for the Delivery of Nucleic Acids. Book: Nanoparticulate Drug Delivery Systems: Strategies, Technologies, and Applications. 2013. 29 pages.
Wang et al., Enhanced bioavailability and efficiency of curcumin for the treatment of asthma by its formulation in solid lipid nanoparticles. Int J Nanomedicine. 2012;7:3667-77. doi: 10.2147/IJN.S30428. Epub Jul. 17, 2012.
Wang et al., Purification of the messenger ribonucleic acid for the lipoprotein of the *Escherichia coli* outer membrane. Biochemistry. Oct. 2, 1979;18(20):4270-7.
Wang et al., Structural Definition of a Neutralization-sensitive Epitope on the MERS-CoV S1-NTD. Cell Rep. Sep. 24, 2019;28(13):3395-3405.e6. doi:10.1016/j.celrep.2019.08.052. Author's Manuscript, 29 pages.

(56) References Cited

OTHER PUBLICATIONS

Wang Y. et al., "Systemic delivery of modified mRNA encoding herpes simplex virus 1 thymidine kinase for targeted cancer gene therapy", Molecular Therapy, vol. 21(2):358-367 (2012).
Weaver., Molecular Biology. 1999. WCB/McGraw-Hill. Chapter 15:456. 5 pages.
Weilhammer et al., The use of nanolipoprotein particles to enhance the immunostimulatory properties of innate immune agonists against lethal influenza challenge. Biomaterials. Dec. 2013;34(38):10305-18. doi: 10.1016/j.biomaterials.2013.09.038. Epub Sep. 27, 2013.
Weissman et al., HPLC purification of in vitro transcribed long RNA. Methods Mol Biol. 2013;969:43-54. doi: 10.1007/978-1-62703-260-5 3.
WHO Drug Information, International Nonproprietary Names for Pharmaceutical Substances (INN), 1993, vol. 7, No. 4, pp. 1-16.
Woodward et al., Varicella Virus Vaccine Live: A 22-Year Review of Postmarketing Safety Data. Open Forum Infect Dis. Aug. 1, 2019 ;6(8):ofz295. 13 pages.
Wrapp et al. "Cryo-EM structure of the 2019-nCoV spike in the prefusion conformation," Science (Mar. 2020) 367:1260-1263.
Wussow et al., Human cytomegalovirus vaccine based on the envelope gH/gL pentamer complex. PLoS Pathog. Nov. 20, 2014;10(11):e1004524, 23 pages. doi:10.1371/journal.ppat.1004524. eCollection Nov. 2014.
Yadav et al., Predicting Immunogenic Tumour Mutations by Combining Mass Spectrometry and Exome Sequencing. Nature. Nov. 27, 2014;515(7528):572-6. doi: 10.1038/nature14001.
Yamamoto et al., Current prospects for mRNA gene delivery, European Journal of Pharmaceutics and Biopharmaceutics 71 (2009) 484-489.
Yang, Xiaoming, et al., Effect of CD44 Binding Peptide Conjugated to an Engineered Inert Matrix on Maintenance of Breast Cancer Stem Cells and Tumorsphere Formation, PLOS One, 2013, vol. 8, Issue 3, pp. 1-15.
Yu, Alice et al, Anti-GD2 Antibody with GM-CSF, Interleukin-2, and Isotretinoin for Neuroblastoma, The New England Journal of Medicine, 2010, vol. 363; No. 14, pp. 1324-1334.
Yuan et al., Cryo-EM structures of MERS-Co V and SARS-Co V spike glycoproteins reveal the dynamic receptor binding domains. Nat Commun. Apr. 10, 2017;8:15092, 9 pages. doi: 10.1038/ncomms15092.
Yuan et al., Human Jagged 1 mutants cause liver defect in Alagille syndrome by overexpression of hepatocyte growth factor. J Mol Biol. Feb. 24, 2006;356(3):559-68. Epub Dec. 20, 2005.
Zhang et al., "Assessing the Heterogeneity Level in Lipid Nanoparticles for siRNA Delivery: Size-Based Separation, Compositional heterogeneity, and Impact of Bioperformance", Molecular Pharmaceutics, vol. 10, 2013, pp. 397-405.
Zhang et al., Personalized cancer vaccines: Targeting the cancer mutanome. Vaccine. Feb. 15, 2017;35(7):1094-1100. doi: 10.1016/j.vaccine.2016.05.073. Epub Jul. 20, 2016. Author's Manuscript, 16 pages.
Zhao et al., A frustrating problem: accelerated blood clearance of PEGylated solid lipid nanoparticles following subcutaneous injection in rats. Eur J Pharm Biopharm. Aug. 2012;81(3):506-13. doi: 10.1016/j.ejpb.2012.04.023. Epub May 11, 2012.
Zhao, Y., et al., "Lipid Nanoparticles for Gene Delivery," Advances in genetics, 2014, vol. 88, pp. 13-36.
Zhigaltsev, I.V., et al., Bottom-Up design and synthesis of limit size lipid nanoparticle systems with aqueous and triglyceride cores using millisecond microfluidic mixing. Langmuir. Feb. 21, 2012; 28(7): 3633-3640.
Zimmermann, E. et al., Electrolyte- and pH-stabilities of aqueous solid lipid nanoparticle (SLN) dispersions in artificial gastrointestinal media. Eur J Pharm Biopharm. Sep. 2001;52(2):203-10.
Zohra, F.T., et al., Drastic effect of nanoapatite particles on liposome-mediated mRNA delivery to mammalian cells. Analytical Biochem. Oct. 2005; 345(1): 164-166.
Zohra, F.T., et al., Effective delivery with enhanced translational activity synergistically accelerates mRNA-based transfection. Biochem Biophys Res Comm. Jun. 2007; 358(1 ): 373-378.
Zou et al., Lipid-mediated delivery of RNA is more efficient than delivery of DNA in non-dividing cells. Int J Pharm. Apr. 15, 2010;389(1-2):232-43. doi: 10.1016/j.ijpharm.2010.01.019. Epub Jan. 18, 2010. Author's Manuscript, 26 pages.
Zou, Li-li et al., Cell-Penetrating Peptide-Mediated Therapeutic Molecule Delivery Into the Central Nervous System, Current Neuropharmacology, 2013, vol. 11, No. 2, pp. 197-208.
Balbino, T.A. et al., "Microfluidic devices for continuous production of pDNA/cationic liposome complexes for gene delivery and vaccine therapy," Colloids and Surfaces B: Biointerfaces 111 (2013), pp. 203-210. (Year: 2013).
Beck et al., "Strategies and challenges for the next generation of antibody-drug conjugates," Nature Review Drug Discovery, May 2017, vol. 16, pp. 315-337.
Belliveau et al., "Microfluidic Synthesis of Highly Potent Limit-size Lipid Nanoparticles for in Vivo Delivery of siRNA," Molecular Therapy-Nucleic Acids, 2012, 1, e37, 9 pages.
Buyens et al., "Liposome based systems for systemic siRNA delivery: Stability in blood sets the requirements for optimal carrier design," Journal of Controlled Release, 2012, 158:362-370.
Cullis et al., "Lipid Nanoparticle Systems for Enabling Gene Therapies," Molecular Therapy, 2017, 25(7), 1467-1475.
Sigma-Aldrich, "DMG-Peg 2000," retrieved from https://www.sigmaaldrich.com/catalog/product/avanti/880151p?lang=en®ion=US on Jan. 4, 2021, 2 pages.
Erasmus, "A Nanostructured Lipid Carrier for Delivery of a Replicating Viral RNA Provides Single, Low-Dose Protection against Zika," Molecular Therapy, Oct. 2018, vol. 26, No. 10, pp. 2507-2522.
Gjetting et al., "A simple protocol for preparation of a liposomal vesicle with encapsulated plasmid DNA that mediate high accumulation and reporter gene activity in tumor tissue," Results in Pharma Sciences, 2011, 1:49-56.
Hoarau D et al., "Novel Long-Circulating Lipid Nanocapsules." Pharmaceutical Research, vol. 21, No. 10, Oct. 2004, pp. 1783-1789.
Iden et al., "In vitro and in vivo comparison of immunoliposomes made by conventional coupling techniques with those made by a new post-insertion approach," Biochimica et Biophysica Acta (2001) 1513: 207-216.
Ishida T et al., "A combinatorial approach to producing sterically stabilized (Stealth) immunoliposomal drugs." FEBS Letters, vol. 460, 1999, pp. 129-133. (Year: 1999).
Jeffs et al. (Mar. 2005) "A Scalable, Extrusion-Free Method for Efficient Liposomal Encapsulation of Plasmid DNA" Pharmaceutical Research, vol. 22, No. 3, p. 362-372.
Kauffman et al., "Optimization of Lipid Nanoparticle Formulations for mRNA Delivery in Vivo with Fractional Factorial and Definitive Screening Designs," Nano Letters, 2015, 15(11):7300-7306.
Kulkarni et al., "Lipid Nanoparticles Enabling Gene Therapies: From Concepts to Clinical Utility," Nucleic Acid Ther., 2018, 28(3): 146-157.
Leung et al., "Lipid Nanoparticles Containing siRNA Synthesized by Microfluidic Mixing Exhibit an Electron-Dense Nanostructured Core," The Journal of Physical Chemistry C, 2012, 116:18440-18450.
Sugiyama et al. "Character of Liposomes as a Drug Carrier by Modifying Various Polyethyleneglycol-Lipids," Biological and Pharmaceutical Bulletin, vol. 36(6), 2013, pp. 900-906.
Li and Huang, "Targeted Delivery of Antisense Oligodeoxynucleotide and Small Interference RNA into Lung Cancer Cells," Molecular Pharmaceutics, 2006 vol. 3, No. 5, pp. 579-588.
MacLachlan, I., "Liposomal Formulations for Nucleic Acid Delivery," Antisense Drug Technologies, Second Edition, Chapter 9, 2007, pp. 237-270.
Maurer, N., et al., Spontaneous entrapment of polynucleotides upon electrostatic interaction with ethanol-destabilized cationic liposomes. Biophys J. May 2001; 80(5):2310-2326.

(56) References Cited

OTHER PUBLICATIONS

Perouzel E et al., “Synthesis and Formulation of Neoglycolipids for the Functionalization of Liposomes and Lipoplexes.” Bioconjugate Chemistry, vol. 14, 2003, pp. 884-898.
Santos et al., “Design of peptide-targeted liposomes containing nucleic acids,” Biochimica et Biophysica Acta (2010) 1798: 433-441.
Perrier et al., “Post-insertion into Lipid NanoCapsules (LNCs): From experimental aspects to mechanisms.” International Journal of Pharmaceutics, vol. 396 (2010), pp. 204-209. (Year : 2010).
Wan, C. et al., “Lipid nanoparticle delivery systems for siRNA-based therapeutics,” Drug Deliv. and Transl. Res., (Feb. 2014), 4(1):74-83.
Wang et al., “Delivery of oligonudeotides with lipid nanopartides,” Advanced Drug DeliveryReviews, 2015, 87: 65-80.
Wang et al., “Encapsulating Protein into Preformed Liposomes by EthanolDestabilized Method,” Artificial Cells, Blood Substitutes, and Technology, 2003, 31(3):303-312.
Wilson et al., “Real Time Measurement of PEG Shedding from Lipid Nanoparticles in Serum via Spectroscopy,” Molecular Pharmaceutics, 2015 12(2):386-392.
Xu. H, et al., “Enhanced pH-Responsiveness, Cellular Trafficking, Cytotoxicity and Long-circulation of PEGylated Liposomes with Post-insertion Technique Using Gemcitabine as a Model Drug.” Pharmaceutical Research, vol. 32, 2015, pp. 2428-2438.
Wan et al., “Studies on PEG-modified SLNs loading vinorelbine bitartrate (I): Preparation and evaluation in vitro,” International Journal of Pharmaceutics (2008) 359: 104-110.
Chi et al., “Molecular Targets and Strategies in the Development of Nucleic Acid Cancer Vaccines: from Shared to Personalized Antigens,” Journal of Biomedical Science, 2024, 31:94, 26 pages.
Akinc, et al., “A combinatorial library of lipid-like materials for delivery of RNAi therapeutics,” Nature Biotechnology, Apr. 27, 2008, vol. 26, pp. 561-569 (with supplemental content).
Dean et al., “Lung Alveolar Repair: Not All Cells Are Equal,” 2017, Trends in Molecular Medicine, vol. 23, Issue 1, 871-873).
Falbe. J, et al., “Surfactants in Consumer Products”, Theory, Technology and Application, 1st edition, Jul. 1994, pp. 101-102.
Finn et al., “A Single Administration of CRISPR/Cas9 Lipid Nanoparticles Achieves Robust and Persistent In Vivo Genome Editing,” Cell Reports, Cell Press, 2018, vol. 22, pp. 2227-2235 (with supplemental content).
Gindy et al., Stabilization of Ostwald Ripening in Low Molecular Weight Amino Lipid Nanoparticles for Systemic Delivery of siRNA Therapeutics.
Housecroft, C.E. & Constable, E.C., “Chemistry: An Introduction to Organic, Inorganic and Physical Chemistry”, 3rd Edition; Pearson Education, 2006; ISBN 0131275674; p. 510.
Kulkarni et al. “Fusion-dependent formation of lipid nanoparticles containing macromolecular payloads.” Nanoscale, vol. 11, 2019, pp. 9023-9031. (Year: 2019).
Kono, K., Drug Delivery System, 2008, vol. 23 No.6, p. 644-653.
Shah et al., Shingrix for Herpes Zoster: A Review. Skin Therapy Lett. 2019 Ju 1 ;24(4): 5-7.

* cited by examiner

SEQUENCE LISTING

```
<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
```

-continued

```
<223> OTHER INFORMATION: stem loop sequence

<400> SEQUENCE: 1

caaaggctct tttcagagcc acca                                    24


<210> SEQ ID NO 2
<211> LENGTH: 24
<212> TYPE: RNA
<213> ORGANISM: Artificial Sequence
<220> FEATURE:
<223> OTHER INFORMATION: stem loop sequence

<400> SEQUENCE: 2

caaaggcucu uuucagagcc acca                                    24
```

METHODS OF PREPARING LIPID NANOPARTICLES

RELATED APPLICATIONS

This application is a U.S. National Phase application, filed under 35 U.S.C. § 371, of International Application No. PCT/US2020/016082, filed Jan. 31, 2020, which claims priority to, and the benefit of, U.S. Provisional Application No. 62/799,620, filed Jan. 31, 2019, the entire contents of each of which are incorporated herein by reference in their entireties.

INCORPORATION BY REFERENCE OF SEQUENCE LISTING

The contents of the text file named "MRNA-062_N01US_SeqList.txt", which was created on Jul. 12, 2021, and is 660 bytes in size, are hereby incorporated by reference in its entirety.

FIELD OF DISCLOSURE

The present disclosure provides novel methods of producing nucleic acid lipid nanoparticle (LNP) formulations, the produced formulations thereof, and the related therapeutic and/or diagnostic uses, such as methods involving the nucleic acid lipid nanoparticles to deliver one or more therapeutics and/or prophylactics, such as a nucleic acid, to and/or produce polypeptides in mammalian cells or organs.

BACKGROUND

The effective targeted delivery of biologically active substances such as small molecule drugs, proteins, and nucleic acids represents a continuing medical challenge. In particular, the delivery of nucleic acids to cells is made difficult by the relative instability and low cell permeability of such species. Thus, there exists a need to develop methods and compositions to facilitate the delivery of therapeutics and prophylactics such as nucleic acids to cells.

Lipid-containing nanoparticles or lipid nanoparticles, liposomes, and lipoplexes have proven effective as transport vehicles into cells and/or intracellular compartments for biologically active substances such as small molecule drugs, proteins, and nucleic acids. Though a variety of such lipid-containing nanoparticles have been demonstrated, improvements in safety, efficacy, and specificity are still lacking.

STATEMENT REGARDING SEQUENCE LISTING

The sequence listing associated with this application is provided in text format in lieu of a paper copy, and is hereby incorporated by reference into the specification. The name of the text file containing the sequence listing is MRNA_062_001WO_ST25.txt. The text file is 614 bytes, and was created on Jan. 30, 2020, and is being submitted electronically.

SUMMARY

In some aspects, the present disclosure provides a method of producing a lipid nanoparticle (LNP) formulation, the method comprising: i) mixing a lipid solution comprising an ionizable lipid with an aqueous buffer solution comprising a first buffering agent thereby forming a lipid nanoparticle solution comprising a lipid nanoparticle; and ii) adding a nucleic acid solution comprising a nucleic acid to the lipid nanoparticle solution thereby forming a lipid nanoparticle (LNP) formulation comprising the lipid nanoparticle associated with the nucleic acid.

In some aspects, the present disclosure provides a method of administering a lipid nanoparticle (LNP) formulation to a patient, the method comprising: i) providing an active agent solution having a pH in a range of about 4.5 to about 8.0 comprising a therapeutic and/or prophylactic agent and a lipid nanoparticle solution having a pH in a range of about 4.5 to about 6.5 comprising a lipid nanoparticle, the lipid nanoparticle comprising an ionizable lipid: ii) forming a lipid nanoparticle formulation comprising the lipid nanoparticle associated with the therapeutic and/or prophylactic agent by mixing the lipid nanoparticle solution and the active agent solution such that the lipid nanoparticle formulation has a pH in a range of about 4.5 to about less than 8.0; and iii) administering the lipid nanoparticle formulation to the patient after the mixing.

According to another aspect, the present disclosure relates to a lipid nanoparticle (LNP) formulation being prepared by the method of any of the embodiments described herein.

According to another aspect, the present disclosure relates to a method of treating or preventing a disease or disorder, the method comprising administering a lipid nanoparticle (LNP) formulation to a subject in need thereof according to the method of any one of the embodiments described herein.

According to another aspect, the present disclosure relates to a method of treating or preventing a disease or disorder, the method comprising administering a lipid nanoparticle (LNP) formulation prepared by the method of any one of the embodiments described herein to a subject in need thereof.

According to another aspect, the present disclosure relates to an active agent solution according to any of the embodiments described herein, a lipid nanoparticle solution according to any of the embodiments described herein, and a kit comprising an active agent solution, a lipid nanoparticle solution and/or a mixing and administration device according to any of the embodiments described herein.

In some aspects, the present disclosure provides a lipid nanoparticle being prepared by a method disclosed herein.

In some aspects, the present disclosure provides a lipid nanoparticle solution being prepared by a method disclosed herein.

In some aspects, the present disclosure provides a lipid nanoparticle (LNP) formulation being prepared by a method disclosed herein.

In some aspects, the present disclosure provides a method of treating or preventing a disease or disorder, the method comprising administering a lipid nanoparticle described herein to a subject in need thereof.

In some aspects, the present disclosure provides a method of treating or preventing a disease or disorder, the method comprising administering a lipid nanoparticle solution nanoparticle described herein to a subject in need thereof.

In some aspects, the present disclosure provides a method of treating or preventing a disease or disorder, the method comprising administering a lipid nanoparticle formulation nanoparticle described herein to a subject in need thereof.

In some aspects, the present disclosure provides a lipid nanoparticle described herein for treating or preventing a disease or disorder in a subject.

In some aspects, the present disclosure provides a lipid nanoparticle solution described herein for treating or preventing a disease or disorder in a subject.

In some aspects, the present disclosure provides a lipid nanoparticle formulation described herein for treating or preventing a disease or disorder in a subject.

In some aspects, the present disclosure provides a use of a lipid nanoparticle described herein in the manufacture of a medicament for treating or preventing a disease or disorder in a subject.

In some aspects, the present disclosure provides a use of a lipid nanoparticle solution described herein in the manufacture of a medicament for treating or preventing a disease or disorder in a subject.

In some aspects, the present disclosure provides a use of a lipid nanoparticle formulation described herein in the manufacture of a medicament for treating or preventing a disease or disorder in a subject.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the disclosure will be apparent from the following detailed description and claims.

DETAILED DESCRIPTION

Figure 1:
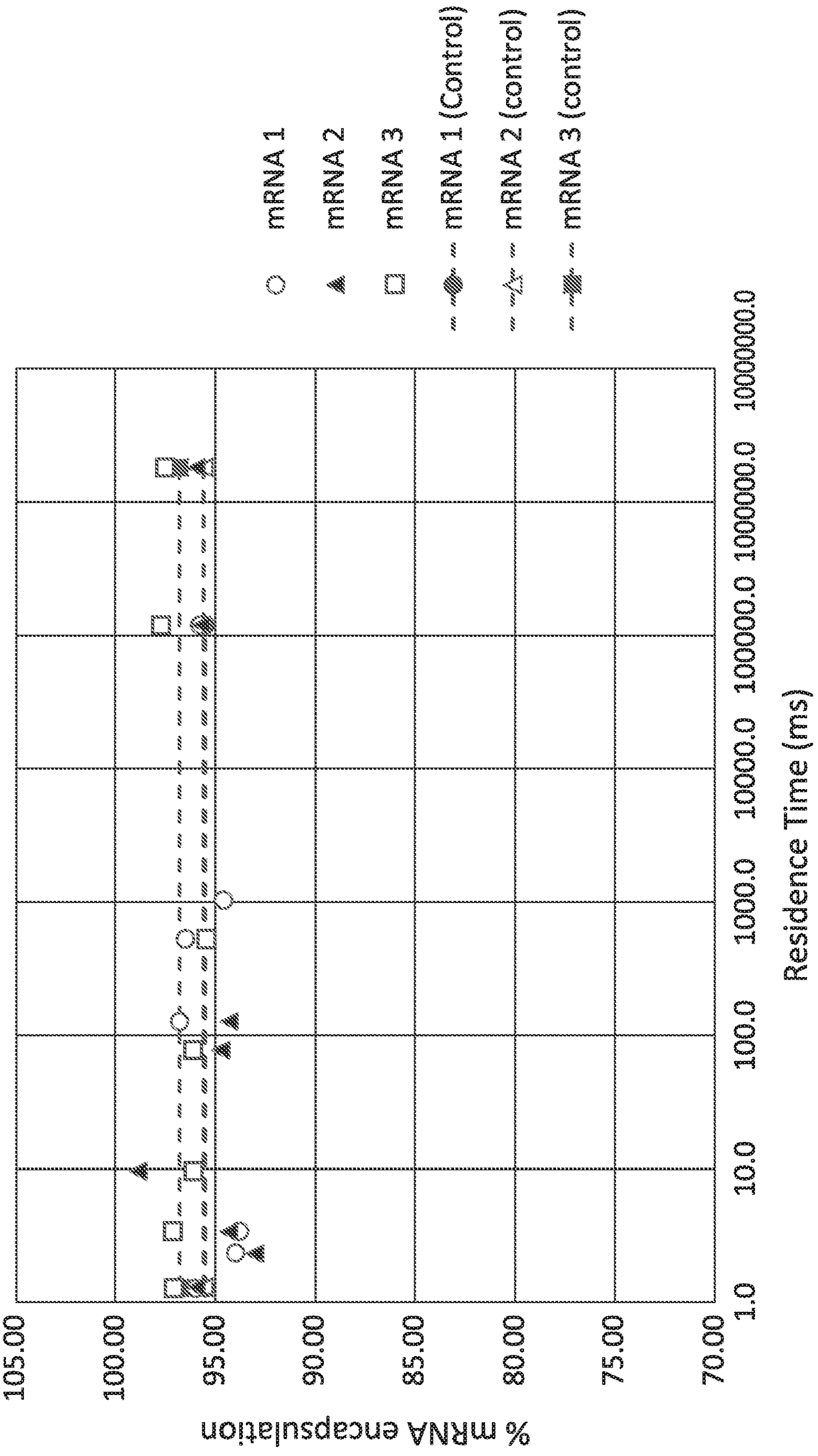
FIG. 1 is a graph showing that comparable or increased mRNA encapsulation is observed when mRNA is introduced at longer timescales after LNP generation (i.e., increased residence times). Encapsulation was evaluated via the Ribogreen fluorescence assay.

The present disclosure is based, in part, on the discovery that the method of producing the lipid nanoparticle (LNP) or lipid nanoparticle (LNP) formulation, as disclosed herein, can influence and/or dictate distribution of certain components within the lipid nanoparticles, and that this distribution can influence and/or dictate physical (e.g., stability) and/or biological (e.g. efficacy, intracellular delivery, immunogenicity) properties of the lipid nanoparticles.

In some embodiments, the method of the present disclosure mitigate an undesired property change from the produced lipid nanoparticle (LNP) or lipid nanoparticle (LNP) formulation. In some embodiments, the methods of the present disclosure mitigate an undesired property change from the produced lipid nanoparticle (LNP) or lipid nanoparticle (LNP) formulation as compared to the LNP or LNP formulation produced by a comparable method (e.g., a method without one or more of the steps as disclosed herein).

In some embodiments, the undesired property change is caused by a stress upon the lipid nanoparticle formulation or the lipid nanoparticle. In some embodiments, the stress is induced during producing, purifying, packing, storing, transporting, and/or using the lipid nanoparticle formulation or lipid nanoparticle. In some embodiments, the stress is heat, shear, excessive agitation, membrane concentration polarization (change in charge state), dehydration, freezing stress, drying stress, freeze/thaw stress, and/or nebulization stress. In some embodiments, the stress is induced during storing a lipid nanoparticle formulation or lipid nanoparticle.

In some embodiments, the undesired property change is a reduction of the physical stability of the LNP formulation. In some embodiments, the undesired property change is an increase of the amount of impurities and/or sub-visible particles, or an increase in the average size of the LNP in the LNP formulation.

In some embodiments, the method of the present disclosure mitigates a reduction of the physical stability (e.g., an increase in the average size of the LNP) from the produced LNP formulation as compared to the LNP formulation produced by a comparable method as disclosed herein.

In some embodiments, the LNP formulation produced by the method of the present disclosure has an average LNP diameter being about 99% or less, about 98% or less, about 97% or less, about 96% or less, about 95% or less, about 90% or less, about 85% or less, about 80% or less, about 75% or less, about 70% or less, about 65% or less, about 60% or less, about 55% or less, about 50% or less, about 40% or less, about 30% or less, about 20% or less, or about 10% or less as compared to the average LNP diameter of the LNP formulation produced by a comparable method as disclosed herein.

In some embodiments, the undesired property change is a reduction of the chemical stability of the LNP formulation. In some embodiments, the undesired property change is a reduction of the integrity of the nucleic acid (e.g., RNA (e.g., mRNA)) in the LNP formulation.

In some embodiments, the undesired property change is a reduction of the biological property of the LNP formulation. In some embodiments, the undesired property change is a reduction of efficacy, intracellular delivery, and/or immunogenicity of the LNP formulation.

In some embodiments, the LNP formulation produced by the method of the present disclosure has an efficacy, intracellular delivery, and/or immunogenicity being higher than the efficacy, intracellular delivery, and/or immunogenicity of the LNP formulation produced by a comparable method as disclosed herein.

In some embodiments, the LNP formulation produced by the method of the present disclosure has an efficacy, intracellular delivery, and/or immunogenicity being higher than the efficacy, intracellular delivery, and/or immunogenicity of the LNP formulation produced by a comparable method by about 5% or higher, about 10% or more, about 15% or more, about 20% or more, about 30% or more, about 40% or more, about 50% or more, about 60% or more, about 70% or more, about 80% or more, about 90% or more, about 1 folds or more, about 2 folds or more, about 3 folds or more, about 4 folds or more, about 5 folds or more, about 10 folds or more, about 20 folds or more, about 30 folds or more, about 40 folds or more, about 50 folds or more, about 100 folds or more, about 200 folds or more, about 300 folds or more, about 400 folds or more, about 500 folds or more, about 1000 folds or more, about 2000 folds or more, about 3000 folds or more, about 4000 folds or more, about 5000 folds or more, or about 10000 folds or more.

In some embodiments, the LNP formulation produced by the method of the present disclosure exhibits a nucleic acid expression (e.g., the mRNA expression) higher than the nucleic acid expression (e.g., the mRNA expression) of the LNP formulation produced by a comparable method.

In some embodiments, the LNP formulation produced by the method of the present disclosure exhibits a nucleic acid expression (e.g., the mRNA expression) higher than the nucleic acid expression (e.g., the mRNA expression) of the LNP formulation produced by a comparable method by about 5% or higher, about 10% or more, about 15% or more, about 20% or more, about 30% or more, about 40% or more, about 50% or more, about 60% or more, about 70% or more, about 80% or more, about 90% or more, about 1 folds or more, about 2 folds or more, about 3 folds or more, about 4 folds or more, about 5 folds or more, about 10 folds or more, about 20 folds or more, about 30 folds or more, about 40 folds or more, about 50) folds or more, about 100 folds or more, about 200 folds or more, about 300) folds or more, about 400 folds or more, about 500 folds or more, about 1000 folds or more, about 2000 folds or more, about 3000 folds or more, about 4000 folds or more, about 5000 folds or more, or about 10000 folds or more.

Traditionally, messenger RNA-loaded lipid nanoparticles (mRNA-LNPs) have been produced via high-energy mixing of aqueous mRNA and a solution of lipids in ethanol. Aqueous solutions are poor solvents of the lipids used in the process, which most often are a mixture of a cationic lipid, a phospholipid, a structural lipid, and a PEG lipid. Mixing the lipids, therefore, results in the self-assembly of the lipids into nanoparticles, e.g., of diameter less than 100 nm.

Additionally, recent efforts towards "bedside" and/or "point-of-care" formulations have been encouraging, whereby mRNA may be encapsulated within preformed vesicles that were prepared at an earlier date. This mode of production offers advantages in the context of clinical supply, as empty LNP vesicles may be produced and stored separately prior to recombination with mRNA in a clinical compound setting. Specifically, bedside formulations may promote increased stability since mRNA and empty raw materials can be stored in separately optimized conditions. Process complexity and cost of goods may be reduced since the LNP preparation occurs independent of cargo, enabling a platform approach for multiple mRNA or active agent constructs. The empty LNP plus mRNA modality may be referred to as "post hoc loading" (PHL), "post-hoc addition", or "post-hoc".

The present disclosure is based, in part, on efforts exploring the fundamental principles of post hoc loading and investigating the impact and conditions of mRNA addition at timescales after empty LNP generation. The time of m RNA addition after lipid precipitation has been varied by upwards of seven orders of magnitude (e.g., 1 ms to 10,000,000 ms) without detrimentally impacting the physicochemical properties of the formulation (e.g., particle size, encapsulation, morphology, and/or structural integrity). Similarities in physicochemical properties were surprising and non-intuitive, given that mRNA is conventionally included as a critical component within inlet aqueous streams of lipid precipitation reactions. Further, oligonucleotides are often described participating in the early particle assembly steps. Outcomes from empirical experiments suggest that mRNA encapsulation may occur at timescales significantly longer than lipid precipitation/particle formation, without detrimentally affecting LNP physicochemical properties. Those experiments demonstrated that the lipid particle formation and subsequent mRNA encapsulation may be separated into two reaction steps. The concept of post hoc loading as described herein may enable control and/or optimization of each step separately. Further, the post hoc loading may enable mRNA addition at timescales that enable point-of-care formulation (e.g., months or years following empty LNP production.

Historically, processes have not been developed to generate pre-formed empty lipid nanoparticles (LNPs) at scales appropriate for clinical supply. The present disclosure is based, in part, on efforts to ascertain a multitude of process parameters advantageous for scaled production including, but not limited to, lipid concentrations, temperature, buffer composition (e.g., ionic strength, pH, counterion), and ethanol content allow for particle size control while The present disclosure is based, in part, on the discovery that the method of producing the lipid nanoparticle (LNP) or lipid nanoparticle (LNP) formulation, as disclosed herein, can influence and/or dictate distribution of certain components within the lipid nanoparticles, and that this distribution can influence and/or dictate physical (e.g., stability) and/or biological (e.g. efficacy, intracellular delivery, immunogenicity) properties of the lipid nanoparticles.

In some embodiments, the present disclosure yields compositions comprising lipid nanoparticles having an advantageous distribution of components.

In some embodiments, the LNP formulation produced by the method of the present disclosure exhibits a nucleic acid expression (e.g., the mRNA expression) higher than the nucleic acid expression (e.g., the mRNA expression) of the LNP formulation produced by a comparable method.

In some embodiments, the LNP formulation produced by the method of the present disclosure displays desirable structural features by small x-ray scattering analysis for in vitro/in vivo activity compared to that of the LNP formulation produced by a comparable method.

In some embodiments, the LNP formulation produced by the method of the present disclosure displays desirable structural features by small x-ray scattering analysis for in vitro/in vivo activity compared to that of the LNP formulation produced by a comparable method.

In some embodiments, the LNP formulation produced by the method of the present disclosure displays more homogeneous structural features by Cryo-TEM analysis compared to that of the LNP formulation produced by a comparable method.

In some embodiments, the LNP formulation produced by the method of the present disclosure exhibits a nucleic acid expression (e.g., the mRNA expression) higher than the nucleic acid expression (e.g., the mRNA expression) of the LNP formulation prepared by a comparable method by about 5% or higher, about 10% or more about 15% or more, about 20% or more, about 30% or more, about 40% or more, about 50% or more, about 60% or more, about 70% or more, about 80% or more, about 90% or more, about 1 folds or more, about 2 folds or more, about 3 folds or more, about 4 folds or more, about 5 folds or more, about 10 folds or more, about 20 folds or more, about 30 folds or more, about 40 folds or more, about 50 folds or more, about 100 folds or more, about 200 folds or more, about 300 folds or more, about 400 folds or more, about 500 folds or more, about 1000 folds or more, about 2000 folds or more, about 3000 folds or more, about 4000 folds or more, about 5000 folds or more, or about 10000 folds or more.

Methods of Producing Lipid Nanoparticle (LNP) Compositions and LNP Compositions Produced Thereof In contrast to other techniques for production (e.g., thin film rehydration/extrusion), ethanol-drop precipitation has been the industry standard for generating stable nucleic acid lipid nanoparticles (SNALPs). Precipitation reactions are favored due to their continuous nature, scalability, and ease of adoption. Those processes usually high energy mixers (e.g., T-junction, confined impinging jets, vortex mixers) to introduce lipids (in ethanol) to a suitable anti-solvent (i.e. water) in a controllable fashion, driving liquid supersaturation and spontaneous precipitation into lipid particles.

The present disclosure provides method of producing a lipid nanoparticle composition, the method comprising: i) mixing a lipid solution comprising an ionizable lipid with an aqueous buffer solution comprising a first aqueous buffer thereby forming an empty lipid nanoparticle; and ii) adding a nucleic acid solution comprising a nucleic acid to the lipid nanoparticle thereby forming a lipid nanoparticle (LNP) formulation comprising a lipid nanoparticle encapsulating the nucleic acid.

Lipid Solution

In some embodiments, the methods of the present disclosure provide a lipid solution.

In some embodiments, the lipid solution may comprise an ionizable lipid. In some embodiments, the lipid solution may comprise the ionizable lipid at a concentration of greater than about 0.01 mg/mL, 0.05 mg/mL, 0.06 mg/mL, 0.07 mg/mL, 0.08 mg/mL, 0.09 mg/mL, 0.1 mg/mL, 0.15 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL, or 1.0 mg/mL. In some embodiments, the lipid solution may comprise a ionizable lipid at a concentration ranging from about 0.01-1.0 mg/mL, 0.01-0.9 mg/mL, 0.01-0.8 mg/mL, 0.01-0.7 mg/mL, 0.01-0.6 mg/mL, 0.01-0.5 mg/mL, 0.01-0.4 mg/mL, 0.01-0.3 mg/mL, 0.01-0.2 mg/mL, 0.01-0.1 mg/mL, 0.05-1.0 mg/mL, 0.05-0.9 mg/mL, 0.05-0.8 mg/mL, 0.05-0.7 mg/mL, 0.05-0.6 mg/mL, 0.05-0.5 mg/mL, 0.05-0.4 mg/mL, 0.05-0.3 mg/mL, 0.05-0.2 mg/mL, 0.05-0.1 mg/mL, 0.1-1.0 mg/mL, 0.2-0.9 mg/mL, 0.3-0.8 mg/mL, 0.4-0.7 mg/mL, or 0.5-0.6 mg/mL. In some embodiments, the lipid solution may comprise an ionizable lipid at a concentration up to about 5.0 mg/mL, 4.0 mg/mL, 3.0 mg/mL, 2.0 mg/mL, 1.0 mg/mL, 0.09 mg/mL, 0.08 mg/mL, 0.07 mg/mL, 0.06 mg/mL, or 0.05 mg/mL.

In some embodiments, the lipid solution may comprise an ionizable lipid. In some embodiments, the lipid solution may comprise the ionizable lipid at a concentration of greater than about 0.1 mg/mL, 0.5 mg/mL, 0.6 mg/mL, 0.7 mg/mL, 0.8 mg/mL, 0.9 mg/mL, 1.0 mg/mL, 1.5 mg/mL, 2.0 mg/mL, 3.0 mg/mL, 4.0 mg/mL, 5.0 mg/mL, 6.0 mg/mL, 7.0 mg/mL, 8.0 mg/mL, 9.0 mg/mL, 10 mg/mL, 11 mg/mL, 12 mg/mL, 13 mg/mL, 14 mg/mL, 15 mg/mL, 20 mg/mL, 25 mg/mL or 30 mg/mL. In some embodiments, the lipid solution may comprise a ionizable lipid at a concentration ranging from about 0.1-20.0 mg/mL, 0.1-19 mg/mL, 0.1-18 mg/mL, 0.1-17 mg/mL, 0.1-16 mg/mL, 0.1-15 mg/mL, 0.1-14 mg/mL, 01-13 mg/mL, 0.1-12 mg/mL, 0.1-11 mg/mL, 0.5-10.0 mg/mL, 0.5-9 mg/mL, 0.5-8 mg/mL, 0.5-7 mg/mL, 0.5-6 mg/mL, 0.5-5.0 mg/mL, 0.5-4 mg/mL, 0.5-3 mg/mL, 0.5-2 mg/mL, 0.5-1 mg/mL, 1-20 mg/mL, 1-15 mg/mL, 1-12 mg/mL, 1-10 mg/mL, or 1-8 mg/mL. In some embodiments, the lipid solution may comprise an ionizable lipid at a concentration up to about 30 mg/mL, 25, mg/mL, 20 mg/mL, 18 mg/mL, 16 mg/mL, 15 mg/mL, 14 mg/mL, 12 mg/mL, 10 mg/mL, 8 mg/mL, 6 mg/mL, 5.0 mg/mL, 4.0 mg/mL, 3.0 mg/mL, 2.0 mg/mL, 1.0 mg/mL, 0.09 mg/mL, 0.08 mg/mL, 0.07 mg/mL, 0.06 mg/mL, or 0.05 mg/mL.

In some embodiments, the lipid solution comprises an ionizable lipid in an aqueous buffer and/or organic solution. In some embodiments, the lipid nanoparticle solution may further comprise a buffering agent and/or a salt. Exemplary suitable buffering agents include, but are not limited to, ammonium sulfate, sodium bicarbonate, sodium citrate, sodium acetate, potassium phosphate, sodium phosphate, HEPES, and the like. In some embodiments, the lipid solution comprises a buffering agent at a concentration ranging from about 0.1-100 mM, from about 0.5-90 mM, from about 1.0-80 mM, from about 2-70 mM, from about 3-60 mM, from about 4-50 mM, from about 5-40 mM, from about 6-30 mM, from about 7-20 mM, from about 8-15 mM, from about 9-12 mM. In some embodiments, the lipid solution comprises a buffering agent at a concentration of or greater than about 0.1 mM, 0.5 mM, 1 mM, 2 mM, 4 mM, 6 mM, 8 mM, 10 mM, 15 mM, 20 mM, 25 mM, 30 mM, 35 mM, 40 mM, 45 mM, or 50 mM. Exemplary suitable salts include, but are not limited to, potassium chloride, magnesium chloride, sodium chloride, and the like. In some embodiments, the lipid solution comprises a salt at a concentration ranging from about 1-500 mM, from about 5-400 mM, from about 10-350 mM, from about 15-300 mM, from about 20)-250 mM, from about 30-200 mM, from about 40-190 mM, from about 50-180 mM, from about 50-170 mM, from about 50-160 mM, from about 50-150 mM, or from about 50-100 mM. In some embodiments, the lipid nanoparticle solution comprises a salt at a concentration of or greater than about 1 mM, 5 mM, 10 mM, 20 mM, 30 mM, 40 mM, 50 mM, 60 mM, 70 mM, 80 mM, 90 mM, or 100 mM.

In some embodiments, the lipid solution may have a pH ranging from about 4.5 to about 7.0, about 4.6 to about 7.0, about 4.8 to about 7.0, about 5.0 to about 7.0, about 5.5 to about 7.0, about 6.0 to about 7.0, about 6.0 to about 6.9, about 6.0 to about 6.8, about 6.0 to about 6.7, about 6.0 to about 6.6, about 6.0 to about 6.5. In some embodiments, a suitable lipid solution may have a pH of or no greater than 4.5, 4.6, 4.7, 4.8, 4.9 5.0, 5.2, 5.4, 5.6, 5.8, 6.0, 6.1, 6.2, 6.3, 6.4, 6.5, 6.6, 6.7, 6.8, 6.9, and 7.0.

Aqueous Buffer Solution

In some embodiments, the aqueous buffer solution comprises a aqueous buffering agent. In some embodiments, a suitable solution may further comprise one or more buffering agent and/or a salt. Exemplary suitable buffering agents include, but are not limited to, ammonium sulfate, sodium bicarbonate, sodium citrate, sodium acetate, potassium phosphate, sodium phosphate, HEPES, and the like. In some embodiments, the aqueous buffer solution comprises a buffering agent at a concentration ranging from about 0.1-100 mM, from about 0.5-90 mM, from about 1.0-80 mM, from about 2-70 mM, from about 3-60 mM, from about 4-50 mM, from about 5-40 mM, from about 6-30 mM, from about 7-20 mM, from about 8-15 mM, from about 9-12 mM. In some embodiments, the aqueous buffer solution comprises a buffering agent at a concentration of or greater than about 0.1 mM, 0.5 mM, 1 mM, 2 mM, 4 mM, 6 mM, 8 mM, 10 mM, 15 mM, 20 mM, 25 mM, 30 mM, 35 mM, 40 mM, 45 mM, or 50 mM. Exemplary suitable salts include, but are not limited to, potassium chloride, magnesium chloride, sodium chloride, and the like. In some embodiments, the aqueous buffer solution comprises a salt at a concentration ranging from about 1-500 mM, from about 5-400 mM, from about 10-350 mM, from about 15-300 mM, from about 20-250 mM, from about 30-200 mM, from about 40-190 mM, from about 50-180 mM, from about 50-170 mM, from about 50-160 mM, from about 50-150 mM, or from about 50-100 mM. In some embodiments, the nucleic acid solution comprises a salt at a concentration of or greater than about 1 mM, 5 mM, 10 mM, 20 mM, 30 mM, 40 mM, 50 mM, 60 mM, 70 mM, 80 mM, 90 mM, or 100 mM.

In some embodiments, the aqueous buffer solution may have a pH ranging from about 4.5 to about 7.0, about 4.6 to about 7.0, about 4.8 to about 7.0, about 5.0 to about 7.0, about 5.5 to about 7.0, about 6.0 to about 7.0, about 6.0 to about 6.9, about 6.0 to about 6.8, about 6.0 to about 6.7, about 6.0 to about 6.6, about 6.0 to about 6.5. In some embodiments, a suitable aqueous buffer solution may have a pH of or no greater than 4.5, 4.6, 4.7, 4.8, 4.9 5.0, 5.2, 5.4, 5.6, 5.8, 6.0, 6.1, 6.2, 6.3, 6.4, 6.5, 6.6, 6.7, 6.8, 6.9, and 7.0.

Nucleic Acid or Active Agent Solution

In some embodiments, the methods of the present disclosure provide an active agent solution comprising a therapeutic and/or prophylactic agent. The therapeutic and/or prophylactic agent may be provided in a solution to be mixed or added to a lipid nanoparticle or lipid nanoparticle solution such that the therapeutic and/or prophylactic agent may be encapsulated in the lipid nanoparticle.

In some embodiments, the therapeutic and/or prophylactic agent is a vaccine or a compound capable of eliciting an immune response.

In some embodiments, the therapeutic and/or prophylactic agent is a nucleic acid.

In some embodiments, the methods of the present disclosure provide a nucleic acid solution comprising a nucleic acid. The nucleic acid may be provided in a solution to be mixed or added to a lipid nanoparticle or lipid nanoparticle solution such that the nucleic acid may be encapsulated in the lipid nanoparticle.

In some embodiments, the nucleic acid solution may comprise the nucleic acid to be encapsulated at various concentrations. In some embodiments, the nucleic acid solution may comprise a nucleic acid at a concentration of greater than about 0.01 mg/mL, 0.05 mg/mL, 0.06 mg/mL, 0.07 mg/mL, 0.08 mg/mL, 0.09 mg/mL, 0.1 mg/mL, 0.15 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL, or 1.0 mg/mL. In some embodiments, the nucleic acid solution may comprise a nucleic acid at a concentration ranging from about 0.01-1.0 mg/mL, 0.01-0.9 mg/mL, 0.01-0.8 mg/mL, 0.01-0.7 mg/mL, 0.01-0.6 mg/mL, 0.01-0.5 mg/mL, 0.01-0.4 mg/mL, 0.01-0.3 mg/mL, 0.01-0.2 mg/mL, 0.01-0.1 mg/mL, 0.05-1.0 mg/mL, 0.05-0.9 mg/mL, 0.05-0.8 mg/mL, 0.05-0.7 mg/mL, 0.05-0.6 mg/mL, 0.05-0.5 mg/mL, 0.05-0.4 mg/mL, 0.05-0.3 mg/mL, 0.05-0.2 mg/mL, 0.05-0.1 mg/mL, 0.1-1.0 mg/mL, 0.2-0.9 mg/mL, 0.3-0.8 mg/mL, 0.4-0.7 mg/mL, or 0.5-0.6 mg/mL. In some embodiments, the nucleic acid solution my comprise a nucleic acid at a concentration up to about 5.0 mg/mL, 4.0 mg/mL, 3.0 mg/mL, 2.0 mg/mL, 1.0 mg/mL, 0.09 mg/mL, 0.08 mg/mL, 0.07 mg/mL, 0.06 mg/mL, or 0.05 mg/mL.

In some embodiments, the nucleic acid solution comprises a nucleic acid in an aqueous buffer. In some embodiments, a suitable nucleic acid solution may further comprise a buffering agent and/or a salt. Exemplary suitable buffering agents include, but are not limited to, ammonium sulfate, sodium bicarbonate, sodium citrate, sodium acetate, potassium phosphate, sodium phosphate, HEPES, and the like. In some embodiments, the nucleic acid solution comprises a buffering agent at a concentration ranging from about 0.1-100 mM, from about 0.5-90 mM, from about 1.0-80 mM, from about 2-70 mM, from about 3-60 mM, from about 4-50 mM, from about 5-40 mM, from about 6-30 mM, from about 7-20 mM, from about 8-15 mM, from about 9-12 mM. In some embodiments, the nucleic acid solution comprises a buffering agent at a concentration of or greater than about 0.1 mM, 0.5 mM, 1 mM, 2 mM, 4 mM, 6 mM, 8 mM, 10 mM, 15 mM, 20 mM, 25 mM, 30 mM, 35 mM, 40 mM, 45 mM, or 50 mM. Exemplary suitable salts include, but are not limited to, potassium chloride, magnesium chloride, sodium chloride, and the like. In some embodiments, the nucleic acid solution comprises a salt at a concentration ranging from about 1-500 mM, from about 5-400 mM, from about 10-350 mM, from about 15-300 mM, from about 20-250 mM, from about 30-200 mM, from about 40-190 mM, from about 50-180 mM, from about 50-170 mM, from about 50-160 mM, from about 50-150 mM, or from about 50-100 mM. In some embodiments, the nucleic acid solution comprises a salt at a concentration of or greater than about 1 mM, 5 mM, 10 mM, 20 mM, 30 mM, 40 mM, 50 mM, 60 mM, 70 mM, 80 mM, 90 mM, or 100 mM.

In some embodiments, the nucleic acid solution may have a pH ranging from about 4.5 to about 7.0, about 4.6 to about 7.0, about 4.8 to about 7.0, about 5.0 to about 7.0, about 5.5 to about 7.0, about 6.0 to about 7.0, about 6.0 to about 6.9, about 6.0 to about 6.8, about 6.0 to about 6.7, about 6.0 to about 6.6, about 6.0 to about 6.5. In some embodiments, a suitable nucleic acid solution may have a pH of or no greater than 4.5, 4.6, 4.7, 4.8, 4.9 5.0, 5.2, 5.4, 5.6, 5.8, 6.0, 6.1, 6.2, 6.3, 6.4, 6.5, 6.6, 6.7, 6.8, 6.9, and 7.0.

Lipid Nanoparticle Solution

In some embodiments, the methods of the present disclosure provide lipid nanoparticle solution comprising a therapeutic and/or prophylactic agent. The therapeutic and/or prophylactic agent may be provided in a solution to be mixed or added to a lipid nanoparticle or lipid nanoparticle solution such that the therapeutic and/or prophylactic agent may be encapsulated in the lipid nanoparticle.

In some embodiments, the methods of the present disclosure provide a lipid nanoparticle solution comprising an empty lipid nanoparticle. The lipid nanoparticle may be provided in a solution to be mixed or added to a lipid nanoparticle or lipid nanoparticle solution such that the nucleic acid may be encapsulated in the lipid nanoparticle.

In some embodiments, the lipid nanoparticle solution may comprise the empty lipid nanoparticle. In some embodiments, the lipid nanoparticle solution may comprise the lipid nanoparticle at a concentration of greater than about 0.01 mg/mL, 0.05 mg/mL, 0.06 mg/mL, 0.07 mg/mL, 0.08 mg/mL, 0.09 mg/mL, 0.1 mg/mL, 0.15 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL, or 1.0 mg/mL. In some embodiments, the lipid nanoparticle solution may comprise the lipid nanoparticle at a concentration ranging from about 0.01-1.0 mg/mL, 0.01-0.9 mg/mL, 0.01-0.8 mg/mL, 0.01-0.7 mg/mL, 0.01-0.6 mg/mL, 0.01-0.5 mg/mL, 0.01-0.4 mg/mL, 0.01-0.3 mg/mL, 0.01-0.2 mg/mL, 0.01-0.1 mg/mL, 0.05-1.0 mg/mL, 0.05-0.9 mg/mL, 0.05-0.8 mg/mL, 0.05-0.7 mg/mL, 0.05-0.6 mg/mL, 0.05-0.5 mg/mL, 0.05-0.4 mg/mL, 0.05-0.3 mg/mL, 0.05-0.2 mg/mL, 0.05-0.1 mg/mL, 0.1-1.0 mg/mL, 0.2-0.9 mg/mL, 0.3-0.8 mg/mL, 0.4-0.7 mg/mL, or 0.5-0.6 mg/mL. In some embodiments, the lipid nanoparticle solution may comprise an empty lipid nanoparticle at a concentration up to about 5.0 mg/mL, 4.0 mg/mL, 3.0 mg/mL, 2.0 mg/mL, 1.0 mg/mL, 0.09 mg/mL, 0.08 mg/mL, 0.07 mg/mL, 0.06 mg/mL, or 0.05 mg/mL.

In some embodiments, the lipid nanoparticle solution comprises a lipid nanoparticle in an aqueous buffer. In some embodiments, the lipid nanoparticle solution may further comprise a buffering agent and/or a salt. Exemplary suitable buffering agents include, but are not limited to, ammonium sulfate, sodium bicarbonate, sodium citrate, sodium acetate, potassium phosphate, sodium phosphate, HEPES, and the like. In some embodiments, the lipid nanoparticle solution comprises a buffering agent at a concentration ranging from about 0.1-100 mM, from about 0.5-90 mM, from about 1.0-80 mM, from about 2-70 mM, from about 3-60 mM, from about 4-50 mM, from about 5-40 mM, from about 6-30 mM, from about 7-20 mM, from about 8-15 mM, from about 9-12 mM. In some embodiments, the lipid nanoparticle solution comprises a buffering agent at a concentration of or greater than about 0.1 mM, 0.5 mM, 1 mM, 2 mM, 4 mM, 6 mM, 8 mM, 10 mM, 15 mM, 20 mM, 25 mM, 30 mM, 35 mM, 40 mM, 45 mM, or 50 mM. Exemplary suitable salts include, but are not limited to, potassium chloride, magnesium chloride, sodium chloride, and the like. In some embodiments, the lipid nanoparticle solution comprises a salt at a concentration ranging from about 1-500 mM, from about 5-400 mM, from about 10-350 mM, from about 15-300 mM, from about 20-250 mM, from about 30-200 mM, from about 40-190 mM, from about 50-180 mM, from about 50-170 mM, from about 50-160 mM, from about 50-150 mM, or from about 50-100 mM. In some embodiments, the lipid nanoparticle solution comprises a salt at a concentration of or greater than about 1 mM, 5 mM, 10 mM, 20 mM, 30 mM, 40 mM, 50 mM, 60 mM, 70 mM, 80 mM, 90 mM, or 100 mM.

In some embodiments, the lipid nanoparticle solution may have a pH ranging from about 4.5 to about 7.0, about 4.6 to about 7.0, about 4.8 to about 7.0, about 5.0 to about 7.0, about 5.5 to about 7.0, about 6.0 to about 7.0, about 6.0 to about 6.9, about 6.0 to about 6.8, about 6.0 to about 6.7, about 6.0 to about 6.6, about 6.0 to about 6.5. In some embodiments, a suitable lipid nanoparticle solution may have a pH of or no greater than 4.5, 4.6, 4.7, 4.8, 4.9 5.0, 5.2, 5.4, 5.6, 5.8, 6.0, 6.1, 6.2, 6.3, 6.4, 6.5, 6.6, 6.7, 6.8, 6.9, and 7.0.

Providing LNP Solutions

In some aspects, the present disclosure provides A method of producing a lipid nanoparticle (LNP) formulation, the method comprising: (i) mixing a lipid solution comprising an ionizable lipid with an aqueous buffer solution comprising a first buffering agent thereby forming a lipid nanoparticle solution comprising a lipid nanoparticle; and (ii) adding a nucleic acid solution comprising a nucleic acid to the lipid nanoparticle solution thereby forming a lipid nanoparticle (LNP) formulation comprising the lipid nanoparticle encapsulating the nucleic acid.

Suitable nucleic acids for the method of the present disclosure are further disclosed herein. In some embodiments, the nucleic acid is an RNA (e.g., mRNA).

Suitable ionizable lipids for the methods of the present disclosure are further disclosed herein.

In some embodiments, the LNP further comprises a phospholipid, a PEG lipid, a structural lipid, or any combination thereof. Suitable phospholipids, PEG lipids, and structural lipids for the methods of the present disclosure are further disclosed herein.

In some embodiments, the step of providing the LNP solution comprises mixing an aqueous buffer solution and an lipid solution wherein the lipid solution comprises an ionizable lipid in an organic solvent.

Processing LNP Solutions

The term "processing", as used herein, includes one or more steps to purify, pH adjust, buffer exchange, and/or concentrate LNPs.

In some embodiments, the step of processing the LNP solution comprises:

iia) filtering the LNP solution.

In some embodiments, the filtration removes an organic solvent (e.g., an alcohol or ethanol) from the LNP solution. In some embodiments, the processing comprises a tangential flow filtration (TFF). In some embodiments, upon removal of the organic solvent (e.g. an alcohol or ethanol), the LNP solution is converted to a solution buffered at a neutral pH, pH 6.5 to 7.8, pH 6.8 to pH 7.5, e.g., pH 7.0 to pH 7.2 (e.g., a phosphate or HEPES buffer). In some embodiments, the resulting LNP solution is sterilized before storage or use, e.g., by filtration (e.g., through a 0.1-0.5 μm filter).

In some embodiments, the step of processing the LNP solution further comprises packing the LNP solution.

As used herein, "packing" may refer to storing a drug product in its final state or in-process storage of LNPs before they are placed into final packaging. Modes of storage and/or packing include, but are not limited to, refrigeration in sterile bags, refrigerated or frozen formulations in vials, lyophilized formulations in vials and syringes, etc.

In some embodiments, the step of packing the LNP solution comprises one or more of the following steps:

iib) adding a cryoprotectant to the LNP solution;

iic) lyophilizing the LNP solution, thereby forming a lyophilized LNP composition;

iid) storing the LNP solution of the lyophilized LNP composition; and iie) adding a buffering solution to the LNP solution or the lyophilized LNP composition, thereby forming the LNP formulation.

In some embodiments, the cryoprotectant is added to the LNP solution prior to the lyophilization. In some embodiments, the cryoprotectant comprises one or more cryoprotective agents, and each of the one or more cryoprotective agents is independently a polyol (e.g., a diol or a triol such as propylene glycol (i.e., 1,2-propanediol), 1,3-propanediol, glycerol, (+/−)-2-methyl-2,4-pentanediol, 1,6-hexanediol, 1,2-butanediol, 2,3-butanediol, ethylene glycol, or diethylene glycol), a nondetergent sulfobetaine (e.g., NDSB-201 (3-(1-pyridino)-1-propane sulfonate), an osmolyte (e.g., L-proline or trimethylamine N-oxide dihydrate), a polymer (e.g., polyethylene glycol 200 (PEG 200), PEG 400, PEG 600, PEG 1000, PEG 3350, PEG 4000, PEG 8000, PEG 10000, PEG 20000, polyethylene glycol monomethyl ether 550) (mPEG 550), mPEG 600, mPEG 2000, mPEG 3350, MPEG 4000, mPEG 5000, polyvinylpyrrolidone (e.g., polyvinylpyrrolidone K 15), pentaerythritol propoxylate, or polypropylene glycol P 400), an organic solvent (e.g., dimethyl sulfoxide (DMSO) or ethanol), a sugar (e.g., D-(+)-sucrose, D-sorbitol, trehalose, D-(+)-maltose monohydrate, meso-erythritol, xylitol, myo-inositol, D-(+)-raffinose pentahydrate, D-(+)-trehalose dihydrate, or D-(+)-glucose monohydrate), or a salt (e.g., lithium acetate, lithium chloride, lithium formate, lithium nitrate, lithium sulfate, magnesium acetate, sodium chloride, sodium formate, sodium malonate, sodium nitrate, sodium sulfate, or any hydrate thereof), or any combination thereof. In some embodiments, the cryoprotectant comprises sucrose. In some embodiments, the cryoprotectant and/or excipient is sucrose.

In some embodiments, the lyophilization is carried out in a suitable glass receptacle (e.g., a 10) mL cylindrical glass vial). In some embodiments, the glass receptacle withstands extreme changes in temperatures between lower than −40° C. and higher than room temperature in short periods of time, and/or be cut in a uniform shape. In some embodiments, the step of lyophilizing comprises freezing the LNP solution at a temperature higher than about −40° C. and, e.g., lower than about −30° C., thereby forming a frozen LNP solution; and drying the frozen LNP solution to form the lyophilized LNP composition. In some embodiments, the freezing step results in a linear decrease in temperature to the final over about 6 minutes, e.g., at about 1° C. per minute from 20° C. to −40° C. In some embodiments, sucrose at 12-15% may be used, and the drying step is performed at a vacuum ranging from about 50 mTorr to about 150 mTorr, e.g., first at a low temperature ranging from about −35° C. to about −15° C., and then at a higher temperature ranging from room temperature to about 25° C., and e.g., the drying step is completed in three to seven days. In some embodiments, the drying step is performed at a vacuum ranging from about 50 mTorr to about 100 mTorr, e.g., first at a low temperature ranging from about −15° C. to about (° C.), and then at a higher temperature.

In some embodiment, the LNP solution or the lyophilized LNP composition is stored at a temperature of about −80° C., about −78° C., about −76° C., about −74° C., about −72° C., about −70° C., about −65° C., about −60° C., about −55° C., about −50° C., about −45° C., about −40° C., about −35° C., or about −30° C. prior to adding the buffering solution.

In some embodiment, the LNP solution or the lyophilized LNP composition is stored at a temperature of about −40° C., about −35° C., about −30° C., about −25° C., about −20° C., about −15° C., about −10° C., about −5° C., about 0° C., about 5° C., about 10° C., about 15° C., about 20° C., or about 25° C. prior to adding the buffering solution.

In some embodiments, the LNP solution or the lyophilized LNP composition is stored at a temperature of ranging from about −40° C. to about 0° C., from about −35° C. to about −5° C., from about −30° C. to about −10° C., from about −25° C. to about −15° C., from about −22° C. to about −18° C., or from about −21° C. to about −19° C. prior to adding the buffering solution.

In some embodiments, the LNP solution or the lyophilized LNP composition is stored at a temperature of about −20° C. prior to adding the buffering solution.

Administering LNP Formulations

In some aspects, the present disclosure relates to a method of administering a lipid nanoparticle (LNP) formulation to a patient, the method comprising: (i) providing an active agent solution having a pH in a range of about 4.5 to about 7.0 comprising a therapeutic and/or prophylactic agent and a lipid nanoparticle solution having a pH in a range of about 4.5 to about 6.5 comprising a lipid nanoparticle, the lipid nanoparticle comprising an ionizable lipid: (ii) forming a lipid nanoparticle formulation comprising the lipid nanoparticle encapsulating the therapeutic and/or prophylactic agent by mixing the lipid nanoparticle solution and the active agent solution such that the lipid nanoparticle formulation has a pH in a range of about 4.5 to about less than 7.0; and (iii) administering the lipid nanoparticle formulation to the patient less than about 72 hours after the mixing.

In some embodiments, the first pH and the second pH are in a range of about 7.0 to about 8.1, or about 7.1 to about 7.8, or about 7.2 to about 7.7, or about 7.3 to about 7.6, or about 7.4 to about 7.5.

In some embodiments, the first pH and the second pH are in a range of about 4.5 to about 6.5, or about 4.6 to about 6.0, or about 4.8 to about 5.5.

In some embodiments, the administering is performed less than about 72 hours after the mixing, e.g., less than about 60 hours after the mixing, e.g., less than about 48 hours after the mixing, e.g., less than about 36 hours after the mixing, e.g., less than about 24 hours after the mixing, e.g., less than about 20 hours after the mixing, e.g., less than about 16 hours after the mixing, e.g., less than about 12 hours after the mixing, e.g., less than about 8 hours after the mixing.

In some embodiments, the administering is performed less than about 120 minutes after the mixing, e.g., less than about 100 minutes after the mixing, e.g., less than about 90 minutes after the mixing, e.g., less than about 80 minutes after the mixing, e.g., less than about 70 minutes after the mixing, e.g., less than about 60 minutes after the mixing, e.g., less than about 50 minutes after the mixing, e.g., less than about 40 minutes after the mixing, e.g., less than about 30 minutes after the mixing, e.g., less than about 20 minutes after the mixing, e.g., less than about 15 minutes after the mixing, e.g., less than about 10 minutes after the mixing.

In some embodiments, the lipid nanoparticle formulation is not processed between the mixing and the administering.

In some embodiments, the method of the present disclosure does not comprise a pH adjustment between the mixing and the administering.

In some embodiments, the lipid nanoparticle formulation is not filtered between the mixing and the administering.

In some embodiments, the method further comprises receiving at a first inlet of a mixing and administration device the organic solution.

In some embodiments, the method further comprises receiving at a second inlet of a mixing and administration device the aqueous buffer solution.

In some embodiments, the mixing is performed at a mixer site of a mixing and administration device.

In some embodiments, the lipid nanoparticle formulation is administered via an outlet of a mixing and administration device.

In some embodiments, the providing, the forming, the mixing and the administering are all performed employing a single mixing and administration device, e.g., a fluidly connected mixing and administration device.

In some embodiments, the mixing and administration device comprises a double-barrel syringe.

In some embodiments, the mixing and administration device comprises a least one selected from the group consisting of a K-syringe and a L-syringe.

In some embodiments, the mixing and administration device comprises a static mixer at the mixer site.

In some embodiments, the static mixer is a helical static mixer.

In some embodiments, the pH of the aqueous buffer solution and the pH of the lipid nanoparticle formulation are about the same.

In some embodiments, the lipid nanoparticle formulation comprises about 1% by volume to about 50% by volume of the organic solvent relative to the total volume of the lipid nanoparticle formulation, e.g., about 2% by volume to about 45% by volume, e.g., about 3% by volume to about 40% by volume, e.g., about 4% by volume to about 35% by volume, e.g., about 5% by volume to about 33% by volume of the organic solvent relative to the total volume of the lipid nanoparticle formulation.

In some embodiments, the organic solvent is an alcohol.

In some embodiments, the organic solvent is ethanol.

In some embodiments, the organic solvent comprise a first organic solvent and a second organic solvent.

In some embodiments, the first organic solvent is an alcohol and the second organic solvent is an alcohol.

In some embodiments, the first organic solvent is ethanol and the second organic solvent is benzyl alcohol.

In some embodiments, a wt/wt ratio of the first organic solvent to the second organic solvent is in a range of about 100:1 to about 1:1, or about 50:1 to about 1:1, or about 20:1 to about 1:1, or about 10:1 to about 1:1.

In some embodiments, the organic solution further comprises a wetting agent. As used herein, a wetting agent may refer to an agent that increases, decreases or improves the ability of a liquid to maintain contact with a surface, such as a solid surface and/or liquid surface.

In some embodiments, the wetting agent is an organic solvent.

In some embodiments, the wetting agent is dimethyl sulfoxide (DMSO).

In some embodiments, a wt/wt ratio of the wetting agent to the organic solvent is in a range of about 1000:1 to about 1:1, or about 500:1 to about 5:1, or about 100:1 to about 10:1.

In some embodiments, the aqueous buffer solution is at least one selected from the group consisting of an acetate buffer, citrate buffer, phosphate buffer, and a tris buffer. In some embodiments, the aqueous buffer solution may be any buffer suitable for maintaining a physiological pH. In some embodiments, the aqueous buffer solution may be any buffer suitable for maintaining a pH suitable for administering to a patient, e.g., a mammalian patient, e.g., a human patient.

In some embodiments, the aqueous buffer solution further comprises a tonicity agent. As used herein, a tonicity agent may refer to an agent that increases, decreases, or improves the effective osmotic pressure gradient, as defined by the water potential of two solutions, or a relative concentration of solutes dissolve in solution impacting the direction and extent of diffusion.

In some embodiments, the tonicity agent is a sugar.

In some embodiments, the sugar is sucrose.

Stabilizing Salts

The term "stabilizing salt" as used herein, refers to a salt that is suitable for the methods of the present disclosure and/or the LNP formulations of the present disclosure. In some embodiments, the stabilizing salt, when used according to the methods of the present disclosure, mitigates an undesired property change from the produced lipid nanoparticle LNP formulation as compared to an LNP formulation produced by a comparable method (e.g., a method not involving the use of the stabilizing salt (e.g., a method without step ia) and/or step iia) without step ia), step iia), step iic) and/or step iid)).

In some embodiments, the stabilizing salt has an affinity to the nucleic acid (e.g., the PO4- backbone of the mRNA) that is higher than the affinity of a comparable sodium salt (e.g., a sodium salt having the same anion as the stabilizing salt) to the nucleic acid.

In some embodiments, the stabilizing salt has an affinity to the nucleic acid (e.g., the PO4- backbone of the mRNA) that is than the affinity of a comparable sodium salt (e.g., a sodium salt having the same anion as the stabilizing salt) to the nucleic acid by about 5% or higher, about 10% or more, about 15% or more, about 20% or more, about 30% or more, about 40% or more, about 50% or more, about 60% or more, about 70% or more, about 80% or more, about 90% or more, about 1 folds or more, about 2 folds or more, about 3 folds or more, about 4 folds or more, about 5 folds or more, about 10 folds or more, about 20 folds or more, about 30 folds or more, about 40 folds or more, about 50 folds or more, about 100 folds or more, about 200 folds or more, about 300 folds or more, about 400 folds or more, about 500 folds or more, about 1000 folds or more, about 2000 folds or more, about 3000 folds or more, about 4000 folds or more, about 5000 folds or more, or about 10000 folds or more.

In some embodiments, the stabilizing salt is an alkali salt or an alkaline earth salt, e.g., a lithium salt, a sodium salt, a potassium salt, a beryllium salt, a magnesium salt, or a calcium salt.

In some embodiments, the stabilizing salt is an alkali salt, e.g., a lithium salt, a sodium salt, or a potassium salt.

In some embodiments, the stabilizing salt is a lithium salt.

In some embodiments, the stabilizing salt is a fluoride salt, a bromide salt, a bromate salt, a perbromate salt, chloride salt, a chlorite salt, a hydroxide salt, a hyperchlorite salt, a perchlorate salt, an iodide salt, an iodate salt, a periodate salt, an azide salt, a carbonate salt, a phosphate salt, or a sulfate salt. In some embodiments, the stabilizing salt is a fluoride salt, a chloride salt, a bromide salt, or an iodide salt.

In some embodiments, the stabilizing salt is a chloride salt.

In some embodiments, the stabilizing salt is lithium fluoride, lithium bromide, lithium bromate, lithium perbromatet, lithium chloride, lithium chlorite, lithium hydroxide, lithium hyperchlorite, lithium perchlorate, lithium iodide, lithium iodate, lithium periodate, lithium azide, lithium carbonate, lithium phosphate, or lithium sulfate. In some embodiments, the stabilizing salt is lithium fluoride, lithium chloride, lithium bromide, or lithium iodide.

In some embodiments, the stabilizing salt is lithium chloride.

In some embodiments, the stabilizing salt is an acetate salt, an adipate salt, an anthranilate salt, an ascorbate salt, a benzoate salt, a butyrate salt, a cinnamate salt, a citrate salt, a decanoate salt, an ethylhexanoate salt, a formate salt, a fumarate salt, a gluconate salt, a glutamate salt, an isobutyrate salt, a lactate salt, a laurate salt, a malate salt, a malonate salt, an octanoate salt, an oxalate salt, a palmitate salt, a phthalate salt, a pivalate salt, a propionate salt, a salicylate salt, a sorbate salt, a stearate salt, a succinate salt, a tartrate salt, or a valerate salt.

In some embodiments, the stabilizing salt is an acetate salt.

In some embodiments, the stabilizing salt is lithium acetate, lithium adipate, lithium anthranilate, lithium ascorbate, lithium benzoate, lithium butyrate, lithium cinnamate, lithium citrate, lithium decanoate, lithium ethylhexanoate, lithium formate, lithium fumarate, lithium gluconate, lithium glutamate, lithium isobutyrate, lithium lactate, lithium laurate, lithium malate, lithium malonate, lithium octanoate, lithium oxalate, lithium palmitate, lithium phthalate, lithium pivalate, lithium propionate, lithium salicylate, lithium sorbate, lithium stearate, lithium succinate, lithium tartrate, or lithium valerate.

In some embodiments, the stabilizing salt is lithium acetate.

In some embodiments, the stabilizing salt is an alkaline earth salt, e.g., a berylium salt, a magnesium salt, or a calcium salt.

In some embodiments, the stabilizing salt is a calcium salt.

In some embodiments, the stabilizing salt is calcium fluoride, calcium bromide, calcium bromate, calcium perbromatet, calcium chloride, calcium chlorite, calcium hydroxide, calcium hyperchlorite, calcium perchlorate, calcium iodide, calcium iodate, calcium periodate, calcium azide, calcium carbonate, calcium phosphate, or calcium sulfate.

In some embodiments, the stabilizing salt is calcium acetate, calcium adipate, calcium anthranilate, calcium ascorbate, calcium benzoate, calcium butyrate, calcium cinnamate, calcium citrate, calcium decanoate, calcium ethylhexanoate, calcium formate, calcium fumarate, calcium gluconate, calcium glutamate, calcium isobutyrate, calcium lactate, calcium laurate, calcium malate, calcium malonate, calcium octanoate, calcium oxalate, calcium palmitate, calcium phthalate, calcium pivalate, calcium propionate, calcium salicylate, calcium sorbate, calcium stearate, calcium succinate, calcium tartrate, or calcium valerate.

It is understood that, in addition to the salts specifically disclosed herein, a variety of salts known in the art (e.g., commercially available) may be suitable for being the stabilizing salt. The effectiveness of a salt with regard to the methods or LNP formulations of the present disclosure may be determined by a skilled artisan, e.g., by comparing the produced LNP formulation with a LNP formulation produced by a comparable method.

First and Second Buffers

In some embodiments, the pH value of the first buffer is greater than the pH value of the second buffer.

In some embodiments, the pH value of the first buffer is about 7.0 or higher, about 7.25 or higher, about 7.5 or higher, about 7.75 or higher, or about 8.0 or higher.

In some embodiments, the pH value of the first buffer ranges from about 7.0 to about 10, from about 7.5 to about 9.5, from about 7.75 to about 9.25, or from about 8 to about 9.

In some embodiments, the first buffer comprises a first buffering agent.

In some embodiments, the first buffering agent is capable of being substantially removed by the lyophilization.

In some embodiments, the first buffering agent is capable of being completely removed by the lyophilization.

In some embodiments, the first buffering agent is substantially removed by the lyophilization.

In some embodiments, about 50% or higher, about 60% or higher, about 70% or higher, about 80% or higher, about 90% or higher, about 95% or higher, about 98% or higher, about 99% or higher, about 99.5% or higher, about 99.8% or higher, about 99.9% or higher, or about 99.95% or higher of the first buffering agent is removed by the lyophilization.

In some embodiments, the first buffering agent has a sublimation point of  or lower,  or lower, or  or lower at  mm Hg.

In some embodiments, the first buffering agent is a triethylammonium salt.

In some embodiments, the first buffering agent is triethylammonium bicarbonate.

In some embodiments, the concentration of triethylammonium bicarbonate in first buffer ranges from about 1 mM to about 200 mM, from about 5 mM to about 100 mM, from about 10 mM to about 50 mM, or from about 15 mM to about 25 mM.

In some embodiments, the concentration of triethylammonium bicarbonate in first buffer is about 20 mM.

In some embodiments, the pH value of the second buffer is about 9.0 or lower, about 8.75 or lower, about 8.5 or lower, about 8.25 lower or higher, about 8.0 or lower, about 7.75 or lower, about 7.5 or lower, about 7.25 or lower, or about 7.0 or lower.

In some embodiments, the pH value of the second buffer ranges from about 7.0 to about 9.0, from about 7.25 to about 8.75, from about 7.5 to about 8.5, or from about 7.75 to about 8.25.

In some embodiments, the second buffer is water. In some embodiments, the second buffer comprises tris(hydroxymethyl)aminomethane.

In some embodiments, the concentration of tris(hydroxymethyl)aminomethane in the second buffer ranges from about 1 mM to about 200 mM, from about 5 mM to about 100 mM, from about 10 mM to about 50 mM, or from about 15 mM to about 25 mM.

In some embodiments, the concentration of tris(hydroxymethyl)aminomethane in the second buffer is about 20 mM.

LNP Formulations and Lipid Nanoparticles (LNPs)

In some aspects, the LNP formulation of the present disclosure is prepared by a method disclosed herein.

In some aspects, the LNP formulation of the present disclosure comprises a plurality of LNPs, wherein the LNPs comprise a nucleic acid and an ionizable lipid.

Suitable nucleic acids for the methods of the present disclosure are further disclosed herein. In some embodiments, the nucleic acid is RNA (e.g., mRNA).

Suitable ionizable lipids for the methods of the present disclosure are further disclosed herein.

In some embodiments, the LNP further comprises a phospholipid, a PEG lipid, a structural lipid, or any combination thereof. Suitable phospholipids, PEG lipids, and structural lipids for the methods of the present disclosure are further disclosed herein.

In some embodiments, the LNP formulation of the disclosure includes at least one lipid nanoparticle component. Lipid nanoparticles may include a lipid component and one or more additional components, such as a therapeutic and/or prophylactic, such as a nucleic acid. A LNP may be designed for one or more specific applications or targets. The elements of a LNP may be selected based on a particular application or target, and/or based on the efficacy, toxicity, expense, ease of use, availability, or other feature of one or more elements. Similarly, the particular formulation of a LNP may be selected for a particular application or target according to, for example, the efficacy and toxicity of particular combination of elements. The efficacy and tolerability of a LNP formulation may be affected by the stability of the formulation.

The lipid component of a LNP may include, for example, a lipid according to Formula (IL-I), (IL-IA), (IL-IB), (IL-II), (IL-IIa), (IL-IIb), (IL-IIc), (IL-IId), (IL-IIe), (IL-IIf), (IL-IIg), (IL-III), (IL-IIIa1), (IL-IIIa2), (IL-IIIa3), (IL-IIIa4), (IL-IIIa5), (IL-IIIa6), (IL-IIIa7), or (IL-IIIa8), a phospholipid (such as an unsaturated lipid, e.g., DOPE or DSPC), a PEG lipid, and a structural lipid. The lipid component of a LNP may include, for example, a lipid according to Formula (IL-I), (IL-IA), (IL-IB), (IL-II), (IL-IIa), (IL-IIb), (IL-IIc), (IL-IId), (IL-IIe), (IL-IIf), (IL-IIg), (IL-III), (IL-IIIa1), (IL-IIIa2), (IL-IIIa3), (IL-IIIa4), (IL-IIIa5), (IL-IIIa6), (IL-IIIa7), or (IL-IIIa8), a phospholipid (such as an unsaturated lipid, e.g., DOPE or DSPC), and a structural lipid. The elements of the lipid component may be provided in specific fractions.

In some embodiments, the lipid component of a LNP includes a lipid according to Formula (IL-I), (IL-IA), (IL-IB), (IL-II), (IL-IIa), (IL-IIb), (IL-IIc), (IL-IId), (IL-IIe), (IL-IIf), (IL-IIg), (IL-III), (IL-IIIa1), (IL-IIIa2), (IL-IIIa3), (IL-IIIa4), (IL-IIIa5), (IL-IIIa6), (IL-IIIa7), or (IL-IIIa8), a phospholipid, a PEG lipid, and a structural lipid. In some embodiments, the lipid component of the lipid nanoparticle includes about 30 mol % to about 60 mol % compound of Formula (IL-I), (IL-IA), (IL-IB), (IL-II), (IL-IIa), (IL-IIb), (IL-IIc), (IL-IId), (IL-IIe), (IL-IIf), (IL-IIg), (IL-III), (IL-IIIa1), (IL-IIIa2), (IL-IIIa3), (IL-IIIa4), (IL-IIIa5), (IL-IIIa6), (IL-IIIa7), or (IL-IIIa8), about 0) mol % to about 30 mol % phospholipid, about 18.5 mol % to about 48.5 mol % structural lipid, and about 0 mol % to about 10 mol % of PEG lipid, provided that the total mol % does not exceed 100%. In some embodiments, the lipid component of the lipid nanoparticle includes about 35 mol % to about 55 mol % compound of Formula (IL-I), (IL-IA), (IL-IB), (IL-II), (IL-IIa), (IL-IIb), (IL-IIc), (IL-IId), (IL-IIe), (IL-IIf), (IL-IIg), (IL-III), (IL-IIIa1), (IL-IIIa2), (IL-IIIa3), (IL-IIIa4), (IL-IIIa5), (IL-IIIa6), (IL-IIIa7), or (IL-IIIa8), about 5 mol % to about 25 mol % phospholipid, about 30 mol % to about 40 mol % structural lipid, and about 0 mol % to about 10 mol % of PEG lipid. In a particular embodiment, the lipid component includes about 50 mol % said compound, about 10 mol % phospholipid, about 38.5 mol % structural lipid, and about 1.5 mol % of PEG lipid. In another particular embodiment, the lipid component includes about 40 mol % said compound, about 20 mol % phospholipid, about 38.5 mol % structural lipid, and about 1.5 mol % of PEG lipid. In some embodiments, the phospholipid may be DOPE or DSPC. In some embodiments, the PEG lipid may be PEG-DMG and/or the structural lipid may be cholesterol.

Lipid nanoparticles may be designed for one or more specific applications or targets. In some embodiments, a LNP may be designed to deliver a therapeutic and/or prophylactic such as an RNA to a particular cell, tissue, organ, or system or group thereof in a mammal's body. Physiochemical properties of lipid nanoparticles may be altered in order to increase selectivity for particular bodily targets. For instance, particle sizes may be adjusted based on the fenestration sizes of different organs. The therapeutic and/or prophylactic included in a LNP may also be selected based on the desired delivery target or targets. In some embodiments, a therapeutic and/or prophylactic may be selected for a particular indication, condition, disease, or disorder and/or for delivery to a particular cell, tissue, organ, or system or group thereof (e.g., localized or specific delivery). In some embodiments, a LNP may include an mRNA encoding a polypeptide of interest capable of being translated within a cell to produce the polypeptide of interest. Such a composition may be designed to be specifically delivered to a particular organ. In some embodiments, a composition may be designed to be specifically delivered to a mammalian liver.

The amount of a therapeutic and/or prophylactic in a LNP may depend on the size, composition, desired target and/or application, or other properties of the lipid nanoparticle as well as on the properties of the therapeutic and/or prophylactic. In some embodiments, the amount of an RNA useful in a LNP may depend on the size, sequence, and other characteristics of the RNA. The relative amounts of a therapeutic and/or prophylactic and other elements (e.g., lipids) in a LNP may also vary. In some embodiments, the wt/wt ratio of the lipid component to a therapeutic and/or prophylactic, such as a nucleic acid, in a LNP may be from about 5:1 to about 60:1, such as 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 45:1, 50:1, and 60:1. In some embodiments, the wt/wt ratio of the lipid component to a therapeutic and/or prophylactic may be from about 10:1 to about 40:1. In some embodiments, the wt/wt ratio is about 20:1. The amount of a therapeutic and/or prophylactic in a LNP may, for example, be measured using absorption spectroscopy (e.g., ultraviolet-visible spectroscopy).

In some embodiments, a LNP includes one or more RNAs, and the one or more RNAs, lipids, and amounts thereof may be selected to provide a specific N: P ratio. The N: P ratio of the composition refers to the molar ratio of nitrogen atoms in one or more lipids to the number of phosphate groups in an RNA. In general, a lower N: P ratio is preferred. The one or more RNA, lipids and amounts thereof may be selected to provide an N: P ratio from about 2:1 to about 30:1, such as 2:1, 3:1, 4:1, 5:1, 6:1, 7:1, 8:1, 9:1, 10:1, 12:1, 14:1, 16:1, 18:1, 20:1, 22:1, 24:1, 26:1, 28:1, or 30:1. In some embodiments, the N: P ratio may be from about 2:1 to about 8:1. In some embodiments, the N: P ratio is from about 5:1 to about 8:1. In some embodiments, the N: P ratio may be about 5.0:1, about 5.5:1, about 5.67:1, about 6.0:1, about 6.5:1, or about 7.0:1. In some embodiments, the N: P ratio may be about 5.67:1.

In some embodiments, the formulation including a LNP may further include a salt, such as a chloride salt.

In some embodiments, the formulation including a LNP may further include a sugar such as a disaccharide. In some embodiments, the formulation further includes a sugar but not a salt, such as a chloride salt.

Physical Properties

The physical properties of the LNP of the present disclosure may be characterized by a variety of methods. In some embodiments, microscopy (e.g., transmission electron microscopy or scanning electron microscopy) may be used to examine the morphology and size distribution of a LNP. Dynamic light scattering or potentiometry (e.g., potentiometric titrations) may be used to measure zeta potentials. Dynamic light scattering may also be utilized to determine particle sizes. Instruments such as the Zetasizer Nano ZS (Malvern Instruments Ltd, Malvern, Worcestershire, UK) may also be used to measure multiple characteristics of a LNP, such as particle size, polydispersity index, and zeta potential.

The average LNP diameter of the LNP formulation may be between 10s of nm and 100s of nm, e.g., measured by dynamic light scattering (DLS). In some embodiments, the average LNP diameter of the LNP formulation may be from about 40 nm to about 150 nm, such as about 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm. In some embodiments, the average LNP diameter of the LNP formulation may be from about 50 nm to about 100 nm, from about 50 nm to about 90 nm, from about 50 nm to about 80 nm, from about 50 nm to about 70 nm, from about 50 nm to about 60 nm, from about 60 nm to about 100 nm, from about 60 nm to about 90 nm, from about 60 nm to about 80 nm, from about 60 nm to about 70 nm, from about 70 nm to about 100 nm, from about 70 nm to about 90 nm, from about 70 nm to about 80 nm, from about 80 nm to about 100 nm, from about 80 nm to about 90 nm, or from about 90 nm to about 100 nm. In some embodiments, the average LNP diameter of the LNP formulation may be from about 70 nm to about 100 nm. In a particular embodiment, the average LNP diameter of the LNP formulation may be about 80 nm. In some embodiments, the average LNP diameter of the LNP formulation may be about 100 nm.

In some embodiments, the average LNP diameter of the LNP formulation ranges from about 1 mm to about 500 mm, from about 5 mm to about 200 mm, from about 10 mm to about 100 mm, from about 20 mm to about 80 mm, from about 25 mm to about 60 mm, from about 30 mm to about 55 mm, from about 35 mm to about 50 mm, or from about 38 mm to about 42 mm.

In some embodiments, the average LNP diameter of the LNP formulation is about 99% or less, about 98% or less, about 97% or less, about 96% or less, about 95% or less, about 90% or less, about 85% or less, about 80% or less, about 75% or less, about 70% or less, about 65% or less, about 60% or less, about 55% or less, about 50% or less, about 40% or less, about 30% or less, about 20% or less, or about 10% or less as compared to the LNP formulation produced by a comparable method.

A LNP may be relatively homogenous. A polydispersity index may be used to indicate the homogeneity of a LNP, e.g., the particle size distribution of the lipid nanoparticles. A small (e.g., less than 0.3) polydispersity index generally indicates a narrow particle size distribution. A LNP may have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25. In some embodiments, the polydispersity index of a LNP may be from about 0.10 to about 0.20.

The zeta potential of a LNP may be used to indicate the electrokinetic potential of the composition. In some embodiments, the zeta potential may describe the surface charge of a LNP. Lipid nanoparticles with relatively low charges, positive or negative, are generally desirable, as more highly charged species may interact undesirably with cells, tissues, and other elements in the body. In some embodiments, the zeta potential of a LNP may be from about −10 mV to about +20 mV, from about −10 mV to about +15 mV, from about −10 mV to about +10 mV, from about −10 mV to about +5 mV, from about −10 mV to about 0 mV, from about −10 mV to about −5 mV, from about −5 mV to about +20 mV, from about −5 mV to about +15 mV, from about −5 mV to about +10 mV, from about −5 mV to about +5 mV, from about −5 mV to about 0 mV, from about 0 mV to about +20 mV, from about 0 mV to about +15 mV, from about 0) mV to about +10 mV, from about 0 mV to about +5 mV, from about +5 mV to about +20 mV, from about +5 mV to about +15 mV, or from about +5 mV to about +10 mV.

The efficiency of encapsulation of a therapeutic and/or prophylactic, such as a nucleic acid describes the amount of therapeutic and/or prophylactic that is encapsulated or otherwise associated with a LNP after preparation, relative to the initial amount provided. The encapsulation efficiency is desirably high (e.g., close to 100%). The encapsulation efficiency may be measured, for example, by comparing the amount of therapeutic and/or prophylactic in a solution containing the lipid nanoparticle before and after breaking up the lipid nanoparticle with one or more organic solvents or detergents. An anion exchange resin may be used to measure the amount of free therapeutic and/or prophylactic (e.g., RNA) in a solution. Fluorescence may be used to measure the amount of free therapeutic and/or prophylactic (e.g., RNA) in a solution. For the lipid nanoparticles described herein, the encapsulation efficiency of a therapeutic and/or prophylactic may be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency may be at least 80%. In some embodiments, the encapsulation efficiency may be at least 90%. In some embodiments, the encapsulation efficiency may be at least 95%.

A LNP may optionally comprise one or more coatings. In some embodiments, a LNP may be formulated in a capsule, film, or table having a coating. A capsule, film, or tablet including a composition described herein may have any useful size, tensile strength, hardness or density.

Chemical Properties

The chemical properties of the LNP, LNP solution, lyophilized LNP composition, or LNP formulation of the present disclosure may be characterized by a variety of methods. In some embodiments, electrophoresis (e.g., capillary electrophoresis) or chromatography (e.g., reverse phase liquid chromatography) may be used to examine the mRNA integrity.

In some embodiments, the LNP integrity of the LNP, LNP solution, lyophilized LNP composition, or LNP formulation of the present disclosure is about 20% or higher, about 25% or higher, about 30% or higher, about 35% or higher, about 40% or higher, about 45% or higher, about 50% or higher, about 55% or higher, about 60% or higher, about 65% or higher, about 70% or higher, about 75% or higher, about 80% or higher, about 85% or higher, about 90% or higher, about 95% or higher, about 96% or higher, about 97% or higher, about 98% or higher, or about 99% or higher.

In some embodiments, the LNP integrity of the LNP, LNP solution, lyophilized LNP composition, or LNP formulation of the present disclosure is higher than the LNP integrity of the LNP, LNP solution, lyophilized LNP composition, or LNP formulation produced by a comparable method by about 5% or higher, about 10% or more, about 15% or more, about 20% or more, about 30% or more, about 40% or more, about 50% or more, about 60% or more, about 70% or more, about 80% or more, about 90% or more, about 1 folds or more, about 2 folds or more, about 3 folds or more, about 4 folds or more, about 5 folds or more, about 10 folds or more, about 20 folds or more, about 30 folds or more, about 40 folds or more, about 50 folds or more, about 100 folds or more, about 200 folds or more, about 300 folds or more, about 400 folds or more, about 500 folds or more, about 1000 folds or more, about 2000 folds or more, about 3000 folds or more, about 4000 folds or more, about 5000 folds or more, or about 10000 folds or more.

In some embodiments, the $T_{80\%}$ of the LNP, LNP solution, lyophilized LNP composition, or LNP formulation of the present disclosure is about 12 months or longer, about 15 months or longer, about 18 months or longer, about 21 months or longer, about 24 months or longer, about 27 months or longer, about 30 months or longer, about 33 months or longer, about 36 months or longer, about 48 months or longer, about 60 months or longer, about 72 months or longer, about 84 months or longer, about 96 months or longer, about 108 months or longer, about 120 months or longer.

In some embodiments, the $T_{80\%}$ of the LNP, LNP solution, lyophilized LNP composition, or LNP formulation of the present disclosure is longer than the $T_{80\%}$ of the LNP, LNP solution, lyophilized LNP composition, or LNP formulation produced by a comparable method by about 5% or higher, about 10% or more, about 15% or more, about 20% or more, about 30% or more, about 40% or more, about 50% or more, about 60% or more, about 70% or more, about 80% or more, about 90% or more, about 1 folds or more, about 2 folds or more, about 3 folds or more, about 4 folds or more, about 5 folds or more.

In some embodiments, the $T_{1/2}$ of the LNP, LNP solution, lyophilized LNP composition, or LNP formulation of the present disclosure is about 12 months or longer, about 15 months or longer, about 18 months or longer, about 21 months or longer, about 24 months or longer, about 27 months or longer, about 30 months or longer, about 33 months or longer, about 36 months or longer, about 48 months or longer, about 60 months or longer, about 72 months or longer, about 84 months or longer, about 96 months or longer, about 108 months or longer, about 120 months or longer.

In some embodiments, the $T_{1/2}$ of the LNP, LNP solution, lyophilized LNP composition, or LNP formulation of the present disclosure is longer than the Tin of the LNP, LNP solution, lyophilized LNP composition, or LNP formulation produced by a comparable method by about 5% or higher, about 10% or more, about 15% or more, about 20% or more, about 30% or more, about 40% or more, about 50% or more, about 60% or more, about 70% or more, about 80% or more, about 90% or more, about 1 folds or more, about 2 folds or more, about 3 folds or more, about 4 folds or more, about 5 folds or more

Definitions

As used herein, the term "alkyl" or "alkyl group" means a linear or branched, saturated hydrocarbon including one or more carbon atoms (e.g., one, two, three, four, five, six, seven, eight, nine, ten, eleven, twelve, thirteen, fourteen, fifteen, sixteen, seventeen, eighteen, nineteen, twenty, or more carbon atoms), which is optionally substituted. The notation "$C_{1-14}$ alkyl" means an optionally substituted linear or branched, saturated hydrocarbon including 1-14 carbon atoms. Unless otherwise specified, an alkyl group described herein refers to both unsubstituted and substituted alkyl groups.

As used herein, the term "alkenyl" or "alkenyl group" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one double bond, which is optionally substituted. The notation "$C_{2-14}$ alkenyl" means an optionally substituted linear or branched hydrocarbon including 2-14 carbon atoms and at least one carbon-carbon double bond. An alkenyl group may include one, two, three, four, or more carbon-carbon double bonds. In some embodiments, $C_{18}$ alkenyl may include one or more double bonds. A $C_{18}$ alkenyl group including two double bonds may be a linoleyl group. Unless otherwise specified, an alkenyl group described herein refers to both unsubstituted and substituted alkenyl groups.

As used herein, the term "carbocycle" or "carbocyclic group" means an optionally substituted mono- or multi-cyclic system including one or more rings of carbon atoms. Rings may be three, four, five, six, seven, eight, nine, ten, eleven, twelve, thirteen, fourteen, fifteen, sixteen, seventeen, eighteen, nineteen, or twenty membered rings. The notation "$C_{3-6}$ carbocycle" means a carbocycle including a single ring having 3-6 carbon atoms. Carbocycles may include one or more carbon-carbon double or triple bonds and may be non-aromatic or aromatic (e.g., cycloalkyl or aryl groups). Examples of carbocycles include cyclopropyl, cyclopentyl, cyclohexyl, phenyl, naphthyl, and 1,2-dihydronaphthyl groups. The term "cycloalkyl" as used herein means a non-aromatic carbocycle and may or may not include any double or triple bond. Unless otherwise specified, carbocycles described herein refers to both unsubstituted and substituted carbocycle groups, i.e., optionally substituted carbocycles.

As used herein, the term "heterocycle" or "heterocyclic group" means an optionally substituted mono- or multi-cyclic system including one or more rings, where at least one ring includes at least one heteroatom. Heteroatoms may be, for example, nitrogen, oxygen, or sulfur atoms. Rings may be three, four, five, six, seven, eight, nine, ten, eleven, twelve, thirteen, or fourteen membered rings. Heterocycles may include one or more double or triple bonds and may be non-aromatic or aromatic (e.g., heterocycloalkyl or heteroaryl groups). Examples of heterocycles include imidazolyl, imidazolidinyl, oxazolyl, oxazolidinyl, thiazolyl, thiazolidinyl, pyrazolidinyl, pyrazolyl, isoxazolidinyl, isoxazolyl, isothiazolidinyl, isothiazolyl, morpholinyl, pyrrolyl, pyrrolidinyl, furyl, tetrahydrofuryl, thiophenyl, pyridinyl, piperidinyl, quinolyl, and isoquinolyl groups. The term "heterocycloalkyl" as used herein means a non-aromatic heterocycle and may or may not include any double or triple bond. Unless otherwise specified, heterocycles described herein refers to both unsubstituted and substituted heterocycle groups, i.e., optionally substituted heterocycles.

As used herein, a "biodegradable group" is a group that may facilitate faster metabolism of a lipid in a mammalian entity. A biodegradable group may be selected from the group consisting of, but is not limited to, —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, an aryl group, and a heteroaryl group. As used herein, an "aryl group" is an optionally substituted carbocyclic group including one or more aromatic rings. Examples of aryl groups include phenyl and naphthyl groups. As used herein, a "heteroaryl group" is an optionally substituted heterocyclic group including one or more aromatic rings. Examples of heteroaryl groups include pyrrolyl, furyl, thiophenyl, imidazolyl, oxazolyl, and thiazolyl. Both aryl and heteroaryl groups may be optionally substituted. In some embodiments, M and M' can be selected from the non-limiting group consisting of optionally substituted phenyl, oxazole, and thiazole. In the formulas herein, M and M' can be independently selected from the list of biodegradable groups above. Unless otherwise specified, aryl or heteroaryl groups described herein refers to both unsubstituted and substituted groups, i.e., optionally substituted aryl or heteroaryl groups.

Alkyl, alkenyl, and cyclyl (e.g., carbocyclyl and heterocyclyl) groups may be optionally substituted unless otherwise specified. Optional substituents may be selected from the group consisting of, but are not limited to, a halogen atom (e.g., a chloride, bromide, fluoride, or iodide group), a carboxylic acid (e.g., —C(O)OH), an alcohol (e.g., a hydroxyl, —OH), an ester (e.g., —C(O)OR or —OC(O)R), an aldehyde (e.g., —C(O)H), a carbonyl (e.g., —C(O)R, alternatively represented by C═O), an acyl halide (e.g., —C(O)X, in which X is a halide selected from bromide, fluoride, chloride, and iodide), a carbonate (e.g., —OC(O)OR), an alkoxy (e.g., —OR), an acetal (e.g., $—C(OR)_2R''''$, in which each OR are alkoxy groups that can be the same or different and R'''' is an alkyl or alkenyl group), a phosphate (e.g., $P(O)_4^{3-}$), a thiol (e.g., —SH), a sulfoxide (e.g., —S(O)R), a sulfinic acid (e.g., —S(O)OH), a sulfonic acid (e.g., $—S(O)_2OH$), a thial (e.g., —C(S)H), a sulfate (e.g., $S(O)_4^{2-}$), a sulfonyl (e.g., $—S(O)_2—$), an amide (e.g., $—C(O)NR_2$, or —N(R)C(O)R), an azido (e.g., $—N_3$), a nitro (e.g., $—NO_2$), a cyano (e.g., —CN), an isocyano (e.g., —NC), an acyloxy (e.g., —OC(O)R), an amino (e.g., $—NR_2$, —NRH, or $—NH_2$), a carbamoyl (e.g., $—OC(O)NR_2$, —OC(O)NRH, or $—OC(O)NH_2$), a sulfonamide (e.g., $—S(O)_2NR_2$, $—S(O)_2NRH$, $—S(O)_2NH_2$, $—N(R)S(O)_2R$, $—N(H)S(O)_2R$, $—N(R)S(O)_2H$, or $—N(H)S(O)_2H$), an alkyl group, an alkenyl group, and a cyclyl (e.g., carbocyclyl or heterocyclyl) group. In any of the preceding, R is an alkyl or alkenyl group, as defined herein. In some embodiments, the substituent groups themselves may be further substituted with, for example, one, two, three, four, five, or six substituents as defined herein. In some embodiments, a $C_{1-6}$ alkyl group may be further substituted with one, two, three, four, five, or six substituents as described herein.

About, Approximately: As used herein, the terms "approximately" and "about," as applied to one or more values of interest, refer to a value that is similar to a stated reference value. In some embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). In some embodiments, when used in the context of an amount of a given compound in a lipid component of a LNP, "about" may mean+/−10% of the recited value. For instance, a LNP including a lipid component having about 40% of a given compound may include 30-50% of the compound.

As used herein, the term "compound," is meant to include all isomers and isotopes of the structure depicted. "Isotopes" refers to atoms having the same atomic number but different mass numbers resulting from a different number of neutrons in the nuclei. In some embodiments, isotopes of hydrogen include tritium and deuterium. Further, a compound, salt, or complex of the present disclosure can be prepared in combination with solvent or water molecules to form solvates and hydrates by routine methods.

As used herein, the term "contacting" means establishing a physical connection between two or more entities. In some embodiments, contacting a mammalian cell with a LNP means that the mammalian cell and a nanoparticle are made to share a physical connection. Methods of contacting cells with external entities both in vivo and ex vivo are well known in the biological arts. In some embodiments, contacting a LNP and a mammalian cell disposed within a mammal may be performed by varied routes of administration (e.g., intravenous, intramuscular, intradermal, and subcutaneous) and may involve varied amounts of lipid nanoparticles. Moreover, more than one mammalian cell may be contacted by a LNP.

As used herein, the term "comparable method" refers to a method with comparable parameters or steps, as of the method being compared (e.g., the producing the LNP formulation of the present disclosure). In some embodiments, the "comparable method" is a method with one or more of steps i), ia), iaa), ib), ii), iia), iib), iic), iid), and iie) of the method being compared. In some embodiments, the "comparable method" is a method without one or more of steps i), ia), iaa), ib), ii), iia), iib), iic), iid), and iie) of the method being compared. In some embodiments, the "comparable method" is a method without one or more of steps ia) and ib) of the method being compared. In some embodiments, the "comparable method" is a method employing a water-soluble salt of a nucleic acid. In some embodiments, the "comparable method" is a method employing an organic solution that does not comprise an organic solvent-soluble nucleic acid. In some embodiments, the "comparable method" is a method comprising processing the lipid nanoparticle prior to administering the lipid nanoparticle formulation.

As used herein, the term "delivering" means providing an entity to a destination. In some embodiments, delivering a therapeutic and/or prophylactic to a subject may involve administering a LNP including the therapeutic and/or prophylactic to the subject (e.g., by an intravenous, intramuscular, intradermal, or subcutaneous route). Administration of a LNP to a mammal or mammalian cell may involve contacting one or more cells with the lipid nanoparticle.

As used herein, the term "enhanced delivery" means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a therapeutic and/or prophylactic by a nanoparticle to a target tissue of interest (e.g., mammalian liver) compared to the level of delivery of a therapeutic and/or prophylactic by a control nanoparticle to a target tissue of interest (e.g., MC3, KC2, or DLinDMA). The level of delivery of a nanoparticle to a particular tissue may be measured by comparing the amount of protein produced in a tissue to the weight of said tissue, comparing the amount of therapeutic and/or prophylactic in a tissue to the weight of said tissue, comparing the amount of protein produced in a tissue to the amount of total protein in said tissue, or comparing the amount of therapeutic and/or prophylactic in a tissue to the amount of total therapeutic and/or prophylactic in said tissue. It will be understood that the enhanced delivery of a nanoparticle to a target tissue need not be determined in a subject being treated, it may be determined in a surrogate such as an animal model (e.g., a rat model).

As used herein, the term "specific delivery." "specifically deliver," or "specifically delivering" means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a therapeutic and/or prophylactic by a nanoparticle to a target tissue of interest (e.g., mammalian liver) compared to an off-target tissue (e.g., mammalian spleen). The level of delivery of a nanoparticle to a particular tissue may be measured by comparing the amount of protein produced in a tissue to the weight of said tissue, comparing the amount of therapeutic and/or prophylactic in a tissue to the weight of said tissue, comparing the amount of protein produced in a tissue to the amount of total protein in said tissue, or comparing the amount of therapeutic and/or prophylactic in a tissue to the amount of total therapeutic and/or prophylactic in said tissue. In some embodiments, for renovascular targeting, a therapeutic and/or prophylactic is specifically provided to a mammalian kidney as compared to the liver and spleen if 1.5, 2-fold, 3-fold, 5-fold, 10-fold, 15 fold, or 20 fold more therapeutic and/or prophylactic per 1 g of tissue is delivered to a kidney compared to that delivered to the liver or spleen following systemic administration of the therapeutic and/or prophylactic. It will be understood that the ability of a nanoparticle to specifically deliver to a target tissue need not be determined in a subject being treated, it may be determined in a surrogate such as an animal model (e.g., a rat model).

As used herein, "encapsulation efficiency" refers to the amount of a therapeutic and/or prophylactic that becomes part of a LNP, relative to the initial total amount of therapeutic and/or prophylactic used in the preparation of a LNP. In some embodiments, if 97 mg of therapeutic and/or prophylactic are encapsulated in a LNP out of a total 100 mg of therapeutic and/or prophylactic initially provided to the composition, the encapsulation efficiency may be given as 97%.

As used herein, "encapsulation", "encapsulated", "loaded", and "associated" may refer to complete, substantial, or partial enclosure, confinement, surrounding, or encasement. As used herein, "encapsulation" or "association" may refer to the process of confining an individual nucleic acid molecule within a nanoparticle and/or establishing a physiochemical relationship between an individual nucleic acid molecule and a nanoparticle. As used herein, an "empty nanoparticle" may refer to a nanoparticle that is substantially free of a therapeutic or prophylactic agent. As used herein, an "empty nanoparticle" may refer to a nanoparticle that is substantially free of a nucleic acid. As used herein, an "empty nanoparticle" may refer to a nanoparticle that consists substantially of only lipid components.

As used herein, "expression" of a nucleic acid sequence refers to translation of an mRNA into a polypeptide or protein and/or post-translational modification of a polypeptide or protein.

As used herein, the term "in vitro" refers to events that occur in an artificial environment, e.g., in a test tube or reaction vessel, in cell culture, in a Petri dish, etc., rather than within an organism (e.g., animal, plant, or microbe).

As used herein, the term "in vivo" refers to events that occur within an organism (e.g., animal, plant, or microbe or cell or tissue thereof).

As used herein, the term "ex vivo" refers to events that occur outside of an organism (e.g., animal, plant, or microbe or cell or tissue thereof). Ex vivo events may take place in an environment minimally altered from a natural (e.g., in vivo) environment.

As used herein, the term "isomer" means any geometric isomer, tautomer, zwitterion, stereoisomer, enantiomer, or diastereomer of a compound. Compounds may include one or more chiral centers and/or double bonds and may thus exist as stereoisomers, such as double-bond isomers (i.e., geometric E/Z isomers) or diastereomers (e.g., enantiomers (i.e., (+) or (−)) or cis/trans isomers). The present disclosure encompasses any and all isomers of the compounds described herein, including stereomerically pure forms (e.g., geometrically pure, enantiomerically pure, or diastereomerically pure) and enantiomeric and stereoisomeric mixtures, e.g., racemates. Enantiomeric and stereometric mixtures of compounds and means of resolving them into their component enantiomers or stereoisomers are well-known.

As used herein, a "lipid component" is that component of a lipid nanoparticle that includes one or more lipids. In some embodiments, the lipid component may include one or more cationic/ionizable, PEGylated, structural, or other lipids, such as phospholipids.

As used herein, a "linker" is a moiety connecting two moieties, for example, the connection between two nucleosides of a cap species. A linker may include one or more groups including but not limited to phosphate groups (e.g., phosphates, boranophosphates, thiophosphates, selenophosphates, and phosphonates), alkyl groups, amidates, or glycerols. In some embodiments, two nucleosides of a cap analog may be linked at their 5' positions by a triphosphate group or by a chain including two phosphate moieties and a boranophosphate moiety.

As used herein, "methods of administration" may include intravenous, intramuscular, intradermal, subcutaneous, or other methods of delivering a composition to a subject. A method of administration may be selected to target delivery (e.g., to specifically deliver) to a specific region or system of a body.

As used herein, "modified" means non-natural. In some embodiments, an RNA may be a modified RNA. That is, an RNA may include one or more nucleobases, nucleosides, nucleotides, or linkers that are non-naturally occurring. A "modified" species may also be referred to herein as an "altered" species. Species may be modified or altered chemically, structurally, or functionally. In some embodiments, a modified nucleobase species may include one or more substitutions that are not naturally occurring.

As used herein, the "N: P ratio" is the molar ratio of ionizable (in the physiological pH range) nitrogen atoms in a lipid to phosphate groups in an RNA, e.g., in a LNP including a lipid component and an RNA.

As used herein, a "lipid nanoparticle" is a composition comprising one or more lipids. Lipid nanoparticles are typically sized on the order of micrometers or smaller and may include a lipid bilayer. Lipid nanoparticles, as used herein, unless otherwise specified, encompass lipid nanoparticles (LNPs), liposomes (e.g., lipid vesicles), and lipoplexes. In some embodiments, a LNP may be a liposome having a lipid bilayer with a diameter of 500 nm or less.

As used herein, "naturally occurring" means existing in nature without artificial aid.

As used herein, "patient" refers to a subject who may seek or be in need of treatment, requires treatment, is receiving treatment, will receive treatment, or a subject who is under care by a trained professional for a particular disease or condition.

As used herein, a "PEG lipid" or "PEGylated lipid" refers to a lipid comprising a polyethylene glycol component.

The phrase "pharmaceutically acceptable" is used herein to refer to those compounds, materials, composition, and/or dosage forms which are, within the scope of sound medical judgment, suitable for use in contact with the tissues of human beings and animals without excessive toxicity, irritation, allergic response, or other problems or complication, commensurate with a reasonable benefit/risk ratio.

The phrase "pharmaceutically acceptable excipient," as used herein, refers to any ingredient other than the compounds described herein (for example, a vehicle capable of suspending, complexing, or dissolving the active compound) and having the properties of being substantially nontoxic and non-inflammatory in a patient. Excipients may include, for example: anti-adherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E (alpha-tocopherol), vitamin C, xylitol, and other species disclosed herein.

Compositions may also include salts of one or more compounds. Salts may be pharmaceutically acceptable salts. As used herein, "pharmaceutically acceptable salts" refers to derivatives of the disclosed compounds wherein the parent compound is altered by converting an existing acid or base moiety to its salt form (e.g., by reacting a free base group with a suitable organic acid). Examples of pharmaceutically acceptable salts include, but are not limited to, mineral or organic acid salts of basic residues such as amines: alkali or organic salts of acidic residues such as carboxylic acids; and the like. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, $17^{th}$ ed., Mack Publishing Company, Easton, Pa., 1985, p. 1418, Pharmaceutical Salts: Properties, Selection, and Use, P. H. Stahl and C. G. Wermuth (eds.), Wiley-VCH, 2008, and Berge et al., Journal of Pharmaceutical Science, 66, 1-19 (1977), each of which is incorporated herein by reference in its entirety.

As used herein, a "phospholipid" is a lipid that includes a phosphate moiety and one or more carbon chains, such as unsaturated fatty acid chains. A phospholipid may include one or more multiple (e.g., double or triple) bonds (e.g., one or more unsaturations). A phospholipid or an analog or derivative thereof may include choline. A phospholipid or an analog or derivative thereof may not include choline. Particular phospholipids may facilitate fusion to a membrane. In some embodiments, a cationic phospholipid may interact with one or more negatively charged phospholipids of a membrane (e.g., a cellular or intracellular membrane). Fusion of a phospholipid to a membrane may allow one or more elements of a lipid-containing composition to pass through the membrane permitting, e.g., delivery of the one or more elements to a cell.

As used herein, the "polydispersity index" is a ratio that describes the homogeneity of the particle size distribution of a system. A small value, e.g., less than 0.3, indicates a narrow particle size distribution.

As used herein, an amphiphilic "polymer" is an amphiphilic compound that comprises an oligomer or a polymer. In some embodiments, an amphiphilic polymer can comprise an oligomer fragment, such as two or more PEG monomer units. In some embodiments, an amphiphilic polymer described herein can be PS 20.

As used herein, the term "polypeptide" or "polypeptide of interest" refers to a polymer of amino acid residues typically joined by peptide bonds that can be produced naturally (e.g., isolated or purified) or synthetically.

As used herein, an "RNA" refers to a ribonucleic acid that may be naturally or non-naturally occurring. In some embodiments, an RNA may include modified and/or non-naturally occurring components such as one or more nucleobases, nucleosides, nucleotides, or linkers. An RNA may include a cap structure, a chain terminating nucleoside, a stem loop, a poly A sequence, and/or a polyadenylation signal. An RNA may have a nucleotide sequence encoding a polypeptide of interest. In some embodiments, an RNA may be a messenger RNA (mRNA). Translation of an mRNA encoding a particular polypeptide, for example, in vivo translation of an mRNA inside a mammalian cell, may produce the encoded polypeptide. RNAs may be selected from the non-liming group consisting of small interfering RNA (siRNA), asymmetrical interfering RNA (aiRNA), microRNA (miRNA), Dicer-substrate RNA (dsRNA), small hairpin RNA (shRNA), mRNA, long non-coding RNA (lncRNA) and mixtures thereof.

As used herein, a “single unit dose” is a dose of any therapeutic administered in one dose/at one time/single route/single point of contact, i.e., single administration event.

As used herein, a “split dose” is the division of a single unit dose or total daily dose into two or more doses.

As used herein, a “total daily dose” is an amount given or prescribed in a 24 hour period. It may be administered as a single unit dose.

As used herein, the term “subject” refers to any organism to which a composition or formulation in accordance with the disclosure may be administered, e.g., for experimental, diagnostic, prophylactic, and/or therapeutic purposes. Typical subjects include animals (e.g., mammals such as mice, rats, rabbits, non-human primates, and humans) and/or plants.

As used herein, “$T_x$” refers to the amount of time lasted for the nucleic acid integrity (e.g., mRNA integrity) of a LNP, LNP solution, lyophilized LNP composition, or LNP formulation to degrade to about X of the initial integrity of the nucleic acid (e.g., mRNA) used for the preparation of the LNP, LNP solution, lyophilized LNP composition, or LNP formulation. For example, “$T_{80\%}$” refers to the amount of time lasted for the nucleic acid integrity (e.g., mRNA integrity) of a LNP, LNP solution, lyophilized LNP composition, or LNP formulation to degrade to about 80% of the initial integrity of the nucleic acid (e.g., mRNA) used for the preparation of the LNP, LNP solution, lyophilized LNP composition, or LNP formulation. For another example, “$T_{1/2}$” refers to the amount of time lasted for the nucleic acid integrity (e.g., mRNA integrity) of a LNP, LNP solution, lyophilized LNP composition, or LNP formulation to degrade to about ½ of the initial integrity of the nucleic acid (e.g., mRNA) used for the preparation of the LNP, LNP solution, lyophilized LNP composition, or LNP formulation.

As used herein, “targeted cells” refers to any one or more cells of interest. The cells may be found in vitro, in vivo, in situ, or in the tissue or organ of an organism. The organism may be an animal, e.g., a mammal, e.g., a human, e.g., a patient.

As used herein, “target tissue” refers to any one or more tissue types of interest in which the delivery of a therapeutic and/or prophylactic would result in a desired biological and/or pharmacological effect. Examples of target tissues of interest include specific tissues, organs, and systems or groups thereof. In particular applications, a target tissue may be a kidney, a lung, a spleen, vascular endothelium in vessels (e.g., intra-coronary or intra-femoral), or tumor tissue (e.g., via intratumoral injection). An “off-target tissue” refers to any one or more tissue types in which the expression of the encoded protein does not result in a desired biological and/or pharmacological effect. In particular applications, off-target tissues may include the liver and the spleen.

The term “therapeutic agent” or “prophylactic agent” refers to any agent that, when administered to a subject, has a therapeutic, diagnostic, and/or prophylactic effect and/or elicits a desired biological and/or pharmacological effect. Therapeutic agents are also referred to as “actives” or “active agents.” Such agents include, but are not limited to, cytotoxins, radioactive ions, chemotherapeutic agents, small molecule drugs, proteins, and nucleic acids.

As used herein, the term “therapeutically effective amount” means an amount of an agent to be delivered (e.g., nucleic acid, drug, composition, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

As used herein, “transfection” refers to the introduction of a species (e.g., an RNA) into a cell. Transfection may occur, for example, in vitro, ex vivo, or in vivo.

As used herein, the term “treating” refers to partially or completely alleviating, ameliorating, improving, relieving, delaying onset of, inhibiting progression of, reducing severity of, and/or reducing incidence of one or more symptoms or features of a particular infection, disease, disorder, and/or condition. In some embodiments, “treating” cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

As used herein, the “zeta potential” is the electrokinetic potential of a lipid, e.g., in a particle composition.

Ionizable Lipids

The present disclosure provides ionizable lipids, e.g., ionizable lipids including a central amine moiety and at least one biodegradable group. The lipids described herein may be advantageously used in lipid nanoparticles and lipid nanoparticle formulations for the delivery of therapeutic and/or prophylactics, such as a nucleic acid, to mammalian cells or organs.

In some aspects, the ionizable lipids of the present disclosure may be one or more of compounds of Formula (IL-1):

(IL-1)

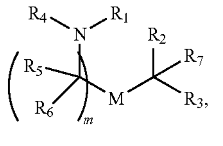

or their N-oxides, or salts or isomers thereof, wherein:

$R^1$ is selected from the group consisting of $C_{5-30}$ alkyl, $C_{5-20}$ alkenyl, —R*YR", —YR", and —R"M'R';

$R^2$ and $R^3$ are independently selected from the group consisting of H, $C_{1-14}$ alkyl, $C_{2-14}$ alkenyl, —R*YR", —YR", and —R*OR", or $R^2$ and $R^3$, together with the atom to which they are attached, form a heterocycle or carbocycle;

$R^4$ is selected from the group consisting of hydrogen, a $C_{3-6}$ carbocycle, $—(CH_2)_nQ$, $—(CH_2)_nCHQR$, $—(CH_2)_oC(R^{10})_2(CH_2)_{n-o}Q$, —CHQR, $—CQ(R)_2$, and unsubstituted $C_{1-6}$ alkyl, where Q is selected from a carbocycle, heterocycle, —OR, $—O(CH_2)_nN(R)_2$, —C(O)OR, —OC(O)R, $—CX_3$, $—CX_2H$, $—CXH_2$, —CN, $—N(R)_2$, $—C(O)N(R)_2$, —N(R)C(O)R, $—N(R)S(O)_2R$, $—N(R)C(O)N(R)_2$, $—N(R)C(S)N(R)_2$, $—N(R)R^8$, $—N(R)S(O)_2R^8$, $—O(CH_2)_nOR$, $—N(R)C(=NR^9)N(R)_2$, $—N(R)C(=CHR^9)N(R)_2$, $—OC(O)N(R)_2$, —N(R)C(O)OR, —N(OR)C(O)R, $—N(OR)S(O)_2R$, —N(OR)C(O)OR, $—N(OR)C(O)N(R)_2$, $—N(OR)C(S)N(R)_2$, $—N(OR)C(=NR^9)N(R)_2$, $—N(OR)C(=CHR^9)N(R)_2$, $—C(=NR^9)N(R)_2$, $—C(=NR^9)R$, —C(O)N(R) OR, and $—C(R)N(R)_2C(O)OR$, each o is independently selected from 1, 2, 3, and 4, and each n is independently selected from 1, 2, 3, 4, and 5;

each $R^5$ is independently selected from the group consisting of OH, $C_{1-3}$ alkyl, $C_{2-3}$ alkenyl, and H;

each $R^6$ is independently selected from the group consisting of OH, $C_{1-3}$ alkyl, $C_{2-3}$ alkenyl, and H;

M and M' are independently selected from —C(O)O—, —OC(O)—, —OC(O)-M"—C(O)O—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group, in which M" is a bond, $C_{1-13}$ alkyl or $C_{2-13}$ alkenyl;

$R^7$ is selected from the group consisting of $C_{1-3}$ alkyl, $C_{2-3}$ alkenyl, and H;

$R^8$ is selected from the group consisting of $C_{3-6}$ carbocycle and heterocycle;

$R^9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

$R^{10}$ is selected from the group consisting of H, OH, $C_{1-3}$ alkyl, and $C_{2-3}$ alkenyl;

each R is independently selected from the group consisting of $C_{1-3}$ alkyl, $C_{2-3}$ alkenyl, $(CH_2)_qOR^*$, and H, and each q is independently selected from 1, 2, and 3;

each R' is independently selected from the group consisting of $C_{1-18}$ alkyl, $C_{2-18}$ alkenyl, —R*YR", —YR", and H;

each R" is independently selected from the group consisting of $C_{3-15}$ alkyl and $C_{3-15}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13; and wherein when $R^4$ is —$(CH_2)_nQ$, $(CH_2)_nCHQR$, —CHQR, or —$CQ(R)_2$, then (i) Q is not —$N(R)_2$ when n is 1, 2, 3, 4 or 5, or (ii) Q is not 5, 6, or 7-membered heterocycloalkyl when n is 1 or 2.

In some aspects, the ionizable lipids of the present disclosure may be one or more of compounds of Formula (IL-X):

(IL-X)

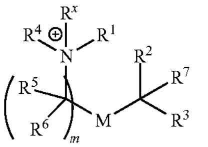

or its N-oxide, or a salt or isomer thereof, wherein or a salt or isomer thereof, wherein $R^1$ is selected from the group consisting of $C_{5-30}$ alkyl, $C_{5-20}$ alkenyl, —R*YR", —YR", and —R"M'R';

$R^2$ and $R^3$ are independently selected from the group consisting of H, $C_{1-14}$ alkyl, $C_{2-14}$ alkenyl, —R*YR", —YR", and —R*OR", or $R^2$ and $R^3$, together with the atom to which they are attached, form a heterocycle or carbocycle;

$R^4$ is selected from the group consisting of hydrogen, a $C_{3-6}$ carbocycle, —$(CH_2)_nQ$, —$(CH_2)_nCHQR$, —$(CH_2)_oC(R^{10})_2(CH_2)_{n-o}Q$, —CHQR, —$CQ(R)_2$, and unsubstituted $C_{1-6}$ alkyl, where Q is selected from a carbocycle, heterocycle, —OR, —$O(CH_2)_nN(R)_2$, —C(O)OR, —OC(O)R, —$CX_3$, —$CX_2H$, —$CXH_2$, —CN, —$N(R)_2$, —$C(O)N(R)_2$, —N(R)C(O)R, —$N(R)S(O)_2R$, —$N(R)C(O)N(R)_2$, —$N(R)C(S)N(R)_2$, $N(R)R^8$, —$N(R)S(O)_2R^8$, —$O(CH_2)_nOR$, —$N(R)C(=NR^9)N(R)_2$, —$N(R)C(=CHR^9)N(R)_2$, —$OC(O)N(R)_2$, —N(R)C(O)OR, —N(OR)C(O)R, —$N(OR)S(O)_2R$, —N(OR)C(O)OR, —$N(OR)C(O)N(R)_2$, —$N(OR)C(S)N(R)_2$, —$N(OR)C(=NR^9)N(R)_2$, —$N(OR)C(=CHR^9)N(R)_2$, —$C(=NR^9)N(R)_2$, —$C(=NR^9)R$, —C(O)N(R) OR, and —$C(R)N(R)_2C(O)OR$, each o is independently selected from 1, 2, 3, and 4, and each n is independently selected from 1, 2, 3, 4, and 5;

$R^x$ is selected from the group consisting of $C_{1-6}$ alkyl, $C_{2-6}$ alkenyl, —$(CH_2)$ OH, and —$(CH_2)_vN(R)_2$, wherein v is selected from 1, 2, 3, 4, 5, and 6;

each $R^5$ is independently selected from the group consisting of OH, $C_{1-3}$ alkyl, $C_{2-3}$ alkenyl, and H;

each $R^6$ is independently selected from the group consisting of OH, $C_{1-3}$ alkyl, $C_{2-3}$ alkenyl, and H;

M and M' are independently selected from —C(O)O—, —OC(O)—, —OC(O)-M"—C(O)O—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group, in which M" is a bond, $C_{1-13}$ alkyl or $C_{2-13}$ alkenyl;

$R^7$ is selected from the group consisting of $C_{1-3}$ alkyl, $C_{2-3}$ alkenyl, and H;

$R^8$ is selected from the group consisting of $C_{3-6}$ carbocycle and heterocycle;

$R^9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

$R^{10}$ is selected from the group consisting of H, OH, $C_{1-3}$ alkyl, and $C_{2-3}$ alkenyl;

each R is independently selected from the group consisting of $C_{1-3}$ alkyl, $C_{2-3}$ alkenyl, $(CH_2)_qOR^*$, and H, and each q is independently selected from 1, 2, and 3;

each R' is independently selected from the group consisting of $C_{1-18}$ alkyl, $C_{2-18}$ alkenyl, —R*YR", —YR", and H;

each R" is independently selected from the group consisting of $C_{3-15}$ alkyl and $C_{3-15}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

In some embodiments, a subset of compounds of Formula (IL-I) includes those of Formula (IL-IA):

(IL-IA)

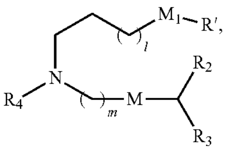

or its N-oxide, or a salt or isomer thereof, wherein 1 is selected from 1, 2, 3, 4, and 5; m is selected from 5, 6, 7, 8, and 9; $M_1$ is a bond or M'; $R^4$ is hydrogen, unsubstituted $C_{1-3}$ alkyl, —$(CH_2)_oC(R^{10})_2(CH_2)_{n-o}Q$, or —$(CH_2)_nQ$, in which Q is OH, —$NHC(S)N(R)_2$, —$NHC(O)N(R)_2$, —N(R)C(O)

R, —N(R)S(O)$_2$R, —N(R)$R^8$, —NHC(=N$R^9$)N(R)$_2$, —NHC(=CH$R^9$)N(R)$_2$, —OC(O)N(R)$_2$, —N(R)C(O)OR, heteroaryl or heterocycloalkyl; M and M' are independently selected from —C(O)O—, —OC(O)—, —OC(O)-M"—C(O)O—, —C(O)N(R')—, —P(O)(OR)O—, —S—S—, an aryl group, and a heteroaryl group; and $R^2$ and $R^3$ are independently selected from the group consisting of H, $C_{1-14}$ alkyl, and $C_{2-14}$ alkenyl. For example, m is 5, 7, or 9. For example, Q is OH, —NHC(S)N(R)$_2$, or —NHC(O)N(R)$_2$. For example, Q is —N(R)C(O)R, or —N(R)S(O)$_2$R.

In some embodiments, a subset of compounds of Formula (I) includes those of Formula (IL-IB):

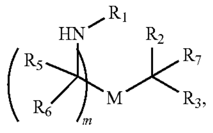

(IL-IB)

or its N-oxide, or a salt or isomer thereof, in which all variables are as defined herein. In some embodiments, m is selected from 5, 6, 7, 8, and 9; $R^4$ is hydrogen, unsubstituted $C_{1-3}$ alkyl, or —$(CH_2)_n$Q, in which Q is —OH, —NHC(S)N(R)$_2$, —NHC(O)N(R)$_2$, —N(R)C(O)R, —N(R)S(O)$_2$R, —N(R)$R_8$, —NHC(=N$R_9$)N(R)$_2$, —NHC(=CH$R_9$)N(R)$_2$, —OC(O)N(R)$_2$, —N(R)C(O)OR, heteroaryl or heterocycloalkyl; M and M' are independently selected from —C(O)O—, —OC(O)—, —OC(O)-M"—C(O)O—, —C(O)N(R')—, —P(O)(OR')O—, —S—S—, an aryl group, and a heteroaryl group; and $R^2$ and $R^3$ are independently selected from the group consisting of H, $C_{1-14}$ alkyl, and $C_{2-14}$ alkenyl. In some embodiments, m is 5, 7, or 9. In some embodiments, Q is OH, —NHC(S)N(R)$_2$, or —NHC(O)N(R)$_2$. In some embodiments, Q is —N(R)C(O)R, or —N(R)S(O)$_2$R.

In some embodiments, a subset of compounds of Formula (IL-I) includes those of Formula (IL-II):

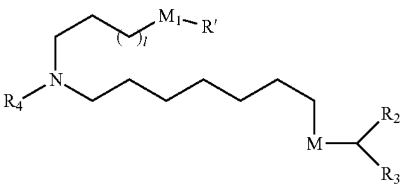

(IL-II)

or its N-oxide, or a slat or isomer thereof, wherein 1 is selected from 1, 2, 3, 4 and 5; M1 is a bond or M'; $R^4$ is hydrogen, unsubstituted $C_{1-3}$ alkyl, or —$(CH_2)_n$Q, in which n is 2, 3, or 4, and Q is —OH, —NHC(S)N(R)$_2$, —NHC(O)N(R)$_2$, —N(R)C(O)R, —N(R)S(O)$_2$R, —N(R)$R^8$, —NHC(=N$R_9$)N(R)$_2$, —NHC(=CH$R^9$)N(R)$_2$, —OC(O)N(R)$_2$, —N(R)C(O)OR, heteroaryl or heterocycloalkyl; M and M' are independently selected from —C(O)O—, —OC(O)—, —OC(O)-M"—C(O)O—, —C(O)N(R')—, —P(O)(OR')O—, —S—S—, an aryl group, and a heteroaryl group; and $R^2$ and $R_3$ are independently selected from the group consisting of H, $C_{1-14}$ alkyl, and $C_{2-14}$ alkenyl.

In some aspects, the ionizable lipids of the present disclosure may be one or more of compounds of Formula (IL-VI):

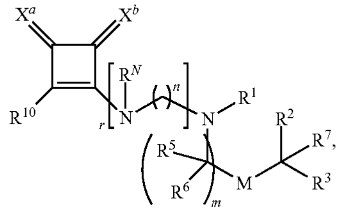

(IL-VI)

or its N-oxide, or a salt or isomer thereof, wherein $R^1$ is selected from the group consisting of $C_{5-30}$ alkyl, $C_{5-20}$ alkenyl, —R*YR", —YR", and —R"M'R';

$R^2$ and $R^3$ are independently selected from the group consisting of H, $C_{1-14}$ alkyl, $C_{2-14}$ alkenyl, —R*YR", —YR", and —R*OR", or $R^2$ and $R^3$, together with the atom to which they are attached, form a heterocycle or carbocycle;

each $R^5$ is independently selected from the group consisting of OH, $C_{1-3}$ alkyl, $C_{2-3}$ alkenyl, and H;

each $R^6$ is independently selected from the group consisting of OH, $C_{1-3}$ alkyl, $C_{2-3}$ alkenyl, and H;

M and M' are independently selected from —C(O)O—, —OC(O)—, —OC(O)-M"—C(O)O—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group, in which M" is a bond, $C_{1-13}$ alkyl or $C_{2-13}$ alkenyl;

$R^7$ is selected from the group consisting of $C_{1-3}$ alkyl, $C_{2-3}$ alkenyl, and H;

each R is independently selected from the group consisting of H, $C_{1-3}$ alkyl, and $C_{2-3}$ alkenyl;

$R^N$ is H, or $C_{1-3}$ alkyl;

each R' is independently selected from the group consisting of $C_{1-18}$ alkyl, $C_{2-18}$ alkenyl, —R*YR", —YR", and H;

each R" is independently selected from the group consisting of $C_{3-15}$ alkyl and $C_{3-15}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I;

$X^a$ and $X^b$ are each independently O or S;

$R^{10}$ is selected from the group consisting of H, halo, —OH, R, —N(R)$_2$, —CN, —$N_3$, —C(O)OH, —C(O)OR, —OC(O)R, —OR, —SR, —S(O)R, —S(O)OR, —S(O)$_2$OR, —$NO_2$, —S(O)$_2$N(R)$_2$, —N(R)S(O)$_2$R, —NH$(CH_2)_{t1}$N(R)$_2$, —NH$(CH_2)_{p1}$O$(CH_2)_{q1}$N(R)$_2$, —NH$(CH_2)_{s1}$OR, —N($(CH_2)_{s1}$OR)$_2$, a carbocycle, a heterocycle, aryl and heteroaryl;

m is selected from 5, 6, 7, 8, 9, 10, 11, 12, and 13;

n is selected from 1, 2, 3, 4, 5, 6, 7, 8, 9, and 10;

r is 0 or 1;

$t^1$ is selected from 1, 2, 3, 4, and 5;

$p^1$ is selected from 1, 2, 3, 4, and 5;

$q^1$ is selected from 1, 2, 3, 4, and 5; and $s^1$ is selected from 1, 2, 3, 4, and 5.

In some embodiments, a subset of compounds of Formula (IL-VI) includes those of Formula (IL-VI-a):

(IL-VI-a)

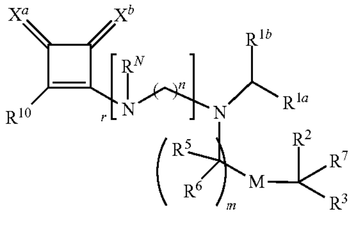

or its N-oxide, or a salt or isomer thereof, wherein $R^{1a}$ and $R^{1b}$ are independently selected from the group consisting of $C_{1-14}$ alkyl and $C_{2-14}$ alkenyl; and $R^2$ and $R^3$ are independently selected from the group consisting of $C_{1-14}$ alkyl, $C_{2-14}$ alkenyl, —R*YR", —YR", and —R*OR", or $R^2$ and $R^3$, together with the atom to which they are attached, form a heterocycle or carbocycle.

In another embodiment, a subset of compounds of Formula (IL-VI) includes those of Formula (IL-VII):

(IL-VII)

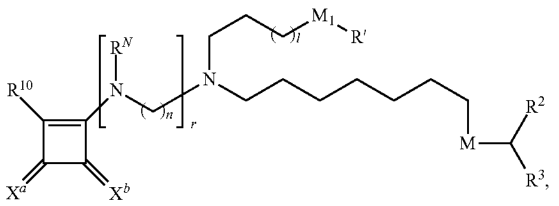

or its N-oxide, or a salt or isomer thereof, wherein 1 is selected from 1, 2, 3, 4, and 5;

$M_1$ is a bond or M'; and $R^2$ and $R^3$ are independently selected from the group consisting of H, $C_{1-14}$ alkyl, and $C_{2-14}$ alkenyl.

In another embodiment, a subset of compounds of Formula (IL-VI) includes those of Formula (IL-VIII):

(L-VIII)

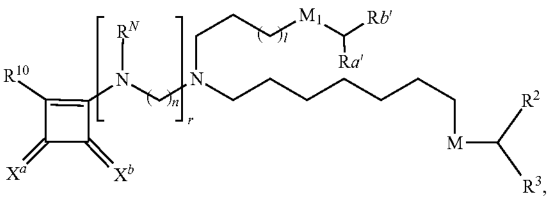

or its N-oxide, or a salt or isomer thereof, wherein 1 is selected from 1, 2, 3, 4, and 5;

$M_1$ is a bond or M'; and $R^{a'}$ and $R^{b'}$ are independently selected from the group consisting of $C_{1-14}$ alkyl and $C_{2-14}$ alkenyl; and $R^2$ and $R^3$ are independently selected from the group consisting of $C_{1-14}$ alkyl, and C2-14 alkenyl.

The compounds of any one of formula (IL-I), (IL-IA), (IL-VI), (IL-VI-a), (IL-VII) or (IL-VIII) include one or more of the following features when applicable.

In some embodiments, $M_1$ is M'.

In some embodiments, M and M' are independently —C(O)O— or —OC(O)—.

In some embodiments, at least one of M and M' is —C(O)O— or —OC(O)—.

In certain embodiments, at least one of M and M' is —OC(O)—.

In certain embodiments, M is —OC(O)— and M' is —C(O)O—. In some embodiments, M is —C(O)O— and M' is —OC(O)—. In certain embodiments, M and M' are each —OC(O)—. In some embodiments, M and M' are each —C(O)O—.

In certain embodiments, at least one of M and M' is —OC(O)-M"—C(O)O—.

In some embodiments, M and M' are independently —S—S—.

In some embodiments, at least one of M and M' is —S—S—.

In some embodiments, one of M and M' is —C(O)O— or —OC(O)— and the other is —S—S—. For example, M is —C(O)O— or —OC(O)— and M' is —S—S— or M' is —C(O)O—, or —OC(O)— and M is —S—S—.

In some embodiments, one of M and M' is —OC(O)-M"—C(O)O—, in which M" is a bond, $C_{1-13}$ alkyl or $C_{2-13}$ alkenyl. In other embodiments, M" is $C_{1-6}$ alkyl or $C_{2-6}$ alkenyl. In certain embodiments, M" is $C_{1-4}$ alkyl or $C_{2-4}$ alkenyl. For example, in some embodiments, M" is $C_1$ alkyl. For example, in some embodiments, M" is $C_2$ alkyl. For example, in some embodiments, M" is $C_3$ alkyl. For example, in some embodiments, M" is $C_4$ alkyl. For example, in some embodiments, M" is $C_2$ alkenyl. For example, in some embodiments, M" is $C_3$ alkenyl. For example, in some embodiments, M" is $C_4$ alkenyl.

In some embodiments, 1 is 1, 3, or 5.

In some embodiments, $R^4$ is hydrogen.

In some embodiments, $R^4$ is not hydrogen.

In some embodiments, $R^4$ is unsubstituted methyl or $—(CH_2)_nQ$, in which Q is OH, $—NHC(S)N(R)_2$, $—NHC(O)N(R)_2$, —N(R)C(O)R, or $—N(R)S(O)_2R$.

In some embodiments, Q is OH.

In some embodiments, Q is $—NHC(S)N(R)_2$.

In some embodiments, Q is $—NHC(O)N(R)_2$.

In some embodiments, Q is —N(R)C(O)R.

In some embodiments, Q is $—N(R)S(O)_2R$.

In some embodiments, Q is $—O(CH_2)_nN(R)_2$.

In some embodiments, Q is $—O(CH_2)_nOR$.

In some embodiments, Q is $—N(R)R^8$.

In some embodiments, Q is $—NHC(=NR^9)N(R)_2$.

In some embodiments, Q is $—NHC(=CHR^9)N(R)_2$.

In some embodiments, Q is $—OC(O)N(R)_2$.

In some embodiments, Q is —N(R)C(O)OR.

In some embodiments, n is 2.

In some embodiments, n is 3.

In some embodiments, n is 4.

In some embodiments, $M_1$ is absent.

In some embodiments, at least one $R^5$ is hydroxyl. For example, one $R^5$ is hydroxyl.

In some embodiments, at least one $R^6$ is hydroxyl. For example, one $R^6$ is hydroxyl.

In some embodiments one of $R^5$ and $R^6$ is hydroxyl. For example, one $R^5$ is hydroxyl and each $R^6$ is hydrogen. For example, one $R^6$ is hydroxyl and each $R^5$ is hydrogen.

In some embodiments, $R^x$ is $C_{1-6}$ alkyl. In some embodiments, $R^x$ is $C_{1-3}$ alkyl. For example, $R^x$ is methyl. For example, $R^x$ is ethyl. For example, $R^x$ is propyl.

In some embodiments, $R^x$ is $—(CH_2)$ OH and, v is 1, 2 or 3. For example, $R^x$ is methanol. For example, $R^x$ is ethanoyl. For example, $R^x$ is propanoyl.

In some embodiments, $R^x$ is $—(CH_2)_vN(R)_2$, v is 1, 2 or 3 and each R is H or methyl. For example, $R^x$ is methanamino, methylmethanamino, or dimethylmethanamino. For example, RX is aminomethanyl, methylaminomethanyl, or dimethylaminomethanyl. For example, RX is aminoethanyl, methylaminoethanyl, or dimethylaminoethanyl. For example, $R^x$ is aminopropanyl, methylaminopropanyl, or dimethylaminopropanyl.

In some embodiments, R' is $C_{1-18}$ alkyl, $C_{2-18}$ alkenyl, —R*YR", or —YR".

In some embodiments, $R^2$ and $R^3$ are independently $C_{3-14}$ alkyl or $C_{3-14}$ alkenyl.

In some embodiments, $R^{1b}$ is $C_{1-14}$ alkyl. In some embodiments, $R^{1b}$ is $C_{2-14}$ alkyl. In some embodiments, $R^{1b}$ is $C_{3-14}$ alkyl. In some embodiments, $R^{1b}$ is $C_{1-8}$ alkyl. In some embodiments, $R^{1b}$ is $C_{1-5}$ alkyl. In some embodiments, $R^{1b}$ is $C_{1-3}$ alkyl. In some embodiments, $R^{1b}$ is selected from $C_1$ alkyl, $C_2$ alkyl, $C_3$ alkyl, $C_4$ alkyl, and $C_5$ alkyl. For example, in some embodiments, $R^{1b}$ is $C_1$ alkyl. For example, in some embodiments, $R^{1b}$ is $C_2$ alkyl. For example, in some embodiments, $R^{1b}$ is $C_3$ alkyl. For example, in some embodiments, $R^{1b}$ is $C_4$ alkyl. For example, in some embodiments, $R^{1b}$ is $C_5$ alkyl.

In some embodiments, $R^1$ is different from —$(CHR^5R^6)_m$-M-$CR^2R^3R^7$.

In some embodiments, —$CHR^{1a}R^{1b}$— is different from —$(CHR^5R^6)_m$-M-$CR^2R^3R^7$.

In some embodiments, $R^7$ is H. In some embodiments, $R^7$ is selected from $C_{1-3}$ alkyl. For example, in some embodiments, $R^7$ is $C_1$ alkyl. For example, in some embodiments, $R^7$ is $C_2$ alkyl. For example, in some embodiments, $R^7$ is $C_3$ alkyl. In some embodiments, $R^7$ is selected from $C_4$ alkyl, $C_4$ alkenyl, $C_5$ alkyl, $C_5$ alkenyl, $C_6$ alkyl, $C_6$ alkenyl, $C_7$ alkyl, $C_7$ alkenyl, $C_9$ alkyl, $C_9$ alkenyl, $C_{11}$ alkyl, $C_{11}$ alkenyl, $C_{17}$ alkyl, $C_{17}$ alkenyl, $C_{18}$ alkyl, and $C_{18}$ alkenyl.

In some embodiments, Rb' is C1-14 alkyl. In some embodiments, Rb' is C2-14 alkyl. In some embodiments, $R^{b'}$ is $C_{3-14}$ alkyl. In some embodiments, $R^{b'}$ is $C_{1-8}$ alkyl. In some embodiments, $R^{b'}$ is $C_{1-5}$ alkyl. In some embodiments, $R^{b'}$ is $C_{1-3}$ alkyl. In some embodiments, $R^{b'}$ is selected from $C_1$ alkyl, $C_2$ alkyl, $C_3$ alkyl, $C_4$ alkyl and $C_5$ alkyl. For example, in some embodiments, $R^{b'}$ is $C_1$ alkyl. For example, in some embodiments, $R^{b'}$ is $C_2$ alkyl. For example, some embodiments, $R^{b'}$ is $C_3$ alkyl. For example, some embodiments, $R^{b'}$ is $C_4$ alkyl.

In some embodiments, the compounds of Formula (IL-I) are of Formula (IL-IIa):

(IL-IIa)

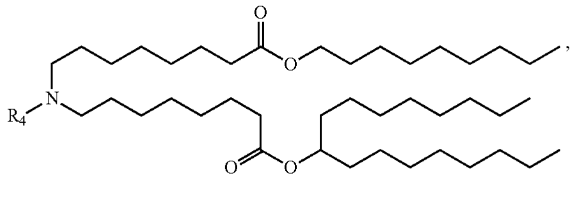

or their N-oxides, or salts or isomers thereof, wherein $R_4$ is as described herein.

In another embodiment, the compounds of Formula (IL-I) are of Formula (IL-IIb):

(IL-IIb)

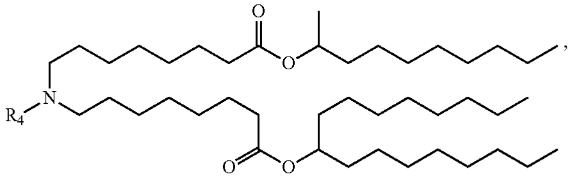

or their N-oxides, or salts or isomers thereof, wherein $R_4$ is as described herein.

In another embodiment, the compounds of Formula (IL-I) are of Formula (IL-IIc) or (IL-IIe):

(IL-IIc)

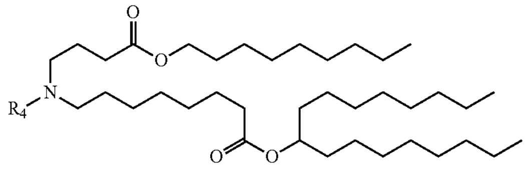

or (IL-IIe)

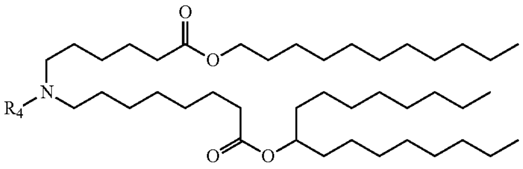

or their N-oxides, or salts or isomers thereof, wherein $R_4$ is as described herein.

In another embodiment, the compounds of Formula (IL-I) are of Formula (IL-IIf):

(IL-IIf)

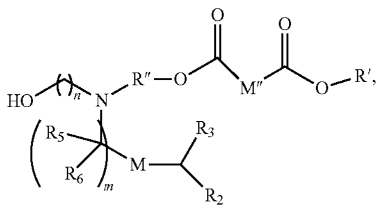

or their N-oxides, or salts or isomers thereof, wherein M is —C(O)O— or —OC(O)—, M" is $C_{1-6}$ alkyl or $C_{2-6}$ alkenyl, $R_2$ and $R_3$ are independently selected from the group consisting of $C_{5-14}$ alkyl and $C_{5-14}$ alkenyl, and n is selected from 2, 3, and 4.

In a further embodiment, the compounds of Formula (IL-I) are of Formula (IL-IId):

(IL-IId)

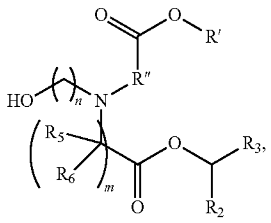

or their N-oxides, or salts or isomers thereof, wherein n is 2, 3, or 4; and m, R', R", and $R_2$ through $R_6$ are as described herein. In some embodiments, each of $R_2$ and $R_3$ may be independently selected from the group consisting of $C_{5-14}$ alky and $C_{5-14}$ alkenyl.

In a further embodiment, the compounds of Formula (IL-I) are of Formula (IL-IIg):

(IL-IIg)

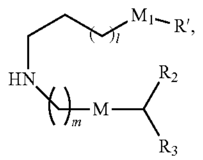

or their N-oxides, or salts or isomers thereof, wherein 1 is selected from 1, 2, 3, 4, and 5; m is selected from 5, 6, 7, 8, and 9; $M_1$ is a bond or M'; M and M' are independently selected from —C(O)O—, —OC(O)—, —OC(O)-M"—C(O)O—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl. In some embodiments, M" is $C_{1-6}$ alkyl (e.g., $C_{1-4}$ alkyl) or $C_{2-6}$ alkenyl (e.g. $C_{2-4}$ alkenyl). In some embodiments, $R_2$ and $R_3$ are independently selected from the group consisting of $C_{5-14}$ alkyl and $C_{5-14}$ alkenyl.

In another embodiment, a subset of compounds of Formula (IL-VI) includes those of Formula (IL-VIIa):

(L-VIIa)

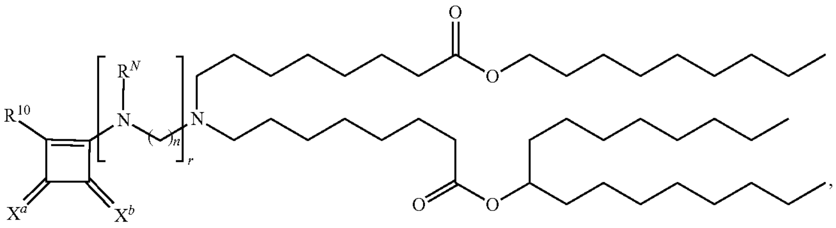

or its N-oxide, or a salt or isomer thereof.

In another embodiment, a subset of compounds of Formula (VI) includes those of Formula (IL-VIIIa):

(IL-VIIIa)

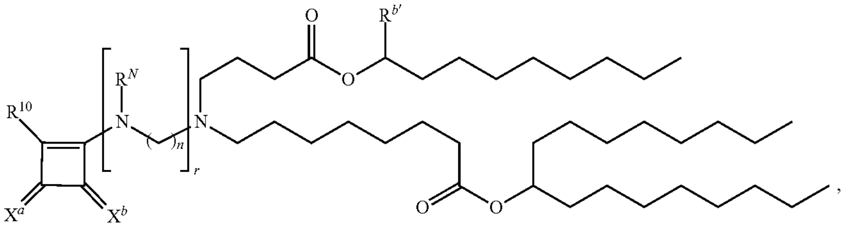

or its N-oxide, or a salt or isomer thereof.

In another embodiment, a subset of compounds of Formula (IL-VI) includes those of Formula (IL-VIIIb):

(IL-VIIIb)

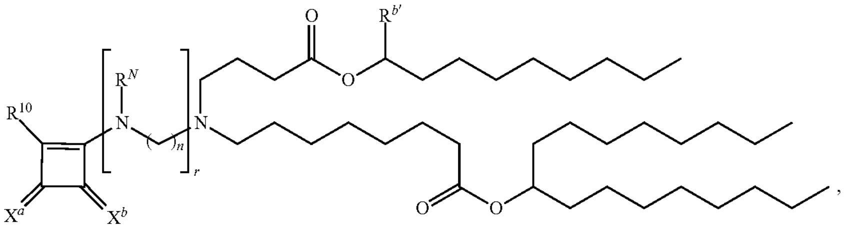

or its N-oxide, or a salt or isomer thereof.

In another embodiment, a subset of compounds of Formula (IL-VI) includes those of Formula (IL-VIIb-1):

(IL-VIIb-1)

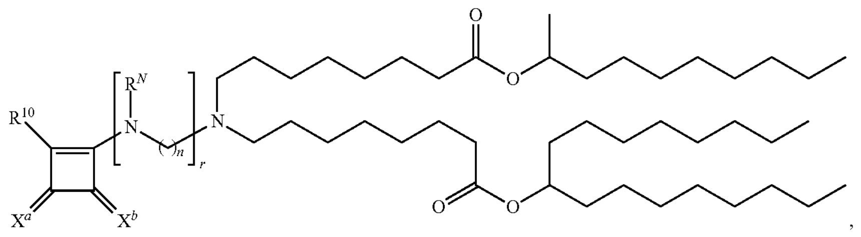

or its N-oxide, or a salt or isomer thereof.

In another embodiment, a subset of compounds of Formula (IL-VI) includes those of Formula (IL-VIIb-2):

(L-VIIb-2)

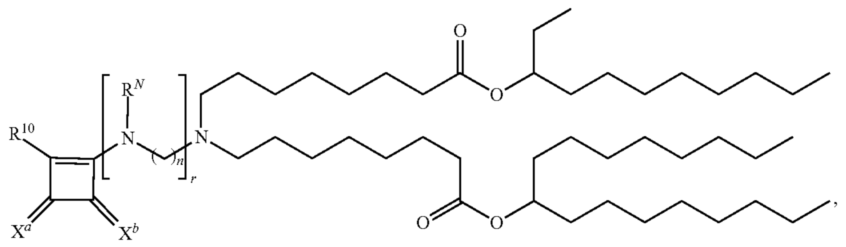

or its N-oxide, or a salt or isomer thereof.

In another embodiment, a subset of compounds of Formula (IL-VI) includes those of Formula (IL-VIIb-3):

(IL-VIIb-3)

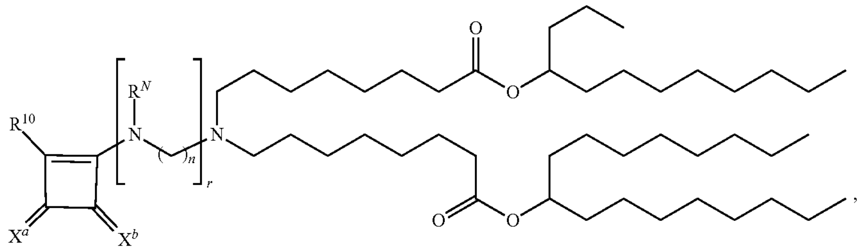

or its N-oxide, or a salt or isomer thereof.

In another embodiment, a subset of compounds of Formula (IL-VI) includes those of Formula (IL-VIIc):

(IL-VIIc)

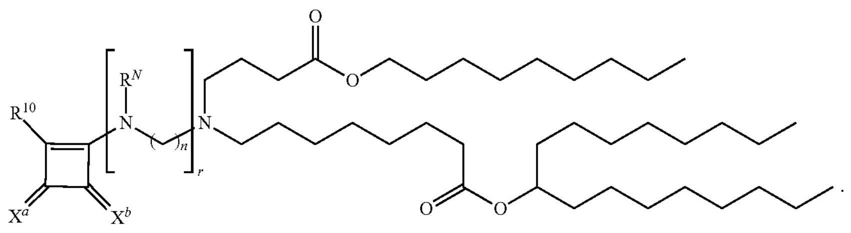

In another embodiment, a subset of compounds of Formula (IL-VI) includes those of Formula (IL-VIId):

(IL-VIId)

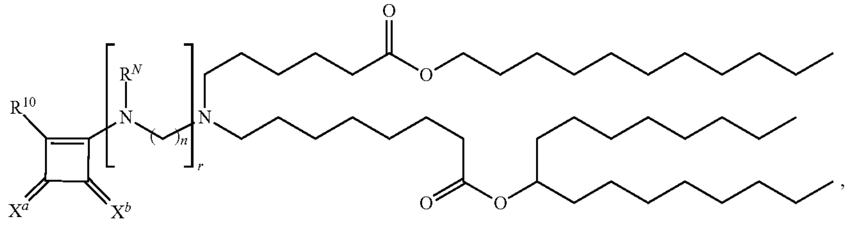

or its N-oxide, or a salt or isomer thereof.

In another embodiment, a subset of compounds of Formula (IL-VI) includes those of Formula (IL-VIIIc):

(IL-VIIIc)

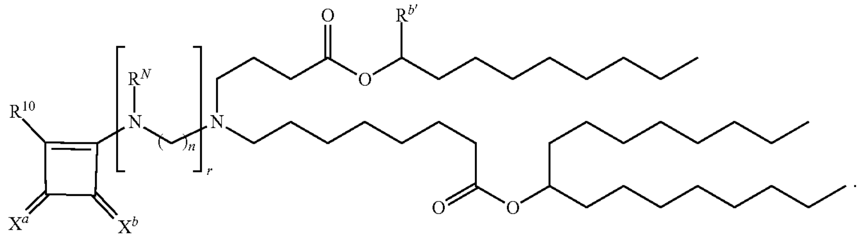

In another embodiment, a subset of compounds of Formula (IL-VI) includes those of Formula (IL-VIIId):

(IL-VIIId)

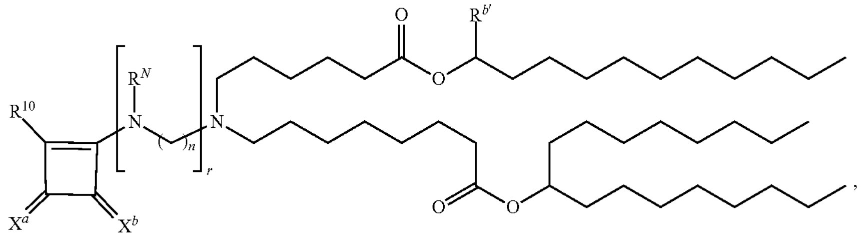

or its N-oxide, or a salt or isomer thereof.

The compounds of any one of formulae (IL-I), (IL-IA), (IL-IB), (IL-II), (IL-IIa), (IL-IIb), (IL-IIc), (IL-IId), (IL-IIe), (IL-IIf), (IL-IIg), (IL-III), (IL-VI), (IL-VI-a), (IL-VII), (IL-VIII), (IL-VIIa), (IL-VIIIa), (IL-VIIIb), (IL-VIIb-1), (IL-VIIb-2), (IL-VIIb-3), (IL-VIIc), (IL-VIId), (IL-VIIIc), or (IL-VIIId) include one or more of the following features when applicable.

In some embodiments, the ionizable lipids are one or more of the compounds described in U.S. Application Nos. 62/220,091, 62/252,316, 62/253,433, 62/266,460, 62/333,557, 62/382,740, 62/393,940, 62/471,937, 62/471,949, 62/475,140, and 62/475,166, and PCT Application No. PCT/US2016/052352.

In some embodiments, the ionizable lipids are selected from Compounds 1-280 described in U.S. Application No. 62/475,166.

In some embodiments, the ionizable lipid is

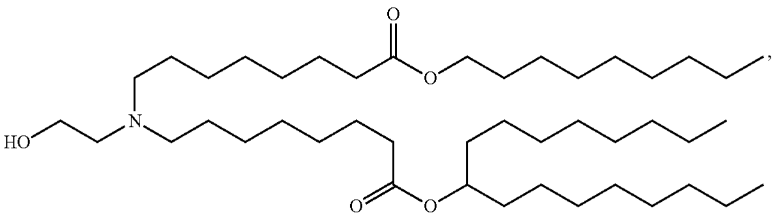 [SMILES: CCCCCCCCCOC(=O)CCCCCCCN(CCO)CCCCCCCC(=O)OC(CCCCCCCC)CCCCCCCC]

or a salt thereof.

In some embodiments, the ionizable lipid is

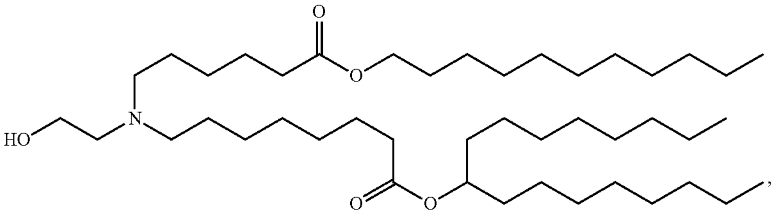 [SMILES: CCCCCCCCCCCOC(=O)CCCCCN(CCO)CCCCCCCC(=O)OC(CCCCCCCC)CCCCCCCC ; ","]

or a salt thereof.

In some embodiments, the ionizable lipid is

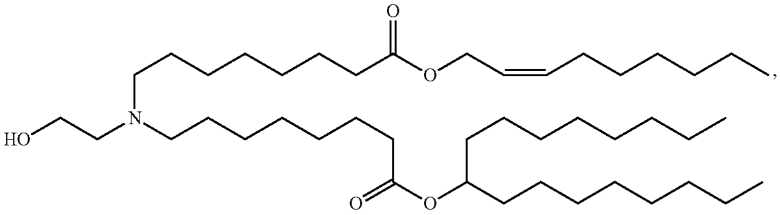 [SMILES: CCCCCC/C=C\COC(=O)CCCCCCCN(CCO)CCCCCCCC(=O)OC(CCCCCCCC)CCCCCCCC ; ","]

or a salt thereof.

In some embodiments, the ionizable lipid is

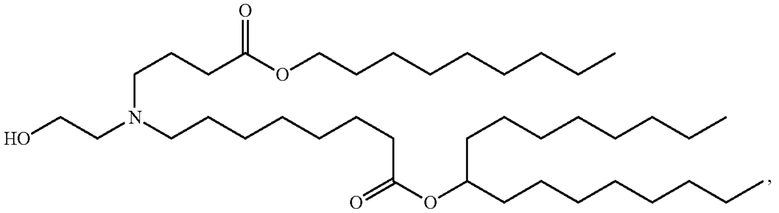 [SMILES: CCCCCCCCCOC(=O)CCCN(CCO)CCCCCCCC(=O)OC(CCCCCCCC)CCCCCCCC ; ","]

or a salt thereof.

In some aspects, the ionizable lipids of the present disclosure may be one or more of compounds of formula (IL-III):

(IL-III)

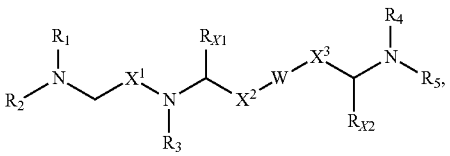

or salts or isomers thereof, wherein,

W is

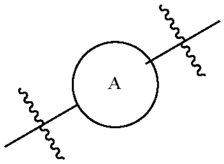

or

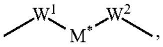

ring A is

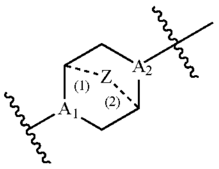

or

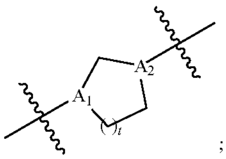

;

t is 1 or 2;

$A_1$ and $A_2$ are each independently selected from CH or N;

Z is $CH_2$ or absent wherein when Z is $CH_2$, the dashed lines (1) and (2) each represent a single bond; and when Z is absent, the dashed lines (1) and (2) are both absent;

$R_1$, $R_2$, $R_3$, $R_4$, and $R_5$ are independently selected from the group consisting of $C_{5-20}$ alkyl, $C_{5-20}$ alkenyl, —R"MR", —R*YR", —YR", and —R*OR";

$R_{X1}$ and $R_{X2}$ are each independently H or $C_{1-3}$ alkyl;

each M is independently selected from the group consisting of —C(O)O—, —OC(O)—, —OC(O)O—, —C(O)N(R')—, —N(R')C(O)—, —C(O)—, —C(S)—, —C(S)S—, —SC(S)—, —CH(OH)—, —P(O)(OR')O—, —$S(O)_2$—, —C(O)S—, —SC(O)—, an aryl group, and a heteroaryl group;

M* is $C_1$-$C_6$ alkyl, $W^1$ and $W^2$ are each independently selected from the group consisting of —O— and —$N(R_6)$—;

each $R^6$ is independently selected from the group consisting of H and $C_{1-5}$ alkyl;

$X^1$, $X^2$, and $X^3$ are independently selected from the group consisting of a bond, —$CH_2$—, —$(CH_2)_2$—, —CHR—, —CHY—, —C(O)—, —C(O)O—, —OC(O)—, —$(CH_2)_n$—C(O)—, —C(O)—$(CH_2)_n$—, —$(CH_2)_n$—C(O)O—, —OC(O)—$(CH_2)_n$—, —$(CH_2)_n$—OC(O)—, —C(O)O—$(CH_2)_n$—, —CH(OH)—, —C(S)—, and —CH(SH)—;

each Y is independently a $C_{3-6}$ carbocycle;

each R* is independently selected from the group consisting of $C_{1-12}$ alkyl and $C_{2-12}$ alkenyl;

each R is independently selected from the group consisting of $C_{1-3}$ alkyl and a $C_{3-6}$ carbocycle;

each R' is independently selected from the group consisting of $C_{1-12}$ alkyl, $C_{2-12}$ alkenyl, and H;

each R" is independently selected from the group consisting of $C_{3-12}$ alkyl, $C_{3-12}$ alkenyl and —R*MR'; and n is an integer from 1-6;

wherein when ring A is

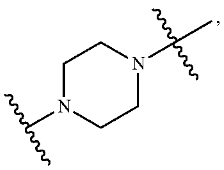 [SMILES: *N1CCN(*)CC1]

, then i) at least one of $X^1$, $X^2$, and $X^3$ is not —$CH_2$—; and/or ii) at least one of $R_1$, $R_2$, $R_3$, $R_4$, and $R_5$ is —R"MR".

In some embodiments, the compound is of any of formulae (IL-IIIa1)-(IL-IIIa8):

(IL-IIIa1)

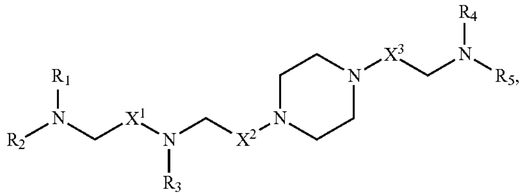

(IL-IIIa2)

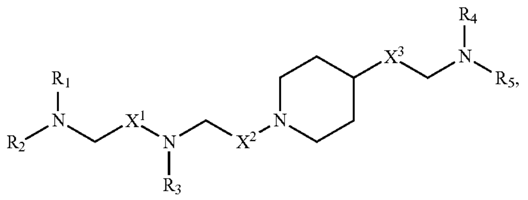

(IL-IIIa3)

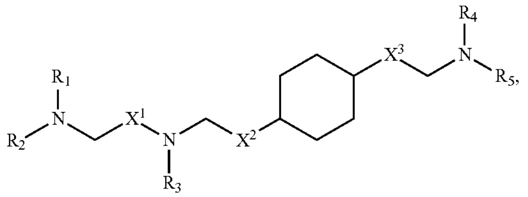

(IL-IIIa4)

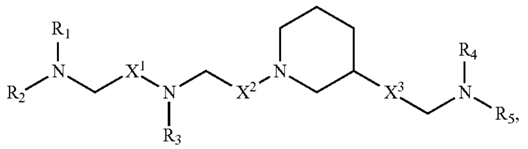

(IL-IIIa5)

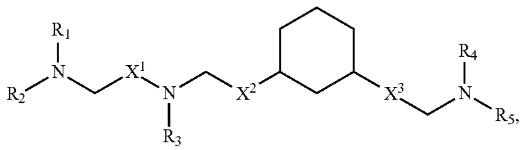

(IL-IIIa6)

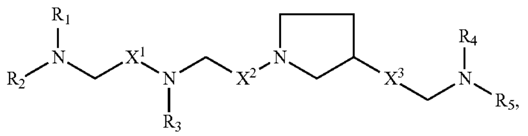

(IL-IIIa7)

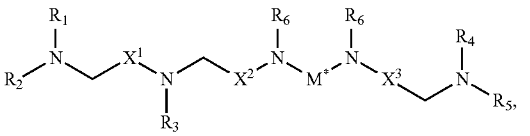

or (IL-IIIa8)

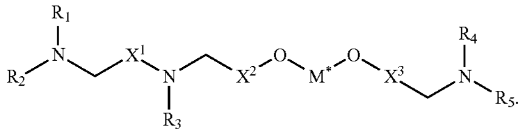

In some embodiments, the ionizable lipids are one or more of the compounds described in U.S. Application Nos. 62/271,146, 62/338,474, 62/413,345, and 62/519,826, PCT Application No. PCT/US2019/052009, and Internation Publication Nos. WO 2017/112865, WO 2017/049245, and WO 2018/170306.

In some embodiments, the ionizable lipids are selected from Compound 1-156 described in U.S. Application No. 62/519,826.

In some embodiments, the ionizable lipids are selected from Compounds 1-16, 42-66, 68-76, and 78-156 described in U.S. Application No. 62/519,826.

In some embodiments, the ionizable lipid is

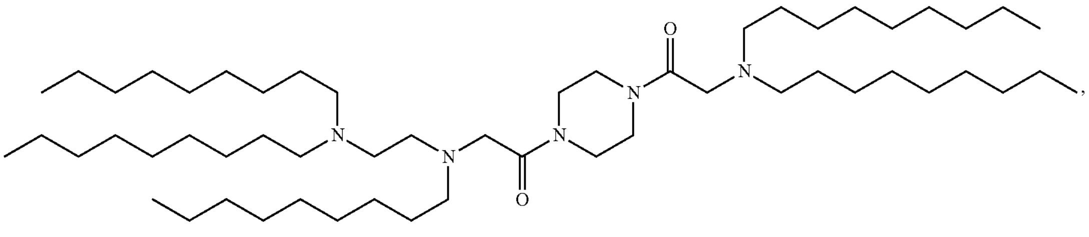 [SMILES: CCCCCCCCCN(CCCCCCCCC)CCN(CCCCCCCCC)CC(=O)N1CCN(C(=O)CN(CCCCCCCCC)CCCCCCCCC)CC1]

or a salt thereof.

The central amine moiety of a lipid according to Formula (IL-1), (IL-IA), (IL-IB), (IL-II), (IL-IIa), (IL-IIb), (IL-IIc), (IL-IId), (IL-IIe), (IL-IIf), (IL-IIg), (IL-III), (IL-IIIa1), (IL-IIIa2), (IL-IIIa3), (IL-IIIa4), (IL-IIIa5), (IL-IIIa6), (IL-IIIa7), or (IL-IIIa8) may be protonated at a physiological pH. Thus, a lipid may have a positive or partial positive charge at physiological pH. Such lipids may be referred to as cationic or ionizable (amino) lipids. Lipids may also be zwitterionic, i.e., neutral molecules having both a positive and a negative charge.

In some embodiments, the ionizable lipid is selected from the group consisting of 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino) butanoate (DLin-MC3-DMA), 2,2-dilinoleyl-4-(2-dimethylaminoethyl)-[1,3]-dioxolane (DLin-KC2-DMA), 1,2-dioleyloxy-N,N-dimethylaminopropane (DODMA), 2-({8-[(3)-cholest-5-en-3-yloxy]octyl}oxy)-N,N-dimethyl-3-[(9Z,12Z)-octadeca-9,12-dien-1-yloxy]propan-1-amine (Octyl-CLinDMA), (2R)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2R)), and (2S)—2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2S)).

Polyethylene Glycol (PEG) Lipids

As used herein, the term "PEG lipid" refers to polyethylene glycol (PEG)-modified lipids. Non-limiting examples of PEG lipids include PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Such lipids are also referred to as PEGylated lipids. In some embodiments, a PEG lipid can be PEG-c-DOMG, PEG-DMG, PEG-DLPE, PEG-DMPE, PEG-DPPC, or a PEG-DSPE lipid.

In some embodiments, the PEG lipid includes, but are not limited to, 1,2-dimyristoyl-sn-glycerol methoxypolyethylene glycol (PEG-DMG), 1,2-distearoyl-sn-glycero-3-phosphoethanolamine-N-[amino (polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA).

In some embodiments, the PEG lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.

In some embodiments, the lipid moiety of the PEG lipids includes those having lengths of from about $C_{14}$ to about $C_{22}$, e.g., from about $C_{14}$ to about $C_{16}$. In some embodiments, a PEG moiety, for example an $mPEG-NH_2$, has a size of about 1000, 2000, 5000, 10,000, 15,000 or 20,000 daltons. In some embodiments, the PEG lipid is $PEG_{2k}$-DMG.

In some embodiments, the lipid nanoparticles described herein can comprise a PEG lipid which is a non-diffusible PEG. Non-limiting examples of non-diffusible PEGs include PEG-DSG and PEG-DSPE.

PEG lipids are known in the art, such as those described in U.S. Pat. No. 8,158,601 and International Publ. No. WO 2015/130584 A2, which are incorporated herein by reference in their entirety.

In general, some of the other lipid components (e.g., PEG lipids) of various formulae, described herein may be synthesized as described International Patent Application No. PCT/US2016/000129, filed Dec. 10, 2016, entitled "Compositions and Methods for Delivery of Therapeutic Agents," which is incorporated by reference in its entirety.

The lipid component of a lipid nanoparticle or lipid nanoparticle formulation may include one or more molecules comprising polyethylene glycol, such as PEG or PEG-modified lipids. Such species may be alternately referred to as PEGylated lipids. A PEG lipid is a lipid modified with polyethylene glycol. A PEG lipid may be selected from the non-limiting group including PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. In some embodiments, a PEG lipid may be PEG-c-DOMG, PEG-DMG, PEG-DLPE, PEG-DMPE, PEG-DPPC, or a PEG-DSPE lipid.

In some embodiments, the PEG-modified lipids are a modified form of PEG DMG. PEG-DMG has the following structure:

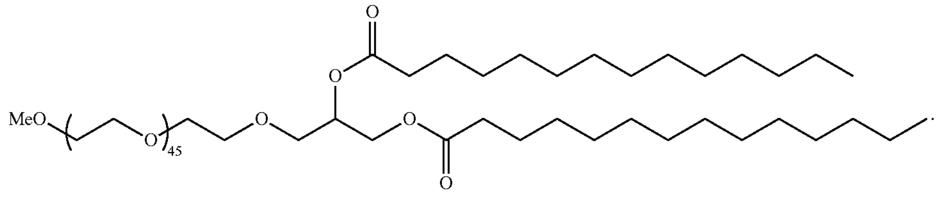

In some embodiments, PEG lipids useful in the present invention can be PEGylated lipids described in International Publication No. WO2012099755, the contents of which is herein incorporated by reference in its entirety. Any of these exemplary PEG lipids described herein may be modified to comprise a hydroxyl group on the PEG chain. In some embodiments, the PEG lipid is a PEG-OH lipid. As generally defined herein, a "PEG-OH lipid" (also referred to herein as "hydroxy-PEGylated lipid") is a PEGylated lipid having one or more hydroxyl (—OH) groups on the lipid. In some embodiments, the PEG-OH lipid includes one or more hydroxyl groups on the PEG chain. In some embodiments, a PEG-OH or hydroxy-PEGylated lipid comprises an —OH group at the terminus of the PEG chain. Each possibility represents a separate embodiment of the present invention.

In some embodiments, a PEG lipid useful in the present invention is a compound of Formula (PL-I). Provided herein are compounds of Formula (PL-I):

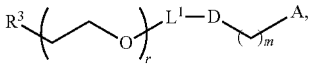

(PL-I)

or salts thereof, wherein:

$R^3$ is —$OR^O$;

$R^O$ is hydrogen, optionally substituted alkyl, or an oxygen protecting group;

r is an integer between 1 and 100, inclusive;

$L^1$ is optionally substituted $C_{1-10}$ alkylene, wherein at least one methylene of the optionally substituted $C_{1-10}$ alkylene is independently replaced with optionally substituted carbocyclylene, optionally substituted heterocyclylene, optionally substituted arylene, optionally substituted heteroarylene, O, $N(R^N)$, S, C(O), $C(O)N(R^N)$, $NR^NC(O)$, C(O)O, —OC(O), OC(O)O, $OC(O)N(R^N)$, $NR^NC(O)O$, or $NR^NC(O)N(R^N)$;

D is a moiety obtained by click chemistry or a moiety cleavable under physiological conditions;

m is 0, 1, 2, 3, 4, 5, 6, 7, 8, 9, or 10;

A is of the formula:

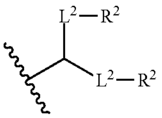

or

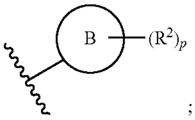

;

each instance of $L^2$ is independently a bond or optionally substituted $C_{1-6}$ alkylene, wherein one methylene unit of the optionally substituted $C_{1-6}$ alkylene is optionally replaced with O, $N(R^N)$, S, C(O), $C(O)N(R^N)$, $NR^NC(O)$, C(O)O, OC(O), OC(O)O, $OC(O)N(R^N)$, —$NR^NC(O)O$, or $NR^NC(O)N(R^N)$;

each instance of $R^2$ is independently optionally substituted $C_{1-30}$ alkyl, optionally substituted $C_{1-30}$ alkenyl, or optionally substituted $C_{1-30}$ alkynyl: optionally wherein one or more methylene units of $R^2$ are independently replaced with optionally substituted carbocyclylene, optionally substituted heterocyclylene, optionally substituted arylene, optionally substituted heteroarylene, $N(R^N)$, O, S, C(O), $C(O)N(R^N)$, $NR^NC(O)$, —$NR^NC(O)N(R^N)$, C(O)O, OC(O), OC(O)O, $OC(O)N(R^N)$, $NR^NC(O)O$, C(O)S, SC(O), —$C(=NR^N)$, $C(=NR^N)N(R^N)$, $NR^NC(=NR^N)$, $NR^NC(=NR^N)N(R^N)$, C(S), $C(S)N(R^N)$, $NR^NC(S)$, $NR^NC(S)N(R^N)$, S(O), OS(O), S(O)O, OS(O)O, $OS(O)_2$, $S(O)_2O$, $OS(O)_2O$, $N(R^N)S(O)$, —$S(O)N(R^N)$, $N(R^N)S(O)N(R^N)$, $OS(O)N(R^N)$, $N(R^N)S(O)O$, $S(O)_2$, $N(R^N)S(O)_2$, $S(O)_2N(R^N)$, $N(R^N)S(O)_2N(R^N)$, $OS(O)_2N(R^N)$, or $N(R^N)S(O)_2O$;

each instance of $R^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2.

In some embodiments, the compound of Formula (PL-I) is a PEG-OH lipid (i.e., $R^3$ is —$OR^O$, and $R^O$ is hydrogen). In some embodiments, the compound of Formula (PL-I) is of Formula (PL-I-OH):

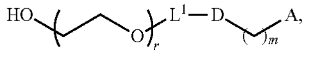

(PL-I-OH)

or a salt thereof.

In some embodiments, a PEG lipid useful in the present invention is a PEGylated fatty acid. In some embodiments, a PEG lipid useful in the present invention is a compound of Formula (PL-II). Provided herein are compounds of Formula (PL-II):

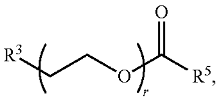

(PL-II)

or a salt thereof, wherein:

$R^3$ is —$OR^O$;

$R^O$ is hydrogen, optionally substituted alkyl or an oxygen protecting group;

r is an integer between 1 and 100, inclusive;

$R^5$ is optionally substituted $C_{10-40}$ alkyl, optionally substituted $C_{10-40}$ alkenyl, or optionally substituted $C_{10-40}$ alkynyl; and optionally one or more methylene groups of $R^5$ are replaced with optionally substituted carbocyclylene, optionally substituted heterocyclylene, optionally substituted arylene, optionally substituted heteroarylene, $N(R^N)$, O, S, C(O), —$C(O)N(R^N)$, $NR^NC(O)$, $NR^NC(O)N(R^N)$, C(O)O, OC(O), OC(O)O, $OC(O)N(R^N)$, —$NR^NC(O)O$, C(O)S, SC(O), $C(=NR^N)$, $C(=NR^N)N(R^N)$, $NR^NC(=NR^N)$, $NR^NC(=NR^N)N(R^N)$, C(S), $C(S)N(R^N)$, $NR^NC(S)$, $NR^NC(S)N(R^N)$, S(O), OS(O), S(O)O, OS(O)O, $OS(O)_2$, —$S(O)_2O$, $OS(O)_2O$, $N(R^N)S(O)$, $S(O)N(R^N)$, $N(R^N)S(O)N(R^N)$, $OS(O)_2O$, $N(R^N)S(O)$, $S(O)N(R^N)$, $N(R^N)S(O)N(R^N)$, $OS(O)N(R^N)$, $N(R^N)S(O)O$, $S(O)_2$, $N(R^N)S(O)_2$, $S(O)_2N(R^N)$, $N(R^N)S(O)_2N(R^N)$, $OS(O)_2N(R^N)$, or $N(R^N)S(O)_2O$; and each instance of $R^N$ is independently hydrogen, optionally substituted alkyl, or a nitrogen protecting group.

In some embodiments, r is an integer between 10 to 80, between 20 to 70, between 30 to 60, or between 40 to 50.

In some embodiments, r is 45.

In some embodiments, $R^5$ is $C_{17}$ alkyl.

In yet other embodiments the compound of Formula (PL-II) is:

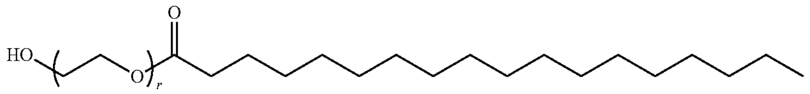

$OS(O)N(R^N)$, $N(R^N)S(O)O$, $S(O)_2$, $N(R^N)S(O)_2$, $S(O)_2N(R^N)$, $N(R^N)S(O)_2N(R^N)$, $OS(O)_2N(R^N)$, or $N(R^N)S(O)_2O$; and or a salt thereof.

In some embodiments, the compound of Formula (PL-II) is (PEG-1)

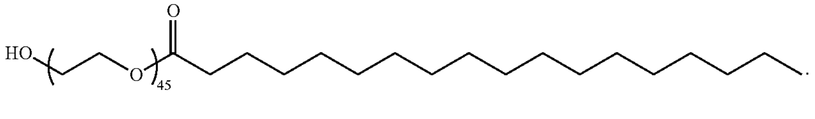

each instance of $R^N$ is independently hydrogen, optionally substituted alkyl, or a nitrogen protecting group.

In some embodiments, the compound of Formula (PL-II) is of Formula (PL-II-OH):

(PL-II-OH)

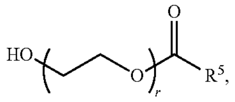

or a salt thereof, wherein:

r is an integer between 1 and 100;

$R^5$ is optionally substituted $C_{10-40}$ alkyl, optionally substituted $C_{10-40}$ alkenyl, or optionally substituted $C_{10-40}$ alkynyl; and optionally one or more methylene groups of $R^5$ are replaced with optionally substituted carbocyclylene, optionally substituted heterocyclylene, optionally substituted arylene, optionally substituted heteroarylene, $N(R^N)$, O, S, C(O), —$C(O)N(R^N)$, $NR^NC(O)$, $NR^NC(O)N(R^N)$, C(O)O, OC(O), OC(O)O, $OC(O)N(R^N)$, —$NR^NC(O)O$, C(O)S, SC(O), $C(=NR^N)$, $C(=NR^N)N(R^N)$, $NR^NC(=NR^N)$, $NR^NC(=NR^N)N(R^N)$, C(S), $C(S)N(R^N)$, $NR^NC(S)$, $NR^NC(S)N(R^N)$, S(O), OS(O), S(O)O, OS(O)O, $OS(O)_2$, —$S(O)_2O$, In some aspects, the lipid composition of the pharmaceutical compositions described herein does not comprise a PEG lipid.

In some embodiments, the PEG lipids may be one or more of the PEG lipids described in U.S. Application No. 62/520,530.

In some embodiments, the PEG lipid is a compound of Formula (PL-III):

(PL-III)

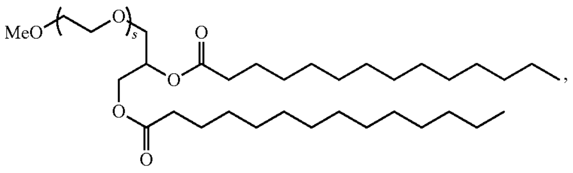

or a salt or isomer thereof, wherein s is an integer between 1 and 100.

In some embodiments, the PEG lipid is a compound of the following formula:

(PEG-2)

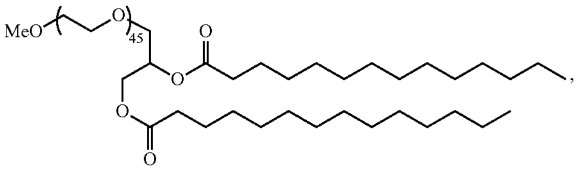

or a salt or isomer thereof.

Structural Lipids

As used herein, the term "structural lipid" refers to sterols and also to lipids containing sterol moieties.

Incorporation of structural lipids in the lipid nanoparticle may help mitigate aggregation of other lipids in the particle. Structural lipids can be selected from the group including but not limited to, cholesterol, fecosterol, sitosterol, ergosterol, campesterol, stigmasterol, brassicasterol, tomatidine, tomatine, ursolic acid, alpha-tocopherol, hopanoids, phytosterols, steroids, and mixtures thereof. In some embodiments, the structural lipid is a mixture of two or more components each independently selected from cholesterol, fecosterol, sitosterol, ergosterol, campesterol, stigmasterol, brassicasterol, tomatidine, tomatine, ursolic acid, alpha-tocopherol, hopanoids, phytosterols, and steroids. In some embodiments, the structural lipid is a sterol. In some embodiments, the structural lipid is a mixture of two or more sterols. As defined herein, "sterols" are a subgroup of steroids consisting of steroid alcohols. In some embodiments, the structural lipid is a steroid. In some embodiments, the structural lipid is cholesterol. In some embodiments, the structural lipid is an analog of cholesterol. In some embodiments, the structural lipid is alpha-tocopherol.

In some embodiments, the structural lipids may be one or more structural lipids described in U.S. Application No. 62/520,530.

Encapsulation Agent

In some embodiments of the present disclosure, the encapsulation agent is a compound of Formula (EA-I):

(EA-I)

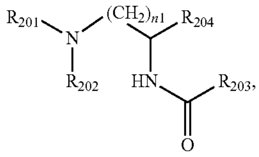

or salts or isomers thereof, wherein $R_{201}$ and $R_{202}$ are each independently selected from the group consisting of H, $C_1$-$C_6$ alkyl, $C_2$-$C_6$ alkenyl, and $(C{=}NH)N(R_{101})_2$ wherein each $R_{101}$ is independently selected from the group consisting of H, $C_1$-$C_6$ alkyl, and $C_2$-$C_6$ alkenyl;

$R_{203}$ is selected from the group consisting of $C_1$-$C_{20}$ alkyl and $C_2$-$C_{20}$ alkenyl;

$R_{204}$ is selected from the group consisting of H, $C_1$-$C_{20}$ alkyl, $C_2$-$C_{20}$ alkenyl, C(O)(O$C_1$-$C_{20}$ alkyl), C(O)(O$C_2$-$C_{20}$ alkenyl), C(O)(NH$C_1$-$C_{20}$ alkyl), and C(O)(NH$C_2$-$C_{20}$ alkenyl);

n1 is selected from 1, 2, 3, 4, 5, 6, 7, 8, 9, and 10.

In some embodiments, $R_{201}$ and $R_{202}$ are each independently selected from the group consisting of H and $CH_3$.

In some embodiments, $R_{201}$ and $R_{202}$ are each independently selected from the group consisting of $(C{=}NH)NH_2$ and $(C{=}NH)N(CH_3)_2$ In some embodiments, $R_{203}$ is selected from the group consisting of $C_1$-$C_{20}$ alkyl, $C_8$-$C_{18}$ alkyl, and $C_{12}$-$C_{16}$ alkyl.

In some embodiments, $R_{204}$ is selected from the group consisting of H, $C_1$-$C_{20}$ alkyl, $C_2$-$C_{20}$ alkenyl, C(O)(O$C_1$-$C_{20}$ alkyl), C(O)(O$C_2$-$C_{20}$ alkenyl), C(O)(NH$C_1$-$C_{20}$ alkyl), and C(O)(NH$C_2$-$C_{20}$ alkenyl); $C_8$-$C_{18}$ alkyl, $C_8$-$C_{18}$ alkenyl, C(O)(O$C_8$-$C_{18}$ alkyl), C(O)(O$C_8$-$C_{18}$ alkenyl), C(O)(NH$C_8$-$C_{18}$ alkyl), and C(O)(NH$C_8$-$C_{18}$ alkenyl); and $C_{12}$-$C_{16}$ alkyl, $C_{12}$-$C_{16}$ alkenyl, C(O)(O$C_{12}$-$C_{16}$ alkyl), C(O)(O$C_{12}$-$C_{16}$ alkenyl), C(O)(NH$C_{12}$-$C_{16}$ alkyl), and C(O)(NH$C_{12}$-$C_{16}$ alkenyl);

In some embodiments, n1 is selected from 1, 2, 3, 4, 5, 6, 7, 8, 9, and 10; n1 is selected from 1, 2, 3, 4, 5, and 6; n1 is selected from 2, 3, and 4.

In some embodiments, n1 is 3.

In some embodiments of the present disclosure, the encapsulation agent is a compound of Formula (EA-II):

(EA-II)

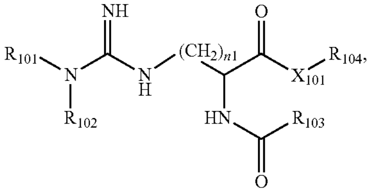

or salts or isomers thereof, wherein $X_{101}$ is a bond, NH, or O;

$R_{101}$ and $R_{102}$ are each independently selected from the group consisting of H, $C_1$-$C_6$ alkyl, and $C_2$-$C_6$ alkenyl;

$R_{103}$ and $R_{104}$ are each independently selected from the group consisting of $C_1$-$C_{20}$ alkyl and $C_2$-$C_{20}$ alkenyl; and n1 is selected from 1, 2, 3, 4, 5, 6, 7, 8, 9, and 10.

In some embodiments, $X_{101}$ is a bond.

In some embodiments, $X_{101}$ is NH.

In some embodiments, $X_{101}$ is O.

In some embodiments, $R_{101}$ and $R_{102}$ are each independently selected from the group consisting of H and $CH_3$.

In some embodiments, Rios is selected from the group consisting of $C_1$-$C_{20}$ alkyl, $C_8$-$C_{18}$ alkyl, and $C_{12}$-$C_{16}$ alkyl.

In some embodiments, $R_{104}$ is selected from the group consisting of $C_1$-$C_{20}$ alkyl, $C_8$-$C_{18}$ alkyl, and $C_{12}$-$C_{16}$ alkyl.

In some embodiments, n1 is selected from 1, 2, 3, 4, 5, 6, 7, 8, 9, and 10; n1 is selected from 1, 2, 3, 4, 5, and 6; n1 is selected from 2, 3, and 4.

In some embodiments, n1 is 3.

Exemplary encapsulation agents include, but are not limited to, ethyl lauroyl arginate, ethyl myristoyl arginate, ethyl palmitoyl arginate, ethyl cholesterol-arginate, ethyl oleic arginate, ethyl capric arginate, and ethyl carprylic arginate.

In certain embodiments, the encapsulation agent is ethyl lauroyl arginate, (ELA-1)

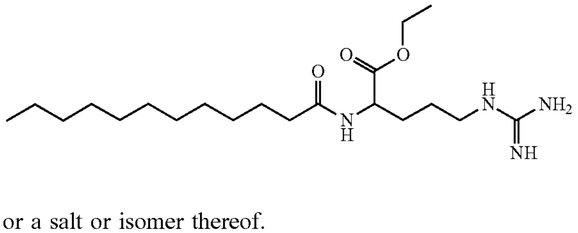

or a salt or isomer thereof.

In certain embodiments, the encapsulation agent is at least one compound selected from the group consisting of:

(EA-2)

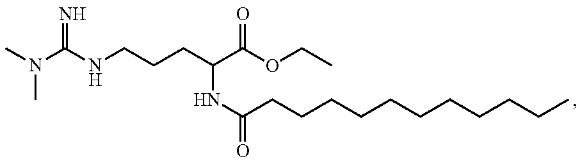, (EA-3)

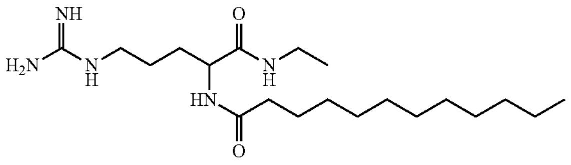, (EL-4)

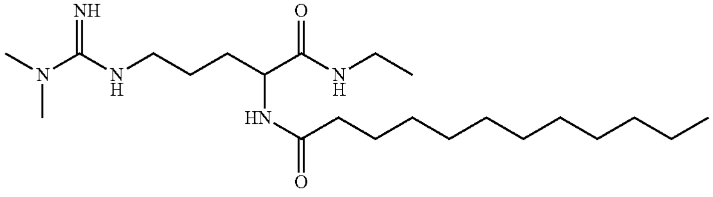, (EA-5)

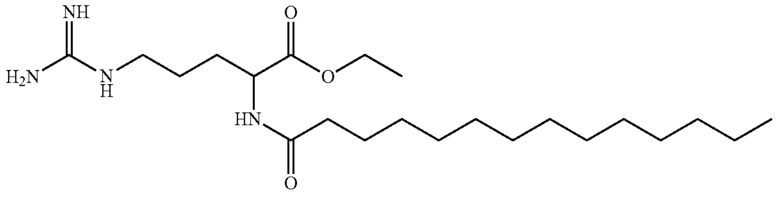, (EA-6)

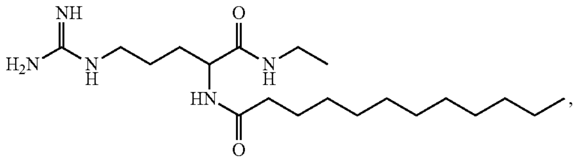, (EA-7)

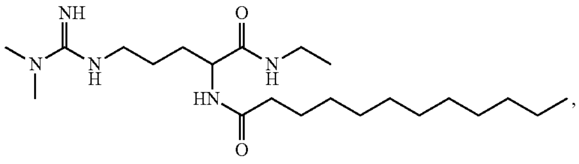, (EA-8)

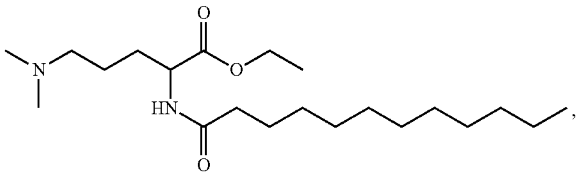, (EA-9)

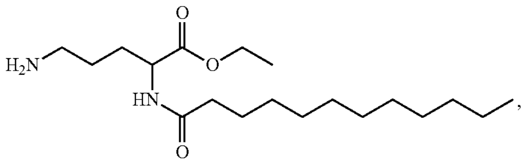, and (EA-10)

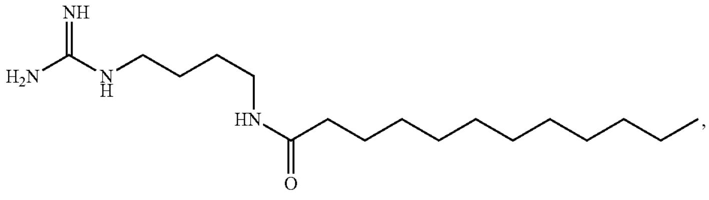, or salts and isomers thereof, such as, for example free bases, TFA salts, and/or HCl salts.

Phospholipids

Phospholipids may assemble into one or more lipid bilayers. In general, phospholipids comprise a phospholipid moiety and one or more fatty acid moieties.

A phospholipid moiety can be selected, for example, from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin.

A fatty acid moiety can be selected, for example, from the non-limiting group consisting of lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, and docosahexaenoic acid.

Particular phospholipids can facilitate fusion to a membrane. In some embodiments, a cationic phospholipid can interact with one or more negatively charged phospholipids of a membrane (e.g., a cellular or intracellular membrane). Fusion of a phospholipid to a membrane can allow one or more elements (e.g., a therapeutic agent) of a lipid-containing composition (e.g., LNPs) to pass through the membrane permitting, e.g., delivery of the one or more elements to a target tissue.

Non-natural phospholipid species including natural species with modifications and substitutions including branching, oxidation, cyclization, and alkynes are also contemplated. In some embodiments, a phospholipid can be functionalized with or cross-linked to one or more alkynes (e.g., an alkenyl group in which one or more double bonds is replaced with a triple bond). Under appropriate reaction conditions, an alkyne group can undergo a copper-catalyzed cycloaddition upon exposure to an azide. Such reactions can be useful in functionalizing a lipid bilayer of a nanoparticle composition to facilitate membrane permeation or cellular recognition or in conjugating a nanoparticle composition to a useful component such as a targeting or imaging moiety (e.g., a dye).

Phospholipids include, but are not limited to, glycerophospholipids such as phosphatidylcholines, phosphatidylethanolamines, phosphatidylserines, phosphatidylinositols, phosphatidy glycerols, and phosphatidic acids. Phospholipids also include phosphosphingolipid, such as sphingomyelin.

In some embodiments, a phospholipid useful or potentially useful in the present invention is an analog or variant of DSPC. In some embodiments, a phospholipid useful or potentially useful in the present invention is a compound of Formula (PL-I):

(PL-I)

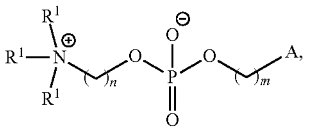

or a salt thereof, wherein:

each $R^1$ is independently optionally substituted alkyl; or optionally two $R^1$ are joined together with the intervening atoms to form optionally substituted monocyclic carbocyclyl or optionally substituted monocyclic heterocyclyl: or optionally three $R^1$ are joined together with the intervening atoms to form optionally substituted bicyclic carbocyclyl or optionally substitute bicyclic heterocyclyl;

n is 1, 2, 3, 4, 5, 6, 7, 8, 9, or 10;

m is 0, 1, 2, 3, 4, 5, 6, 7, 8, 9, or 10;

A is of the formula:

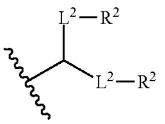

or

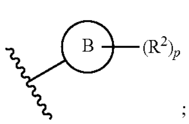

;

each instance of $L^2$ is independently a bond or optionally substituted $C_{1-6}$ alkylene, wherein one methylene unit of the optionally substituted $C_{1-6}$ alkylene is optionally replaced with —O—, —N($R^N$)—, —S—, —C(O)—, —C(O)N($R^N$)—, —$NR^N$C(O)—, —C(O)O—, —OC(O)—, —OC(O)O—, —OC(O)N($R^N$)—, —$NR^N$C(O)O—, or —$NR^N$C(O)N($R^N$)—;

each instance of $R^2$ is independently optionally substituted $C_{1-30}$ alkyl, optionally substituted $C_{1-30}$ alkenyl, or optionally substituted $C_{1-30}$ alkynyl: optionally wherein one or more methylene units of $R^2$ are independently replaced with optionally substituted carbocyclylene, optionally substituted heterocyclylene, optionally substituted arylene, optionally substituted heteroarylene, —N($R^N$)—, —O—, —S—, —C(O)—, —C(O)N($R^N$)—, —$NR^N$C(O)—, —$NR^N$C(O)N($R^N$)—, —C(O)O—, —OC(O)—, —OC(O)O—, —OC(O)N($R^N$)—, —$NR^N$C(O)O—, —C(O)S—, —SC(O)—, —C(=$NR^N$)—, —C(=$NR^N$)N($R^N$)—, —$NR^N$C(=$NR^N$)—, —$NR^N$C(=$NR^N$)N($R^N$)—, —C(S)—, —C(S)N($R^N$)—, —$NR^N$C(S)—, —$NR^N$C(S)N($R^N$)—, —S(O)—, —OS(O)—, —S(O)O—, —OS(O)O—, —$OS(O)_2$—, —$S(O)_2O$—, —$OS(O)_2O$—, —N($R^N$)S(O)—, —S(O)N($R^N$)—, —N($R^N$)S(O)N($R^N$)—, —OS(O)N($R^N$)—, —N($R^N$)S(O)O—, —$S(O)_2$—, —N($R^N$)$S(O)_2$—, —$S(O)_2$N($R^N$)—, —N($R^N$)$S(O)_2$N($R^N$)—, —$OS(O)_2$N($R^N$)—, or —N($R^N$)$S(O)_2O$—;

each instance of $R^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2;

provided that the compound is not of the formula:

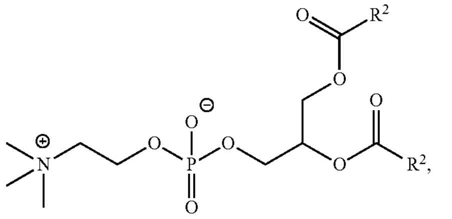

wherein each instance of $R^2$ is independently unsubstituted alkyl, unsubstituted alkenyl, or unsubstituted alkynyl.

In some embodiments, the phospholipids may be one or more of the phospholipids described in U.S. Application No. 62/520,530.

In some embodiments, the phospholipids may be selected from the non-limiting group consisting of 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), and sphingomyelin. In some embodiments, a LNP includes DSPC. In some embodiments, a LNP includes DOPE. In some embodiments, a LNP includes both DSPC and DOPE.

i) Phospholipid Head Modifications

In some embodiments, a phospholipid useful or potentially useful in the present invention comprises a modified phospholipid head (e.g., a modified choline group). In some embodiments, a phospholipid with a modified head is DSPC, or analog thereof, with a modified quaternary amine. In some embodiments, in embodiments of Formula (PL-I), at least one of $R^1$ is not methyl. In some embodiments, at least one of $R^1$ is not hydrogen or methyl. In some embodiments, the compound of Formula (PL-I) is one of the following formulae:

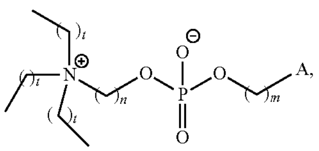

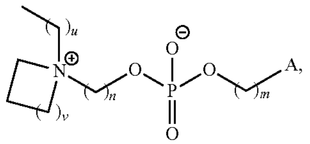

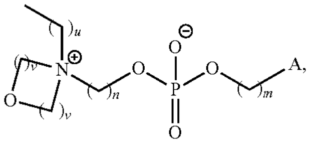

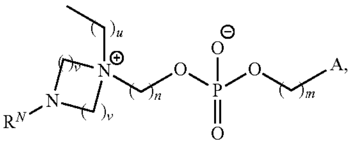

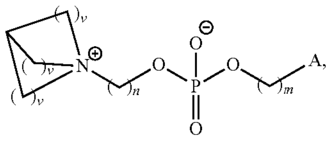

or a salt thereof, wherein:

each t is independently 1, 2, 3, 4, 5, 6, 7, 8, 9, or 10;

each u is independently 0, 1, 2, 3, 4, 5, 6, 7, 8, 9, or 10; and each v is independently 1, 2, or 3.

In some embodiments, a compound of Formula (PL-I) is of Formula (PL-I-a):

(PL-I-a)

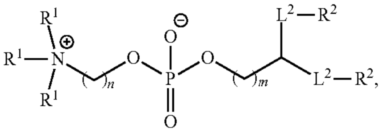

or a salt thereof.

In some embodiments, a phospholipid useful or potentially useful in the present invention comprises a cyclic moiety in place of the glyceride moiety. In some embodiments, a phospholipid useful in the present invention is DSPC, or analog thereof, with a cyclic moiety in place of the glyceride moiety. In some embodiments, the compound of Formula (PL-I) is of Formula (PL-I-b):

(PL-I-b)

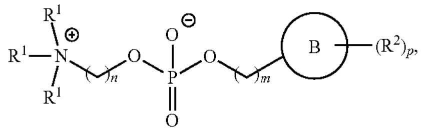

or a salt thereof.

ii) Phospholipid Tail Modifications

In some embodiments, a phospholipid useful or potentially useful in the present invention comprises a modified tail. In some embodiments, a phospholipid useful or potentially useful in the present invention is DSPC, or analog thereof, with a modified tail. As described herein, a "modified tail" may be a tail with shorter or longer aliphatic chains, aliphatic chains with branching introduced, aliphatic chains with substituents introduced, aliphatic chains wherein one or more methylenes are replaced by cyclic or heteroatom groups, or any combination thereof. In some embodiments, the compound of (PL-I) is of Formula (PL-I-a), or a salt thereof, wherein at least one instance of $R^2$ is each instance of $R^2$ is optionally substituted $C_{1-30}$ alkyl, wherein one or more methylene units of $R^2$ are independently replaced with optionally substituted carbocyclylene, optionally substituted heterocyclylene, optionally substituted arylene, optionally substituted heteroarylene, $—N(R^N)—$, $—O—$, $—S—$, $—C(O)—$, $—C(O)N(R^N)—$, $—NR^NC(O)—$, $—NR^NC(O)N(R^N)—$, $—C(O)O—$, $—OC(O)—$, $—OC(O)O—$, $—OC(O)N(R^N)—$, $—NR^NC(O)O—$, $—C(O)S—$, $—SC(O)—$, $—C(=NR^N)—$, $—C(=NR^N)N(R^N)—$, $—NR^NC(=NR^N)—$, $—NR^NC(=NR^N)N(R^N)—$, $—C(S)—$, $—C(S)N(R^N)—$, $—NR^NC(S)—$, $—NR^NC(S)N(R^N)—$, $—S(O)—$, $—OS(O)—$, $—S(O)O—$, $—OS(O)O—$, $—OS(O)_2—$, $—S(O)_2O—$, $—OS(O)_2O—$, $—N(R^N)S(O)—$, $—S(O)N(R^N)—$, $—N(R^N)S(O)N(R^N)—$, $—OS(O)N(R^N)—$, $—N(R^N)S(O)O—$, $—S(O)_2—$, $—N(R^N)S(O)_2—$, $—S(O)_2N(R^N)—$, $—N(R^N)S(O)_2N(R^N)—$, $—OS(O)_2N(R^N)—$, or $—N(R^N)S(O)_2O—$.

In some embodiments, the compound of Formula (PL-I) is of Formula (PL-I-c):

(PL-I-c)

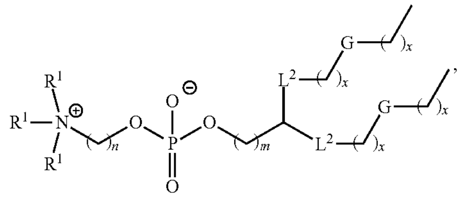

or a salt thereof, wherein:

each x is independently an integer between 0-30, inclusive; and each instance is G is independently selected from the group consisting of optionally substituted carbocyclylene, optionally substituted heterocyclylene, optionally substituted arylene, optionally substituted heteroarylene, $—N(R^N)—$, $—O—$, $—S—$, $—C(O)—$, $—C(O)N(R^N)—$, $—NR^NC(O)—$, $—NR^NC(O)N(R^N)—$, $—C(O)O—$, $—OC(O)—$, $—OC(O)O—$, $—OC(O)N(R^N)—$, $—NR^NC(O)O—$, $—C(O)S—$, $—SC(O)—$, $—C(=NR^N)—$, $—C(=NR^N)N(R^N)—$, $—NR^NC(=NR^N)—$, $—NR^NC(=NR^N)N(R^N)—$, $—C(S)—$, $—C(S)N(R^N)—$, $—NR^NC(S)—$, $—NR^NC$ (S)N($R^N$)—, —S(O)—, —OS(O)—, —S(O)O—, —OS(O)O—, —OS$(O)_2$—, —S$(O)_2$O—, —OS$(O)_2$O—, —N($R^N$)S(O)—, —S(O)N($R^N$)—, —N($R^N$)S(O)N($R^N$)—, —OS(O)N($R^N$)—, —N($R^N$)S(O)O—, —S$(O)_2$—, —N($R^N$)S$(O)_2$—, —S$(O)_2$N($R^N$)—, —N($R^N$)S$(O)_2$N($R^N$)—, —OS$(O)_2$N($R^N$)—, or —N($R^N$)S$(O)_2$O—. Each possibility represents a separate embodiment of the present invention.

In some embodiments, a phospholipid useful or potentially useful in the present invention comprises a modified phosphocholine moiety, wherein the alkyl chain linking the quaternary amine to the phosphoryl group is not ethylene (e.g., n is not 2). Therefore, in some embodiments, a phospholipid useful or potentially useful in the present invention is a compound of Formula (PL-I), wherein n is 1, 3, 4, 5, 6, 7, 8, 9, or 10. In some embodiments, a compound of Formula (PL-I) is of one of the following formulae:

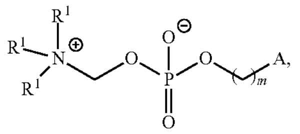

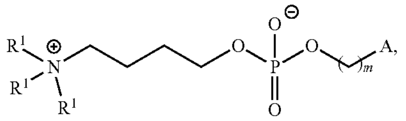

or a salt thereof.

Alternative Lipids

In some embodiments, an alternative lipid is used in place of a phospholipid of the present disclosure. Non-limiting examples of such alternative lipids include the following:

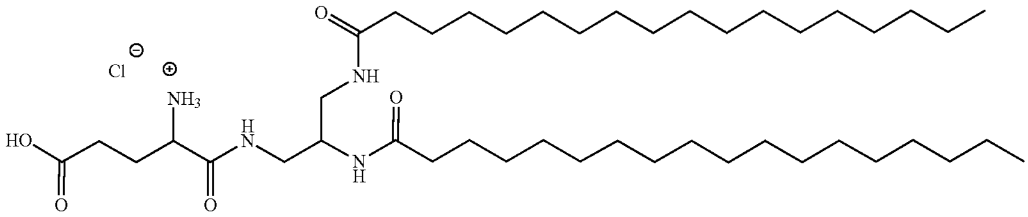

,

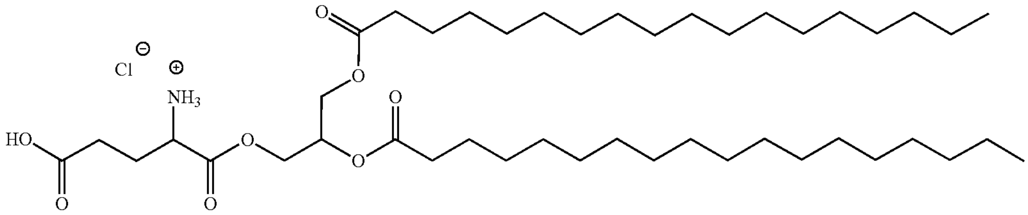

,

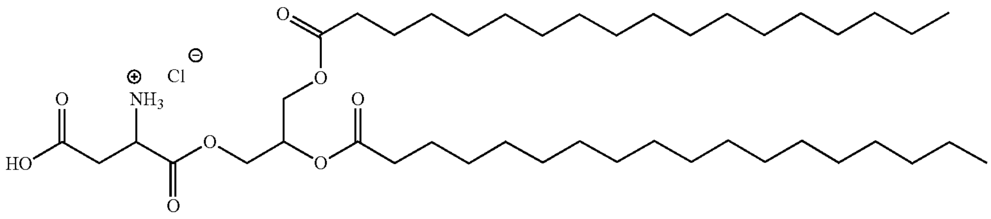

,

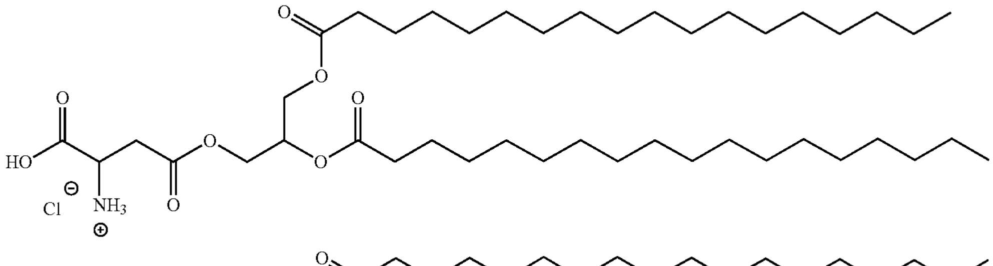

,

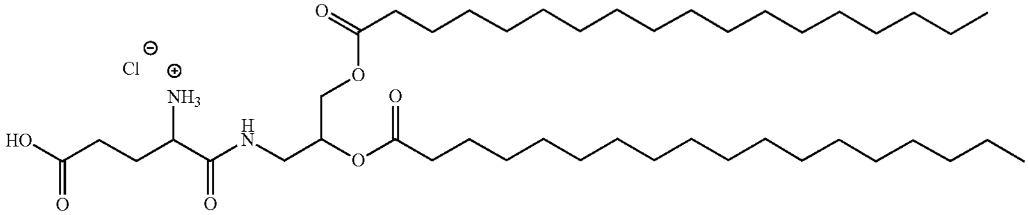

,

-continued

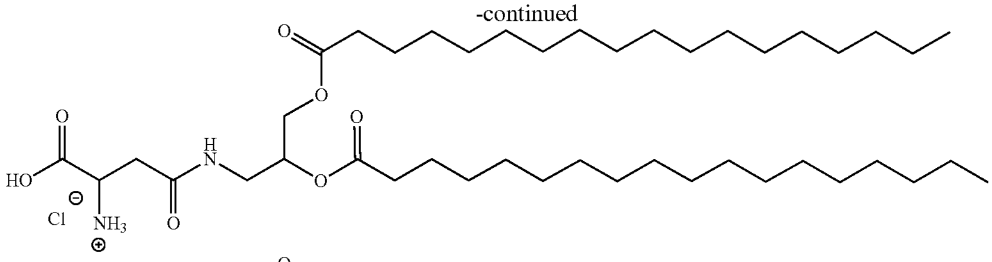

, and

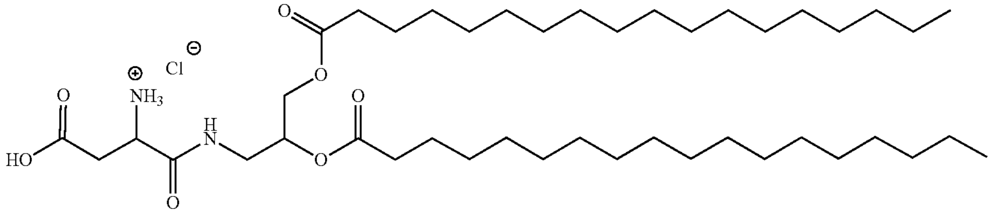

.

Adjuvants

In some embodiments, a LNP that includes one or more lipids described herein may further include one or more adjuvants, e.g., Glucopyranosyl Lipid Adjuvant (GLA), CpG oligodeoxynucleotides (e.g., Class A or B), poly (I:C), aluminum hydroxide, and Pam3CSK4.

Therapeutic Agents

Lipid nanoparticles may include one or more therapeutics and/or prophylactics, such as a nucleic acid. The disclosure features methods of delivering a therapeutic and/or prophylactic, such as a nucleic acid to a mammalian cell or organ, producing a polypeptide of interest in a mammalian cell, and treating a disease or disorder in a mammal in need thereof comprising administering to a mammal and/or contacting a mammalian cell with a LNP including a therapeutic and/or prophylactic, such as a nucleic acid.

Therapeutics and/or prophylactics include biologically active substances and are alternately referred to as "active agents". A therapeutic and/or prophylactic may be a substance that, once delivered to a cell or organ, brings about a desirable change in the cell, organ, or other bodily tissue or system. Such species may be useful in the treatment of one or more diseases, disorders, or conditions. In some embodiments, a therapeutic and/or prophylactic is a small molecule drug useful in the treatment of a particular disease, disorder, or condition. Examples of drugs useful in the lipid nanoparticles include, but are not limited to, antineoplastic agents (e.g., vincristine, doxorubicin, mitoxantrone, camptothecin, cisplatin, bleomycin, cyclophosphamide, methotrexate, and streptozotocin), antitumor agents (e.g., actinomycin D, vincristine, vinblastine, cytosine arabinoside, anthracyclines, alkylating agents, platinum compounds, antimetabolites, and nucleoside analogs, such as methotrexate and purine and pyrimidine analogs), anti-infective agents, local anesthetics (e.g., dibucaine and chlorpromazine), beta-adrenergic blockers (e.g., propranolol, timolol, and labetalol), antihypertensive agents (e.g., clonidine and hydralazine), anti-depressants (e.g., imipramine, amitriptyline, and doxepin), anti-conversants (e.g., phenytoin), antihistamines (e.g., diphenhydramine, chlorpheniramine, and promethazine), antibiotic/antibacterial agents (e.g., gentamycin, ciprofloxacin, and cefoxitin), antifungal agents (e.g., miconazole, terconazole, econazole, isoconazole, butaconazole, clotrimazole, itraconazole, nystatin, naftifine, and amphotericin B), antiparasitic agents, hormones, hormone antagonists, immunomodulators, neurotransmitter antagonists, antiglaucoma agents, vitamins, narcotics, and imaging agents.

In some embodiments, a therapeutic and/or prophylactic is a cytotoxin, a radioactive ion, a chemotherapeutic, a vaccine, a compound that elicits an immune response, and/or another therapeutic and/or prophylactic. A cytotoxin or cytotoxic agent includes any agent that may be detrimental to cells. Examples include, but are not limited to, taxol, cytochalasin B, gramicidin D, ethidium bromide, emetine, mitomycin, etoposide, teniposide, vincristine, vinblastine, colchicine, doxorubicin, daunorubicin, dihydroxyanthracinedione, mitoxantrone, mithramycin, actinomycin D. 1-dehydrotestosterone, glucocorticoids, procaine, teracaine, lidocaine, propranolol, puromycin, maytansinoids, e.g., maytansinol, rachelmycin (CC-1065), and analogs or homologs thereof. Radioactive ions include, but are not limited to iodine (e.g., iodine 125 or iodine 131), strontium 89, phosphorous, palladium, cesium, iridium, phosphate, cobalt, yttrium 90, samarium 153, and praseodymium. Vaccines include compounds and preparations that are capable of providing immunity against one or more conditions related to infectious diseases such as influenza, measles, human papillomavirus (HPV), rabies, meningitis, whooping cough, tetanus, plague, hepatitis, and tuberculosis and can include mRNAs encoding infectious disease derived antigens and/or epitopes. Vaccines also include compounds and preparations that direct an immune response against cancer cells and can include mRNAs encoding tumor cell derived antigens, epitopes, and/or neoepitopes. Compounds eliciting immune responses may include, but are not limited to, vaccines, corticosteroids (e.g., dexamethasone), and other species.

In some embodiments, a therapeutic and/or prophylactic is a protein. Therapeutic proteins useful in the nanoparticles in the disclosure include, but are not limited to, gentamycin, amikacin, insulin, erythropoietin (EPO), granulocyte-colony stimulating factor (G-CSF), granulocyte-macrophage colony stimulating factor (GM-CSF), Factor VIR, luteinizing hormone-releasing hormone (LHRH) analogs, interferons, heparin, Hepatitis B surface antigen, typhoid vaccine, and cholera vaccine. In some embodiments, a vaccine and/or a compound capable of eliciting an immune response is administered intramuscularly via a composition including a compound according to Formula (IL-I), (IL-IA), (IL-IB), (IL-II), (IL-IIa), (IL-IIb), (IL-IIc), (IL-IId), (IL-IIe), (IL-IIf), (IL-IIg), (IL-III), (IL-IIIa1), (IL-IIIa2), (IL-IIIa3), (IL-IIIa4), (IL-IIIa5), (IL-IIIa6), (IL-IIIa7), or (IL-IIIa8) (e.g., Compound 3, 18, 20, 26, or 29). Other therapeutics and/or prophylactics include, but are not limited to, antimetabolites (e.g., methotrexate, 6-mercaptopurine, 6-thioguanine, cytarabine, 5-fluorouracil dacarbazine), alkylating agents (e.g., mechlorethamine, thiotepa chlorambucil, rachelmycin (CC-1065), melphalan, carmustine (BSNU), lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids).

Polynucleotides and Nucleic Acids

In some embodiments, a therapeutic agent is a polynucleotide or nucleic acid (e.g., ribonucleic acid or deoxyribonucleic acid). The term "polynucleotide", in its broadest sense, includes any compound and/or substance that is or can be incorporated into an oligonucleotide chain. Exemplary polynucleotides for use in accordance with the present disclosure include, but are not limited to, one or more of deoxyribonucleic acid (DNA), ribonucleic acid (RNA) including messenger RNA (mRNA), hybrids thereof, RNAi-inducing agents, RNAi agents, siRNAs, shRNAs, miRNAs, antisense RNAs, ribozymes, catalytic DNA, RNAs that induce triple helix formation, aptamers, vectors, etc. In some embodiments, a therapeutic and/or prophylactic is an RNA. RNAs useful in the compositions and methods described herein can be selected from the group consisting of, but are not limited to, shortmers, antagomirs, antisense, ribozymes, small interfering RNA (siRNA), asymmetrical interfering RNA (aiRNA), microRNA (miRNA), Dicer-substrate RNA (dsRNA), small hairpin RNA (shRNA), transfer RNA (tRNA), messenger RNA (mRNA), and mixtures thereof. In some embodiments, the RNA is an mRNA.

In some embodiments, a therapeutic and/or prophylactic is an mRNA. An mRNA may encode any polypeptide of interest, including any naturally or non-naturally occurring or otherwise modified polypeptide. A polypeptide encoded by an mRNA may be of any size and my have any secondary structure or activity. In some embodiments, a polypeptide encoded by an mRNA may have a therapeutic effect when expressed in a cell.

In some embodiments, a therapeutic and/or prophylactic is an siRNA. An siRNA may be capable of selectively knocking down or down regulating expression of a gene of interest. In some embodiments, an siRNA could be selected to silence a gene associated with a particular disease, disorder, or condition upon administration to a subject in need thereof of a LNP including the siRNA. An siRNA may comprise a sequence that is complementary to an mRNA sequence that encodes a gene or protein of interest. In some embodiments, the siRNA may be an immunomodulatory siRNA.

In some embodiments, a therapeutic and/or prophylactic is an shRNA or a vector or plasmid encoding the same. An shRNA may be produced inside a target cell upon delivery of an appropriate construct to the nucleus. Constructs and mechanisms relating to shRNA are well known in the relevant arts.

Nucleic acids and polynucleotides useful in the disclosure typically include a first region of linked nucleosides encoding a polypeptide of interest (e.g., a coding region), a first flanking region located at the 5"-terminus of the first region (e.g., a 5'-UTR), a second flanking region located at the 3'-terminus of the first region (e.g., a 3'-UTR) at least one 5'-cap region, and a 3'-stabilizing region. In some embodiments, a nucleic acid or polynucleotide further includes a poly-A region or a Kozak sequence (e.g., in the 5'-UTR). In some cases, polynucleotides may contain one or more intronic nucleotide sequences capable of being excised from the polynucleotide. In some embodiments, a polynucleotide or nucleic acid (e.g., an mRNA) may include a 5' cap structure, a chain terminating nucleotide, a stem loop, a poly A sequence, and/or a polyadenylation signal. Any one of the regions of a nucleic acid may include one or more alternative components (e.g., an alternative nucleoside). In some embodiments, the 3'-stabilizing region may contain an alternative nucleoside such as an L-nucleoside, an inverted thymidine, or a 2'-O-methyl nucleoside and/or the coding region, 5-UTR, 3'-UTR, or cap region may include an alternative nucleoside such as a 5-substituted uridine (e.g., 5-methoxyuridine), a 1-substituted pseudouridine (e.g., 1-methyl-pseudouridine), and/or a 5-substituted cytidine (e.g., 5-methyl-cytidine).

Generally, the shortest length of a polynucleotide can be the length of the polynucleotide sequence that is sufficient to encode for a dipeptide. In another embodiment, the length of the polynucleotide sequence is sufficient to encode for a tripeptide. In another embodiment, the length of the polynucleotide sequence is sufficient to encode for a tetrapeptide. In another embodiment, the length of the polynucleotide sequence is sufficient to encode for a pentapeptide. In another embodiment, the length of the polynucleotide sequence is sufficient to encode for a hexapeptide. In another embodiment, the length of the polynucleotide sequence is sufficient to encode for a heptapeptide. In another embodiment, the length of the polynucleotide sequence is sufficient to encode for an octapeptide. In another embodiment, the length of the polynucleotide sequence is sufficient to encode for a nonapeptide. In another embodiment, the length of the polynucleotide sequence is sufficient to encode for a decapeptide.

Examples of dipeptides that the alternative polynucleotide sequences can encode for include, but are not limited to, carnosine and anserine.

In some cases, a polynucleotide is greater than 30 nucleotides in length. In another embodiment, the polynucleotide molecule is greater than 35 nucleotides in length. In another embodiment, the length is at least 40 nucleotides. In another embodiment, the length is at least 45 nucleotides. In another embodiment, the length is at least 50 nucleotides. In another embodiment, the length is at least 55 nucleotides. In another embodiment, the length is at least 60 nucleotides. In another embodiment, the length is at least 80 nucleotides. In another embodiments, the length is at least 90 nucleotides. In another embodiment, the length is at least 100 nucleotides. In another embodiment, the length is at least 120 nucleotides. In another embodiment, the length is at least 140 nucleotides. In another embodiment, the length is at least 160 nucleotides. In another embodiment, the length is at least 180 nucleotides. In another embodiment, the length is at least 200 nucleotides. In another embodiment, the length is at least 250 nucleotides. In another embodiment, the length is at least 300 nucleotides. In another embodiment, the length is at least 350 nucleotides. In another embodiment, the length is at least 400 nucleotides. In another embodiment, the length is at least 450 nucleotides. In another embodiment, the length is at least 500 nucleotides. In another embodiment, the length is at least 600 nucleotides. In another embodiment, the length is at least 700 nucleotides. In another embodiment, the length is at least 800 nucleotides. In another embodiment, the length is at least 900 nucleotides. In another embodiment, the length is at least 1000 nucleotides. In another embodiment, the length is at least 1100 nucleotides. In another embodiment, the length is at least 1200 nucleotides. In another embodiment, the length is at least 1300 nucleotides. In another embodiment, the length is at least 1400 nucleotides. In another embodiment, the length is at least 1500 nucleotides. In another embodiment, the length is at least 1600 nucleotides. In another embodiment, the length is at least 1800 nucleotides. In another embodiment, the length is at least 2000 nucleotides. In another embodiment, the length is at least 2500 nucleotides. In another embodiment, the length is at least 3000 nucleotides. In another embodiment, the length is at least 4000 nucleotides. In another embodiment, the length is at least 5000 nucleotides, or greater than 5000 nucleotides.

Nucleic acids and polynucleotides may include one or more naturally occurring components, including any of the canonical nucleotides A (adenosine), G (guanosine), C (cytosine), U (uridine), or T (thymidine). In some embodiments, all or substantially all of the nucleotides comprising (a) the 5'-UTR, (b) the open reading frame (ORF), (c) the 3'-UTR, (d) the poly A tail, and any combination of (a, b, c, or d above) comprise naturally occurring canonical nucleotides A (adenosine), G (guanosine), C (cytosine), U (uridine), or T (thymidine).

Nucleic acids and polynucleotides may include one or more alternative components, as described herein, which impart useful properties including increased stability and/or the lack of a substantial induction of the innate immune response of a cell into which the polynucleotide is introduced. In some embodiments, an alternative polynucleotide or nucleic acid exhibits reduced degradation in a cell into which the polynucleotide or nucleic acid is introduced, relative to a corresponding unaltered polynucleotide or nucleic acid. These alternative species may enhance the efficiency of protein production, intracellular retention of the polynucleotides, and/or viability of contacted cells, as well as possess reduced immunogenicity.

Polynucleotides and nucleic acids may be naturally or non-naturally occurring. Polynucleotides and nucleic acids may include one or more modified (e.g., altered or alternative) nucleobases, nucleosides, nucleotides, or combinations thereof. The nucleic acids and polynucleotides useful in a LNP can include any useful modification or alteration, such as to the nucleobase, the sugar, or the internucleoside linkage (e.g., to a linking phosphate, to a phosphodiester linkage, to the phosphodiester backbone). In some embodiments, alterations (e.g., one or more alterations) are present in each of the nucleobase, the sugar, and the internucleoside linkage. Alterations according to the present disclosure may be alterations of ribonucleic acids (RNAs) to deoxyribonucleic acids (DNAs), e.g., the substitution of the 2'-OH of the ribofuranosyl ring to 2'-H, threose nucleic acids (TNAs), glycol nucleic acids (GNAs), peptide nucleic acids (PNAs), locked nucleic acids (LNAs), or hybrids thereof. Additional alterations are described herein.

Polynucleotides and nucleic acids may or may not be uniformly altered along the entire length of the molecule. In some embodiments, one or more or all types of nucleotide (e.g., purine or pyrimidine, or any one or more or all of A, G, U. C) may or may not be uniformly altered in a polynucleotide or nucleic acid, or in a given predetermined sequence region thereof. In some instances, all nucleotides X in a polynucleotide (or in a given sequence region thereof) are altered, wherein X may be any one of nucleotides A, G, U, C, or any one of the combinations A+G, A+U, A+C, G+U, G+C, U+C, A+G+U, A+G+C, G+U+C, or A+G+U+C.

Different sugar alterations and/or internucleoside linkages (e.g., backbone structures) may exist at various positions in a polynucleotide. One of ordinary skill in the art will appreciate that the nucleotide analogs or other alteration(s) may be located at any position(s) of a polynucleotide such that the function of the polynucleotide is not substantially decreased. An alteration may also be a 5'- or 3'-terminal alteration. In some embodiments, the polynucleotide includes an alteration at the 3'-terminus. The polynucleotide may contain from about 1% to about 100% alternative nucleotides (either in relation to overall nucleotide content, or in relation to one or more types of nucleotide, i.e., any one or more of A, G, U, or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100% from 90% to 95%, from 90% to 100%, and from 95% to 100%). It will be understood that any remaining percentage is accounted for by the presence of a canonical nucleotide (e.g., A, G, U, or C).

Polynucleotides may contain at a minimum zero and at a maximum 100% alternative nucleotides, or any intervening percentages, such as at least 5% alternative nucleotides, at least 10% alternative nucleotides, at least 25% alternative nucleotides, at least 50% alternative nucleotides, at least 80% alternative nucleotides, or at least 90% alternative nucleotides. In some embodiments, polynucleotides may contain an alternative pyrimidine such as an alternative uracil or cytosine. In some embodiments, at least 5%, at least 10%, at least 25%, at least 50%, at least 80%, at least 90% or 100% of the uracil in a polynucleotide is replaced with an alternative uracil (e.g., a 5-substituted uracil). The alternative uracil can be replaced by a compound having a single unique structure, or can be replaced by a plurality of compounds having different structures (e.g., 2, 3, 4 or more unique structures). In some instances, at least 5%, at least 10%, at least 25%, at least 50%, at least 80%, at least 90% or 100% of the cytosine in the polynucleotide is replaced with an alternative cytosine (e.g., a 5-substituted cytosine). The alternative cytosine can be replaced by a compound having a single unique structure, or can be replaced by a plurality of compounds having different structures (e.g., 2, 3, 4 or more unique structures).

In some embodiments, nucleic acids do not substantially induce an innate immune response of a cell into which the polynucleotide (e.g., mRNA) is introduced. Features of an induced innate immune response include 1) increased expression of pro-inflammatory cytokines, 2) activation of intracellular PRRs (RIG-I, MDA5, etc.), and/or 3) termination or reduction in protein translation.

The nucleic acids can optionally include other agents (e.g., RNAi-inducing agents, RNAi agents, siRNAs, shRNAs, miRNAs, antisense RNAs, ribozymes, catalytic DNA, tRNA, RNAs that induce triple helix formation, aptamers, vectors). In some embodiments, the nucleic acids may include one or more messenger RNAs (mRNAs) having one or more alternative nucleoside or nucleotides (i.e., alternative mRNA molecules).

In some embodiments, a nucleic acid (e.g., mRNA) molecule, formula, composition or method associated therewith comprises one or more polynucleotides comprising features as described in WO2002/098443, WO2003/051401, WO2008/052770, WO2009127230, WO2006122828, WO2008/083949, WO2010088927, WO2010/037539, WO2004/004743, WO2005/016376, WO2006/024518, WO2007/095976, WO2008/014979, WO2008/077592, WO2009/030481, WO2009/095226, WO2011069586, WO2011026641, WO2011/144358, WO2012019780, WO2012013326, WO2012089338, WO2012113513, WO2012116811, WO2012116810, WO2013113502, WO2013113501, WO2013113736, WO2013143698, WO2013143699, WO2013143700, WO2013/120626, WO2013120627, WO2013120628, WO2013120629, WO2013174409, WO2014127917, WO2015/024669, WO2015/024668, WO2015/024667, WO2015/024665, WO2015/024666, WO2015/024664, WO2015101415, WO2015101414, WO2015024667, WO2015062738, WO2015101416, all of which are incorporated by reference herein.

Nucleobase Alternatives

The alternative nucleosides and nucleotides can include an alternative nucleobase. A nucleobase of a nucleic acid is an organic base such as a purine or pyrimidine or a derivative thereof. A nucleobase may be a canonical base (e.g., adenine, guanine, uracil, thymine, and cytosine). These nucleobases can be altered or wholly replaced to provide polynucleotide molecules having enhanced properties, e.g., increased stability such as resistance to nucleases. Non-canonical or modified bases may include, for example, one or more substitutions or modifications including, but not limited to, alkyl, aryl, halo, oxo, hydroxyl, alkyloxy, and/or thio substitutions: one or more fused or open rings: oxidation; and/or reduction.

Alternative nucleotide base pairing encompasses not only the standard adenine-thymine, adenine-uracil, or guanine-cytosine base pairs, but also base pairs formed between nucleotides and/or alternative nucleotides including non-standard or alternative bases, wherein the arrangement of hydrogen bond donors and hydrogen bond acceptors permits hydrogen bonding between a non-standard base and a standard base or between two complementary non-standard base structures. One example of such non-standard base pairing is the base pairing between the alternative nucleotide inosine and adenine, cytosine, or uracil.

In some embodiments, the nucleobase is an alternative uracil. Exemplary nucleobases and nucleosides having an alternative uracil include, but are not limited to, pseudouridine (ψ), pyridin-4-one ribonucleoside, 5-aza-uracil, 6-aza-uracil, 2-thio-5-aza-uracil, 2-thio-uracil ($s^2U$), 4-thio-uracil ($s^4U$), 4-thio-pseudouridine, 2-thio-pseudouridine, 5-hydroxy-uracil ($ho^5U$), 5-aminoallyl-uracil, 5-halo-uracil (e.g., 5-iodo-uracil or 5-bromo-uracil), 3-methyl-uracil ($m^3U$), 5-methoxy-uracil ($mo^5U$), uracil 5-oxyacetic acid ($cmo^5U$), uracil 5-oxyacetic acid methyl ester ($mcmo^5U$), 5-carboxymethyl-uracil ($cm^5U$), 1-carboxymethyl-pseudouridine, 5-carboxyhydroxymethyl-uracil ($chm^5U$), 5-carboxy hydroxymethyl-uracil methyl ester ($mchm^5U$), 5-methoxy-carbonylmethyl-uracil ($mcm^5U$), 5-methoxy carbonylmethyl-2-thio-uracil ($mcm^5s^2U$), 5-aminomethyl-2-thio-uracil ($nm^5s^2U$), 5-methylaminomethyl-uracil ($mnm^3U$), 5-methylaminomethyl-2-thio-uracil ($mnm^5s^2U$), 5-methylaminomethyl-2-seleno-uracil ($mnm^3se^2U$), 5-carbamoylmethyl-uracil ($ncm^5U$), 5-carboxymethylaminomethyl-uracil ($cmnm^5U$), 5-carboxy methylaminomethyl-2-thio-uracil ($cmnm^5s^2U$), 5-propynyl-uracil, 1-propynyl-pseudouracil, 5-taurinomethyl-uracil ($\tau m^5U$), 1-taurinomethyl-pseudouridine, 5-taurinomethyl-2-thio-uracil ($\tau m^5s^2U$), 1-taurinomethyl-4-thio-pseudouridine, 5-methyl-uracil ($m^5U$, i.e., having the nucleobase deoxythymine), 1-methyl-pseudouridine ($m^1\psi$), 5-methyl-2-thio-uracil ($m^5s^2U$), 1-methyl-4-thio-pseudouridine ($m^1s^4\psi$), 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydrouracil (D), dihydropseudouridine, 5,6-dihydrouracil, 5-methyl-dihydrouracil ($m^5D$), 2-thio-dihydrouracil, 2-thio-dihydropseudouridine, 2-methoxy-uracil, 2-methoxy-4-thio-uracil. 4-methoxy-pseudouridine, 4-methoxy-2-thio-pseudouridine, N1-methyl-pseudouridine, 3-(3-amino-3-carboxypropyl) uracil ($acp^3U$), 1-methyl-3-(3-amino-3-carboxypropyl) pseudouridine ($acp^3\psi$). 5-(isopentenylaminomethyl) uracil ($inm^5U$), 5-(isopentenylaminomethyl)-2-thio-uracil ($inm^5s^2U$), 5,2'-O-dimethyl-uridine ($m^5Um$), 2-thio-2'-O_methyl-uridine ($s^2Um$), 5-methoxy carbonylmethyl-2'-O-methyl-uridine ($mcm^5Um$), 5-carbamoylmethyl-2'-O-methyl-uridine ($ncm^5Um$), 5-carboxymethylaminomethyl-2'-O-methyl-uridine ($cmnm^5Um$), 3,2'-O-dimethyl-uridine ($m^3Um$), and 5-(isopentenylaminomethyl)-2'-O-methyl-uridine ($inm^5Um$), 1-thio-uracil, deoxythymidine, 5-(2-carbomethoxyvinyl)-uracil, 5-(carbamoylhydroxy methyl)-uracil, 5-carbamoylmethyl-2-thio-uracil, 5-carboxymethyl-2-thio-uracil, 5-cyanomethyl-uracil, 5-methoxy-2-thio-uracil, and 5-[3-(1-E-propenylamino)]uracil.

In some embodiments, the nucleobase is an alternative cytosine. Exemplary nucleobases and nucleosides having an alternative cytosine include, but are not limited to, 5-aza-cytosine. 6-aza-cytosine, pseudoisocytidine, 3-methyl-cytosine (m3C), N4-acetyl-cytosine (ac4C), 5-formyl-cytosine (f5C), N4-methyl-cytosine (m4C), 5-methyl-cytosine (m5C), 5-halo-cytosine (e.g., 5-iodo-cytosine), 5-hydroxymethyl-cytosine (hm5C), 1-methyl-pseudoisocytidine, pyrrolo-cytosine, pyrrolo-pseudoisocytidine, 2-thio-cytosine (s2C), 2-thio-5-methyl-cytosine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytosine. 2-methoxy-5-methyl-cytosine, 4-methoxy-pseudoisocytidine, 4-methoxy-1-methyl-pseudoisocytidine, lysidine (k2C), 5,2'-O-dimethyl-cytidine (m5Cm), N4-acetyl-2'-O-methyl-cytidine (ac4Cm), N4,2'-O-dimethyl-cytidine (m4Cm), 5-formyl-2'-O-methyl-cytidine (f5Cm), N4,N4,2'-O-trimethyl-cytidine (m42Cm), 1-thio-cytosine, 5-hydroxy-cytosine, 5-(3-azidopropyl)-cytosine, and 5-(2-azidoethyl)-cytosine.

In some embodiments, the nucleobase is an alternative adenine. Exemplary nucleobases and nucleosides having an alternative adenine include, but are not limited to, 2-amino-purine, 2,6-diaminopurine, 2-amino-6-halo-purine (e.g., 2-amino-6-chloro-purine), 6-halo-purine (e.g., 6-chloro-purine), 2-amino-6-methyl-purine, 8-azido-adenine, 7-deaza-adenine, 7-deaza-8-aza-adenine, 7-deaza-2-amino-purine, 7-deaza-8-aza-2-amino-purine, 7-deaza-2,6-diaminopurine, 7-deaza-8-aza-2,6-diaminopurine, 1-methyl-adenine (m1A), 2-methyl-adenine (m2A), N6-methyl-adenine (m6A), 2-methylthio-N6-methyl-adenine (ms2m6A), N6-isopentenyl-adenine (16A), 2-methylthio-N6-isopentenyl-adenine (ms216A), N6-(cis-hydroxyisopentenyl)adenine (io6A), 2-methylthio-N6-(cis-hydroxyisopentenyl)adenine (ms2106A), N6-glycinylcarbamoyl-adenine (g6A), N6-threonylcarbamoyl-adenine (16A), N6-methyl-N6-threonylcarbamoyl-adenine (m6t6A), 2-methylthio-N6-threonylcarbamoyl-adenine (ms2g6A), N6,N6-dimethyl-adenine (m62A), N6-hydroxynorvalylcarbamoyl-adenine (hn6A), 2-methylthio-N6-hydroxynorvalylcarbamoyl-adenine (ms2hn6A), N6-acetyl-adenine (ac6A), 7-methyl-adenine, 2-methylthio-adenine, 2-methoxy-adenine, N6,2'-O-dimethyl-adenosine (m6Am), N6,N6,2'-O-trimethyl-adenosine (m62Am), 1,2'-O-dimethyl-adenosine (m1Am), 2-amino-N6-methyl-purine, 1-thio-adenine, 8-azido-adenine, N6-(19-amino-pentaoxanonadecyl)-adenine, 2,8-dimethyl-adenine, N6-formyl-adenine, and N6-hydroxymethyl-adenine.

In some embodiments, the nucleobase is an alternative guanine. Exemplary nucleobases and nucleosides having an alternative guanine include, but are not limited to, inosine (I), 1-methyl-inosine (m1I), wyosine (imG), methylwyosine (mimG), 4-demethyl-wyosine (imG-14), isowyosine (imG2), wybutosine (yW), peroxywybutosine (o2yW), hydroxywybutosine (OHyW), undermodified hydroxywybutosine (OHyW*), 7-deaza-guanine, queuosine (Q), epoxy queuosine (oQ), galactosyl-queuosine (galQ), mannosyl-queuosine (manQ), 7-cyano-7-deaza-guanine (preQ0), 7-aminomethyl-7-deaza-guanine (preQ1), archaeosine (G+), 7-deaza-8-aza-guanine, 6-thio-guanine, 6-thio-7-deaza-guanine, 6-thio-7-deaza-8-aza-guanine, 7-methyl-guanine (m7G), 6-thio-7-methyl-guanine, 7-methyl-inosine, 6-methoxy-guanine, 1-methyl-guanine (m1G), N2-methyl-guanine (m2G), N2,N2-dimethyl-guanine (m22G), N2,7-dimethyl-guanine (m2,7G), N2,N2,7-dimethyl-guanine (m2,2,7G), 8-oxo-guanine, 7-methyl-8-oxo-guanine, 1-methyl-6-thio-guanine, N2-methyl-6-thio-guanine, N2,N2-dimethyl-6-thio-guanine, N2-methyl-2'-O-methyl-guanosine (m2Gm), N2,N2-dimethyl-2'-O-methyl-guanosine (m22Gm), 1-methyl-2'-O-methyl-guanosine (m1Gm), N2,7-dimethyl-2'-O-methyl-guanosine (m2,7Gm), 2'-O-methyl-inosine (Im), 1,2'-O-dimethyl-inosine (m1Im), 1-thio-guanine, and O—6-methyl-guanine.

The alternative nucleobase of a nucleotide can be independently a purine, a pyrimidine, a purine or pyrimidine analog. In some embodiments, the nucleobase can be an alternative to adenine, cytosine, guanine, uracil, or hypoxanthine. In another embodiment, the nucleobase can also include, for example, naturally-occurring and synthetic derivatives of a base, including, but not limited to, pyrazolo [3,4-d]pyrimidines, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-propynyl uracil and cytosine, 6-azo uracil, cytosine and thymine, 5-uracil (pseudouracil), 4-thiouracil, 8-halo (e.g., 8-bromo), 8-amino, 8-thiol, 8-thioalkyl, 8-hydroxy and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, deazaguanine, 7-deazaguanine, 3-deazaguanine, deazaadenine, 7-deazaadenine, 3-deazaadenine, pyrazolo[3,4-d]pyrimidine, imidazo[1,5-a]1,3,5 triazinones, 9-deazapurines, imidazo[4,5-d]pyrazines, thiazolo[4,5-d]pyrimidines, pyrazin-2-ones, 1,2,4-triazine, pyridazine: or 1,3,5 triazine. When the nucleotides are depicted using the shorthand A, G, C, T or U, each letter refers to the representative base and/or derivatives thereof, e.g., A includes adenine or adenine analogs, e.g., 7-deaza adenine).

Alterations on the Sugar

Nucleosides include a sugar molecule (e.g., a 5-carbon or 6-carbon sugar, such as pentose, ribose, arabinose, xylose, glucose, galactose, or a deoxy derivative thereof) in combination with a nucleobase, while nucleotides are nucleosides containing a nucleoside and a phosphate group or alternative group (e.g., boranophosphate, thiophosphate, selenophosphate, phosphonate, alkyl group, amidate, and glycerol). A nucleoside or nucleotide may be a canonical species, e.g., a nucleoside or nucleotide including a canonical nucleobase, sugar, and, in the case of nucleotides, a phosphate group, or may be an alternative nucleoside or nucleotide including one or more alternative components. In some embodiments, alternative nucleosides and nucleotides can be altered on the sugar of the nucleoside or nucleotide. In some embodiments, the alternative nucleosides or nucleotides include the structure:

Formula IV

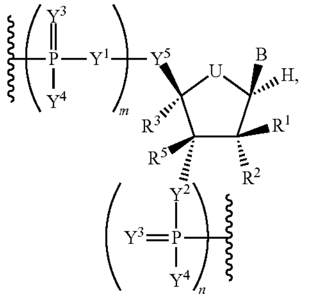

Formula V

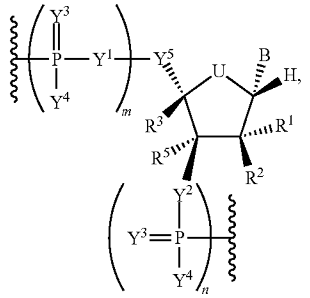

Formula VI

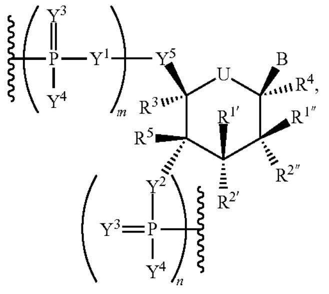

or

Formula VII

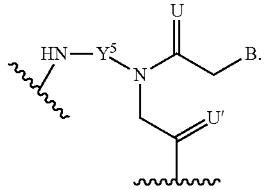

In each of the Formulae IV, V, VI and VII, each of m and n is independently, an integer from 0 to 5, each of U and U' independently, is O, S, $N(RU)_{nu}$, or $C(RU)_{nu}$, wherein nu is an integer from 0 to 2 and each $R^U$ is, independently, H, halo, or optionally substituted alkyl;

each of $R^{1'}$, $R^{2'}$, $R^{1''}$, $R^{2''}$, $R^1$, $R^2$, $R^3$, $R^4$, and $R^5$ is, independently, if present, H, halo, hydroxy, thiol, optionally substituted alkyl, optionally substituted alkoxy, optionally substituted alkenyloxy, optionally substituted alkynyloxy, optionally substituted aminoalkoxy, optionally substituted alkoxyalkoxy, optionally substituted hydroxyalkoxy, optionally substituted amino, azido, optionally substituted aryl, optionally substituted aminoalkyl, optionally substituted aminoalkenyl, optionally substituted aminoalkynyl, or absent; wherein the combination of $R^3$ with one or more of $R^{1'}$, $R^{1''}$, $R^{2'}$, $R^{2''}$, or $R^5$ (e.g., the combination of $R^{1'}$ and $R^3$, the combination of $R^{1''}$ and $R^3$, the combination of $R^{2'}$ and $R^3$, the combination of $R^{2''}$ and $R^3$, or the combination of $R^5$ and $R^3$) can join together to form optionally substituted alkylene or optionally substituted heteroalkylene and, taken together with the carbons to which they are attached, provide an optionally substituted heterocyclyl (e.g., a bicyclic, tricyclic, or tetracyclic heterocyclyl); wherein the combination of $R^5$ with one or more of $R^{1'}$, $R^{1''}$, $R^{2'}$, or $R^{2''}$ (e.g., the combination of $R^{1'}$ and $R^5$, the combination of $R^{1''}$ and $R^5$, the combination of $R^{2'}$ and $R^5$, or the combination of $R^{2''}$ and $R^5$) can join together to form optionally substituted alkylene or optionally substituted heteroalkylene and, taken together with the carbons to which they are attached, provide an optionally substituted heterocyclyl (e.g., a bicyclic, tricyclic, or tetracyclic heterocyclyl); and wherein the combination of $R^4$ and one or more of $R^{1'}$, $R^{1''}$, $R^{2'}$, $R^{2''}$, $R^3$, or $R^5$ can join together to form optionally substituted alkylene or optionally substituted heteroalkylene and, taken together with the carbons to which they are attached, provide an optionally substituted heterocyclyl (e.g., a bicyclic, tricyclic, or tetracyclic heterocyclyl); each of m' and m'' is, independently, an integer from 0 to 3 (e.g., from 0 to 2, from 0 to 1, from 1 to 3, or from 1 to 2);

each of $Y^1$, $Y^2$, and $Y^3$, is, independently, O, S, Se, —$NR^{N1}$—, optionally substituted alkylene, or optionally substituted heteroalkylene, wherein $R^{N1}$ is H, optionally substituted alkyl, optionally substituted alkenyl, optionally substituted alkynyl, optionally substituted aryl, or absent;

each $Y^4$ is, independently, H, hydroxy, thiol, boranyl, optionally substituted alkyl, optionally substituted alkenyl, optionally substituted alkynyl, optionally substituted alkoxy, optionally substituted alkenyloxy, optionally substituted alkynyloxy, optionally substituted thioalkoxy, optionally substituted alkoxyalkoxy, or optionally substituted amino:

each $Y^5$ is, independently, O, S, Se, optionally substituted alkylene (e.g., methylene), or optionally substituted heteroalkylene; and B is a nucleobase, either modified or unmodified.

In some embodiments, the 2'-hydroxy group (OH) can be modified or replaced with a number of different substituents. Exemplary substitutions at the 2'-position include, but are not limited to, H, azido, halo (e.g., fluoro), optionally substituted $C_{1-6}$ alkyl (e.g., methyl); optionally substituted $C_{1-6}$ alkoxy (e.g., methoxy or ethoxy); optionally substituted $C_{6-10}$ aryloxy; optionally substituted $C_{3-8}$ cycloalkyl; optionally substituted $C_{6-10}$ aryl-$C_{1-6}$ alkoxy, optionally substituted $C_{1-12}$ (heterocyclyl)oxy; a sugar (e.g., ribose, pentose, or any described herein): a polyethyleneglycol (PEG), —$O(CH_2CH_2O)_nCH_2CH_2OR$, where R is H or optionally substituted alkyl, and n is an integer from 0) to 20 (e.g., from 0) to 4, from 0) to 8, from 0 to 10, from 0 to 16, from 1 to 4, from 1 to 8, from 1 to 10, from 1 to 16, from 1 to 20, from 2 to 4, from 2 to 8, from 2 to 10, from 2 to 16, from 2 to 20, from 4 to 8, from 4 to 10, from 4 to 16, and from 4 to 20); "locked" nucleic acids (LNA) in which the 2'-hydroxy is connected by a $C_{1-6}$ alkylene or $C_{1-6}$ heteroalkylene bridge to the 4'-carbon of the same ribose sugar, where exemplary bridges included methylene, propylene, ether, or amino bridges; aminoalkyl, as defined herein: aminoalkoxy, as defined herein: amino as defined herein; and amino acid, as defined herein.

Generally, RNA includes the sugar group ribose, which is a 5-membered ring having an oxygen. Exemplary, non-limiting alternative nucleotides include replacement of the oxygen in ribose (e.g., with S, Se, or alkylene, such as methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for anhydrohexitol, altritol, mannitol, cyclohexanyl, cyclohexenyl, and morpholino (that also has a phosphoramidate backbone)); multicyclic forms (e.g., tricyclo and "unlocked" forms, such as glycol nucleic acid (GNA) (e.g., R-GNA or S-GNA, where ribose is replaced by glycol units attached to phosphodiester bonds), threose nucleic acid (TNA, where ribose is replace with a-L-threofuranosyl-(3'→2')), and peptide nucleic acid (PNA, where 2-amino-ethyl-glycine linkages replace the ribose and phosphodiester backbone).

In some embodiments, the sugar group contains one or more carbons that possess the opposite stereochemical configuration of the corresponding carbon in ribose. Thus, a polynucleotide molecule can include nucleotides containing, e.g., arabinose or L-ribose, as the sugar.

In some embodiments, the polynucleotide includes at least one nucleoside wherein the sugar is L-ribose, 2'-O-methyl-ribose, 2'-fluoro-ribose, arabinose, hexitol, an LNA, or a PNA.

Alterations on the Internucleoside Linkage

Alternative nucleotides can be altered on the internucleoside linkage (e.g., phosphate backbone). Herein, in the context of the polynucleotide backbone, the phrases "phosphate" and "phosphodiester" are used interchangeably. Backbone phosphate groups can be altered by replacing one or more of the oxygen atoms with a different substituent.

The alternative nucleotides can include the wholesale replacement of an unaltered phosphate moiety with another internucleoside linkage as described herein. Examples of alternative phosphate groups include, but are not limited to, phosphorothioate, phosphoroselenates, boranophosphates, boranophosphate esters, hydrogen phosphonates, phosphoramidates, phosphorodiamidates, alkyl or aryl phosphonates, and phosphotriesters. Phosphorodithioates have both non-linking oxygens replaced by sulfur. The phosphate linker can also be altered by the replacement of a linking oxygen with nitrogen (bridged phosphoramidates), sulfur (bridged phosphorothioates), and carbon (bridged methylene-phosphonates).

The alternative nucleosides and nucleotides can include the replacement of one or more of the non-bridging oxygens with a borane moiety ($BH_3$), sulfur (thio), methyl, ethyl, and/or methoxy. As a non-limiting example, two non-bridging oxygens at the same position (e.g., the alpha (α), beta (β) or gamma (γ) position) can be replaced with a sulfur (thio) and a methoxy.

The replacement of one or more of the oxygen atoms at the a position of the phosphate moiety (e.g., a-thio phosphate) is provided to confer stability (such as against exonucleases and endonucleases) to RNA and DNA through the unnatural phosphorothioate backbone linkages. Phosphorothioate DNA and RNA have increased nuclease resistance and subsequently a longer half-life in a cellular environment.

Other internucleoside linkages that may be employed according to the present disclosure, including internucleoside linkages which do not contain a phosphorous atom, are described herein.

Internal Ribosome Entry Sites

Polynucleotides may contain an internal ribosome entry site (IRES). An IRES may act as the sole ribosome binding site, or may serve as one of multiple ribosome binding sites of an mRNA. A polynucleotide containing more than one functional ribosome binding site may encode several peptides or polypeptides that are translated independently by the ribosomes (e.g., multicistronic mRNA). When polynucleotides are provided with an IRES, further optionally provided is a second translatable region. Examples of IRES sequences that can be used according to the present disclosure include without limitation, those from picornaviruses (e.g., FMDV), pest viruses (CFFV), polio viruses (PV), encephalomyocarditis viruses (ECMV), foot-and-mouth disease viruses (FMDV), hepatitis C viruses (HCV), classical swine fever viruses (CSFV), murine leukemia virus (MLV), simian immune deficiency viruses (SIV) or cricket paralysis viruses (CrPV).

5'-Cap Structure

A polynucleotide (e.g., an mRNA) may include a 5'-cap structure. The 5'-cap structure of a polynucleotide is involved in nuclear export and increasing polynucleotide stability and binds the mRNA Cap Binding Protein (CBP), which is responsible for polynucleotide stability in the cell and translation competency through the association of CBP with poly-A binding protein to form the mature cyclic mRNA species. The cap further assists the removal of 5'-proximal introns removal during mRNA splicing.

Endogenous polynucleotide molecules may be 5'-end capped generating a 5'-ppp-5'-triphosphate linkage between a terminal guanosine cap residue and the 5'-terminal transcribed sense nucleotide of the polynucleotide. This 5'-guanylate cap may then be methylated to generate an N7-methyl-guanylate residue. The ribose sugars of the terminal and/or anteterminal transcribed nucleotides of the 5' end of the polynucleotide may optionally also be 2'-O-methylated. 5'-decapping through hydrolysis and cleavage of the guanylate cap structure may target a polynucleotide molecule, such as an mRNA molecule, for degradation.

Alterations to polynucleotides may generate a non-hydrolyzable cap structure preventing decapping and thus increasing polynucleotide half-life. Because cap structure hydrolysis requires cleavage of 5'-ppp-5' phosphorodiester linkages, alternative nucleotides may be used during the capping reaction. In some embodiments, a Vaccinia Capping Enzyme from New England Biolabs (Ipswich, MA) may be used with a-thio-guanosine nucleotides according to the manufacturer's instructions to create a phosphorothioate linkage in the 5'-ppp-5' cap. Additional alternative guanosine nucleotides may be used such as a-methyl-phosphonate and seleno-phosphate nucleotides.

Additional alterations include, but are not limited to, 2'-O-methylation of the ribose sugars of 5'-terminal and/or 5'-anteterminal nucleotides of the polynucleotide (as mentioned above) on the 2'-hydroxy group of the sugar. Multiple distinct 5'-cap structures can be used to generate the 5'-cap of a polynucleotide, such as an mRNA molecule.

5'-Cap structures include those described in International Patent Publication Nos. WO2008127688, WO 2008016473, and WO 2011015347, the cap structures of each of which are incorporated herein by reference.

Cap analogs, which herein are also referred to as synthetic cap analogs, chemical caps, chemical cap analogs, or structural or functional cap analogs, differ from natural (i.e., endogenous, wild-type, or physiological) 5'-caps in their chemical structure, while retaining cap function. Cap analogs may be chemically (i.e., non-enzymatically) or enzymatically synthesized and/linked to a polynucleotide.

For example, the Anti-Reverse Cap Analog (ARCA) cap contains two guanosines linked by a 5'-5'-triphosphate group, wherein one guanosine contains an N7-methyl group as well as a 3'-O-methyl group (i.e., N7,3'-O-dimethyl-guanosine-5'-triphosphate-5'-guanosine, $m^7G$-3'mppp-G, which may equivalently be designated 3' O-Me-$m^7G$(5')ppp (5')G). The 3'-O atom of the other, unaltered, guanosine becomes linked to the 5'-terminal nucleotide of the capped polynucleotide (e.g., an mRNA). The N7- and 3'-O-methylated guanosine provides the terminal moiety of the capped polynucleotide (e.g., mRNA).

Another exemplary cap is mCAP, which is similar to ARCA but has a 2'-O-methyl group on guanosine (i.e., N7,2'-O-dimethyl-guanosine-5'-triphosphate-5'-guanosine, $m^7$Gm-ppp-G).

A cap may be a dinucleotide cap analog. As a non-limiting example, the dinucleotide cap analog may be modified at different phosphate positions with a boranophosphate group or a phophoroselenoate group such as the dinucleotide cap analogs described in U.S. Pat. No. 8,519,110, the cap structures of which are herein incorporated by reference.

Alternatively, a cap analog may be a N7-(4-chlorophenoxyethyl) substituted dinucleotide cap analog known in the art and/or described herein. Non-limiting examples of N7-(4-chlorophenoxyethyl) substituted dinucleotide cap analogs include a N7-(4-chlorophenoxyethyl)-G(5')ppp(5')G and a N7-(4-chlorophenoxyethyl)-m3'-OG(5')ppp(5')G cap analog (see, e.g., the various cap analogs and the methods of synthesizing cap analogs described in Kore et al. Bioorganic & Medicinal Chemistry 2013 21:4570-4574: the cap structures of which are herein incorporated by reference). In other instances, a cap analog useful in the polynucleotides of the present disclosure is a 4-chloro/bromophenoxyethyl analog.

While cap analogs allow for the concomitant capping of a polynucleotide in an in vitro transcription reaction, up to 20% of transcripts remain uncapped. This, as well as the structural differences of a cap analog from endogenous 5'-cap structures of polynucleotides produced by the endogenous, cellular transcription machinery, may lead to reduced translational competency and reduced cellular stability.

Alternative polynucleotides may also be capped post-transcriptionally, using enzymes, in order to generate more authentic 5'-cap structures. As used herein, the phrase "more authentic" refers to a feature that closely mirrors or mimics, either structurally or functionally, an endogenous or wild type feature. That is, a "more authentic" feature is better representative of an endogenous, wild-type, natural or physiological cellular function, and/or structure as compared to synthetic features or analogs of the prior art, or which outperforms the corresponding endogenous, wild-type, natural, or physiological feature in one or more respects. Non-limiting examples of more authentic 5'-cap structures useful in the polynucleotides of the present disclosure are those which, among other things, have enhanced binding of cap binding proteins, increased half-life, reduced susceptibility to 5'-endonucleases, and/or reduced 5'-decapping, as compared to synthetic 5'-cap structures known in the art (or to a wild-type, natural or physiological 5'-cap structure). In some embodiments, recombinant Vaccinia Virus Capping Enzyme and recombinant 2'-O-methyltransferase enzyme can create a canonical 5'-5'-triphosphate linkage between the 5'-terminal nucleotide of a polynucleotide and a guanosine cap nucleotide wherein the cap guanosine contains an N7-methylation and the 5'-terminal nucleotide of the polynucleotide contains a 2'-O-methyl. Such a structure is termed the Cap1 structure. This cap results in a higher translational-competency, cellular stability, and a reduced activation of cellular pro-inflammatory cytokines, as compared, e.g., to other 5' cap analog structures known in the art. Other exemplary cap structures include 7mG(5')ppp(5')N,pN2p (Cap 0), 7mG(5') ppp(5')N1mpNp (Cap 1), 7mG(5')-ppp(5')N1mpN2mp (Cap 2), and m(7)Gpppm(3)(6,6,2')Apm(2')Apm(2')Cpm(2)(3,2') Up (Cap 4).

Because the alternative polynucleotides may be capped post-transcriptionally, and because this process is more efficient, nearly 100% of the alternative polynucleotides may be capped. This is in contrast to ~80% when a cap analog is linked to a polynucleotide in the course of an in vitro transcription reaction.

5'-terminal caps may include endogenous caps or cap analogs. A 5'-terminal cap may include a guanosine analog. Useful guanosine analogs include inosine, N1-methyl-guanosine, 2'-fluoro-guanosine, 7-deaza-guanosine, 8-oxo-guanosine, 2-amino-guanosine, LNA-guanosine, and 2-azido-guanosine.

In some cases, a polynucleotide contains a modified 5'-cap. A modification on the 5'-cap may increase the stability of polynucleotide, increase the half-life of the polynucleotide, and could increase the polynucleotide translational efficiency. The modified 5'-cap may include, but is not limited to, one or more of the following modifications: modification at the 2'- and/or 3'-position of a capped guanosine triphosphate (GTP), a replacement of the sugar ring oxygen (that produced the carbocyclic ring) with a methylene moiety (CH2), a modification at the triphosphate bridge moiety of the cap structure, or a modification at the nucleobase (G) moiety.

5'-UTRs

A 5'-UTR may be provided as a flanking region to polynucleotides (e.g., mRNAs). A 5'-UTR may be homologous or heterologous to the coding region found in a polynucleotide. Multiple 5'-UTRs may be included in the flanking region and may be the same or of different sequences. Any portion of the flanking regions, including none, may be codon optimized and any may independently contain one or more different structural or chemical alterations, before and/or after codon optimization.

Shown in Table 21 in U.S. Provisional Application No. 61/775,509, and in Table 21 and in Table 22 in U.S. Provisional Application No. 61/829,372, of which are incorporated herein by reference, is a listing of the start and stop site of alternative polynucleotides (e.g., mRNA). In Table 21 each 5'-UTR (5'-UTR-005 to 5'-UTR 68511) is identified by its start and stop site relative to its native or wild type (homologous) transcript (ENST; the identifier used in the ENSEMBL database).

To alter one or more properties of a polynucleotide (e.g., mRNA), 5'-UTRs which are heterologous to the coding region of an alternative polynucleotide (e.g., mRNA) may be engineered. The polynucleotides (e.g., mRNA) may then be administered to cells, tissue or organisms and outcomes such as protein level, localization, and/or half-life may be measured to evaluate the beneficial effects the heterologous 5'-UTR may have on the alternative polynucleotides (mRNA). Variants of the 5'-UTRs may be utilized wherein one or more nucleotides are added or removed to the termini, including A, T, C or G. 5'-UTRs may also be codon-optimized, or altered in any manner described herein.

5'-UTRs, 3'-UTRs, and Translation Enhancer Elements (TEEs)

The 5'-UTR of a polynucleotides (e.g., mRNA) may include at least one translation enhancer element. The term "translational enhancer element" refers to sequences that increase the amount of polypeptide or protein produced from a polynucleotide. As a non-limiting example, the TEE may be located between the transcription promoter and the start codon. The polynucleotides (e.g., mRNA) with at least one TEE in the 5'-UTR may include a cap at the 5'-UTR. Further, at least one TEE may be located in the 5'-UTR of polynucleotides (e.g., mRNA) undergoing cap-dependent or cap-independent translation.

In some aspects, TEEs are conserved elements in the UTR which can promote translational activity of a polynucleotide such as, but not limited to, cap-dependent or cap-independent translation. The conservation of these sequences has been previously shown by Panek et al. (Nucleic Acids Research, 2013, 1-10) across 14 species including humans.

In one non-limiting example, the TEEs known may be in the 5'-leader of the Gtx homeodomain protein (Chappell et al., Proc. Natl. Acad. Sci. USA 101:9590-9594, 2004, the TEEs of which are incorporated herein by reference).

In another non-limiting example, TEEs are disclosed in US Patent Publication Nos. 2009/0226470 and 2013/0177581, International Patent Publication Nos. WO2009/075886, WO2012/009644, and WO1999/024595, US Patent Nos. 6,310,197, and 6,849,405, the TEE sequences of each of which are incorporated herein by reference.

In yet another non-limiting example, the TEE may be an internal ribosome entry site (IRES), HCV-IRES or an IRES element such as, but not limited to, those described in U.S. Pat. No. 7,468,275, US Patent Publication Nos. 2007/0048776 and 2011/0124100 and International Patent Publication Nos. WO2007/025008 and WO2001/055369, the IRES sequences of each of which are incorporated herein by reference. The IRES elements may include, but are not limited to, the Gtx sequences (e.g., Gtx9-nt, Gtx8-nt, Gtx7-nt) described by Chappell et al. (Proc. Natl. Acad. Sci. USA 101:9590-9594, 2004) and Zhou et al. (PNAS 102:6273-6278, 2005) and in US Patent Publication Nos. 2007/0048776 and 2011/0124100 and International Patent Publication No. WO2007/025008, the IRES sequences of each of which are incorporated herein by reference.

"Translational enhancer polynucleotides" are polynucleotides which include one or more of the specific TEE exemplified herein and/or disclosed in the art (see e.g., U.S. Pat. Nos. 6,310,197, 6,849,405, 7,456,273, 7,183,395, U.S. Patent Publication Nos. 20090/226470, 2007/0048776, 2011/0124100, 2009/0093049, 2013/0177581, International Patent Publication Nos. WO2009/075886, WO2007/025008, WO2012/009644, WO2001/055371 WO1999/024595, and European Patent Nos. 2610341 and 2610340; the TEE sequences of each of which are incorporated herein by reference) or their variants, homologs or functional derivatives. One or multiple copies of a specific TEE can be present in a polynucleotide (e.g., mRNA). The TEEs in the translational enhancer polynucleotides can be organized in one or more sequence segments. A sequence segment can harbor one or more of the specific TEEs exemplified herein, with each TEE being present in one or more copies. When multiple sequence segments are present in a translational enhancer polynucleotide, they can be homogenous or heterogeneous. Thus, the multiple sequence segments in a translational enhancer polynucleotide can harbor identical or different types of the specific TEEs exemplified herein, identical or different number of copies of each of the specific TEEs, and/or identical or different organization of the TEEs within each sequence segment.

A polynucleotide (e.g., mRNA) may include at least one TEE that is described in International Patent Publication Nos. WO1999/024595, WO2012/009644, WO2009/075886, WO2007/025008, WO1999/024595, European Patent Publication Nos. 2610341 and 2610340, U.S. Pat. Nos. 6,310,197, 6,849,405, 7,456,273, 7,183,395, and US Patent Publication Nos. 2009/0226470, 2011/0124100, 2007/0048776, 2009/0093049, and 2013/0177581 the TEE sequences of each of which are incorporated herein by reference. The TEE may be located in the 5'-UTR of the polynucleotides (e.g., mRNA).

A polynucleotide (e.g., mRNA) may include at least one TEE that has at least 50%, at least 55%, at least 60%, at least 65%, at least 70%, at least 75%, at least 80%, at least 85%, at least 90%, at least 95% or at least 99% identity with the TEEs described in US Patent Publication Nos. 2009/0226470, 2007/0048776, 2013/0177581 and 2011/0124100, International Patent Publication Nos. WO1999/024595, WO2012/009644, WO2009/075886 and WO2007/025008, European Patent Publication Nos. 2610341 and 2610340, U.S. Pat. Nos. 6,310,197, 6,849,405, 7,456,273, 7,183,395, the TEE sequences of each of which are incorporated herein by reference.

The 5'-UTR of a polynucleotide (e.g., mRNA) may include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18 at least 19, at least 20, at least 21, at least 22, at least 23, at least 24, at least 25, at least 30, at least 35, at least 40, at least 45, at least 50, at least 55 or more than 60 TEE sequences. The TEE sequences in the 5'-UTR of a polynucleotide (e.g., mRNA) may be the same or different TEE sequences. The TEE sequences may be in a pattern such as ABABAB, AABBAABBAABB, or ABCABCABC, or variants thereof, repeated once, twice, or more than three times. In these patterns, each letter, A, B, or C represent a different TEE sequence at the nucleotide level.

In some cases, the 5'-UTR may include a spacer to separate two TEE sequences. As a non-limiting example, the spacer may be a 15 nucleotide spacer and/or other spacers known in the art. As another non-limiting example, the 5'-UTR may include a TEE sequence-spacer module repeated at least once, at least twice, at least 3 times, at least 4 times, at least 5 times, at least 6 times, at least 7 times, at least 8 times, at least 9 times, or more than 9 times in the 5'-UTR.

In other instances, the spacer separating two TEE sequences may include other sequences known in the art which may regulate the translation of the polynucleotides (e.g., mRNA) of the present disclosure such as, but not limited to, miR sequences (e.g., miR binding sites and miR seeds). As a non-limiting example, each spacer used to separate two TEE sequences may include a different miR sequence or component of a miR sequence (e.g., miR seed sequence).

In some instances, the TEE in the 5'-UTR of a polynucleotide (e.g., mRNA) may include at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99% or more than 99% of the TEE sequences disclosed in US Patent Publication Nos. 2009/0226470, 2007/0048776, 2013/0177581 and 2011/0124100, International Patent Publication Nos. WO1999/024595, WO2012/009644, WO2009/075886 and WO2007/025008, European Patent Publication Nos. 2610341 and 2610340, and U.S. Pat. Nos. 6,310,197, 6,849,405, 7,456,273, and 7,183,395 the TEE sequences of each of which are incorporated herein by reference. In another embodiment, the TEE in the 5'-UTR of the polynucleotides (e.g., mRNA) of the present disclosure may include a 5-30 nucleotide fragment, a 5-25 nucleotide fragment, a 5-20 nucleotide fragment, a 5-15 nucleotide fragment, a 5-10) nucleotide fragment of the TEE sequences disclosed in US Patent Publication Nos. 2009/0226470, 2007/0048776, 2013/0177581 and 2011/0124100, International Patent Publication Nos. WO1999/024595, WO2012/009644, WO2009/075886 and WO2007/025008, European Patent Publication Nos. 2610341 and 2610340, and U.S. Pat. Nos. 6,310,197, 6,849,405, 7,456,273, and 7,183,395; the TEE sequences of each of which are incorporated herein by reference.

In certain cases, the TEE in the 5'-UTR of the polynucleotides (e.g., mRNA) of the present disclosure may include at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99% or more than 99% of the TEE sequences disclosed in Chappell et al. (Proc. Natl. Acad. Sci. USA 101:9590-9594, 2004) and Zhou et al. (PNAS 102: 6273-6278, 2005), in Supplemental Table 1 and in Supplemental Table 2 disclosed by Wellensiek et al (Genome-wide profiling of human cap-independent translation-enhancing elements, Nature Methods, 2013; DOI: 10.1038/NMETH.2522): the TEE sequences of each of which are herein incorporated by reference. In another embodiment, the TEE in the 5'-UTR of the polynucleotides (e.g., mRNA) of the present disclosure may include a 5-30 nucleotide fragment, a 5-25 nucleotide fragment, a 5-20) nucleotide fragment, a 5-15 nucleotide fragment, a 5-10 nucleotide fragment of the TEE sequences disclosed in Chappell et al. (Proc. Natl. Acad. Sci. USA 101:9590-9594, 2004) and Zhou et al. (PNAS 102:6273-6278, 2005), in Supplemental Table 1 and in Supplemental Table 2 disclosed by Wellensiek et al (Genome-wide profiling of human cap-independent translation-enhancing elements, Nature Methods, 2013; DOI: 10.1038/NMETH.2522); the TEE sequences of each of which is incorporated herein by reference.

In some cases, the TEE used in the 5'-UTR of a polynucleotide (e.g., mRNA) is an IRES sequence such as, but not limited to, those described in U.S. Pat. No. 7,468,275 and International Patent Publication No. WO2001/055369, the TEE sequences of each of which are incorporated herein by reference.

In some instances, the TEEs used in the 5'-UTR of a polynucleotide (e.g., mRNA) may be identified by the methods described in US Patent Publication Nos. 2007/0048776 and 2011/0124100 and International Patent Publication Nos. WO2007/025008 and WO2012/009644, the methods of each of which are incorporated herein by reference.

In some cases, the TEEs used in the 5'-UTR of a polynucleotide (e.g., mRNA) of the present disclosure may be a transcription regulatory element described in U.S. Pat. Nos. 7,456,273 and 7,183,395, US Patent Publication No. 2009/0093049, and International Publication No. WO2001/055371, the TEE sequences of each of which is incorporated herein by reference. The transcription regulatory elements may be identified by methods known in the art, such as, but not limited to, the methods described in U.S. Pat. Nos. 7,456,273 and 7,183,395, US Patent Publication No. 2009/0093049, and International Publication No. WO2001/055371, the methods of each of which is incorporated herein by reference.

In yet other instances, the TEE used in the 5'-UTR of a polynucleotide (e.g., mRNA) is a polynucleotide or portion thereof as described in U.S. Pat. Nos. 7,456,273 and 7,183,395, US Patent Publication No. 2009/0093049, and International Publication No. WO2001/055371, the TEE sequences of each of which are incorporated herein by reference.

The 5'-UTR including at least one TEE described herein may be incorporated in a monocistronic sequence such as, but not limited to, a vector system or a polynucleotide vector. As a non-limiting example, the vector systems and polynucleotide vectors may include those described in U.S. Pat. Nos. 7,456,273 and 7,183,395, US Patent Publication Nos. 2007/0048776, 2009/0093049 and 2011/0124100, and International Patent Publication Nos. WO2007/025008 and WO2001/055371, the TEE sequences of each of which are incorporated herein by reference.

The TEEs described herein may be located in the 5'-UTR and/or the 3'-UTR of the polynucleotides (e.g., mRNA). The TEEs located in the 3'-UTR may be the same and/or different than the TEEs located in and/or described for incorporation in the 5'-UTR.

In some cases, the 3'-UTR of a polynucleotide (e.g., mRNA) may include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18 at least 19, at least 20, at least 21, at least 22, at least 23, at least 24, at least 25, at least 30, at least 35, at least 40, at least 45, at least 50, at least 55 or more than 60 TEE sequences. The TEE sequences in the 3'-UTR of the polynucleotides (e.g., mRNA) of the present disclosure may be the same or different TEE sequences. The TEE sequences may be in a pattern such as ABABAB, AABBAABBAABB, or ABCABCABC, or variants thereof, repeated once, twice, or more than three times. In these patterns, each letter, A, B, or C represent a different TEE sequence at the nucleotide level.

In one instance, the 3'-UTR may include a spacer to separate two TEE sequences. As a non-limiting example, the spacer may be a 15 nucleotide spacer and/or other spacers known in the art. As another non-limiting example, the 3'-UTR may include a TEE sequence-spacer module repeated at least once, at least twice, at least 3 times, at least 4 times, at least 5 times, at least 6 times, at least 7 times, at least 8 times, at least 9 times, or more than 9 times in the 3'-UTR.

In other cases, the spacer separating two TEE sequences may include other sequences known in the art which may regulate the translation of the polynucleotides (e.g., mRNA) of the present disclosure such as, but not limited to, miR sequences described herein (e.g., miR binding sites and miR seeds). As a non-limiting example, each spacer used to separate two TEE sequences may include a different miR sequence or component of a miR sequence (e.g., miR seed sequence).

In some embodiments, a polyribonucleotide of the disclosure comprises a miR and/or TEE sequence. In some embodiments, the incorporation of a miR sequence and/or a TEE sequence into a polyribonucleotide of the disclosure can change the shape of the stem loop region, which can increase and/or decrease translation. See e.g., Kedde et al., Nature Cell Biology 2010 12 (10): 1014-20, herein incorporated by reference in its entirety).

Sensor Sequences and MicroRNA (miRNA) Binding Sites

Sensor sequences include, for example, microRNA (miRNA) binding sites, transcription factor binding sites, structured mRNA sequences and/or motifs, artificial binding sites engineered to act as pseudo-receptors for endogenous nucleic acid binding molecules, and combinations thereof. Non-limiting examples of sensor sequences are described in U.S. Publication 2014/0200261, the contents of which are incorporated herein by reference in their entirety.

In some embodiments, a polyribonucleotide (e.g., a ribonucleic acid (RNA), e.g., a messenger RNA (mRNA)) of the disclosure comprising an open reading frame (ORF) encoding a polypeptide further comprises a sensor sequence. In some embodiments, the sensor sequence is a miRNA binding site.

A miRNA is a 19-25 nucleotide long noncoding RNA that binds to a polyribonucleotide and down-regulates gene expression either by reducing stability or by inhibiting translation of the polyribonucleotide. A miRNA sequence comprises a "seed" region, i.e., a sequence in the region of positions 2-8 of the mature miRNA. A miRNA seed can comprise positions 2-8 or 2-7 of the mature miRNA. In some embodiments, a miRNA seed can comprise 7 nucleotides (e.g., nucleotides 2-8 of the mature miRNA), wherein the seed-complementary site in the corresponding miRNA binding site is flanked by an adenosine (A) opposed to miRNA position 1. In some embodiments, a miRNA seed can comprise 6 nucleotides (e.g., nucleotides 2-7 of the mature miRNA), wherein the seed-complementary site in the corresponding miRNA binding site is flanked by an adenosine (A) opposed to miRNA position 1. See, for example, Grimson A, Farh K K, Johnston W K, Garrett-Engele P, Lim L P, Bartel D P; Mol Cell. 2007 Jul. 6: 27 (1): 91-105. miRNA profiling of the target cells or tissues can be conducted to determine the presence or absence of miRNA in the cells or tissues. In some embodiments, a polyribonucleotide (e.g., a ribonucleic acid (RNA), e.g., a messenger RNA (mRNA)) of the disclosure comprises one or more microRNA target sequences, microRNA sequences, or microRNA seeds. Such sequences can correspond to any known microRNA such as those taught in US Publication US2005/0261218 and US Publication US2005/0059005, the contents of each of which are incorporated herein by reference in their entirety.

As used herein, the term "microRNA (miRNA or miR) binding site" refers to a sequence within a polyribonucleotide, e.g., within a DNA or within an RNA transcript, including in the 5'UTR and/or 3'UTR, that has sufficient complementarity to all or a region of a miRNA to interact with, associate with or bind to the miRNA. In some embodiments, a polyribonucleotide of the disclosure comprising an ORF encoding a polypeptide further comprises a miRNA binding site. In exemplary embodiments, a 5'UTR and/or 3'UTR of the polyribonucleotide (e.g., a ribonucleic acid (RNA), e.g., a messenger RNA (mRNA)) comprises a miRNA binding site.

A miRNA binding site having sufficient complementarity to a miRNA refers to a degree of complementarity sufficient to facilitate miRNA-mediated regulation of a polyribonucleotide, e.g., miRNA-mediated translational repression or degradation of the polyribonucleotide. In exemplary aspects of the disclosure, a miRNA binding site having sufficient complementarity to the miRNA refers to a degree of complementarity sufficient to facilitate miRNA-mediated degradation of the polyribonucleotide, e.g., miRNA-guided RNA-induced silencing complex (RISC)-mediated cleavage of mRNA. The miRNA binding site can have complementarity to, for example, a 19-25 nucleotide miRNA sequence, to a 19-23 nucleotide miRNA sequence, or to a 22 nucleotide miRNA sequence. A miRNA binding site can be complementary to only a portion of a miRNA, e.g., to a portion less than 1, 2, 3, or 4 nucleotides of the full length of a naturally-occurring miRNA sequence. Full or complete complementarity (e.g., full complementarity or complete complementarity over all or a significant portion of the length of a naturally-occurring miRNA) is preferred when the desired regulation is mRNA degradation.

In some embodiments, a miRNA binding site includes a sequence that has complementarity (e.g., partial or complete complementarity) with an miRNA seed sequence. In some embodiments, the miRNA binding site includes a sequence that has complete complementarity with a miRNA seed sequence. In some embodiments, a miRNA binding site includes a sequence that has complementarity (e.g., partial or complete complementarity) with an miRNA sequence. In some embodiments, the miRNA binding site includes a sequence that has complete complementarity with a miRNA sequence. In some embodiments, a miRNA binding site has complete complementarity with a miRNA sequence but for 1, 2, or 3 nucleotide substitutions, terminal additions, and/or truncations.

In some embodiments, the miRNA binding site is the same length as the corresponding miRNA. In some embodiments, the miRNA binding site is one, two, three, four, five, six, seven, eight, nine, ten, eleven or twelve nucleotide(s) shorter than the corresponding miRNA at the 5' terminus, the 3' terminus, or both. In still other embodiments, the microRNA binding site is two nucleotides shorter than the corresponding microRNA at the 5' terminus, the 3' terminus, or both. The miRNA binding sites that are shorter than the corresponding miRNAs are still capable of degrading the mRNA incorporating one or more of the miRNA binding sites or preventing the mRNA from translation.

In some embodiments, the miRNA binding site binds to the corresponding mature miRNA that is part of an active RISC containing Dicer. In another embodiment, binding of the miRNA binding site to the corresponding miRNA in RISC degrades the mRNA containing the miRNA binding site or prevents the mRNA from being translated. In some embodiments, the miRNA binding site has sufficient complementarity to miRNA so that a RISC complex comprising the miRNA cleaves the polyribonucleotide comprising the miRNA binding site. In some embodiments, the miRNA binding site has imperfect complementarity so that a RISC complex comprising the miRNA induces instability in the polyribonucleotide comprising the miRNA binding site. In another embodiment, the miRNA binding site has imperfect complementarity so that a RISC complex comprising the miRNA represses transcription of the polyribonucleotide comprising the miRNA binding site.

In some embodiments, the miRNA binding site has one, two, three, four, five, six, seven, eight, nine, ten, eleven or twelve mismatch(es) from the corresponding miRNA.

In some embodiments, the miRNA binding site has at least about ten, at least about eleven, at least about twelve, at least about thirteen, at least about fourteen, at least about fifteen, at least about sixteen, at least about seventeen, at least about eighteen, at least about nineteen, at least about twenty, or at least about twenty-one contiguous nucleotides complementary to at least about ten, at least about eleven, at least about twelve, at least about thirteen, at least about fourteen, at least about fifteen, at least about sixteen, at least about seventeen, at least about eighteen, at least about nineteen, at least about twenty, or at least about twenty-one, respectively, contiguous nucleotides of the corresponding miRNA.

By engineering one or more miRNA binding sites into a polyribonucleotide of the disclosure, the polyribonucleotide can be targeted for degradation or reduced translation, provided the miRNA in question is available. This can reduce off-target effects upon delivery of the polyribonucleotide. In some embodiments, if a polyribonucleotide of the disclosure is not intended to be delivered to a tissue or cell but ends up there, then a miRNA abundant in the tissue or cell can inhibit the expression of the gene of interest if one or multiple binding sites of the miRNA are engineered into the 5'UTR and/or 3'UTR of the polyribonucleotide.

Conversely, miRNA binding sites can be removed from polyribonucleotide sequences in which they naturally occur in order to increase protein expression in specific tissues. In some embodiments, a binding site for a specific miRNA can be removed from a polyribonucleotide to improve protein expression in tissues or cells containing the miRNA.

In some embodiments, a polyribonucleotide of the disclosure can include at least one miRNA-binding site in the 5'UTR and/or 3'UTR in order to direct cytotoxic or cytoprotective mRNA therapeutics to specific cells such as, but not limited to, normal and/or cancerous cells. In another embodiment, a polyribonucleotide of the disclosure can include two, three, four, five, six, seven, eight, nine, ten, or more miRNA-binding sites in the 5'-UTR and/or 3'-UTR in order to direct cytotoxic or cytoprotective mRNA therapeutics to specific cells such as, but not limited to, normal and/or cancerous cells.

Regulation of expression in multiple tissues can be accomplished through introduction or removal of one or more miRNA binding sites. The decision whether to remove or insert a miRNA binding site can be made based on miRNA expression patterns and/or their profilings in diseases. Identification of miRNAs, miRNA binding sites, and their expression patterns and role in biology have been reported (e.g., Bonauer et al., Curr Drug Targets 2010 11:943-949; Anand and Cheresh Curr Opin Hematol 2011 18:171-176; Contreras and Rao Leukemia 2012 26:404-413 (2011 Dec. 20. doi: 10.1038/leu.2011.356); Bartel Cell 2009 136:215-233; Landgraf et al, Cell, 2007 129:1401-1414; Gentner and Naldini, Tissue Antigens. 2012 80:393-403 and all references therein: each of which is incorporated herein by reference in its entirety).

miRNAs and miRNA binding sites can correspond to any known sequence, including non-limiting examples described in U.S. Publication Nos. 2014/0200261, 2005/0261218, and 2005/0059005, each of which are incorporated herein by reference in their entirety.

Examples of tissues where miRNA are known to regulate mRNA, and thereby protein expression, include, but are not limited to, liver (miR-122), muscle (miR-133, miR-206, miR-208), endothelial cells (miR-17-92, miR-126), myeloid cells (miR-142-3p, miR-142-5p, miR-16, miR-21, miR-223, miR-24, miR-27), adipose tissue (let-7, miR-30c), heart (miR-Id, miR-149), kidney (miR-192, miR-194, miR-204), and lung epithelial cells (let-7, miR-133, miR-126).

Specifically, miRNAs are known to be differentially expressed in immune cells (also called hematopoietic cells), such as antigen presenting cells (APCs) (e.g., dendritic cells and macrophages), macrophages, monocytes, B lymphocytes, T lymphocytes, granulocytes, natural killer cells, etc. Immune cell specific miRNAs are involved in immunogenicity, autoimmunity, the immune-response to infection, inflammation, as well as unwanted immune response after gene therapy and tissue/organ transplantation. Immune cells specific miRNAs also regulate many aspects of development, proliferation, differentiation and apoptosis of hematopoietic cells (immune cells). In some embodiments, miR-142 and miR-146 are exclusively expressed in immune cells, particularly abundant in myeloid dendritic cells. It has been demonstrated that the immune response to a polyribonucleotide can be shut-off by adding miR-142 binding sites to the 3'-UTR of the polyribonucleotide, enabling more stable gene transfer in tissues and cells. miR-142 efficiently degrades exogenous polyribonucleotides in antigen presenting cells and suppresses cytotoxic elimination of transduced cells (e.g., Annoni A et al., blood, 2009, 114, 5152-5161; Brown B D, et al., Nat med. 2006, 12 (5), 585-591; Brown B D, et al., blood, 2007, 110 (13): 4144-4152, each of which is incorporated herein by reference in its entirety).

An antigen-mediated immune response can refer to an immune response triggered by foreign antigens, which, when entering an organism, are processed by the antigen presenting cells and displayed on the surface of the antigen presenting cells. T cells can recognize the presented antigen and induce a cytotoxic elimination of cells that express the antigen.

Introducing a miR-142 binding site into the 5'UTR and/or 3'UTR of a polyribonucleotide of the disclosure can selectively repress gene expression in antigen presenting cells through miR-142 mediated degradation, limiting antigen presentation in antigen presenting cells (e.g., dendritic cells) and thereby preventing antigen-mediated immune response after the delivery of the polyribonucleotide. The polyribonucleotide is then stably expressed in target tissues or cells without triggering cytotoxic elimination.

In some embodiments, binding sites for miRNAs that are known to be expressed in immune cells, in particular, antigen presenting cells, can be engineered into a polyribonucleotide of the disclosure to suppress the expression of the polyribonucleotide in antigen presenting cells through miRNA mediated RNA degradation, subduing the antigen-mediated immune response. Expression of the polyribonucleotide is maintained in non-immune cells where the immune cell specific miRNAs are not expressed. In some embodiments, in some embodiments, to prevent an immunogenic reaction against a liver specific protein, any miR-122 binding site can be removed and a miR-142 (and/or mirR-146) binding site can be engineered into the 5'UTR and/or 3'UTR of a polyribonucleotide of the disclosure.

To further drive the selective degradation and suppression in APCs and macrophage, a polyribonucleotide of the disclosure can include a further negative regulatory element in the 5'UTR and/or 3'UTR, either alone or in combination with miR-142 and/or miR-146 binding sites. As a non-limiting example, the further negative regulatory element is a Constitutive Decay Element (CDE).

Immune cell specific miRNAs include, but are not limited to, hsa-let-7a-2-3p, hsa-let-7a-3p, hsa-7a-5p, hsa-let-7c, hsa-let-7e-3p, hsa-let-7e-5p, hsa-let-7g-3p, hsa-let-7g-5p, hsa-let-7i-3p, hsa-let-7i-5p, miR-10a-3p, miR-10a-5p, miR-1184, hsa-let-7f-1-3p, hsa-let-7f-2-5p, hsa-let-7f-5p, miR-125b-1-3p, miR-125b-2-3p, miR-125b-5p, miR-1279, miR-130a-3p, miR-130a-5p, miR-132-3p, miR-132-5p, miR-142-3p, miR-142-5p, miR-143-3p, miR-143-5p, miR-146a-3p, miR-146a-5p, miR-146b-3p, miR-146b-5p, miR-147a, miR-147b, miR-148a-5p, miR-148a-3p, miR-150-3p, miR-150-5p, miR-151b, miR-155-3p, miR-155-5p, miR-15a-3p, miR-15a-5p, miR-15b-5p, miR-15b-3p, miR-16-1-3p, miR-16-2-3p, miR-16-5p, miR-17-5p, miR-181a-3p, miR-181a-5p, miR-181a-2-3p, miR-182-3p, miR-182-5p, miR-197-3p, miR-197-5p, miR-21-5p, miR-21-3p, miR-214-3p, miR-214-5p, miR-223-3p, miR-223-5p, miR-221-3p, miR-221-5p, miR-23b-3p, miR-23b-5p, miR-24-1-5p, miR-24-2-5p, miR-24-3p, miR-26a-1-3p, miR-26a-2-3p, miR-26a-5p, miR-26b-3p, miR-26b-5p, miR-27a-3p, miR-27a-5p, miR-27b-3p, miR-27b-5p, miR-28-3p, miR-28-5p, miR-2909, miR-29a-3p, miR-29a-5p, miR-29b-1-5p, miR-29b-2-5p, miR-29c-3p, miR-29c-5p, miR-30e-3p, miR-30e-5p, miR-331-5p, miR-339-3p, miR-339-5p, miR-345-3p, miR-345-5p, miR-346, miR-34a-3p, miR-34a-5p, miR-363-3p, miR-363-5p, miR-372, miR-377-3p, miR-377-5p, miR-493-3p, miR-493-5p, miR-542, miR-548b-5p, miR548c-5p, miR-548i, miR-548j, miR-548n, miR-574-3p, miR-598, miR-718, miR-935, miR-99a-3p, miR-99a-5p, miR-99b-3p, and miR-99b-5p. Furthermore, novel miRNAs can be identified in immune cell through micro-array hybridization and microtome analysis (e.g., Jima D D et al, Blood, 2010, 116:e118-e127; Vaz C et al., BMC Genomics, 2010, 11,288, the content of each of which is incorporated herein by reference in its entirety.)

miRNAs that are known to be expressed in the liver include, but are not limited to, miR-107, miR-122-3p, miR-122-5p, miR-1228-3p, miR-1228-5p, miR-1249, miR-129-5p, miR-1303, miR-151a-3p, miR-151a-5p, miR-152, miR-194-3p, miR-194-5p, miR-199a-3p, miR-199a-5p, miR-199b-3p, miR-199b-5p, miR-296-5p, miR-557, miR-581, miR-939-3p, and miR-939-5p. miRNA binding sites from any liver specific miRNA can be introduced to or removed from a polyribonucleotide of the disclosure to regulate expression of the polyribonucleotide in the liver. Liver specific miRNA binding sites can be engineered alone or further in combination with immune cell (e.g., APC) miRNA binding sites in a polyribonucleotide of the disclosure.

miRNAs that are known to be expressed in the lung include, but are not limited to, let-7a-2-3p, let-7a-3p, let-7a-5p, miR-126-3p, miR-126-5p, miR-127-3p, miR-127-5p, miR-130a-3p, miR-130a-5p, miR-130b-3p, miR-130b-5p, miR-133a, miR-133b, miR-134, miR-18a-3p, miR-18a-5p, miR-18b-3p, miR-18b-5p, miR-24-1-5p, miR-24-2-5p, miR-24-3p, miR-296-3p, miR-296-5p, miR-32-3p, miR-337-3p, miR-337-5p, miR-381-3p, and miR-381-5p. MiRNA binding sites from any lung specific miRNA can be introduced to or removed from a polyribonucleotide of the disclosure to regulate expression of the polyribonucleotide in the lung. Lung specific miRNA binding sites can be engineered alone or further in combination with immune cell (e.g., APC) miRNA binding sites in a polyribonucleotide of the disclosure.

miRNAs that are known to be expressed in the heart include, but are not limited to, miR-1, miR-133a, miR-133b, miR-149-3p, miR-149-5p, miR-186-3p, miR-186-5p, miR-208a, miR-208b, miR-210, miR-296-3p, miR-320, miR-451a, miR-451b, miR-499a-3p, miR-499a-5p, miR-499b-3p, miR-499b-5p, miR-744-3p, miR-744-5p, miR-92b-3p, and miR-92b-5p. MiRNA binding sites from any heart specific microRNA can be introduced to or removed from a polyribonucleotide of the disclosure to regulate expression of the polyribonucleotide in the heart. Heart specific miRNA binding sites can be engineered alone or further in combination with immune cell (e.g., APC) miRNA binding sites in a polyribonucleotide of the disclosure.

miRNAs that are known to be expressed in the nervous system include, but are not limited to, miR-124-5p, miR-125a-3p, miR-125a-5p, miR-125b-1-3p, miR-125b-2-3p, miR-125b-5p, miR-1271-3p, miR-1271-5p, miR-128, miR-132-5p, miR-135a-3p, miR-135a-5p, miR-135b-3p, miR-135b-5p, miR-137, miR-139-5p, miR-139-3p, miR-149-3p, miR-149-5p, miR-153, miR-181c-3p, miR-181c-5p, miR-183-3p, miR-183-5p, miR-190a, miR-190b, miR-212-3p, miR-212-5p, miR-219-1-3p, miR-219-2-3p, miR-23a-3p, miR-23a-5p, miR-30a-5p, miR-30b-3p, miR-30b-5p, miR-30c-1-3p, miR-30c-2-3p, miR-30c-5p, miR-30d-3p, miR-30d-5p, miR-329, miR-342-3p, miR-3665, miR-3666, miR-380-3p, miR-380-5p, miR-383, miR-410, miR-425-3p, miR-425-5p, miR-454-3p, miR-454-5p, miR-483, miR-510), miR-516a-3p, miR-548b-5p, miR-548c-5p, miR-571, miR-7-1-3p, miR-7-2-3p, miR-7-5p, miR-802, miR-922, miR-9-3p, and miR-9-5p. MiRNAs enriched in the nervous system further include those specifically expressed in neurons, including, but not limited to, miR-132-3p, miR-132-3p, miR-148b-3p, miR-148b-5p, miR-151a-3p, miR-151a-5p, miR-212-3p, miR-212-5p, miR-320b, miR-320e, miR-323a-3p, miR-323a-5p, miR-324-5p, miR-325, miR-326, miR-328, miR-922 and those specifically expressed in glial cells, including, but not limited to, miR-1250, miR-219-1-3p, miR-219-2-3p, miR-219-5p, miR-23a-3p, miR-23a-5p, miR-3065-3p, miR-3065-5p, miR-30e-3p, miR-30e-5p, miR-32-5p, miR-338-5p, and miR-657. MiRNA binding sites from any CNS specific miRNA can be introduced to or removed from a polyribonucleotide of the disclosure to regulate expression of the polyribonucleotide in the nervous system. Nervous system specific miRNA binding sites can be engineered alone or further in combination with immune cell (e.g., APC) miRNA binding sites in a polyribonucleotide of the disclosure.

miRNAs that are known to be expressed in the pancreas include, but are not limited to, miR-105-3p, miR-105-5p, miR-184, miR-195-3p, miR-195-5p, miR-196a-3p, miR-196a-5p, miR-214-3p, miR-214-5p, miR-216a-3p, miR-216a-5p, miR-30a-3p, miR-33a-3p, miR-33a-5p, miR-375, miR-7-1-3p, miR-7-2-3p, miR-493-3p, miR-493-5p, and miR-944. MiRNA binding sites from any pancreas specific miRNA can be introduced to or removed from a polyribonucleotide of the disclosure to regulate expression of the polyribonucleotide in the pancreas. Pancreas specific miRNA binding sites can be engineered alone or further in combination with immune cell (e.g., APC) miRNA binding sites in a polyribonucleotide of the disclosure.

miRNAs that are known to be expressed in the kidney include, but are not limited to, miR-122-3p, miR-145-5p, miR-17-5p, miR-192-3p, miR-192-5p, miR-194-3p, miR-194-5p, miR-20a-3p, miR-20a-5p, miR-204-3p, miR-204-5p, miR-210, miR-216a-3p, miR-216a-5p, miR-296-3p, miR-30a-3p, miR-30a-5p, miR-30b-3p, miR-30b-5p, miR-30c-1-3p, miR-30c-2-3p, miR30c-5p, miR-324-3p, miR-335-3p, miR-335-5p, miR-363-3p, miR-363-5p, and miR-562. MiRNA binding sites from any kidney specific miRNA can be introduced to or removed from a polyribonucleotide of the disclosure to regulate expression of the polyribonucleotide in the kidney. Kidney specific miRNA binding sites can be engineered alone or further in combination with immune cell (e.g., APC) miRNA binding sites in a polyribonucleotide of the disclosure.

miRNAs that are known to be expressed in the muscle include, but are not limited to, let-7g-3p, let-7g-5p, miR-1, miR-1286, miR-133a, miR-133b, miR-140-3p, miR-143-3p, miR-143-5p, miR-145-3p, miR-145-5p, miR-188-3p, miR-188-5p, miR-206, miR-208a, miR-208b, miR-25-3p, and miR-25-5p. MiRNA binding sites from any muscle specific miRNA can be introduced to or removed from a polyribonucleotide of the disclosure to regulate expression of the polyribonucleotide in the muscle. Muscle specific miRNA binding sites can be engineered alone or further in combination with immune cell (e.g., APC) miRNA binding sites in a polyribonucleotide of the disclosure.

miRNAs are also differentially expressed in different types of cells, such as, but not limited to, endothelial cells, epithelial cells, and adipocytes.

miRNAs that are known to be expressed in endothelial cells include, but are not limited to, let-7b-3p, let-7b-5p, miR-100-3p, miR-100-5p, miR-101-3p, miR-101-5p, miR-126-3p, miR-126-5p, miR-1236-3p, miR-1236-5p, miR-130a-3p, miR-130a-5p, miR-17-5p, miR-17-3p, miR-18a-3p, miR-18a-5p, miR-19a-3p, miR-19a-5p, miR-19b-1-5p, miR-19b-2-5p, miR-19b-3p, miR-20a-3p, miR-20a-5p, miR-217, miR-210, miR-21-3p, miR-21-5p, miR-221-3p, miR-221-5p, miR-222-3p, miR-222-5p, miR-23a-3p, miR-23a-5p, miR-296-5p, miR-361-3p, miR-361-5p, miR-421, miR-424-3p, miR-424-5p, miR-513a-5p, miR-92a-1-5p, miR-92a-2-5p, miR-92a-3p, miR-92b-3p, and miR-92b-5p. Many novel miRNAs are discovered in endothelial cells from deep-sequencing analysis (e.g., Voellenkle C et al., RNA. 2012, 18, 472-484, herein incorporated by reference in its entirety). MiRNA binding sites from any endothelial cell specific miRNA can be introduced to or removed from a polyribonucleotide of the disclosure to regulate expression of the polyribonucleotide in the endothelial cells.

miRNAs that are known to be expressed in epithelial cells include, but are not limited to, let-7b-3p, let-7b-5p, miR-1246, miR-200a-3p, miR-200a-5p, miR-200b-3p, miR-200b-5p, miR-200c-3p, miR-200c-5p, miR-338-3p, miR-429, miR-451a, miR-451b, miR-494, miR-802 and miR-34a, miR-34b-5p, miR-34c-5p, miR-449a, miR-449b-3p, miR-449b-5p specific in respiratory ciliated epithelial cells, let-7 family, miR-133a, miR-133b, miR-126 specific in lung epithelial cells, miR-382-3p, miR-382-5p specific in renal epithelial cells, and miR-762 specific in corneal epithelial cells. MiRNA binding sites from any epithelial cell specific miRNA can be introduced to or removed from a polyribonucleotide of the disclosure to regulate expression of the polyribonucleotide in the epithelial cells.

In addition, a large group of miRNAs are enriched in embryonic stem cells, controlling stem cell self-renewal as well as the development and/or differentiation of various cell lineages, such as neural cells, cardiac, hematopoietic cells, skin cells, osteogenic cells and muscle cells (e.g., Kuppusamy K T et al., Curr. Mol Med, 2013, 13 (5), 757-764; Vidigal J A and Ventura A. Semin Cancer Biol. 2012, 22 (5-6), 428-436; Goff L A et al., PLoS One, 2009, 4:e7192; Morin R D et al., Genome Res, 2008, 18, 610-621; Yoo J K et al., Stem Cells Dev. 2012, 21 (11), 2049-2057, each of which is herein incorporated by reference in its entirety). MiRNAs abundant in embryonic stem cells include, but are not limited to, let-7a-2-3p, let-a-3p, let-7a-5p, let7d-3p, let-7d-5p, miR-103a-2-3p, miR-103a-5p, miR-106b-3p, miR-106b-5p, miR-1246, miR-1275, miR-138-1-3p, miR-138-2-3p, miR-138-5p, miR-154-3p, miR-154-5p, miR-200c-3p, miR-200c-5p, miR-290, miR-301a-3p, miR-301a-5p, miR-302a-3p, miR-302a-5p, miR-302b-3p, miR-302b-5p, miR-302c-3p, miR-302c-5p, miR-302d-3p, miR-302d-

5p, miR-302e, miR-367-3p, miR-367-5p, miR-369-3p, miR-369-5p, miR-370, miR-371, miR-373, miR-380-5p, miR-423-3p, miR-423-5p, miR-486-5p, miR-520c-3p, miR-548e, miR-548f, miR-548g-3p, miR-548g-5p, miR-548i, miR-548k, miR-5481, miR-548m, miR-548n, miR-5480-3p, miR-5480-5p, miR-548p, miR-664a-3p, miR-664a-5p, miR-664b-3p, miR-664b-5p, miR-766-3p, miR-766-5p, miR-885-3p, miR-885-5p, miR-93-3p, miR-93-5p, miR-941, miR-96-3p, miR-96-5p, miR-99b-3p and miR-99b-5p. Many predicted novel miRNAs are discovered by deep sequencing in human embryonic stem cells (e.g., Morin R D et al., Genome Res, 2008, 18, 610-621; Goff L A et al., PLoS One, 2009, 4:e7192; Bar M et al., Stem cells, 2008, 26, 2496-2505, the content of each of which is incorporated herein by reference in its entirety).

In some embodiments, the binding sites of embryonic stem cell specific miRNAs can be included in or removed from the 3'UTR of a polyribonucleotide of the disclosure to modulate the development and/or differentiation of embryonic stem cells, to inhibit the senescence of stem cells in a degenerative condition (e.g., degenerative diseases), or to stimulate the senescence and apoptosis of stem cells in a disease condition (e.g., cancer stem cells).

Many miRNA expression studies are conducted to profile the differential expression of miRNAs in various cancer cells/tissues and other diseases. Some miRNAs are abnormally over-expressed in certain cancer cells and others are under-expressed. In some embodiments, miRNAs are differentially expressed in cancer cells (WO2008/154098, US2013/0059015, US2013/0042333, WO2011/157294); cancer stem cells (US2012/0053224): pancreatic cancers and diseases (US2009/0131348, US2011/0171646, US2010/0286232, U.S. Pat. No. 8,389,210); asthma and inflammation (U.S. Pat. No. 8,415,096): prostate cancer (US2013/0053264): hepatocellular carcinoma (WO2012/151212, US2012/0329672, WO2008/054828, U.S. Pat. No. 8,252,538): lung cancer cells (WO2011/076143, WO2013/033640, WO2009/070653, US2010/0323357): cutaneous T cell lymphoma (WO2013/011378); colorectal cancer cells (WO2011/0281756, WO2011/076142): cancer positive lymph nodes (WO2009/100430, US2009/0263803): nasopharyngeal carcinoma (EP2112235); chronic obstructive pulmonary disease (US2012/0264626, US2013/0053263): thyroid cancer (WO2013/066678); ovarian cancer cells (US2012/0309645, WO2011/095623): breast cancer cells (WO2008/154098, WO2007/081740, US2012/0214699), leukemia and lymphoma (WO2008/073915, US2009/0092974, US2012/0316081, US2012/0283310, WO2010/018563, the content of each of which is incorporated herein by reference in its entirety.)

As a non-limiting example, miRNA binding sites for miRNAs that are over-expressed in certain cancer and/or tumor cells can be removed from the 3'UTR of a polyribonucleotide of the disclosure, restoring the expression suppressed by the over-expressed miRNAs in cancer cells, thus ameliorating the corresponsive biological function, for instance, transcription stimulation and/or repression, cell cycle arrest, apoptosis and cell death. Normal cells and tissues, wherein miRNAs expression is not up-regulated, will remain unaffected.

MiRNA can also regulate complex biological processes such as angiogenesis (e.g., miR-132) (Anand and Cheresh Curr Opin Hematol 2011 18:171-176). In the polyribonucleotides of the disclosure, miRNA binding sites that are involved in such processes can be removed or introduced, in order to tailor the expression of the polyribonucleotides to biologically relevant cell types or relevant biological processes. In this context, the polyribonucleotides of the disclosure are defined as auxotrophic polyribonucleotides.

Stem Loops

Polynucleotides (e.g., mRNAs) may include a stem loop such as, but not limited to, a histone stem loop. The stem loop may be a nucleotide sequence that is about 25 or about 26 nucleotides in length such as, but not limited to, those as described in International Patent Publication No. WO2013/103659, which is incorporated herein by reference. The histone stem loop may be located 3'-relative to the coding region (e.g., at the 3'-terminus of the coding region). As a non-limiting example, the stem loop may be located at the 3'-end of a polynucleotide described herein. In some cases, a polynucleotide (e.g., an mRNA) includes more than one stem loop (e.g., two stem loops). Examples of stem loop sequences are described in International Patent Publication Nos. WO2012/019780 and WO201502667, the stem loop sequences of which are herein incorporated by reference. In some instances, a polynucleotide includes the stem loop sequence CAAAGGCTCTTTTCAGAGCCACCA (SEQ ID NO: 1). In others, a polynucleotide includes the stem loop sequence CAAAGGCUCUUUUCAGAGCCACCA (SEQ ID NO: 2).

A stem loop may be located in a second terminal region of a polynucleotide. As a non-limiting example, the stem loop may be located within an untranslated region (e.g., 3'-UTR) in a second terminal region.

In some cases, a polynucleotide such as, but not limited to mRNA, which includes the histone stem loop may be stabilized by the addition of a 3'-stabilizing region (e.g., a 3'-stabilizing region including at least one chain terminating nucleoside). Not wishing to be bound by theory, the addition of at least one chain terminating nucleoside may slow the degradation of a polynucleotide and thus can increase the half-life of the polynucleotide.

In other cases, a polynucleotide such as, but not limited to mRNA, which includes the histone stem loop may be stabilized by an alteration to the 3'-region of the polynucleotide that can prevent and/or inhibit the addition of oligio(U) (see e.g., International Patent Publication No. WO2013/103659).

In yet other cases, a polynucleotide such as, but not limited to mRNA, which includes the histone stem loop may be stabilized by the addition of an oligonucleotide that terminates in a 3'-deoxynucleoside, 2',3'-dideoxynucleoside 3'-O-methylnucleosides, 3'-O-ethylnucleosides, 3'-arabinosides, and other alternative nucleosides known in the art and/or described herein.

In some instances, the polynucleotides of the present disclosure may include a histone stem loop, a poly-A region, and/or a 5'-cap structure. The histone stem loop may be before and/or after the poly-A region. The polynucleotides including the histone stem loop and a poly-A region sequence may include a chain terminating nucleoside described herein.

In other instances, the polynucleotides of the present disclosure may include a histone stem loop and a 5'-cap structure. The 5'-cap structure may include, but is not limited to, those described herein and/or known in the art.

In some cases, the conserved stem loop region may include a miR sequence described herein. As a non-limiting example, the stem loop region may include the seed sequence of a miR sequence described herein. In another non-limiting example, the stem loop region may include a miR-122 seed sequence.

In certain instances, the conserved stem loop region may include a miR sequence described herein and may also include a TEE sequence.

In some cases, the incorporation of a miR sequence and/or a TEE sequence changes the shape of the stem loop region which may increase and/or decrease translation. (See, e.g., Kedde et al. A Pumilio-induced RNA structure switch in p27-3'UTR controls miR-221 and miR-22 accessibility. Nature Cell Biology. 2010, herein incorporated by reference in its entirety).

Polynucleotides may include at least one histone stem-loop and a poly-A region or polyadenylation signal. Non-limiting examples of polynucleotide sequences encoding for at least one histone stem-loop and a poly-A region or a polyadenylation signal are described in International Patent Publication No. WO2013/120497, WO2013/120629, WO2013/120500, WO2013/120627, WO2013/120498, WO2013/120626, WO2013/120499 and WO2013/120628, the sequences of each of which are incorporated herein by reference. In certain cases, the polynucleotide encoding for a histone stem loop and a poly-A region or a polyadenylation signal may code for a pathogen antigen or fragment thereof such as the polynucleotide sequences described in International Patent Publication No WO2013/120499 and WO2013/120628, the sequences of both of which are incorporated herein by reference. In other cases, the polynucleotide encoding for a histone stem loop and a poly-A region or a polyadenylation signal may code for a therapeutic protein such as the polynucleotide sequences described in International Patent Publication No WO2013/120497 and WO2013/120629, the sequences of both of which are incorporated herein by reference. In some cases, the polynucleotide encoding for a histone stem loop and a poly-A region or a polyadenylation signal may code for a tumor antigen or fragment thereof such as the polynucleotide sequences described in International Patent Publication No WO2013/120500 and WO2013/120627, the sequences of both of which are incorporated herein by reference. In other cases, the polynucleotide encoding for a histone stem loop and a poly-A region or a polyadenylation signal may code for an allergenic antigen or an autoimmune self-antigen such as the polynucleotide sequences described in International Patent Publication No WO2013/120498 and WO2013/120626, the sequences of both of which are incorporated herein by reference.

Poly-A Regions

A polynucleotide or nucleic acid (e.g., an mRNA) may include a poly A sequence and/or polyadenylation signal. A poly A sequence may be comprised entirely or mostly of adenine nucleotides or analogs or derivatives thereof. A polyA sequence may be a tail located adjacent to a 3' untranslated region of a nucleic acid.

During RNA processing, a long chain of adenosine nucleotides (poly-A region) is normally added to messenger RNA (mRNA) molecules to increase the stability of the molecule. Immediately after transcription, the 3'-end of the transcript is cleaved to free a 3'-hydroxy. Then poly-A polymerase adds a chain of adenosine nucleotides to the RNA. The process, called polyadenylation, adds a poly-A region that is between 100 and 250 residues long.

Unique poly-A region lengths may provide certain advantages to the alternative polynucleotides of the present disclosure.

Generally, the length of a poly-A region of the present disclosure is at least 30 nucleotides in length. In another embodiment, the poly-A region is at least 35 nucleotides in length. In another embodiment, the length is at least 40 nucleotides. In another embodiment, the length is at least 45 nucleotides. In another embodiment, the length is at least 55 nucleotides. In another embodiment, the length is at least 60 nucleotides. In another embodiment, the length is at least 70 nucleotides. In another embodiment, the length is at least 80 nucleotides. In another embodiment, the length is at least 90 nucleotides. In another embodiment, the length is at least 100 nucleotides. In another embodiment, the length is at least 120 nucleotides. In another embodiment, the length is at least 140 nucleotides. In another embodiment, the length is at least 160 nucleotides. In another embodiment, the length is at least 180 nucleotides. In another embodiment, the length is at least 200 nucleotides. In another embodiment, the length is at least 250 nucleotides. In another embodiment, the length is at least 300 nucleotides. In another embodiment, the length is at least 350 nucleotides. In another embodiment, the length is at least 400 nucleotides. In another embodiment, the length is at least 450 nucleotides. In another embodiment, the length is at least 500 nucleotides. In another embodiment, the length is at least 600 nucleotides. In another embodiment, the length is at least 700 nucleotides. In another embodiment, the length is at least 800 nucleotides. In another embodiment, the length is at least 900 nucleotides. In another embodiment, the length is at least 1000 nucleotides. In another embodiment, the length is at least 1100 nucleotides. In another embodiment, the length is at least 1200 nucleotides. In another embodiment, the length is at least 1300 nucleotides. In another embodiment, the length is at least 1400 nucleotides. In another embodiment, the length is at least 1500 nucleotides. In another embodiment, the length is at least 1600 nucleotides. In another embodiment, the length is at least 1700 nucleotides. In another embodiment, the length is at least 1800 nucleotides. In another embodiment, the length is at least 1900 nucleotides. In another embodiment, the length is at least 2000 nucleotides. In another embodiment, the length is at least 2500 nucleotides. In another embodiment, the length is at least 3000 nucleotides.

In some instances, the poly-A region may be 80 nucleotides, 120 nucleotides, 160) nucleotides in length on an alternative polynucleotide molecule described herein.

In other instances, the poly-A region may be 20, 40, 80, 100, 120, 140 or 160 nucleotides in length on an alternative polynucleotide molecule described herein.

In some cases, the poly-A region is designed relative to the length of the overall alternative polynucleotide. This design may be based on the length of the coding region of the alternative polynucleotide, the length of a particular feature or region of the alternative polynucleotide (such as mRNA), or based on the length of the ultimate product expressed from the alternative polynucleotide. When relative to any feature of the alternative polynucleotide (e.g., other than the mRNA portion which includes the poly-A region) the poly-A region may be 10, 20, 30, 40, 50, 60, 70, 80, 90 or 100% greater in length than the additional feature. The poly-A region may also be designed as a fraction of the alternative polynucleotide to which it belongs. In this context, the poly-A region may be 10, 20, 30, 40, 50, 60, 70, 80, or 90% or more of the total length of the construct or the total length of the construct minus the poly-A region.

In certain cases, engineered binding sites and/or the conjugation of polynucleotides (e.g., mRNA) for poly-A binding protein may be used to enhance expression. The engineered binding sites may be sensor sequences which can operate as binding sites for ligands of the local microenvironment of the polynucleotides (e.g., mRNA). As a non-limiting example, the polynucleotides (e.g., mRNA) may include at least one engineered binding site to alter the binding affinity of poly-A binding protein (PABP) and analogs thereof. The incorporation of at least one engineered binding site may increase the binding affinity of the PABP and analogs thereof.

Additionally, multiple distinct polynucleotides (e.g., mRNA) may be linked together to the PABP (poly-A binding protein) through the 3'-end using alternative nucleotides at the 3'-terminus of the poly-A region. Transfection experiments can be conducted in relevant cell lines at and protein production can be assayed by ELISA at 12 hours, 24 hours, 48 hours, 72 hours, and day 7 post-transfection. As a non-limiting example, the transfection experiments may be used to evaluate the effect on PABP or analogs thereof binding affinity as a result of the addition of at least one engineered binding site.

In certain cases, a poly-A region may be used to modulate translation initiation. While not wishing to be bound by theory, the poly-A region recruits PABP which in turn can interact with translation initiation complex and thus may be essential for protein synthesis.

In some cases, a poly-A region may also be used in the present disclosure to protect against 3'-5'-exonuclease digestion.

In some instances, a polynucleotide (e.g., mRNA) may include a polyA-G Quartet. The G-quartet is a cyclic hydrogen bonded array of four guanosine nucleotides that can be formed by G-rich sequences in both DNA and RNA. In this embodiment, the G-quartet is incorporated at the end of the poly-A region. The resultant polynucleotides (e.g., mRNA) may be assayed for stability, protein production and other parameters including half-life at various time points. It has been discovered that the poly A-G quartet results in protein production equivalent to at least 75% of that seen using a poly-A region of 120 nucleotides alone.

In some cases, a polynucleotide (e.g., mRNA) may include a poly-A region and may be stabilized by the addition of a 3'-stabilizing region. The polynucleotides (e.g., mRNA) with a poly-A region may further include a 5'-cap structure.

In other cases, a polynucleotide (e.g., mRNA) may include a poly-A-G Quartet. The polynucleotides (e.g., mRNA) with a poly-A-G Quartet may further include a 5'-cap structure.

In some cases, the 3'-stabilizing region which may be used to stabilize a polynucleotide (e.g., mRNA) including a poly-A region or poly-A-G Quartet may be, but is not limited to, those described in International Patent Publication No. WO2013/103659, the poly-A regions and poly-A-G Quartets of which are incorporated herein by reference. In other cases, the 3'-stabilizing region which may be used with the present disclosure include a chain termination nucleoside such as 3'-deoxyadenosine (cordycepin), 3'-deoxyuridine, 3'-deoxycytosine, 3'-deoxyguanosine, 3'-deoxy thymine, 2',3'-dideoxynucleosides, such as 2',3'-dideoxyadenosine, 2',3'-dideoxyuridine, 2',3'-dideoxycytosine, 2',3'-dideoxyguanosine, 2',3'-dideoxy thymine, a 2'-deoxynucleoside, or an O-methylnucleoside.

In other cases, a polynucleotide such as, but not limited to mRNA, which includes a poly A region or a poly-A-G Quartet may be stabilized by an alteration to the 3'-region of the polynucleotide that can prevent and/or inhibit the addition of oligio(U) (see e.g., International Patent Publication No. WO2013/103659).

In yet other instances, a polynucleotide such as, but not limited to mRNA, which includes a poly-A region or a poly-A-G Quartet may be stabilized by the addition of an oligonucleotide that terminates in a 3'-deoxynucleoside, 2',3'-dideoxynucleoside 3'-O-methylnucleosides, 3'-O-ethylnucleosides, 3'-arabinosides, and other alternative nucleosides known in the art and/or described herein.

Chain Terminating Nucleosides

A nucleic acid may include a chain terminating nucleoside. In some embodiments, a chain terminating nucleoside may include those nucleosides deoxygenated at the 2' and/or 3' positions of their sugar group. Such species may include 3'-deoxyadenosine (cordycepin), 3'-deoxyuridine, 3'-deoxycytosine, 3'-deoxyguanosine, 3'-deoxythymine, and 2',3'-dideoxynucleosides, such as 2',3'-dideoxyadenosine, 2',3'-dideoxyuridine, 2',3'-dideoxycytosine, 2',3'-dideoxyguanosine, and 2',3'-dideoxy thymine.

Genome Editing Techniques

In some embodiments, the nucleic acid is suitable for a genome editing technique.

In some embodiments, the genome editing technique is clustered regularly interspaced short palindromic repeats (CRISPR) or transcription activator-like effector nuclease (TALEN).

In some embodiments, the nucleic acid is at least one nucleic acid suitable for a genome editing technique selected from the group consisting of a CRISPR RNA (crRNA), a trans-activating crRNA (tracrRNA), a single guide RNA (sgRNA), and a DNA repair template.

Vaccines

In some embodiments, the therapeutic and/or prophylactic is a ribonucleic acid (RNA) cancer vaccine of an RNA (e.g., messenger RNA (mRNA)) that can safely direct the body's cellular machinery to produce nearly any cancer protein or fragment thereof of interest. In some embodiments, the RNA is a modified RNA. The RNA vaccines of the present disclosure may be used to induce a balanced immune response against cancers, comprising both cellular and humoral immunity, without risking the possibility of insertional mutagenesis, for example.

The RNA vaccines may be utilized in various settings depending on the prevalence of the cancer or the degree or level of unmet medical need. The RNA vaccines may be utilized to treat and/or prevent a cancer of various stages or degrees of metastasis. The RNA vaccines have superior properties in that they produce much larger antibody titers and produce responses earlier than alternative anti-cancer therapies including cancer vaccines. While not wishing to be bound by theory, it is believed that the RNA vaccines, as mRNA polynucleotides, are better designed to produce the appropriate protein conformation upon translation as the RNA vaccines co-opt natural cellular machinery. Unlike traditional vaccines which are manufactured ex vivo and may trigger unwanted cellular responses, the RNA vaccines are presented to the cellular system in a more native fashion.

Some embodiments of the present disclosure provide cancer vaccines that include at least one ribonucleic acid (RNA) polynucleotide having an open reading frame encoding at least one cancer antigenic polypeptide or an immunogenic fragment thereof {e.g., an immunogenic fragment capable of inducing an immune response to cancer). Other embodiments include at least one ribonucleic acid (RNA) polynucleotide having an open reading frame encoding two or more antigens or epitopes capable of inducing an immune response to cancer.

The invention in some aspects is a vaccine of a mRNA having an open reading frame encoding a cancer antigen and a mRNA having an open reading frame encoding an immune checkpoint modulator. In some embodiments the immune checkpoint modulator is an inhibitory checkpoint polypeptide. In some embodiments, the inhibitory checkpoint polypeptide is an antibody or fragment thereof that specifically binds to a molecule selected from the group consisting of PD-1, TIM-3, VISTA, A2AR, B7-H3, B7-H4, BTLA, CTLA-4, IDO, KIR and LAG3. The inhibitory checkpoint polypeptide is an anti-CTLA4 or anti-PDI antibody in some embodiments. Optionally the vaccine includes a lipid nanoparticle. In some embodiments a vaccine of a mRNA having an open reading frame encoding a cancer antigen is administered to a subject. In other embodiments a checkpoint inhibitor 3-10 weeks later. In some embodiments the checkpoint inhibitor is administered 4 weeks later.

In other aspects the invention is a personalized cancer vaccine of a mRNA having an open reading frame encoding at least 2 cancer antigens, wherein the at least 2 cancer antigens are patient specific cancer antigens, and a lipid nanoparticle carrier. In some embodiments the lipid nanoparticle has a mean diameter of 50-200 nm.

In yet other aspects, the invention is a personalized cancer vaccine of a mRNA having an open reading frame encoding at least 2 cancer antigens wherein the at least 2 cancer antigens are representative of antigens of a patient. In some embodiments, the antigens of a patient are exosome identified antigens of the patient. In some embodiments a single mRNA encodes the cancer antigens. In other embodiments a plurality of mRNA encode the cancer antigens.

Each mRNA may encode 5-10 cancer antigens or a single cancer antigen in other embodiments. In some embodiments the mRNA encodes 2-100 cancer antigens. In other embodiments mRNA encodes 10-100, 20-100, 50-100, 100-200, 300-400, 500-600, 600-700, 700-800, 900-1,000, or 1,000-10,000 cancer antigens.

In some embodiments, a) the mRNA encoding each cancer antigen is interspersed by cleavage sensitive sites;
b) the mRNA encoding each cancer antigen is linked directly to one another without a linker;
c) the mRNA encoding each cancer antigen is linked to one another with a single nucleotide linker;
d) each cancer antigen comprises a 25-35 amino acids and includes a centrally located SNP mutation;
e) at least 30% of the cancer antigens have a highest affinity for class I MHC molecules from the subject;
f) at least 30% of the cancer antigens have a highest affinity for class II MHC molecules from the subject;
g) at least 50% of the cancer antigens have a predicted binding affinity of IC >500 nM for HLA-A, HLA-B and/or DRB 1;
h) the mRNA encodes 20 cancer antigens;
i) 50% of the cancer antigens have a binding affinity for class I MHC and 50% of the cancer antigens have a binding affinity for class II MHC; and/or
j) the mRNA encoding the cancer antigens is arranged such that the cancer antigens are ordered to minimize pseudo-epitopes.

In some embodiments, each cancer antigen comprises 31 amino acids and includes a centrally located SNP mutation with 15 flanking amino acids on each side of the SNP mutation.

In some embodiments the vaccine is a personalized cancer vaccine and wherein the cancer antigen is a subject specific cancer antigen. In some embodiments, the subject specific cancer antigen may be representative of an exome of a tumor sample of the subject, or of a transcriptome of a tumor sample of the subject. In some embodiments, the subject specific cancer antigen may be representative of an exosome of the subject.

In some embodiments, the open reading frame further encodes one or more traditional cancer antigens. In some embodiments, the traditional cancer antigen is a non-mutated antigen. In some embodiments, the traditional cancer antigen is a mutated antigen.

In some embodiments, the mRNA vaccine further comprises an mRNA having an open reading frame encoding one or more traditional cancer antigens.

In some embodiments a single mRNA encodes the cancer antigens. In other embodiments a plurality of mRNA encode the cancer antigens. Each cancer antigen is 10-50 amino acids in length in some embodiments. In other embodiments each cancer antigen is 15-20 amino acids in length. In other embodiments the cancer antigen is 20-50, 25-100, 100-200, 200-300, 300-400, 400-500, 500-1,000, or 1,000-10,000 amino acids in length.

In some embodiments, the vaccines further comprise an adjuvant.

Some embodiments of the present disclosure provide a cancer vaccine that includes at least one ribonucleic acid (RNA) polynucleotide having an open reading frame encoding at least one cancer polypeptide, at least one 5' terminal cap and at least one chemical modification, formulated within a lipid nanoparticle. In some embodiments, a 5' terminal cap is 7mG(5')ppp(5')N1mpNp.

In some embodiments, at least one chemical modification is selected from pseudouridine, N1-methylpseudouridine, N1-ethylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methoxyuridine and 2'-O-methyl uridine. In some embodiments the extent of incorporation of chemically modified nucleotides has been optimized for improved immune responses to the vaccine formulation.

In some embodiments, a lipid nanoparticle comprises a cationic lipid, a PEG-modified lipid, a sterol and a non-cationic lipid. In some embodiments, a cationic lipid is an ionizable cationic lipid and the non-cationic lipid is a neutral lipid, and the sterol is a cholesterol. In some embodiments, a cationic lipid is selected from 2,2-dilinoleyl-4-dimethylaminoethyl-[1,3]-dioxolane (DLin-KC2-DMA), dilinoleylmethyl-4-dimethylaminobutyrate (DLin-MC3-DMA), and di((Z)-non-2-en-1-yl) 9-((4-(dimethylamino)butanoyl)oxy) heptadecanedioate (L319).

In some embodiments the lipid nanoparticle formulation includes an immune potentiator (e.g., TLR agonist) to enhance immunogenicity of the vaccine (formulation).

In some embodiments, 100% of the uracil in the open reading frame have a chemical modification. In some embodiments, a chemical modification is in the 5-position of the uracil. In some embodiments, a chemical modification is a N1-methyl pseudouridine.

In other embodiments a mRNA encoding an APC reprograming molecule is included in the vaccine or coadministered with the vaccine. The APC reprograming molecule may be a CIITA, a chaperone protein such as CLIP, HLA-DO, HLA-DM, a costimulatory molecule such as CD40, CD80, CD86, a CIITA fragment such as amino acids 26-137 of CIITA or a protein having 80% sequence identity to CIITA.

In other aspects a method of eliciting an immune response in a subject by identifying at least 2 cancer antigens from a sample of a subject, wherein the at least 2 cancer antigens include mutations selected from the group consisting of frame-shift mutations and recombinations, and administering a mRNA vaccine having an open reading frame encoding the at least 2 cancer antigens to the subject is provided.

In some embodiments, the cancer antigens are identified from an exosome of the subject. In some embodiments 2-100 antigens are identified from the exosome. In other embodiments the mRNA vaccine has an open reading frame encoding the 2-100 antigens. A single mRNA or a plurality of mRNA may encode the antigens.

In some embodiments the antigens are cancer antigens. The cancer antigens may have mutations selected from point mutations, frame-shift mutations and recombinations. The method may further involve confirming that the cancer antigens are subject specific by exome analysis.

In some embodiments the method may further involve confirming that the cancer antigens are subject specific by transcriptome analysis.

In some embodiments the method also involves at least one month after the administration of the mRNA vaccine, identifying at least 2 cancer antigens from a sample of the subject to produce a second set of cancer antigens, and administering to the subject a mRNA vaccine having an open reading frame encoding the second set of cancer antigens to the subject.

In other embodiments the sample of the subject is a tumor sample.

In other aspects the invention comprises a method of eliciting an immune response in a subject by identifying at least 2 cancer antigens from a sample of a subject to produce a first set of cancer antigens, administering to the subject a mRNA vaccine having an open reading frame encoding the first set of cancer antigens to the subject, at least one month after the administration of the mRNA vaccine, identifying at least 2 cancer antigens from a sample of a subject to produce a second set of cancer antigens, and administering to the subject a mRNA vaccine having an open reading frame encoding the second set of cancer antigens to the subject.

The mRNA vaccine having an open reading frame encoding second set of antigens, in some embodiments, is administered to the subject 6 months to 1 year after the mRNA vaccine having an open reading frame encoding first set of cancer antigens. In other embodiments the mRNA vaccine having an open reading frame encoding second set of antigens is administered to the subject 1-2 years after the mRNA vaccine having an open reading frame encoding first set of cancer antigens.

In some embodiments a single mRNA has an open reading frame encoding the cancer antigens. In other embodiments a plurality of mRNA encode the antigens. In some embodiments the second set of cancer antigens includes 2-100 antigens. In other embodiments the cancer antigens have mutations selected from point mutations, frame-shift mutations and recombinations.

In other aspects the invention comprises a method of eliciting an immune response in a subject, by identifying at least 2 cancer antigens from a sample of a subject, administering a mRNA having an open reading frame encoding the at least 2 cancer antigens to the subject, and administering a cancer therapeutic agent to the subject. In some embodiments the cancer therapeutic agent is a targeted therapy. The targeted therapy may be a BRAF inhibitor such as vemurafenib (PLX4032) or dabrafenib.

In other embodiments the cancer therapeutic agent is a T-cell therapeutic agent. The T-cell therapeutic agent may be a checkpoint inhibitor such as an anti-PD-1 antibody or an anti-CTLA-4 antibody. In some embodiments the anti-PD-1 antibody is BMS-936558 (nivolumab). In other embodiments the anti-CTLA-4 antibody is ipilimumab. The T-cell therapeutic agent in other embodiments is OX40L. In yet other embodiments the cancer therapeutic agent is a vaccine comprising a population based tumor specific antigen.

In other embodiments the cancer therapeutic agent is a vaccine comprising an mRNA having an open reading frame encoding one or more traditional cancer antigens.

In some embodiments, the mRNA having an open reading frame encoding the at least 2 cancer antigens is administered to the subject simultaneously with the cancer therapeutic agent. In some embodiments, the mRNA having an open reading frame encoding the at least 2 cancer antigens is administered to the subject before administration of the cancer therapeutic agent. In some embodiments, the mRNA having an open reading frame encoding the at least 2 cancer antigens is administered to the subject after administration of the cancer therapeutic agent.

A method comprising mixing a mRNA having an open reading frame encoding a cancer antigen with a lipid nanoparticle formulation to produce a mRNA cancer vaccine, and administering the mRNA cancer vaccine to a subject within 24 hours of mixing is provided in other aspects of the invention. In some embodiments the mRNA cancer vaccine is administered to the subject within 12 hours of mixing. In other embodiments the mRNA cancer vaccine is administered to the subject within 1 hour of mixing. The mRNA cancer vaccine encodes 2-100 cancer antigens or 10-100 cancer antigens in some embodiments.

In some embodiments the vaccine is a personalized cancer vaccine and wherein the cancer antigen is a subject specific cancer antigen.

In some embodiments a single mRNA encodes the cancer antigens. In other embodiments a plurality of mRNA encode the cancer antigens. Each mRNA encodes 5-10 cancer antigens or a single cancer antigen in other embodiments. In yet other embodiments each cancer antigen is 10-50 amino acids in length or 15-20 amino acids in length.

Further provided herein are uses of cancer vaccines in the manufacture of a medicament for use in a method of inducing an antigen specific immune response in a subject, the method comprising administering the cancer vaccine to the subject in an amount effective to produce an antigen specific immune response.

A method of treating cancer in a subject in need thereof by identifying at least 2 cancer antigens from an exosome isolated from the subject: producing, based on the identified antigens, a mRNA vaccine having an open reading frame encoding the antigens; and administering the mRNA vaccine to the subject, wherein the mRNA vaccine induces a tumor-specific immune response in the subject, thereby treating cancer in the subject is provided in other aspects. The invention in other aspects is a RNA vaccine preparable according to a method involving identifying at least 2 cancer antigens from an exosome isolated from a subject: producing, based on the identified antigens, a mRNA vaccine having an open reading frame encoding the antigens.

A method of eliciting an immune response in a subject against a cancer antigen is provided in aspects of the invention. The method involves administering to the subject a RNA vaccine comprising at least one RNA polynucleotide having an open reading frame encoding at least one antigenic polypeptide or an immunogenic fragment thereof, thereby inducing in the subject an immune response specific to the antigenic polypeptide or an immunogenic fragment thereof, wherein the anti-antigenic polypeptide antibody titer in the subject is increased following vaccination relative to anti-antigenic polypeptide antibody titer in a subject vaccinated with a prophylactically effective dose of a traditional vaccine against the cancer. An "anti-antigenic polypeptide antibody" is a serum antibody the binds specifically to the antigenic polypeptide.

A prophylactically effective dose is a therapeutically effective dose that prevents advancement of cancer at a clinically acceptable level. In some embodiments the therapeutically effective dose is a dose listed in a package insert for the vaccine. A traditional vaccine, as used herein, refers to a vaccine other than the mRNA vaccines of the invention. For instance, a traditional vaccine includes but is not limited to live microorganism vaccines, killed microorganism vaccines, subunit vaccines, protein antigen vaccines, DNA vaccines, etc. In exemplary embodiments, a traditional vaccine is a vaccine that has achieved regulatory approval and/or is registered by a national drug regulatory body, for example the Food and Drug Administration (FDA) in the United States or the European Medicines Agency (EMA.)

In some embodiments the anti-antigenic polypeptide antibody titer in the subject is increased 1 log to 10 log following vaccination relative to anti-antigenic polypeptide antibody titer in a subject vaccinated with a prophylactically effective dose of a traditional vaccine against the cancer.

In some embodiments the anti-antigenic polypeptide antibody titer in the subject is increased 1 log following vaccination relative to anti-antigenic polypeptide antibody titer in a subject vaccinated with a prophylactically effective dose of a traditional vaccine against the cancer.

In some embodiments the anti-antigenic polypeptide antibody titer in the subject is increased 2 log following vaccination relative to anti-antigenic polypeptide antibody titer in a subject vaccinated with a prophylactically effective dose of a traditional vaccine against the cancer.

In some embodiments the anti-antigenic polypeptide antibody titer in the subject is increased 3 log following vaccination relative to anti-antigenic polypeptide antibody titer in a subject vaccinated with a prophylactically effective dose of a traditional vaccine against the cancer.

In some embodiments the anti-antigenic polypeptide antibody titer in the subject is increased 5 log following vaccination relative to anti-antigenic polypeptide antibody titer in a subject vaccinated with a prophylactically effective dose of a traditional vaccine against the or cancer.

In some embodiments the anti-antigenic polypeptide antibody titer in the subject is increased 10 log following vaccination relative to anti-antigenic polypeptide antibody titer in a subject vaccinated with a prophylactically effective dose of a traditional vaccine against the or cancer.

A method of eliciting an immune response in a subject against a cancer antigen is provided in other aspects of the invention. The method involves administering to the subject a RNA vaccine comprising at least one RNA polynucleotide having an open reading frame encoding at least one antigenic polypeptide or an immunogenic fragment thereof, thereby inducing in the subject an immune response specific to antigenic polypeptide or an immunogenic fragment thereof, wherein the immune response in the subject is equivalent to an immune response in a subject vaccinated with a traditional vaccine against the cancer antigen at 2 times to 100 times the dosage level relative to the RNA vaccine.

In some embodiments the immune response in the subject is equivalent to an immune response in a subject vaccinated with a traditional vaccine at twice the dosage level relative to the RNA vaccine.

In some embodiments the immune response in the subject is equivalent to an immune response in a subject vaccinated with a traditional vaccine at three times the dosage level relative to the RNA vaccine.

In some embodiments the immune response in the subject is equivalent to an immune response in a subject vaccinated with a traditional vaccine at 4 times the dosage level relative to the RNA vaccine.

In some embodiments the immune response in the subject is equivalent to an immune response in a subject vaccinated with a traditional vaccine at 5 times the dosage level relative to the RNA vaccine. In some embodiments the immune response in the subject is equivalent to an immune response in a subject vaccinated with a traditional vaccine at 10 times the dosage level relative to the RNA vaccine.

In some embodiments the immune response in the subject is equivalent to an immune response in a subject vaccinated with a traditional vaccine at 50 times the dosage level relative to the RNA vaccine.

In some embodiments the immune response in the subject is equivalent to an immune response in a subject vaccinated with a traditional vaccine at 100 times the dosage level relative to the RNA vaccine.

In some embodiments the immune response in the subject is equivalent to an immune response in a subject vaccinated with a traditional vaccine at 10 times to 1000 times the dosage level relative to the RNA vaccine.

In some embodiments the immune response in the subject is equivalent to an immune response in a subject vaccinated with a traditional vaccine at 100 times to 1000 times the dosage level relative to the RNA vaccine.

In other embodiments the immune response is assessed by determining antibody titer in the subject.

In other aspects the invention comprises a method of eliciting an immune response in a subject against a by administering to the subject a RNA vaccine comprising at least one RNA polynucleotide having an open reading frame encoding at least one cancer antigenic polypeptide or an immunogenic fragment thereof, thereby inducing in the subject an immune response specific to the antigenic polypeptide or an immunogenic fragment thereof, wherein the immune response in the subject is induced 2 days to 10 weeks earlier relative to an immune response induced in a subject vaccinated with a prophylactically effective dose of a traditional vaccine against the cancer antigen. In some embodiments the immune response in the subject is induced in a subject vaccinated with a prophylactically effective dose of a traditional vaccine at 2 times to 100 times the dosage level relative to the RNA vaccine.

In some embodiments the immune response in the subject is induced 2 days earlier relative to an immune response induced in a subject vaccinated with a prophylactically effective dose of a traditional vaccine.

In some embodiments the immune response in the subject is induced 3 days earlier relative to an immune response induced in a subject vaccinated a prophylactically effective dose of a traditional vaccine. In some embodiments the immune response in the subject is induced 1 week earlier relative to an immune response induced in a subject vaccinated with a prophylactically effective dose of a traditional vaccine.

In some embodiments the immune response in the subject is induced 2 weeks earlier relative to an immune response induced in a subject vaccinated with a prophylactically effective dose of a traditional vaccine.

In some embodiments the immune response in the subject is induced 3 weeks earlier relative to an immune response induced in a subject vaccinated with a prophylactically effective dose of a traditional vaccine.

In some embodiments the immune response in the subject is induced 5 weeks earlier relative to an immune response induced in a subject vaccinated with a prophylactically effective dose of a traditional vaccine.

In some embodiments the immune response in the subject is induced 10 weeks earlier relative to an immune response induced in a subject vaccinated with a prophylactically effective dose of a traditional vaccine.

A method of eliciting an immune response in a subject against an cancer by administering to the subject a cancer RNA vaccine having an open reading frame encoding a first antigenic polypeptide, wherein the RNA polynucleotide does not include a stabilization element, and wherein an adjuvant is not coformulated or co-administered with the vaccine.

In yet other aspects the invention comprises a method of producing an mRNA encoding a concatemeric cancer antigen comprising between 1000 and 3000 nucleotides, the method by (a) binding a first polynucleotide comprising an open reading frame encoding the concatemeric cancer antigen and a second polynucleotide comprising a 5'-UTR to a polynucleotide conjugated to a solid support;
(b) ligating the 3 '-terminus of the second polynucleotide to the 5'-terminus of the first polynucleotide under suitable conditions, wherein the suitable conditions comprise a DNA Ligase, thereby producing a first ligation product;
(c) ligating the 5' terminus of a third polynucleotide comprising a 3'-UTR to the 3'-terminus of the first ligation product under suitable conditions, wherein the suitable conditions comprise an RNA Ligase, thereby producing a second ligation product; and
(d) releasing the second ligation product from the solid support, thereby producing an mRNA encoding the concatemeric cancer antigen comprising between 1000 and 3000 nucleotides. In some embodiments of any one of the provided compositions or methods, the mRNA encodes one or more recurrent polymorphisms. In some embodiments, the one or more recurrent polymorphisms comprises a recurrent somatic cancer mutation in p53. In some such embodiments, the one or more recurrent somatic cancer mutation in p53 are selected from the group consisting of:
(1) mutations at the canonical 5' splice site neighboring codon p.T125;
(2) mutations at the canonical 5' splice site neighboring codon p.331;
(3) mutations at the canonical 3' splice site neighboring codon p.126;
(4) mutations at the canonical 5' splice site neighboring codon p.224, inducing a cryptic alternative intronic 5' splice site.

In some embodiments, the invention provides a cancer therapeutic vaccine comprising mRNA encoding an open reading frame (ORF) coding for one or more of neoantigen peptides (1) through (4). In some embodiments, the invention provides the selective administration of a vaccine containing or coding for one or more of peptides (1)-(4), based on the patient's tumor containing any of the above mutations. In some embodiments, the invention provides the selective administration of the vaccine based on the dual criteria of the subject's tumor containing any of the above mutations and the subject's normal HLA type containing the corresponding HLA allele predicted to bind to the resulting neoantigen.

A method for treating a subject with a personalized mRNA cancer vaccine, by isolating a sample from a subject, identifying a set of neoepitopes by analyzing a patient transcriptome and/or a patient exome from the sample to produce a patient specific mutanome, selecting a set of neoepitopes for the vaccine from the mutanome based on MHC binding strength, MHC binding diversity, predicted degree of immunogenicity, low self reactivity, and/or T cell reactivity, preparing the mRNA vaccine to encode the set of neoepitopes and administering the mRNA vaccine to the subject within two months of isolating the sample from the subject is provided in other aspects of the invention. In some embodiments the mRNA vaccine is administered to the subject within one month of isolating the sample from the subject.

In other aspects the invention comprises a method of identifying a set of neoepitopes for use in a personalized mRNA cancer vaccine having one or more polynucleotides that encode the set of neoepitopes by a. identifying a patient specific mutanome by analyzing a patient transcriptome and a patient exome, b. selecting a subset of 15-500 neoepitopes from the mutanome using a weighted value for the neoepitopes based on at least three of: an assessment of gene or transcript-level expression in patient RNA-seq; variant call confidence score: RNA-seq allele-specific expression: conservative vs. non-conservative amino acid substitution: position of point mutation (Centering Score for increased TCR engagement): position of point mutation (Anchoring Score for differential HLA binding): Selfness: <100% core epitope homology with patient WES data: HLA-A and -B IC50 for 8mers-11mers: HLA-DRB 1 IC50 for 15mers-20mers: promiscuity Score (i.e. number of patient HLAs predicted to bind): HLA-C IC50 for 8mers-1 Imers: HLA-DRB3-5 IC50 for 15mers-20mers: HLA-DQB 1/A1 IC50 for 15mers-20mers: HLA-DPB 1/A1 IC50 for 15mers-20mers: Class I vs Class II proportion: Diversity of patient HLA-A, -B and DRB 1 allotypes covered: proportion of point mutation vs complex epitopes (e.g. frameshifts); and/or pseudo-epitope HLA binding scores, and c. selecting the set of neoepitopes for use in a personalized mRNA cancer vaccine from the subset based on the highest weighted value, wherein the set of neoepitopes comprise 15-40 neoepitopes.

In some embodiments the nucleic acid vaccines described herein are chemically modified. In other embodiments the nucleic acid vaccines are unmodified.

Yet other aspects provide compositions for and methods of vaccinating a subject comprising administering to the subject a nucleic acid vaccine comprising one or more RNA polynucleotides having an open reading frame encoding a first antigenic polypeptide or a concatemeric polypeptide, wherein the RNA polynucleotide does not include a stabilization element, and wherein an adjuvant is not coformulated or co-administered with the vaccine.

In other aspects the invention is a composition for or method of vaccinating a subject comprising administering to the subject a nucleic acid vaccine comprising one or more RNA polynucleotides having an open reading frame encoding a first antigenic polypeptide wherein a dosage of between 10 ug/kg and 400 ug/kg of the nucleic acid vaccine is administered to the subject. In some embodiments the dosage of the RNA polynucleotide is 1-5 ug, 5-10 ug, 10-15 ug, 15-20 ug, 10-25 ug, 20-25 ug, 20-50 ug, 30-50 ug, 40-50 ug, 40-60 ug, 60-80 ug, 60-100 ug, 50-100 ug, 80-120 ug, 40-120 ug, 40-150 ug, 50-150 ug, 50-200 ug, 80-200 ug, 100-200 ug, 120-250 ug, 150-250 ug, 180-280 ug, 200-300 ug, 50-300 ug, 80-300 ug, 100-300 ug, 40-300 ug, 50-350 ug, 100-350 ug, 200-350 ug, 300-350 ug, 320-400 ug, 40-380 ug, 40-100 ug, 100-400 ug, 200-400 ug, or 300-400 ug per dose. In some embodiments, the nucleic acid vaccine is administered to the subject by intradermal or intramuscular injection. In some embodiments, the nucleic acid vaccine is administered to the subject on day zero. In some embodiments, a second dose of the nucleic acid vaccine is administered to the subject on day twenty one.

In some embodiments, a dosage of 25 micrograms of the RNA polynucleotide is included in the nucleic acid vaccine administered to the subject. In some embodiments, a dosage of 100 micrograms of the RNA polynucleotide is included in the nucleic acid vaccine administered to the subject. In some embodiments, a dosage of 50 micrograms of the RNA polynucleotide is included in the nucleic acid vaccine administered to the subject. In some embodiments, a dosage of 75 micrograms of the RNA polynucleotide is included in the nucleic acid vaccine administered to the subject. In some embodiments, a dosage of 150 micrograms of the RNA polynucleotide is included in the nucleic acid vaccine administered to the subject. In some embodiments, a dosage of 400 micrograms of the RNA polynucleotide is included in the nucleic acid vaccine administered to the subject. In some embodiments, a dosage of 200 micrograms of the RNA polynucleotide is included in the nucleic acid vaccine administered to the subject. In some embodiments, the RNA polynucleotide accumulates at a 100 fold higher level in the local lymph node in comparison with the distal lymph node. In other embodiments the nucleic acid vaccine is chemically modified and in other embodiments the nucleic acid vaccine is not chemically modified.

Aspects of the invention provide a nucleic acid vaccine comprising one or more RNA polynucleotides having an open reading frame encoding a first antigenic polypeptide or a concatemeric polypeptide, wherein the RNA polynucleotide does not include a stabilization element, and a pharmaceutically acceptable carrier or excipient, wherein an adjuvant is not included in the vaccine. In some embodiments, the stabilization element is a histone stem-loop. In some embodiments, the stabilization element is a nucleic acid sequence having increased GC content relative to wild type sequence.

Aspects of the invention provide nucleic acid vaccines comprising one or more RNA polynucleotides having an open reading frame encoding a first antigenic polypeptide, wherein the RNA polynucleotide is present in the formulation for in vivo administration to a host, which confers an antibody titer superior to the criterion for seroprotection for the first antigen for an acceptable percentage of human subjects. In some embodiments, the antibody titer produced by the mRNA vaccines of the invention is a neutralizing antibody titer. In some embodiments the neutralizing antibody titer is greater than a protein vaccine. In other embodiments the neutralizing antibody titer produced by the mRNA vaccines of the invention is greater than an adjuvanted protein vaccine. In yet other embodiments the neutralizing antibody titer produced by the mRNA vaccines of the invention is 1,000-10,000, 1,200-10,000, 1,400-10,000, 1,500-10,000, 1,000-5,000, 1,000-4,000, 1,800-10,000, 2000-10,000, 2,000-5,000, 2,000-3,000, 2,000-4,000, 3,000-5,000, 3,000-4,000, or 2,000-2,500. A neutralization titer is typically expressed as the highest serum dilution required to achieve a 50% reduction in the number of plaques.

In preferred aspects, vaccines of the invention (e.g., LNP-encapsulated mRNA vaccines) produce prophylactically- and/or therapeutically-efficacious levels, concentrations and/or titers of antigen-specific antibodies in the blood or serum of a vaccinated subject. As defined herein, the term antibody titer refers to the amount of antigen-specific antibody produces in s subject, e.g., a human subject. In exemplary embodiments, antibody titer is expressed as the inverse of the greatest dilution (in a serial dilution) that still gives a positive result. In exemplary embodiments, antibody titer is determined or measured by enzyme-linked immunosorbent assay (ELISA). In exemplary embodiments, antibody titer is determined or measured by neutralization assay, e.g., by microneutralization assay. In certain aspects, antibody titer measurement is expressed as a ratio, such as 1:40, 1:100, etc.

In exemplary embodiments of the invention, an efficacious vaccine produces an antibody titer of greater than 1:40, greater that 1:100, greater than 1:400, greater than 1:1000, greater than 1:2000, greater than 1:3000, greater than 1:4000, greater than 1:500, greater than 1:6000, greater than 1:7500, greater than 1:10000. In exemplary embodiments, the antibody titer is produced or reached by 10 days following vaccination, by 20 days following vaccination, by 30 days following vaccination, by 40 days following vaccination, or by 50 or more days following vaccination. In exemplary embodiments, the titer is produced or reached following a single dose of vaccine administered to the subject. In other embodiments, the titer is produced or reached following multiple doses, e.g., following a first and a second dose (e.g., a booster dose.)

In exemplary aspects of the invention, antigen-specific antibodies are measured in units of μg/ml or are measured in units of IU/L (International Units per liter) or mIU/ml (milli International Units per ml). In exemplary embodiments of the invention, an efficacious vaccine produces >0.5 μg/ml, >0.1 μg/ml, >0.2 μg/ml, >0.35 μg/ml, >0.5 μg/ml, >1 μg/ml, >2 μg/ml, >5 μg/ml or >10 μg/ml. In exemplary embodiments of the invention, an efficacious vaccine produces >10 mIU/ml, >20 mIU/ml, >50 mIU/ml, >100 mIU/ml, >200 mIU/ml, >500 mIU/ml or >1000 mIU/ml. In exemplary embodiments, the antibody level or concentration is produced or reached by 10 days following vaccination, by 20 days following vaccination, by 30 days following vaccination, by 40 days following vaccination, or by 50 or more days following vaccination. In exemplary embodiments, the level or concentration is produced or reached following a single dose of vaccine administered to the subject. In other embodiments, the level or concentration is produced or reached following multiple doses, e.g., following a first and a second dose (e.g., a booster dose.) In exemplary embodiments, antibody level or concentration is determined or measured by enzyme-linked immunosorbent assay (ELISA). In exemplary embodiments, antibody level or concentration is determined or measured by neutralization assay, e.g., by microneutralization assay. Also provided are nucleic acid vaccines comprising one or more RNA polynucleotides having an open reading frame encoding a first antigenic polypeptide or a concatemeric polypeptide, wherein the RNA polynucleotide is present in a formulation for in vivo administration to a host for eliciting a longer lasting high antibody titer than an antibody titer elicited by an mRNA vaccine having a stabilizing element or formulated with an adjuvant and encoding the first antigenic polypeptide. In some embodiments, the RNA polynucleotide is formulated to produce a neutralizing antibodies within one week of a single administration. In some embodiments, the adjuvant is selected from a cationic peptide and an immunostimulatory nucleic acid. In some embodiments, the cationic peptide is protamine.

Aspects provide nucleic acid vaccines comprising one or more RNA polynucleotides having an open reading frame comprising at least one chemical modification or optionally no nucleotide modification, the open reading frame encoding a first antigenic polypeptide or a concatemeric polypeptide, wherein the RNA polynucleotide is present in the formulation for in vivo administration to a host such that the level of antigen expression in the host significantly exceeds a level of antigen expression produced by an mRNA vaccine having a stabilizing element or formulated with an adjuvant and encoding the first antigenic polypeptide.

Other aspects provide nucleic acid vaccines comprising one or more RNA polynucleotides having an open reading frame comprising at least one chemical modification or optionally no nucleotide modification, the open reading frame encoding a first antigenic polypeptide or a concatemeric polypeptide, wherein the vaccine has at least 10 fold less RNA polynucleotide than is required for an unmodified mRNA vaccine to produce an equivalent antibody titer. In some embodiments, the RNA polynucleotide is present in a dosage of 25-100 micrograms.

Aspects of the invention also provide a unit of use vaccine, comprising between 10 ug and 400 ug of one or more RNA polynucleotides having an open reading frame comprising at least one chemical modification or optionally no nucleotide modification, the open reading frame encoding a first antigenic polypeptide or a concatemeric polypeptide, and a pharmaceutically acceptable carrier or excipient, formulated for delivery to a human subject. In some embodiments, the vaccine further comprises a cationic lipid nanoparticle.

Aspects of the invention provide methods of creating, maintaining or restoring antigenic memory to a tumor in an individual or population of individuals comprising administering to said individual or population an antigenic memory booster nucleic acid vaccine comprising (a) at least one RNA polynucleotide, said polynucleotide comprising at least one chemical modification or optionally no nucleotide modification and two or more codon-optimized open reading frames, said open reading frames encoding a set of reference antigenic polypeptides, and (b) optionally a pharmaceutically acceptable carrier or excipient. In some embodiments, the vaccine is administered to the individual via a route selected from the group consisting of intramuscular administration, intradermal administration and subcutaneous administration. In some embodiments, the administering step comprises contacting a muscle tissue of the subject with a device suitable for injection of the composition. In some embodiments, the administering step comprises contacting a muscle tissue of the subject with a device suitable for injection of the composition in combination with electroporation.

Aspects of the invention provide methods of vaccinating a subject comprising administering to the subject a single dosage of between 25 ug/kg and 400 ug/kg of a nucleic acid vaccine comprising one or more RNA polynucleotides having an open reading frame encoding a first antigenic polypeptide or a concatemeric polypeptide in an effective amount to vaccinate the subject.

Other aspects provide nucleic acid vaccines comprising one or more RNA polynucleotides having an open reading frame comprising at least one chemical modification, the open reading frame encoding a first antigenic polypeptide or a concatemeric polypeptide, wherein the vaccine has at least 10 fold less RNA polynucleotide than is required for an unmodified mRNA vaccine to produce an equivalent antibody titer. In some embodiments, the RNA polynucleotide is present in a dosage of 25-100 micrograms.

Other aspects provide nucleic acid vaccines comprising an LNP formulated RNA polynucleotide having an open reading frame comprising no nucleotide modifications (unmodified), the open reading frame encoding a first antigenic polypeptide or a concatemeric polypeptide, wherein the vaccine has at least 10 fold less RNA polynucleotide than is required for an unmodified mRNA vaccine not formulated in a LNP to produce an equivalent antibody titer. In some embodiments, the RNA polynucleotide is present in a dosage of 25-100 micrograms.

In other aspects the invention encompasses a method of treating an elderly subject age 60 years or older comprising administering to the subject a nucleic acid vaccine comprising one or more RNA polynucleotides having an open reading frame encoding an antigenic polypeptide or a concatemeric polypeptide in an effective amount to vaccinate the subject.

In other aspects the invention encompasses a method of treating a young subject age 17 years or younger comprising administering to the subject a nucleic acid vaccine comprising one or more RNA polynucleotides having an open reading frame encoding an antigenic polypeptide or a concatemeric polypeptide in an effective amount to vaccinate the subject.

In other aspects the invention encompasses a method of treating an adult subject comprising administering to the subject a nucleic acid vaccine comprising one or more RNA polynucleotides having an open reading frame encoding an antigenic polypeptide or a concatemeric polypeptide in an effective amount to vaccinate the subject.

In some aspects the invention comprises a method of vaccinating a subject with a combination vaccine including at least two nucleic acid sequences encoding antigens wherein the dosage for the vaccine is a combined therapeutic dosage wherein the dosage of each individual nucleic acid encoding an antigen is a sub therapeutic dosage. In some embodiments, the combined dosage is 25 micrograms of the RNA polynucleotide in the nucleic acid vaccine administered to the subject. In some embodiments, the combined dosage is 100 micrograms of the RNA polynucleotide in the nucleic acid vaccine administered to the subject. In some embodiments the combined dosage is 50 micrograms of the RNA polynucleotide in the nucleic acid vaccine administered to the subject. In some embodiments, the combined dosage is 75 micrograms of the RNA polynucleotide in the nucleic acid vaccine administered to the subject. In some embodiments, the combined dosage is 150 micrograms of the RNA polynucleotide in the nucleic acid vaccine administered to the subject. In some embodiments, the combined dosage is 400 micrograms of the RNA polynucleotide in the nucleic acid vaccine administered to the subject. In some embodiments, the sub therapeutic dosage of each individual nucleic acid encoding an antigen is 1, 2, 3, 4, 5, 6, 7, 8, 9, 10, 11, 12, 13, 14, 15, 16, 17, 18, 19, or 20 micrograms. In other embodiments the nucleic acid vaccine is chemically modified and in other embodiments the nucleic acid vaccine is not chemically modified.

Other Components

A LNP may include one or more components in addition to those described in the preceding sections. In some embodiments, a LNP may include one or more small hydrophobic molecules such as a vitamin (e.g., vitamin A or vitamin E) or a sterol.

Lipid nanoparticles may also include one or more permeability enhancer molecules, carbohydrates, polymers, surface altering agents, or other components. A permeability enhancer molecule may be a molecule described by U.S. patent application publication No. 2005/0222064, for example. Carbohydrates may include simple sugars (e.g., glucose) and polysaccharides (e.g., glycogen and derivatives and analogs thereof).

A polymer may be included in and/or used to encapsulate or partially encapsulate a LNP. A polymer may be biodegradable and/or biocompatible. A polymer may be selected from, but is not limited to, polyamines, polyethers, polyamides, polyesters, polycarbamates, polyureas, polycarbonates, polystyrenes, polyimides, polysulfones, polyurethanes, polyacetylenes, polyethylenes, polyethyleneimines, polyisocyanates, polyacrylates, polymethacrylates, polyacrylonitriles, and polyarylates. In some embodiments, a polymer may include poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacrylate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone (PVP), polysiloxanes, polystyrene, polyurethanes, derivatized celluloses such as alkyl celluloses, hydroxyalkyl celluloses, cellulose ethers, cellulose esters, nitro celluloses, hydroxypropylcellulose, carboxy methylcellulose, polymers of acrylic acids, such as poly(methyl(meth)acrylate) (PMMA), poly(ethyl(meth)acrylate), poly(butyl(meth)acrylate), poly(isobutyl(meth)acrylate), poly(hexyl(meth)acrylate), poly(isodecyl(meth)acrylate), poly(lauryl(meth)acrylate), poly(phenyl(meth)acrylate), poly(methyl acrylate), poly(isopropyl acrylate), poly(isobutyl acrylate), poly(octadecyl acrylate) and copolymers and mixtures thereof, polydioxanone and its copolymers, polyhydroxyalkanoates, polypropylene fumarate, polyoxymethylene, poloxamers, poloxamines, poly(ortho)esters, poly(butyric acid), poly(valeric acid), poly(lactide-co-caprolactone), trimethylene carbonate, poly(N-acryloylmorpholine) (PACM), poly(2-methyl-2-oxazoline) (PMOX), poly(2-ethyl-2-oxazoline) (PEOZ), and polyglycerol.

Surface altering agents may include, but are not limited to, anionic proteins (e.g., bovine serum albumin), surfactants (e.g., cationic surfactants such as dimethyldioctadecyl-ammonium bromide), sugars or sugar derivatives (e.g., cyclodextrin), nucleic acids, polymers (e.g., heparin, polyethylene glycol, and poloxamer), mucolytic agents (e.g., acetylcysteine, mugwort, bromelain, papain, clerodendrum, bromhexine, carbocisteine, eprazinone, mesna, ambroxol, sobrerol, domiodol, letosteine, stepronin, tiopronin, gelsolin, thymosin β4, dornase alfa, neltenexine, and erdosteine), and DNases (e.g., rhDNase). A surface altering agent may be disposed within a nanoparticle and/or on the surface of a LNP (e.g., by coating, adsorption, covalent linkage, or other process).

A LNP may also comprise one or more functionalized lipids. In some embodiments, a lipid may be functionalized with an alkyne group that, when exposed to an azide under appropriate reaction conditions, may undergo a cycloaddition reaction. In particular, a lipid bilayer may be functionalized in this fashion with one or more groups useful in facilitating membrane permeation, cellular recognition, or imaging. The surface of a LNP may also be conjugated with one or more useful antibodies. Functional groups and conjugates useful in targeted cell delivery, imaging, and membrane permeation are well known in the art.

In addition to these components, lipid nanoparticles may include any substance useful in pharmaceutical compositions. In some embodiments, the lipid nanoparticle may include one or more pharmaceutically acceptable excipients or accessory ingredients such as, but not limited to, one or more solvents, dispersion media, diluents, dispersion aids, suspension aids, granulating aids, disintegrants, fillers, glidants, liquid vehicles, binders, surface active agents, isotonic agents, thickening or emulsifying agents, buffering agents, lubricating agents, oils, preservatives, and other species. Excipients such as waxes, butters, coloring agents, coating agents, flavorings, and perfuming agents may also be included. Pharmaceutically acceptable excipients are well known in the art (see for example Remington's *The Science and Practice of Pharmacy,* $21^{st}$ Edition, A. R. Gennaro; Lippincott, Williams & Wilkins, Baltimore, MD, 2006).

Examples of diluents may include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and/or combinations thereof. Granulating and dispersing agents may be selected from the non-limiting list consisting of potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (VEEGUM®), sodium lauryl sulfate, quaternary ammonium compounds, and/or combinations thereof.

Surface active agents and/or emulsifiers may include, but are not limited to, natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite [aluminum silicate] and VEEGUM® [magnesium aluminum silicate]), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxy methyl cellulose, hydroxypropyl cellulose, hydroxypropyl methylcellulose, methylcellulose), sorbitan fatty acid esters (e.g., polyoxyethylene sorbitan monolaurate [TWEEN® 20], polyoxyethylene sorbitan [TWEEN® 60], polyoxyethylene sorbitan monooleate [TWEEN® 80], sorbitan monopalmitate [SPAN®40], sorbitan monostearate [SPAN®60], sorbitan tristearate [SPAN®65], glyceryl monooleate, sorbitan monooleate [SPAN®80]), polyoxyethylene esters (e.g., polyoxyethylene monostearate [MYRJ® 45], polyoxyethylene hydrogenated castor oil, polyethoxylated castor oil, polyoxymethylene stearate, and SOLUTOL®), sucrose fatty acid esters, polyethylene glycol fatty acid esters (e.g., CREMOPHOR®), polyoxyethylene ethers, (e.g., polyoxyethylene lauryl ether [BRIJ® 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, PLURONIC® F 68, POLOXAMER® 188, cetrimonium bromide, cetylpyridinium chloride, benzalkonium chloride, docusate sodium, and/or combinations thereof.

A binding agent may be starch (e.g., cornstarch and starch paste); gelatin; sugars (e.g., sucrose, glucose, dextrose, dextrin, molasses, lactose, lactitol, mannitol); natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (VEEGUM®), and larch arabogalactan); alginates; polyethylene oxide; polyethylene glycol; inorganic calcium salts; silicic acid; polymethacrylates; waxes; water; alcohol; and combinations thereof, or any other suitable binding agent.

Examples of preservatives may include, but are not limited to, antioxidants, chelating agents, antimicrobial preservatives, antifungal preservatives, alcohol preservatives, acidic preservatives, and/or other preservatives. Examples of antioxidants include, but are not limited to, alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and/or sodium sulfite. Examples of chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Examples of antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Examples of antifungal preservatives include, but are not limited to, butyl paraben, methyl paraben, ethyl paraben, propyl paraben, benzoic acid, hydroxy benzoic acid, potassium benzoate, potassium sorbate, sodium benzoate, sodium propionate, and/or sorbic acid. Examples of alcohol preservatives include, but are not limited to, ethanol, polyethylene glycol, benzyl alcohol, phenol, phenolic compounds, bisphenol, chlorobutanol, hydroxybenzoate, and/or phenylethyl alcohol. Examples of acidic preservatives include, but are not limited to, vitamin A, vitamin C, vitamin E, beta-carotene, citric acid, acetic acid, dehydroascorbic acid, ascorbic acid, sorbic acid, and/or phytic acid. Other preservatives include, but are not limited to, tocopherol, tocopherol acetate, deteroxime mesylate, cetrimide, butylated hydroxyanisole (BHA), butylated hydroxytoluene (BHT), ethylenediamine, sodium lauryl sulfate (SLS), sodium lauryl ether sulfate (SLES), sodium bisulfite, sodium metabisulfite, potassium sulfite, potassium metabisulfite, GLYDANT PLUS®, PHENONIP®, methylparaben, GERMALL® 115, GERMABEN® II, NEOLONE™, KATHON™, and/or EUXYL®.

Examples of buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, d-gluconic acid, calcium glycerophosphate, calcium lactate, calcium lactobionate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, amino-sulfonate buffers (e.g., HEPES), magnesium hydroxide, aluminum hydroxide, alginic acid, pyrogen-free water, isotonic saline, Ringer's solution, ethyl alcohol, and/or combinations thereof. Lubricating agents may selected from the non-limiting group consisting of magnesium stearate, calcium stearate, stearic acid, silica, talc, malt, glyceryl behenate, hydrogenated vegetable oils, polyethylene glycol, sodium benzoate, sodium acetate, sodium chloride, leucine, magnesium lauryl sulfate, sodium lauryl sulfate, and combinations thereof.

Examples of oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soy bean, sunflower, tea tree, thistle, tsubaki, vetiver, walnut, and wheat germ oils as well as butyl stearate, caprylic triglyceride, capric triglyceride, cyclomethicone, diethyl sebacate, dimethicone 360, simethicone, isopropyl myristate, mineral oil, octyldodecanol, oleyl alcohol, silicone oil, and/or combinations thereof.

Pharmaceutical Compositions

Formulations comprising lipid nanoparticles may be formulated in whole or in part as pharmaceutical compositions. Pharmaceutical compositions may include one or more lipid nanoparticles. In some embodiments, a pharmaceutical composition may include one or more lipid nanoparticles including one or more different therapeutics and/or prophylactics. Pharmaceutical compositions may further include one or more pharmaceutically acceptable excipients or accessory ingredients such as those described herein. General guidelines for the formulation and manufacture of pharmaceutical compositions and agents are available, for example, in Remington's *The Science and Practice of Pharmacy*, $21^{st}$ Edition, A. R. Gennaro; Lippincott, Williams & Wilkins, Baltimore, MD, 2006. Conventional excipients and accessory ingredients may be used in any pharmaceutical composition, except insofar as any conventional excipient or accessory ingredient may be incompatible with one or more components of a LNP in the formulation of the disclosure. An excipient or accessory ingredient may be incompatible with a component of a LNP of the formulation if its combination with the component or LNP may result in any undesirable biological effect or otherwise deleterious effect.

In some embodiments, one or more excipients or accessory ingredients may make up greater than 50% of the total mass or volume of a pharmaceutical composition including a LNP. In some embodiments, the one or more excipients or accessory ingredients may make up 50%, 60%, 70%, 80%, 90%, or more of a pharmaceutical convention. In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Relative amounts of the one or more lipid nanoparticles, the one or more pharmaceutically acceptable excipients, and/or any additional ingredients in a pharmaceutical composition in accordance with the present disclosure will vary, depending upon the identity, size, and/or condition of the subject treated and further depending upon the route by which the composition is to be administered. By way of example, a pharmaceutical composition may comprise between 0.1% and 100% (wt/wt) of one or more lipid nanoparticles. As another example, a pharmaceutical composition may comprise between 0.1% and 15% (wt/vol) of one or more amphiphilic polymers (e.g., 0.5%, 1%, 2.5%, 5%, 10%, or 12.5% w/v).

In some embodiments, the lipid nanoparticles and/or pharmaceutical compositions of the disclosure are refrigerated or frozen for storage and/or shipment (e.g., being stored at a temperature of 4° C. or lower, such as a temperature between about −150° C. and about 0° C. or between about −80° C. and about −20° C. (e.g., about −5° C., −10° C., −15° C., −20° C., −25° C., −30° C., −40° C., −50° C., −60° C., −70° C., −80° C., −90° C., −130° C. or −150° C.). For example, the pharmaceutical composition comprising one or more lipid nanoparticles is a solution or solid (e.g., via lyophilization) that is refrigerated for storage and/or shipment at, for example, about −20° C., −30° C., −40° C., −50° C., −60° C., −70° C., or −80° C. In certain embodiments, the disclosure also relates to a method of increasing stability of the lipid nanoparticles and by storing the lipid nanoparticles and/or pharmaceutical compositions thereof at a temperature of 4° C. or lower, such as a temperature between about −150° C. and about 0° C. or between about −80° C. and about −20° C., e.g., about −5° C., −10° C., −15° C., −20° C., −25° C., −30° C., −40° C., −50° C., −60° C., −70° C., −80° C., −90° C., −130° C. or −150° C.).

Lipid nanoparticles and/or pharmaceutical compositions including one or more lipid nanoparticles may be administered to any patient or subject, including those patients or subjects that may benefit from a therapeutic effect provided by the delivery of a therapeutic and/or prophylactic to one or more particular cells, tissues, organs, or systems or groups thereof, such as the renal system. Although the descriptions provided herein of lipid nanoparticles and pharmaceutical compositions including lipid nanoparticles are principally directed to compositions which are suitable for administration to humans, it will be understood by the skilled artisan that such compositions are generally suitable for administration to any other mammal. Modification of compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the compositions is contemplated include, but are not limited to, humans, other primates, and other mammals, including commercially relevant mammals such as cattle, pigs, hoses, sheep, cats, dogs, mice, and/or rats.

A pharmaceutical composition including one or more lipid nanoparticles may be prepared by any method known or hereafter developed in the art of pharmacology. In general, such preparatory methods include bringing the active ingredient into association with an excipient and/or one or more other accessory ingredients, and then, if desirable or necessary, dividing, shaping, and/or packaging the product into a desired single- or multi-dose unit.

A pharmaceutical composition in accordance with the present disclosure may be prepared, packaged, and/or sold in bulk, as a single unit dose, and/or as a plurality of single unit doses. As used herein, a "unit dose" is discrete amount of the pharmaceutical composition comprising a predetermined amount of the active ingredient (e.g., lipid nanoparticle). The amount of the active ingredient is generally equal to the dosage of the active ingredient which would be administered to a subject and/or a convenient fraction of such a dosage such as, for example, one-half or one-third of such a dosage.

Pharmaceutical compositions may be prepared in a variety of forms suitable for a variety of routes and methods of administration. In some embodiments, pharmaceutical compositions may be prepared in liquid dosage forms (e.g., emulsions, microemulsions, nanoemulsions, solutions, suspensions, syrups, and elixirs), injectable forms, solid dosage forms (e.g., capsules, tablets, pills, powders, and granules), dosage forms for topical and/or transdermal administration (e.g., ointments, pastes, creams, lotions, gels, powders, solutions, sprays, inhalants, and patches), suspensions, powders, and other forms.

Liquid dosage forms for oral and parenteral administration include, but are not limited to, pharmaceutically acceptable emulsions, microemulsions, nanoemulsions, solutions, suspensions, syrups, and/or elixirs. In addition to active ingredients, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include additional therapeutics and/or prophylactics, additional agents such as wetting agents, emulsifying and suspending agents, sweetening, flavoring, and/or perfuming agents. In certain embodiments for parenteral administration, compositions are mixed with solubilizing agents such as Cremophor®, alcohols, oils, modified oils, glycols, polysorbates, cyclodextrins, polymers, and/or combinations thereof.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of an active ingredient, it is often desirable to slow the absorption of the active ingredient from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are prepared by entrapping the drug in liposomes or microemulsions which are compatible with body tissues.

Compositions for rectal or vaginal administration are typically suppositories which can be prepared by mixing compositions with suitable non-irritating excipients such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, films, powders, and granules. In such solid dosage forms, an active ingredient is mixed with at least one inert, pharmaceutically acceptable excipient such as sodium citrate or dicalcium phosphate and/or fillers or extenders (e.g., starches, lactose, sucrose, glucose, mannitol, and silicic acid), binders (e.g., carboxymethylcellulose, alginates, gelatin, polyvinylpyrrolidone, sucrose, and acacia), humectants (e.g., glycerol), disintegrating agents (e.g., agar, calcium carbonate, potato or tapioca starch, alginic acid, certain silicates, and sodium carbonate), solution retarding agents (e.g., paraffin), absorption accelerators (e.g., quaternary ammonium compounds), wetting agents (e.g., cetyl alcohol and glycerol monostearate), absorbents (e.g., kaolin and bentonite clay, silicates), and lubricants (e.g., talc, calcium stearate, magnesium stearate, solid polyethylene glycols, sodium lauryl sulfate), and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. Solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

Dosage forms for topical and/or transdermal administration of a composition may include ointments, pastes, creams, lotions, gels, powders, solutions, sprays, inhalants, and/or patches. Generally, an active ingredient is admixed under sterile conditions with a pharmaceutically acceptable excipient and/or any needed preservatives and/or buffers as may be required. Additionally, the present disclosure contemplates the use of transdermal patches, which often have the added advantage of providing controlled delivery of a compound to the body. Such dosage forms may be prepared, for example, by dissolving and/or dispensing the compound in the proper medium. Alternatively or additionally, rate may be controlled by either providing a rate controlling membrane and/or by dispersing the compound in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO 99/34850 and functional equivalents thereof. Jet injection devices which deliver liquid compositions to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (wt/wt) active ingredient, although the concentration of active ingredient may be as high as the solubility limit of the active ingredient in the solvent. Formulations for topical administration may further comprise one or more of the additional ingredients described herein.

A pharmaceutical composition may be prepared, packaged, and/or sold in a formulation suitable for pulmonary administration via the buccal cavity. Such a formulation may comprise dry particles which comprise the active ingredient. Such compositions are conveniently in the form of dry powders for administration using a device comprising a dry powder reservoir to which a stream of propellant may be directed to disperse the powder and/or using a self-propelling solvent/powder dispensing container such as a device comprising the active ingredient dissolved and/or suspended in a low-boiling propellant in a sealed container. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50% to 99.9% (wt/wt) of the composition, and active ingredient may constitute 0.1% to 20% (wt/wt) of the composition. A propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide an active ingredient in the form of droplets of a solution and/or suspension. Such formulations may be prepared, packaged, and/or sold as aqueous and/or dilute alcoholic solutions and/or suspensions, optionally sterile, comprising active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. Droplets provided by this route of administration may have an average diameter in the range from about 1 nm to about 200 nm.

Formulations described herein as being useful for pulmonary delivery are useful for intranasal delivery of a pharmaceutical composition. Another formulation suitable for intranasal administration is a coarse powder comprising the active ingredient and having an average particle from about 0.2 μm to 500 μm. Such a formulation is administered in the manner in which snuff is taken, i.e. by rapid inhalation through the nasal passage from a container of the powder held close to the nose.

Formulations suitable for nasal administration may, for example, comprise from about as little as 0.1% (wt/wt) and as much as 100% (wt/wt) of active ingredient, and may comprise one or more of the additional ingredients described herein. A pharmaceutical composition may be prepared, packaged, and/or sold in a formulation suitable for buccal administration. Such formulations may, for example, be in the form of tablets and/or lozenges made using conventional methods, and may, for example, 0.1% to 20% (wt/wt) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising active ingredient. Such powdered, aerosolized, and/or aerosolized formulations, when dispersed, may have an average particle and/or droplet size in the range from about 0.1 nm to about 200 nm, and may further comprise one or more of any additional ingredients described herein.

A pharmaceutical composition may be prepared, packaged, and/or sold in a formulation suitable for ophthalmic administration. Such formulations may, for example, be in the form of eye drops including, for example, a 0.1/1.0% (wt/wt) solution and/or suspension of the active ingredient in an aqueous or oily liquid excipient. Such drops may further comprise buffering agents, salts, and/or one or more other of any additional ingredients described herein. Other ophthalmically-administrable formulations which are useful include those which comprise the active ingredient in microcrystalline form and/or in a liposomal preparation. Ear drops and/or eye drops are contemplated as being within the scope of this present disclosure.

Methods of Producing Polypeptides in Cells

The present disclosure provides methods of producing a polypeptide of interest in a mammalian cell. Methods of producing polypeptides involve contacting a cell with a formulation of the disclosure comprising a LNP including an mRNA encoding the polypeptide of interest. Upon contacting the cell with the lipid nanoparticle, the mRNA may be taken up and translated in the cell to produce the polypeptide of interest.

In general, the step of contacting a mammalian cell with a LNP including an mRNA encoding a polypeptide of interest may be performed in vivo, ex vivo, in culture, or in vitro. The amount of lipid nanoparticle contacted with a cell, and/or the amount of mRNA therein, may depend on the type of cell or tissue being contacted, the means of administration, the physiochemical characteristics of the lipid nanoparticle and the mRNA (e.g., size, charge, and chemical composition) therein, and other factors. In general, an effective amount of the lipid nanoparticle will allow for efficient polypeptide production in the cell. Metrics for efficiency may include polypeptide translation (indicated by polypeptide expression), level of mRNA degradation, and immune response indicators.

The step of contacting a LNP including an mRNA with a cell may involve or cause transfection. A phospholipid including in the lipid component of a LNP may facilitate transfection and/or increase transfection efficiency, for example, by interacting and/or fusing with a cellular or intracellular membrane. Transfection may allow for the translation of the mRNA within the cell.

In some embodiments, the lipid nanoparticles described herein may be used therapeutically. For example, an mRNA included in a LNP may encode a therapeutic polypeptide (e.g., in a translatable region) and produce the therapeutic polypeptide upon contacting and/or entry (e.g., transfection) into a cell. In other embodiments, an mRNA included in a LNP may encode a polypeptide that may improve or increase the immunity of a subject. In some embodiments, an mRNA may encode a granulocyte-colony stimulating factor or trastuzumab.

In some embodiments, an mRNA included in a LNP may encode a recombinant polypeptide that may replace one or more polypeptides that may be substantially absent in a cell contacted with the lipid nanoparticle. The one or more substantially absent polypeptides may be lacking due to a genetic mutation of the encoding gene or a regulatory pathway thereof. Alternatively, a recombinant polypeptide produced by translation of the mRNA may antagonize the activity of an endogenous protein present in, on the surface of, or secreted from the cell. An antagonistic recombinant polypeptide may be desirable to combat deleterious effects caused by activities of the endogenous protein, such as altered activities or localization caused by mutation. In another alternative, a recombinant polypeptide produced by translation of the mRNA may indirectly or directly antagonize the activity of a biological moiety present in, on the surface of, or secreted from the cell. Antagonized biological moieties may include, but are not limited to, lipids (e.g., cholesterol), lipoproteins (e.g., low density lipoprotein), nucleic acids, carbohydrates, and small molecule toxins. Recombinant polypeptides produced by translation of the mRNA may be engineered for localization within the cell, such as within a specific compartment such as the nucleus, or may be engineered for secretion from the cell or for translocation to the plasma membrane of the cell.

In some embodiments, contacting a cell with a LNP including an mRNA may reduce the innate immune response of a cell to an exogenous nucleic acid. A cell may be contacted with a first lipid nanoparticle including a first amount of a first exogenous mRNA including a translatable region and the level of the innate immune response of the cell to the first exogenous mRNA may be determined. Subsequently, the cell may be contacted with a second composition including a second amount of the first exogenous mRNA, the second amount being a lesser amount of the first exogenous mRNA compared to the first amount. Alternatively, the second composition may include a first amount of a second exogenous mRNA that is different from the first exogenous mRNA. The steps of contacting the cell with the first and second compositions may be repeated one or more times. Additionally, efficiency of polypeptide production (e.g., translation) in the cell may be optionally determined, and the cell may be re-contacted with the first and/or second composition repeatedly until a target protein production efficiency is achieved.

Methods of Delivering Therapeutic Agents to Cells and Organs

The present disclosure provides methods of delivering a therapeutic and/or prophylactic, such as a nucleic acid, to a mammalian cell or organ. Delivery of a therapeutic and/or prophylactic to a cell involves administering a formulation of the disclosure that comprises a LNP including the therapeutic and/or prophylactic, such as a nucleic acid, to a subject, where administration of the composition involves contacting the cell with the composition. In some embodiments, a protein, cytotoxic agent, radioactive ion, chemotherapeutic agent, or nucleic acid (such as an RNA, e.g., mRNA) may be delivered to a cell or organ. In the instance that a therapeutic and/or prophylactic is an mRNA, upon contacting a cell with the lipid nanoparticle, a translatable mRNA may be translated in the cell to produce a polypeptide of interest. However, mRNAs that are substantially not translatable may also be delivered to cells. Substantially non-translatable mRNAs may be useful as vaccines and/or may sequester translational components of a cell to reduce expression of other species in the cell.

In some embodiments, a LNP may target a particular type or class of cells (e.g., cells of a particular organ or system thereof). In some embodiments, a LNP including a therapeutic and/or prophylactic of interest may be specifically delivered to a mammalian liver, kidney, spleen, femur, or lung. Specific delivery to a particular class of cells, an organ, or a system or group thereof implies that a higher proportion of lipid nanoparticles including a therapeutic and/or prophylactic are delivered to the destination (e.g., tissue) of interest relative to other destinations, e.g., upon administration of a LNP to a mammal. In some embodiments, specific delivery may result in a greater than 2 fold, 5 fold, 10 fold, 15 fold, or 20 fold increase in the amount of therapeutic and/or prophylactic per 1 g of tissue of the targeted destination (e.g., tissue of interest, such as a liver) as compared to another destination (e.g., the spleen). In some embodiments, the tissue of interest is selected from the group consisting of a liver, kidney, a lung, a spleen, a femur, vascular endothelium in vessels (e.g., intra-coronary or intra-femoral) or kidney, and tumor tissue (e.g., via intratumoral injection).

As another example of targeted or specific delivery, an mRNA that encodes a protein-binding partner (e.g., an antibody or functional fragment thereof, a scaffold protein, or a peptide) or a receptor on a cell surface may be included in a LNP. An mRNA may additionally or instead be used to direct the synthesis and extracellular localization of lipids, carbohydrates, or other biological moieties. Alternatively, other therapeutics and/or prophylactics or elements (e.g., lipids or ligands) of a LNP may be selected based on their affinity for particular receptors (e.g., low density lipoprotein receptors) such that a LNP may more readily interact with a target cell population including the receptors. In some embodiments, ligands may include, but are not limited to, members of a specific binding pair, antibodies, monoclonal antibodies, Fv fragments, single chain Fv (scFv) fragments, Fab fragments, F(ab)2 fragments, single domain antibodies, camelized antibodies and fragments thereof, humanized antibodies and fragments thereof, and multivalent versions thereof; multivalent binding reagents including mono- or bi-specific antibodies such as disulfide stabilized Fv fragments, scFv tandems, diabodies, tribodies, or tetrabodies; and aptamers, receptors, and fusion proteins.

In some embodiments, a ligand may be a surface-bound antibody, which can permit tuning of cell targeting specificity. This is especially useful since highly specific antibodies can be raised against an epitope of interest for the desired targeting site. In some embodiments, multiple antibodies are expressed on the surface of a cell, and each antibody can have a different specificity for a desired target. Such approaches can increase the avidity and specificity of targeting interactions.

A ligand can be selected, e.g., by a person skilled in the biological arts, based on the desired localization or function of the cell. In some embodiments an estrogen receptor ligand, such as tamoxifen, can target cells to estrogen-dependent breast cancer cells that have an increased number of estrogen receptors on the cell surface. Other non-limiting examples of ligand/receptor interactions include CCRI (e.g., for treatment of inflamed joint tissues or brain in rheumatoid arthritis, and/or multiple sclerosis), CCR7, CCR8 (e.g., targeting to lymph node tissue), CCR6, CCR9, CCR10 (e.g., to target to intestinal tissue), CCR4, CCR10) (e.g., for targeting to skin), CXCR4 (e.g., for general enhanced transmigration), HCELL (e.g., for treatment of inflammation and inflammatory disorders, bone marrow), Alpha4beta7 (e.g., for intestinal mucosa targeting), and VLA-4NCAM-1 (e.g., targeting to endothelium). In general, any receptor involved in targeting (e.g., cancer metastasis) can be harnessed for use in the methods and compositions described herein.

Targeted cells may include, but are not limited to, hepatocytes, epithelial cells, hematopoietic cells, epithelial cells, endothelial cells, lung cells, bone cells, stem cells, mesenchymal cells, neural cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes, and tumor cells.

In some embodiments, a LNP may target hepatocytes. Apolipoproteins such as apolipoprotein E (apoE) have been shown to associate with neutral or near neutral lipid-containing lipid nanoparticles in the body, and are known to associate with receptors such as low-density lipoprotein receptors (LDLRs) found on the surface of hepatocytes. Thus, a LNP including a lipid component with a neutral or near neutral charge that is administered to a subject may acquire apoE in a subject's body and may subsequently deliver a therapeutic and/or prophylactic (e.g., an RNA) to hepatocytes including LDLRs in a targeted manner.

Methods of Treating Diseases and Disorders

Lipid nanoparticles may be useful for treating a disease, disorder, or condition. In particular, such compositions may be useful in treating a disease, disorder, or condition characterized by missing or aberrant protein or polypeptide activity. In some embodiments, a formulation of the disclosure that comprises a LNP including an mRNA encoding a missing or aberrant polypeptide may be administered or delivered to a cell. Subsequent translation of the mRNA may produce the polypeptide, thereby reducing or eliminating an issue caused by the absence of or aberrant activity caused by the polypeptide. Because translation may occur rapidly, the methods and compositions may be useful in the treatment of acute diseases, disorders, or conditions such as sepsis, stroke, and myocardial infarction. A therapeutic and/or prophylactic included in a LNP may also be capable of altering the rate of transcription of a given species, thereby affecting gene expression.

Diseases, disorders, and/or conditions characterized by dysfunctional or aberrant protein or polypeptide activity for which a composition may be administered include, but are not limited to, rare diseases, infectious diseases (as both vaccines and therapeutics), cancer and proliferative diseases, genetic diseases (e.g., cystic fibrosis), autoimmune diseases, diabetes, neurodegenerative diseases, cardio- and reno-vascular diseases, and metabolic diseases. Multiple diseases, disorders, and/or conditions may be characterized by missing (or substantially diminished such that proper protein function does not occur) protein activity. Such proteins may not be present, or they may be essentially non-functional. A specific example of a dysfunctional protein is the missense mutation variants of the cystic fibrosis transmembrane conductance regulator (CFTR) gene, which produce a dysfunctional protein variant of CFTR protein, which causes cystic fibrosis. The present disclosure provides a method for treating such diseases, disorders, and/or conditions in a subject by administering a LNP including an RNA and a lipid component including a lipid according to Formula (I), a phospholipid (optionally unsaturated), a PEG lipid, and a structural lipid, wherein the RNA may be an mRNA encoding a polypeptide that antagonizes or otherwise overcomes an aberrant protein activity present in the cell of the subject.

The disclosure provides methods involving administering lipid nanoparticles including one or more therapeutic and/or prophylactic agents, such as a nucleic acid, and pharmaceutical compositions including the same. The terms therapeutic and prophylactic can be used interchangeably herein with respect to features and embodiments of the present disclosure. Therapeutic compositions, or imaging, diagnostic, or prophylactic compositions thereof, may be administered to a subject using any reasonable amount and any route of administration effective for preventing, treating, diagnosing, or imaging a disease, disorder, and/or condition and/or any other purpose. The specific amount administered to a given subject may vary depending on the species, age, and general condition of the subject: the purpose of the administration: the particular composition: the mode of administration; and the like. Compositions in accordance with the present disclosure may be formulated in dosage unit form for ease of administration and uniformity of dosage. It will be understood, however, that the total daily usage of a composition of the present disclosure will be decided by an attending physician within the scope of sound medical judgment. The specific therapeutically effective, prophylactically effective, or otherwise appropriate dose level (e.g., for imaging) for any particular patient will depend upon a variety of factors including the severity and identify of a disorder being treated, if any; the one or more therapeutics and/or prophylactics employed; the specific composition employed; the age, body weight, general health, sex, and diet of the patient; the time of administration, route of administration, and rate of excretion of the specific pharmaceutical composition employed; the duration of the treatment; drugs used in combination or coincidental with the specific pharmaceutical composition employed; and like factors well known in the medical arts.

A LNP including one or more therapeutics and/or prophylactics, such as a nucleic acid, may be administered by any route. In some embodiments, compositions, including prophylactic, diagnostic, or imaging compositions including one or more lipid nanoparticles described herein, are administered by one or more of a variety of routes, including oral, intravenous, intramuscular, intra-arterial, intramedullary, intrathecal, subcutaneous, intraventricular, trans- or intradermal, interdermal, rectal, intravaginal, intraperitoneal, topical (e.g., by powders, ointments, creams, gels, lotions, and/or drops), mucosal, nasal, buccal, enteral, intravitreal, intratumoral, sublingual, intranasal; by intratracheal instillation, bronchial instillation, and/or inhalation; as an oral spray and/or powder, nasal spray, and/or aerosol, and/or through a portal vein catheter. In some embodiments, a composition may be administered intravenously, intramuscularly, intradermally, intra-arterially, intratumorally, subcutaneously, or by inhalation. However, the present disclosure encompasses the delivery or administration of compositions described herein by any appropriate route taking into consideration likely advances in the sciences of drug delivery. In general, the most appropriate route of administration will depend upon a variety of factors including the nature of the lipid nanoparticle including one or more therapeutics and/or prophylactics (e.g., its stability in various bodily environments such as the bloodstream and gastrointestinal tract), the condition of the patient (e.g., whether the patient is able to tolerate particular routes of administration), etc.

In certain embodiments, compositions in accordance with the present disclosure may be administered at dosage levels sufficient to deliver from about 0.0001 mg/kg to about 10 mg/kg, from about 0.001 mg/kg to about 10 mg/kg, from about 0.005 mg/kg to about 10 mg/kg, from about 0.01 mg/kg to about 10 mg/kg, from about 0.05 mg/kg to about 10 mg/kg, from about 0.1 mg/kg to about 10 mg/kg, from about 1 mg/kg to about 10 mg/kg, from about 2 mg/kg to about 10 mg/kg, from about 5 mg/kg to about 10 mg/kg, from about 0.0001 mg/kg to about 5 mg/kg, from about 0.001 mg/kg to about 5 mg/kg, from about 0.005 mg/kg to about 5 mg/kg, from about 0.01 mg/kg to about 5 mg/kg, from about 0.05 mg/kg to about 5 mg/kg, from about 0.1 mg/kg to about 5 mg/kg, from about 1 mg/kg to about 5 mg/kg, from about 2 mg/kg to about 5 mg/kg, from about 0.0001 mg/kg to about 2.5 mg/kg, from about 0.001 mg/kg to about 2.5 mg/kg, from about 0.005 mg/kg to about 2.5 mg/kg, from about 0.01 mg/kg to about 2.5 mg/kg, from about 0.05 mg/kg to about 2.5 mg/kg, from about 0.1 mg/kg to about 2.5 mg/kg, from about 1 mg/kg to about 2.5 mg/kg, from about 2 mg/kg to about 2.5 mg/kg, from about 0.0001 mg/kg to about 1 mg/kg, from about 0.001 mg/kg to about 1 mg/kg, from about 0.005 mg/kg to about 1 mg/kg, from about 0.01 mg/kg to about 1 mg/kg, from about 0.05 mg/kg to about 1 mg/kg, from about 0.1 mg/kg to about 1 mg/kg, from about 0.0001 mg/kg to about 0.25 mg/kg, from about 0.001 mg/kg to about 0.25 mg/kg, from about 0.005 mg/kg to about 0.25 mg/kg, from about 0.01 mg/kg to about 0.25 mg/kg, from about 0.05 mg/kg to about 0.25 mg/kg, or from about 0.1 mg/kg to about 0.25 mg/kg of a therapeutic and/or prophylactic (e.g., an mRNA) in a given dose, where a dose of 1 mg/kg (mpk) provides 1 mg of a therapeutic and/or prophylactic per 1 kg of subject body weight. In some embodiments, a dose of about 0.001 mg/kg to about 10 mg/kg of a therapeutic and/or prophylactic (e.g., mRNA) of a LNP may be administered. In other embodiments, a dose of about 0.005 mg/kg to about 2.5 mg/kg of a therapeutic and/or prophylactic may be administered. In certain embodiments, a dose of about 0.1 mg/kg to about 1 mg/kg may be administered. In other embodiments, a dose of about 0.05 mg/kg to about 0.25 mg/kg may be administered. A dose may be administered one or more times per day, in the same or a different amount, to obtain a desired level of mRNA expression and/or therapeutic, diagnostic, prophylactic, or imaging effect. The desired dosage may be delivered, for example, three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations). In some embodiments, a single dose may be administered, for example, prior to or after a surgical procedure or in the instance of an acute disease, disorder, or condition.

Lipid nanoparticles including one or more therapeutics and/or prophylactics, such as a nucleic acid, may be used in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. In some embodiments, one or more lipid nanoparticles including one or more different therapeutics and/or prophylactics may be administered in combination. Compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of compositions, or imaging, diagnostic, or prophylactic compositions thereof in combination with agents that improve their bioavailability, reduce and/or modify their metabolism, inhibit their excretion, and/or modify their distribution within the body.

It will further be appreciated that therapeutically, prophylactically, diagnostically, or imaging active agents utilized in combination may be administered together in a single composition or administered separately in different compositions. In general, it is expected that agents utilized in combination will be utilized at levels that do not exceed the levels at which they are utilized individually. In some embodiments, the levels utilized in combination may be lower than those utilized individually.

The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, a composition useful for treating cancer may be administered concurrently with a chemotherapeutic agent), or they may achieve different effects (e.g., control of any adverse effects, such as infusion related reactions).

A LNP may be used in combination with an agent to increase the effectiveness and/or therapeutic window of the composition. Such an agent may be, for example, an anti-inflammatory compound, a steroid (e.g., a corticosteroid), a statin, an estradiol, a BTK inhibitor, an S1P1 agonist, a glucocorticoid receptor modulator (GRM), or an anti-histamine. In some embodiments, a LNP may be used in combination with dexamethasone, methotrexate, acetaminophen, an H1 receptor blocker, or an H2 receptor blocker. In some embodiments, a method of treating a subject in need thereof or of delivering a therapeutic and/or prophylactic to a subject (e.g., a mammal) may involve pre-treating the subject with one or more agents prior to administering a LNP. In some embodiments, a subject may be pre-treated with a useful amount (e.g., 10 mg. 20 mg, 30 mg. 40 mg, 50 mg, 60 mg, 70 mg, 80 mg. 90 mg, 100 mg, or any other useful amount) of dexamethasone, methotrexate, acetaminophen, an H1 receptor blocker, or an H2 receptor blocker. Pre-treatment may occur 24 or fewer hours (e.g., 24 hours, 20 hours, 16 hours, 12 hours, 8 hours, 4 hours, 2 hours, 1 hour, 50 minutes, 40 minutes, 30 minutes, 20 minutes, or 10 minutes) before administration of the lipid nanoparticle and may occur one, two, or more times in, for example, increasing dosage amounts.

Those skilled in the art will recognize, or be able to ascertain using no more than routine experimentation, many equivalents to the specific embodiments in accordance with the disclosure described herein. The scope of the present disclosure is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all, of the group members are present in, employed in, or otherwise relevant to a given product or process.

It is also noted that the term "comprising" is intended to be open and permits but does not require the inclusion of additional elements or steps. When the term "comprising" is used herein, the terms "consisting essentially of" and "consisting of" are thus also encompassed and disclosed. Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

Where ranges are given, endpoints are included. Furthermore, it is to be understood that unless otherwise indicated or otherwise evident from the context and understanding of one of ordinary skill in the art, values that are expressed as ranges can assume any specific value or sub-range within the stated ranges in different embodiments of the disclosure, to the tenth of the unit of the lower limit of the range, unless the context clearly dictates otherwise.

In addition, it is to be understood that any particular embodiment of the present disclosure that falls within the prior art may be explicitly excluded from any one or more of the claims. Since such embodiments are deemed to be known to one of ordinary skill in the art, they may be excluded even if the exclusion is not set forth explicitly herein.

All cited sources, for example, references, publications, patent applications, databases, database entries, and art cited herein, are incorporated into this application by reference, even if not expressly stated in the citation. In case of conflicting statements of a cited source and the instant application, the statement in the instant application shall control.

The disclosure having been described, the following examples are offered by way of illustration and not limitation.

EXAMPLES

Example 1: Post-Hoc Loading Studies

Initial experiments were set up to elucidate the post hoc loading (PHL) effect. For instance, experiments describe the addition of mRNA to pre-formed vesicles within the upstream section of the process (i.e. immediately following lipid precipitation, ~1 ms to 1,800,000 ms downstream). For example, see FIGS. 1-5.

FIG. 1 is a graph showing that comparable or increased mRNA encapsulation is observed when mRNA is introduced at longer LNP residence times. Encapsulation was evaluated via the Ribogreen fluorescence assay.

Figure 2:
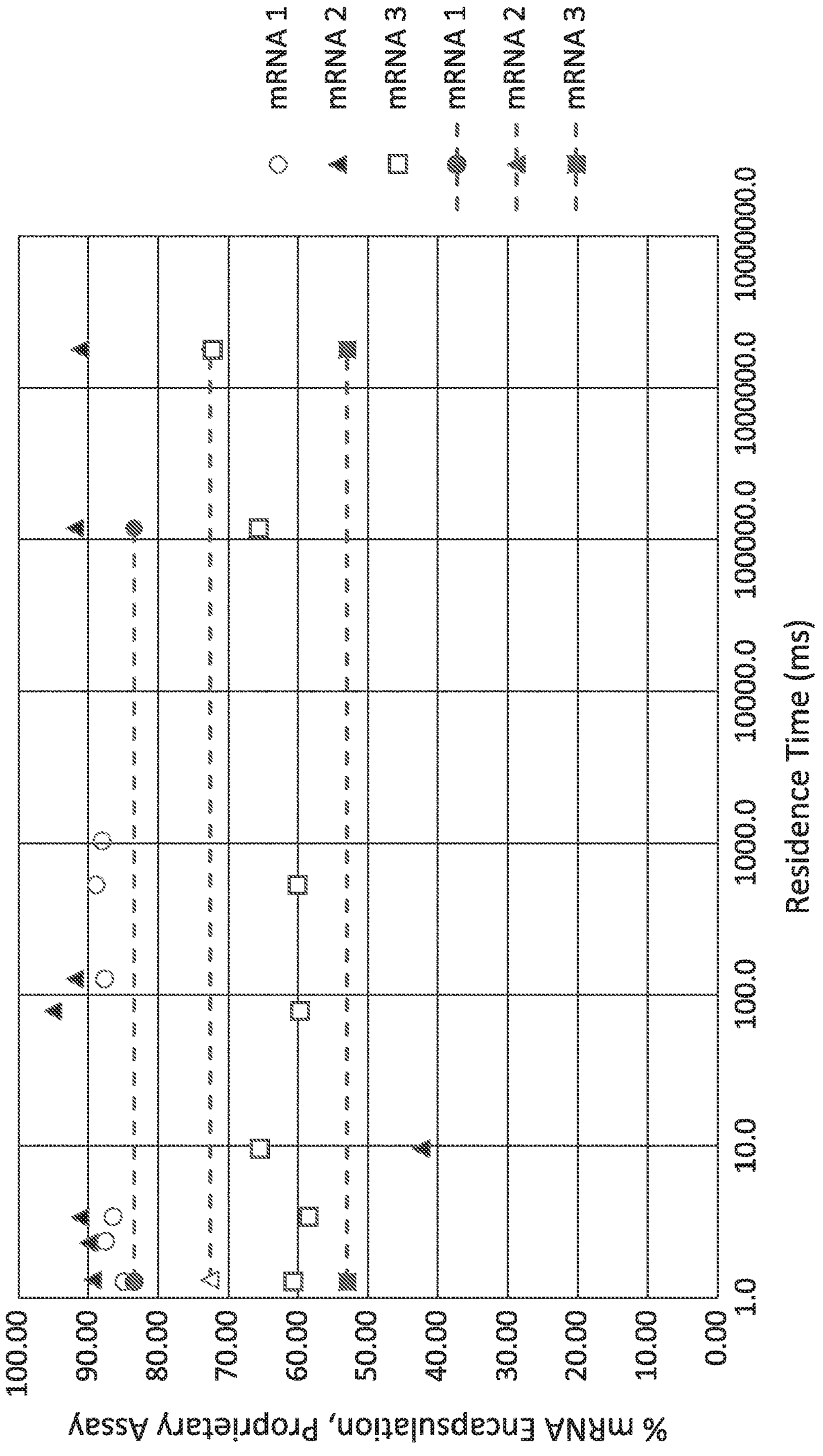
FIG. 2 is a graph showing that comparable or increased mRNA encapsulation is observed when mRNA is introduced at longer timescales after LNP generation (i.e., increased residence times) relative to controls (dotted line). Encapsulation was evaluated via the ion exchange (AEX) assay.

FIG. 2 is a graph showing that comparable or significantly increased mRNA encapsulation is observed when mRNA is introduced at longer LNP residence times relative to controls (dotted line). Encapsulation was evaluated via the ion exchange (AEX) assay.

Figure 3:
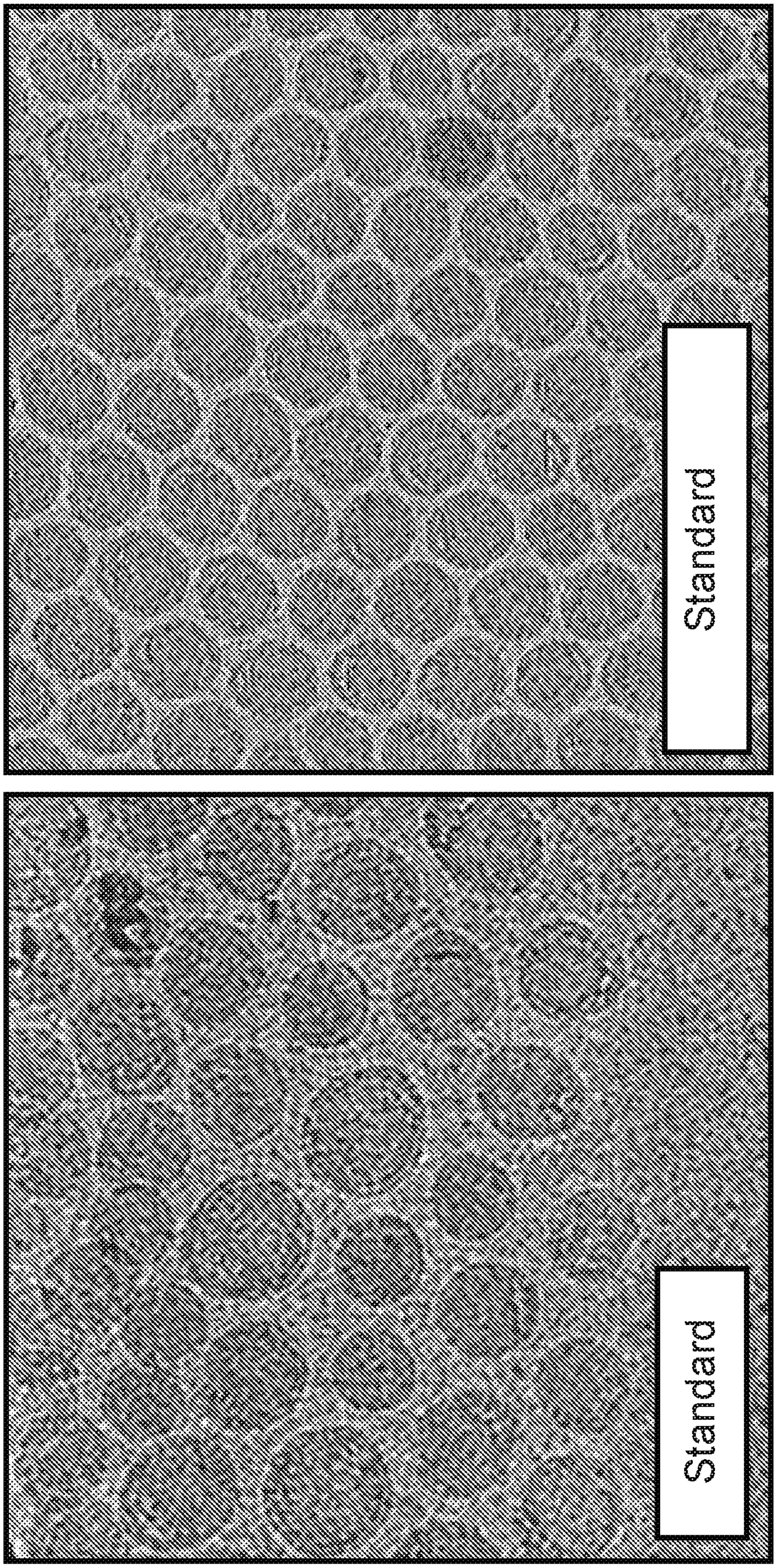
FIG. 3 are cryo-EM images demonstrating that comparable particle morphology is observed with a post-hoc loading ("PHL)" process mode relative to a standard process wherein mRNA is included during an initial particle formation ("Standard").

FIG. 3 are cryo-EM images demonstrating that comparable particle morphology is observed with a post-hoc loading ("PHL)" process mode relative to a standard process wherein mRNA is included during an initial particle formation ("Standard").

Figure 4:
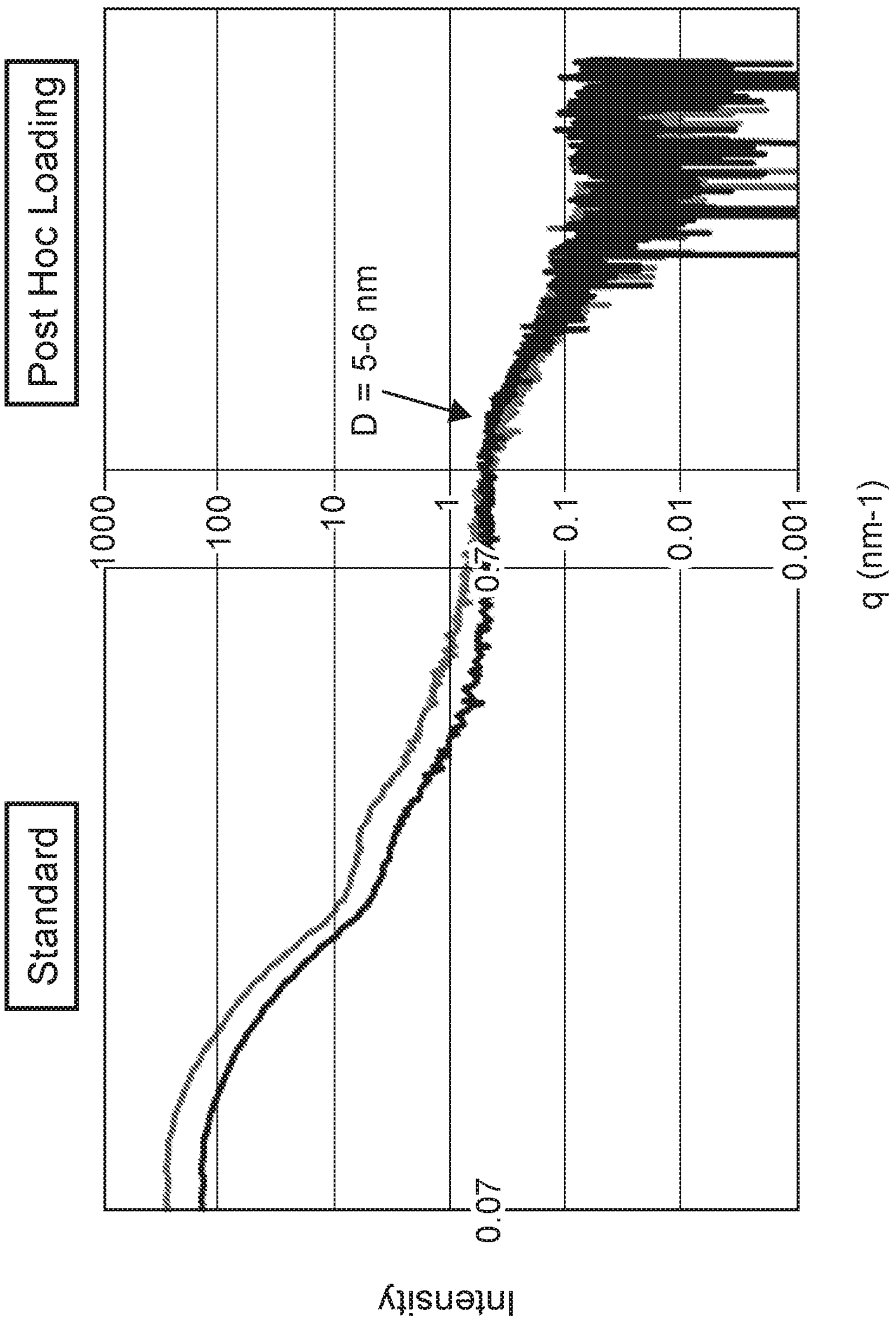
FIG. 4 is an small angle x-ray scatters (SAXS) analysis demonstrating the increase structural features (q=~1.3 nm−1, calculated D-spacing of 5-6 nm) in post-hoc loading process batch relative to standard lot process.

FIG. 4 is an small angle x-ray scatters (SAXS) analysis demonstrating the increase structural features (q=~1.3 nm−1, calculated D-spacing of 5-6 nm) in post-hoc loading process batch relative to standard lot process.

Figure 5:
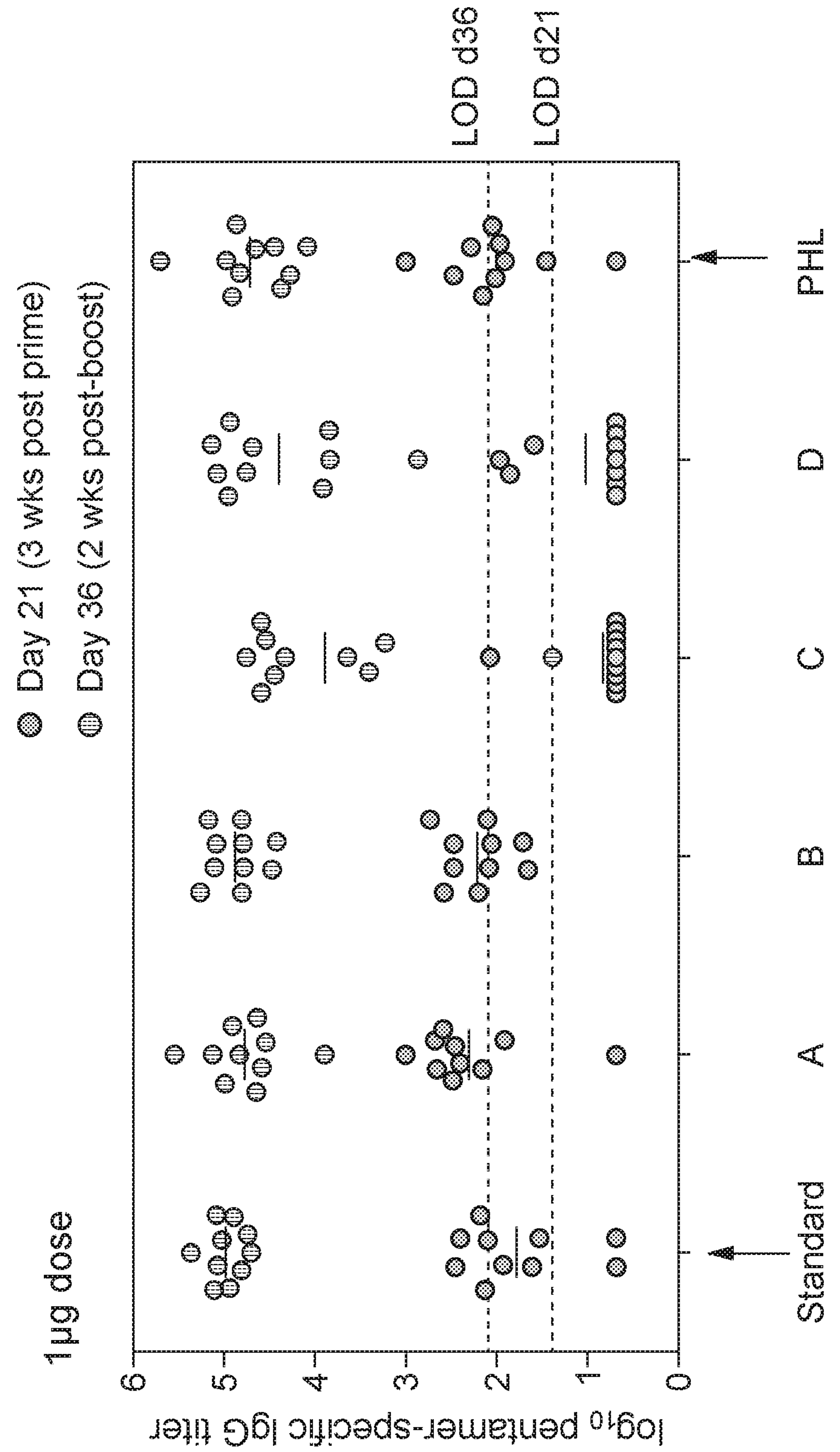
FIG. 5 is a plot demonstrating in vivo performance of a PHL process against a Standard process showing an increased first-dose response (3 weeks post-prime) for a PHL in a prophylactic vaccine context and demonstrating comparable total IgG observed after a 2-week boost. The A-D entries reflect alternate versions of the standard process as a comparison.

FIG. 5 is a plot demonstrating in vivo performance of a PHL process against a Standard process showing an increased first-dose response (3 weeks post-prime) for a PHL in a prophylactic vaccine context and demonstrating comparable total IgG observed after a 2-week boost. The A-D entries reflect alternate versions of the standard process as a comparison.

Example 2: "Bedside" or "Field-Mix" Application of Post-Hoc Loading

Secondly, the PHL concept was applied to the "bedside" or "field mix" embodiment, which involves a more significant time delay between particle formation and mRNA encapsulation (i.e. months to years). Briefly, empty LNPs are processed in the absence of mRNA, stored, and mixed with mRNA cargo prior to use. A scalable empty LNP process was developed. Initially, particle size was a critical parameter for efficient mixing and MRNA encapsulation in the field mix process, whereby LNPs of small diameter (<100) nm) resulted in improved MRNA encapsulation during the field mixing process. A continuous, scalable nanoprecipitation process was developed in an effort to control LNP diameter and polydispersity. Particle maturation (i.e. growth via coalescence) was determined to be a critical factor in driving homogeneity and narrow polydispersity indices. The experimental design for optimization of upstream nanoprecipitation conditions, whereby temperature and % ethanol (mixing ratio) was varied with fixed total residence time prior to a second ethanol drop step (acetate dilution) to target 12.5% ethanol. Particle maturation was arrested at <15% ethanol. The modulation of process Temperature and % ethanol enabled particle size control and decreased polydispersity. For example, see FIGS. 6-35.

Figure 6:
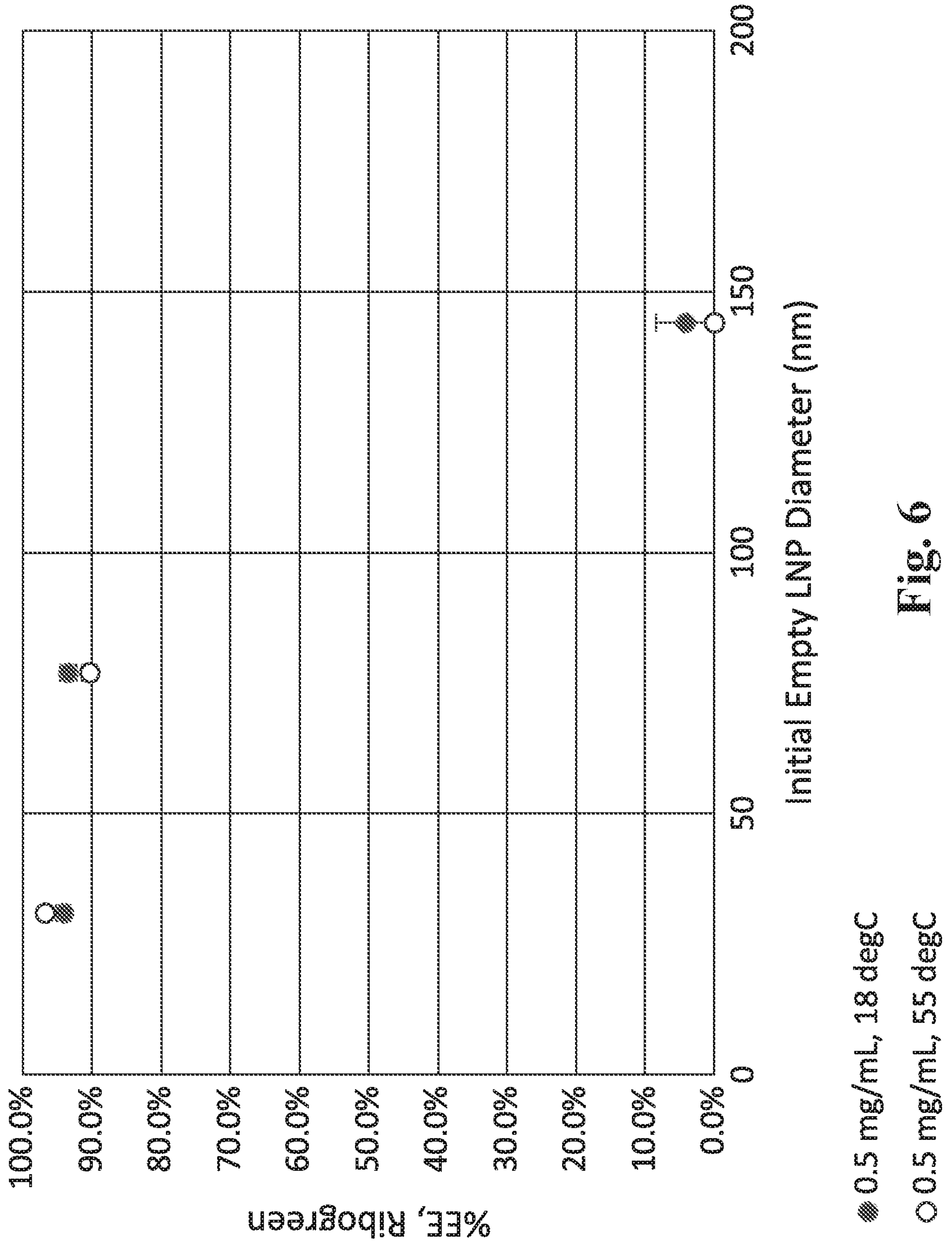
FIG. 6 is a graph demonstrating the effect the initial diameter of an LNP dispersion had on mRNA encapsulation and showing that LNP batches with decreased diameter resulted in increased mRNA encapsulation.

FIG. 6 is a graph demonstrating the effect the initial diameter of an LNP dispersion had on mRNA encapsulation and showing that LNP batches with decreased diameter resulted in increased mRNA encapsulation.

Figure 7:
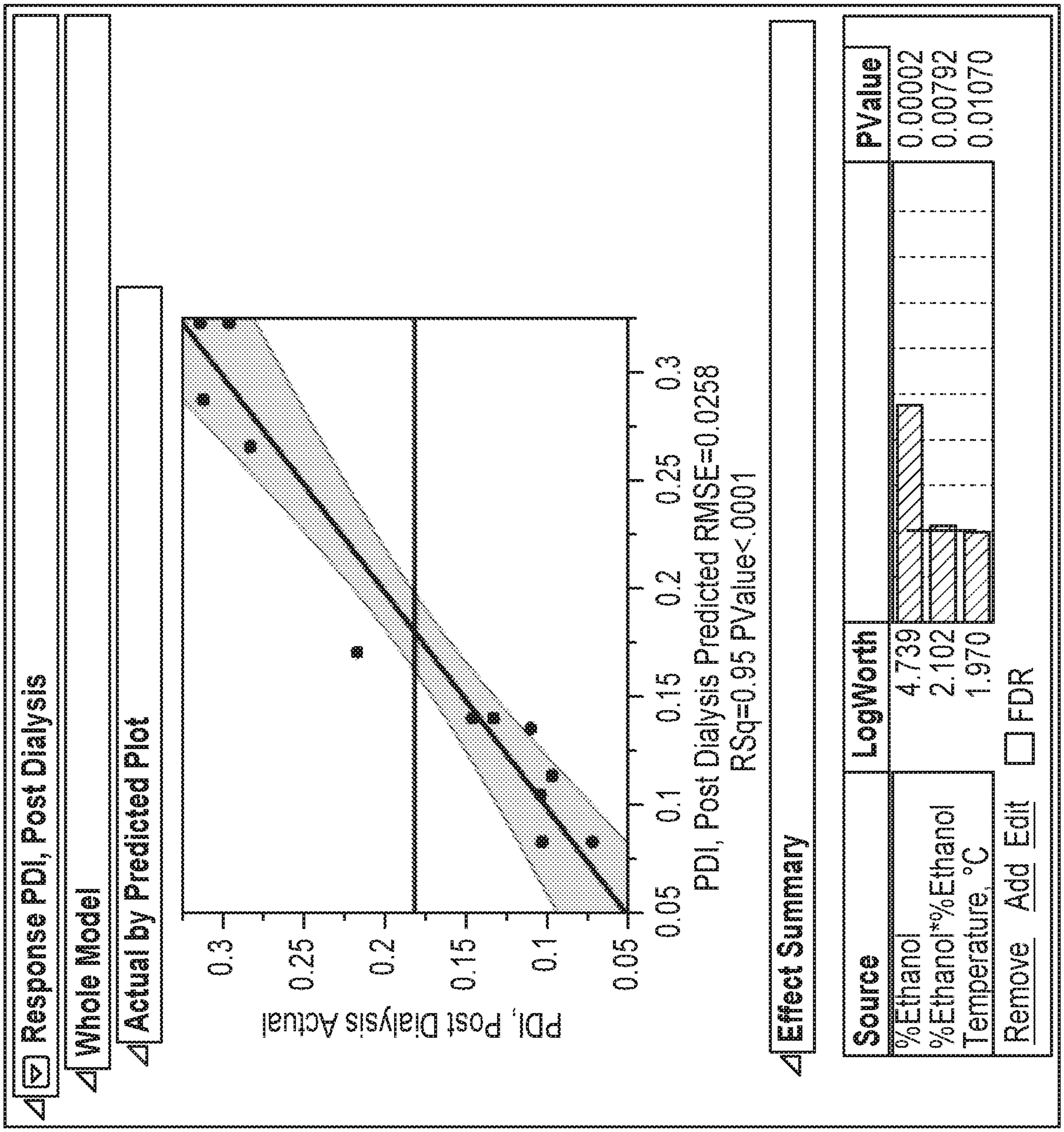
FIG. 7 is a model fitting demonstrating ethanol content and temperature are critical parameters affecting LNP polydispersity index (PDI) via dynamic light scattering (DLS) characterization where the model fitting enabled calculation of an advantageous range of process conditions to favor low PDI (e.g., 30% ethanol, 40° C.) enabling small uniform particles and a favorable composition.

FIG. 7 is a model fitting demonstrating ethanol content and temperature are critical parameters affecting LNP polydispersity index (PDI) via dynamic light scattering (DLS) characterization where the model fitting enabled calculation of an advantageous range of process conditions to favor low PDI (e.g., 30% ethanol, 40° C.).

Figure 8:
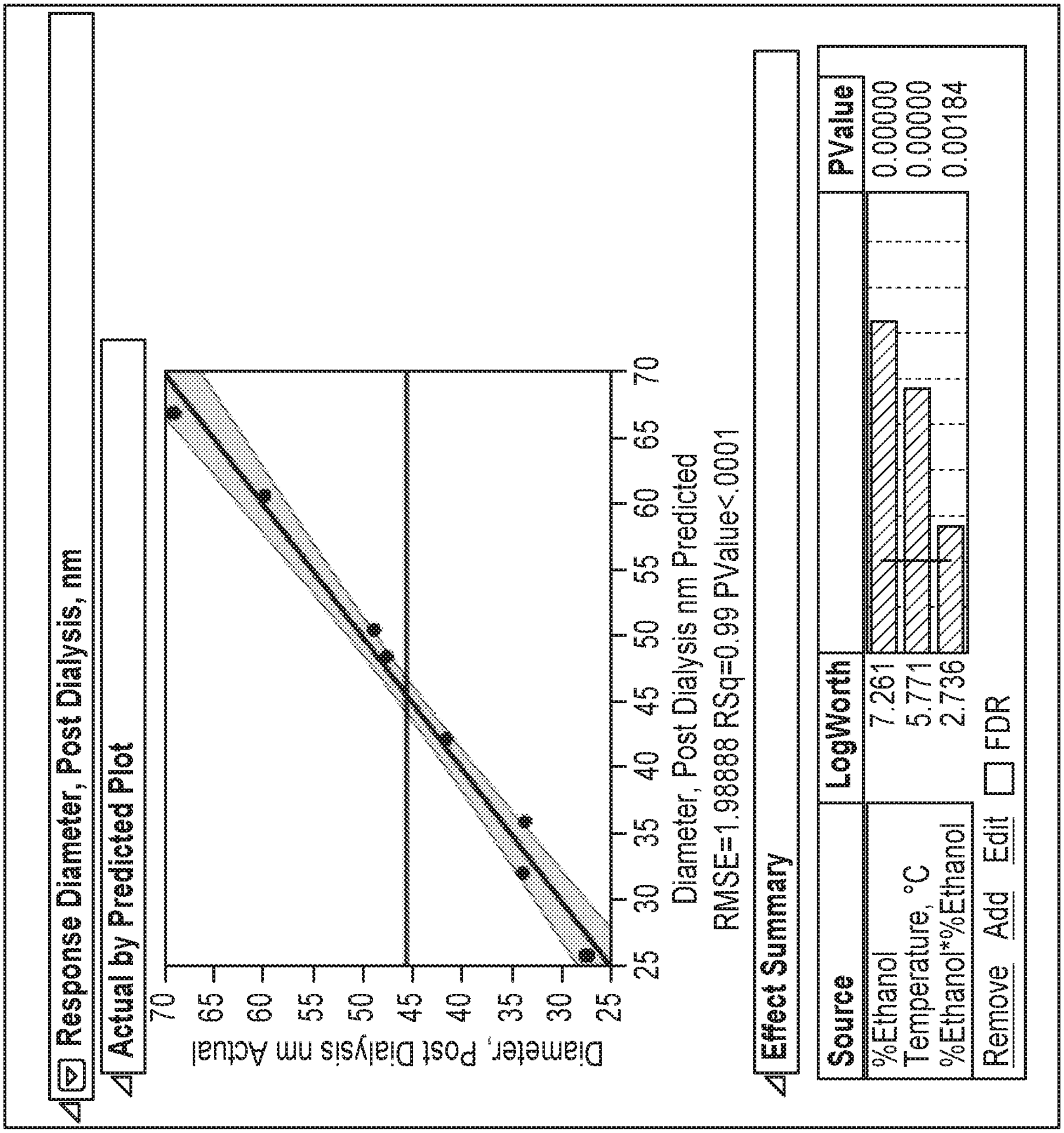
FIG. 8 is a model fitting demonstrating ethanol content and temperature are critical parameters affecting LNP diameter via DLS characterization where the model fitting enabled calculation of an advantageous range of process conditions to favor particle size control in a favorable range for mRNA encapsulation by the processes described herein (<100 nm) enabling small uniform particles and a favorable composition.

FIG. 8 is a model fitting demonstrating ethanol content and temperature are critical parameters affecting LNP diameter via DLS characterization where the model fitting enabled calculation of an advantageous range of process conditions to favor particle size control in a favorable range for mRNA encapsulation by the processes described herein (<100 nm).

Figure 9:
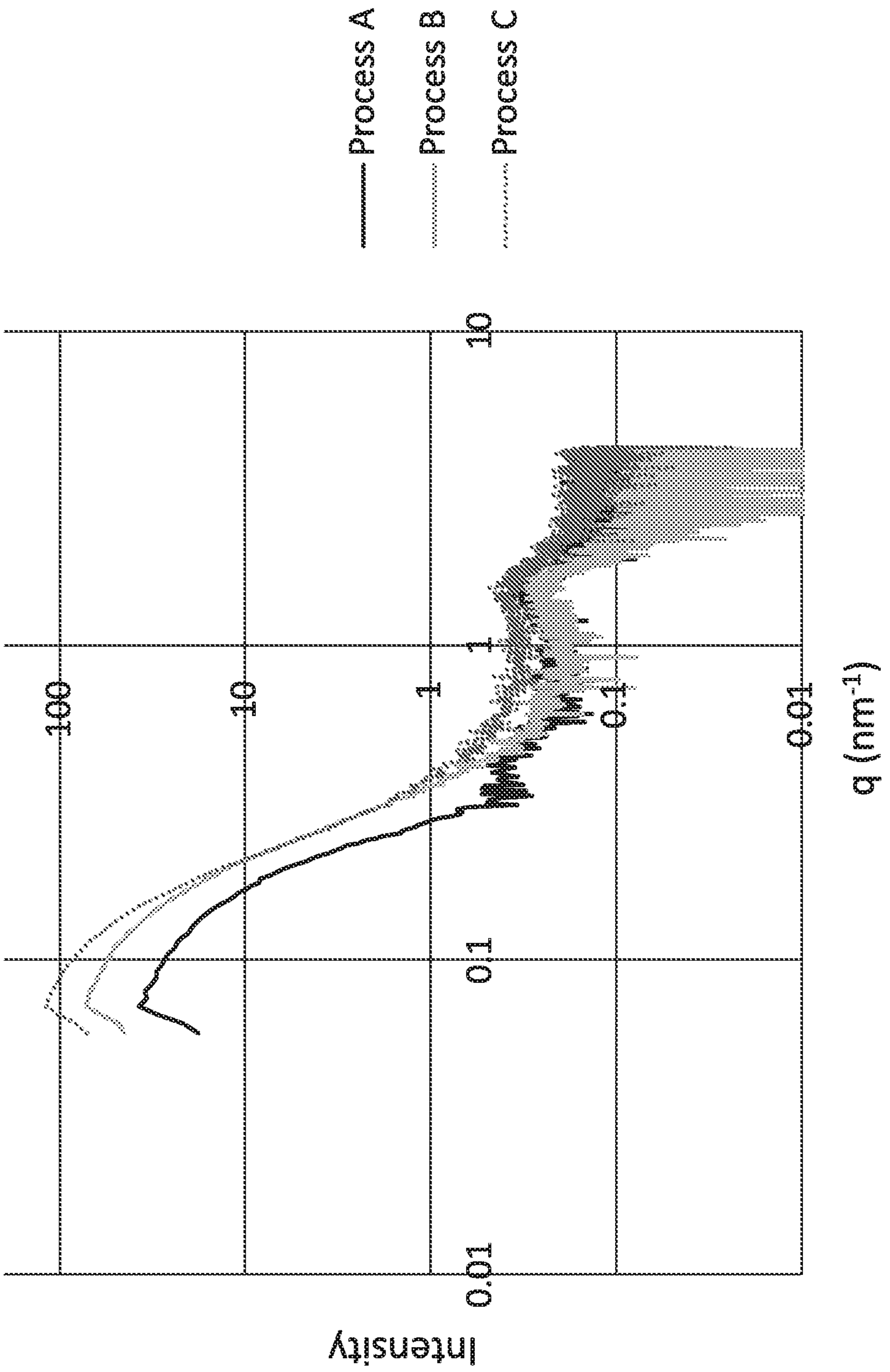
FIG. 9 is a graph demonstrating that the process for empty LNP generation affected structural features by small-angle x-ray scattering (SAXS) analysis showing that all process conditions resulted in particles with a pronounced feature at q=1.4 $nm^{-1}$ (calculated D-spacing ~4 nm). Process A without maturation generated an additional feature at q=0.45 (calculated D-spacing ~14 nm). This feature is associated with a population of small liposomal or micellar structures in the samples via cryo-TEM analysis. Process B and C incorporating a maturation time showed improved polydispersity (via DLS analysis) and structural homogeneity (via cryo-TEM analysis) compared to Process A.

FIG. 9 is a graph demonstrating that the process for empty LNP generation affected structural features by small-angle x-ray scattering (SAXS) analysis showing that all process conditions resulted in particles with a pronounced feature at q=1.4 $nm^{-1}$ (calculated D-spacing ~4 nm). Process A without maturation generated an additional feature at q=0.45 (calculated D-spacing ~14 nm). This feature is associated with a population of small liposomal or micellar structures in the samples via cryo-TEM analysis. Process B and C incorporating a maturation time showed improved polydispersity (via DLS analysis) and structural homogeneity (via cryo-TEM analysis) compared to Process A.

Figure 10:
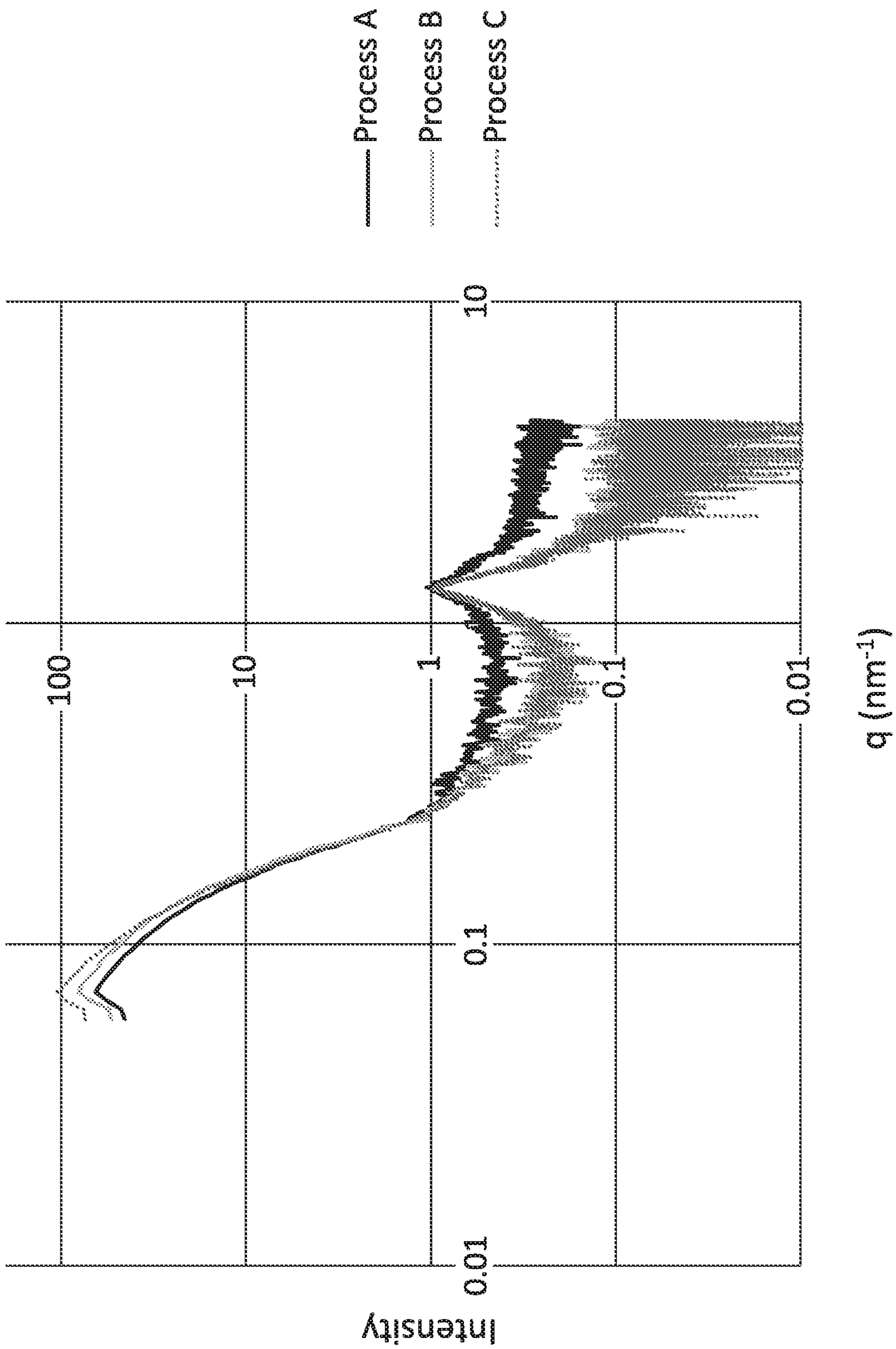
FIG. 10 is a graph demonstrating mRNA loaded via processes described herein produced particles showing a high degree of structure, with a pronounced feature at q=1.3 nm−1 (calculated D-spacing ~5 nm). Process B and C, which leverage optimal process conditions favoring maturation time and low PDI, showed decreased polydispersity and improved structural homogeneity compared to Process A.

FIG. 10 is a graph demonstrating mRNA loaded via processes described herein produced particles showing a high degree of structure, with a pronounced feature at q=1.3 nm−1 (calculated D-spacing ~5 nm). Process B and C, which leverage optimal process conditions favoring maturation time and low PDI, showed decreased polydispersity and improved structural homogeneity compared to Process A.

Figure 11:
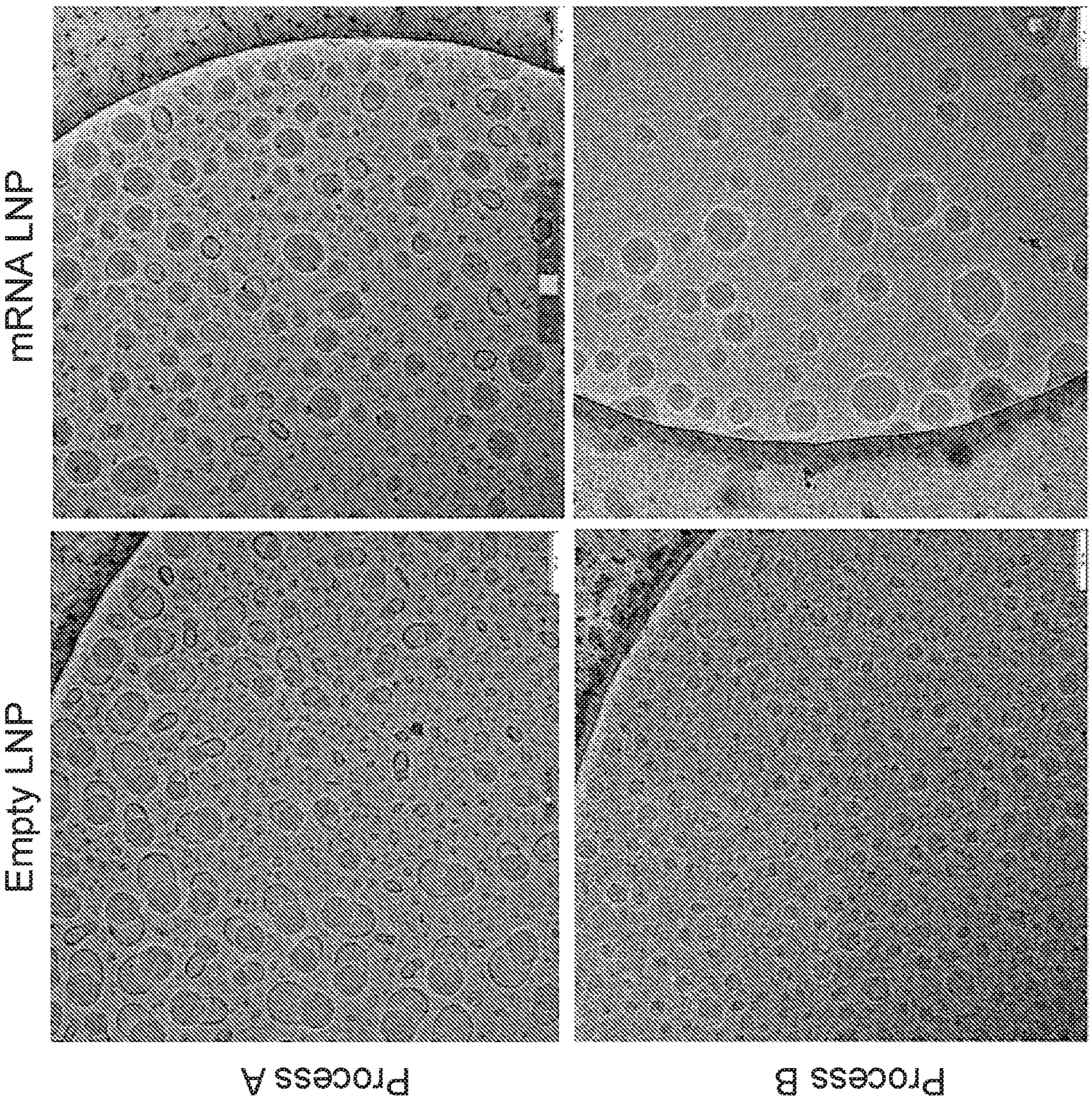
FIG. 11 is cryo-EM images demonstrating improved particle homogeneity observed with Process B (increased maturation) relative to Process A (standard) for batches generated with a procedures described herein.

FIG. 11 is cryo-EM images demonstrating improved particle homogeneity observed with Process B (increased maturation) relative to Process A (standard) for batches generated with a procedures described herein.

Figure 12:
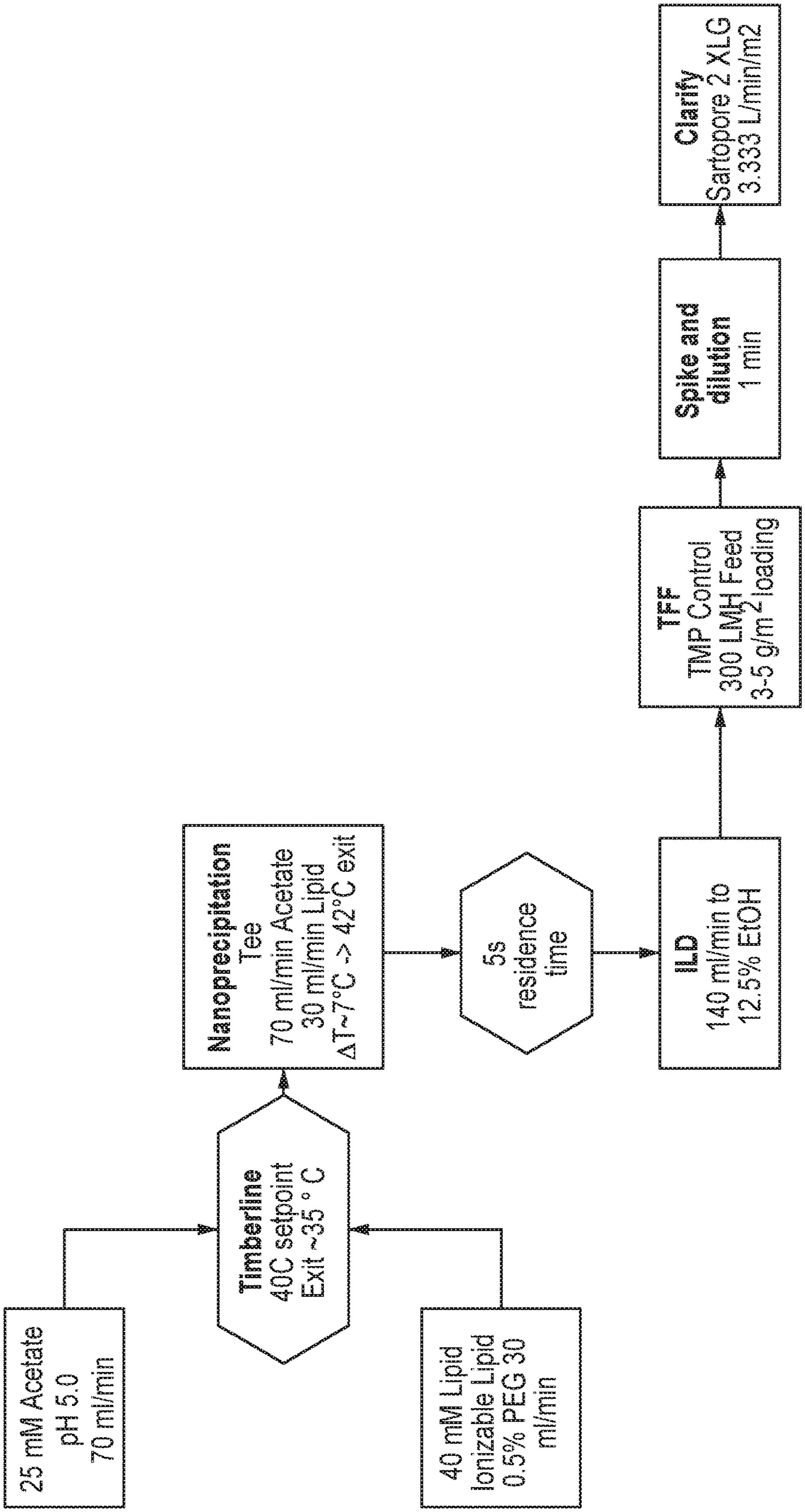
FIG. 12 is an exemplary process flow diagram demonstrating a continuous nanoprecipitation process for LNP formation.

FIG. 12 is an exemplary process flow diagram demonstrating a continuous nanoprecipitation process for LNP formation.

Figure 13:
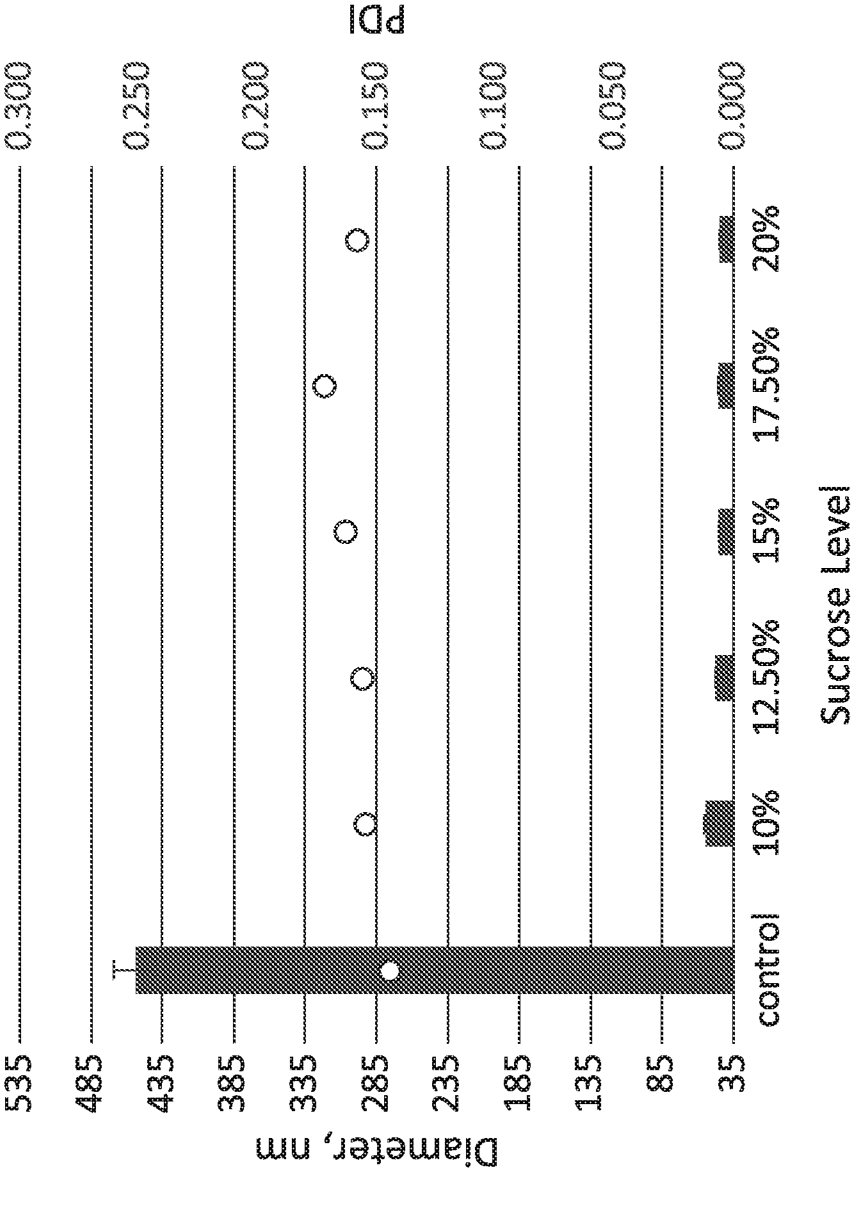
FIG. 13 is a graph demonstrating that sucrose exhibited a cryoprotective effect for LNP dispersions, enabling conservation of particle diameter after freeze/thaw stress, and advantageous sucrose concentration determined to be >15 wt %.

FIG. 13 is a graph demonstrating that sucrose exhibited a cryoprotective effect for LNP dispersions, enabling conservation of particle diameter after freeze/thaw stress, and advantageous sucrose concentration determined to be >15 wt %.

Figure 14:
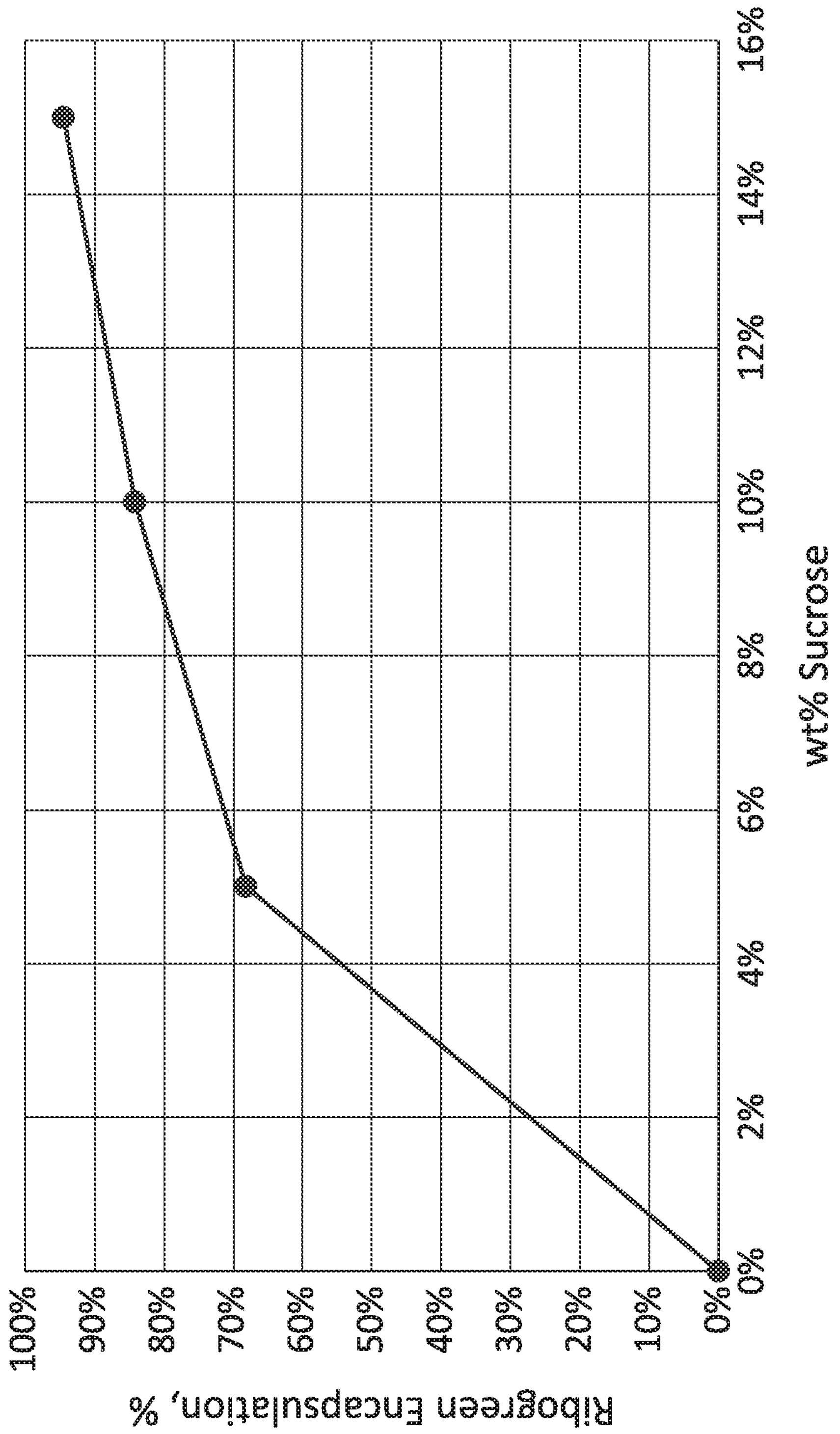
FIG. 14 is a graph demonstrating that inclusion of cryoprotective excipient sucrose enabled complete mRNA encapsulation via the processes described herein (Ribogreen Assay) for lipid nanoparticles that experience a free/thaw stress prior to mRNA addition.

FIG. 14 is a graph demonstrating that inclusion of cryoprotective excipient sucrose enabled complete mRNA encapsulation via the processes described herein (Ribogreen Assay).

Figure 15A:
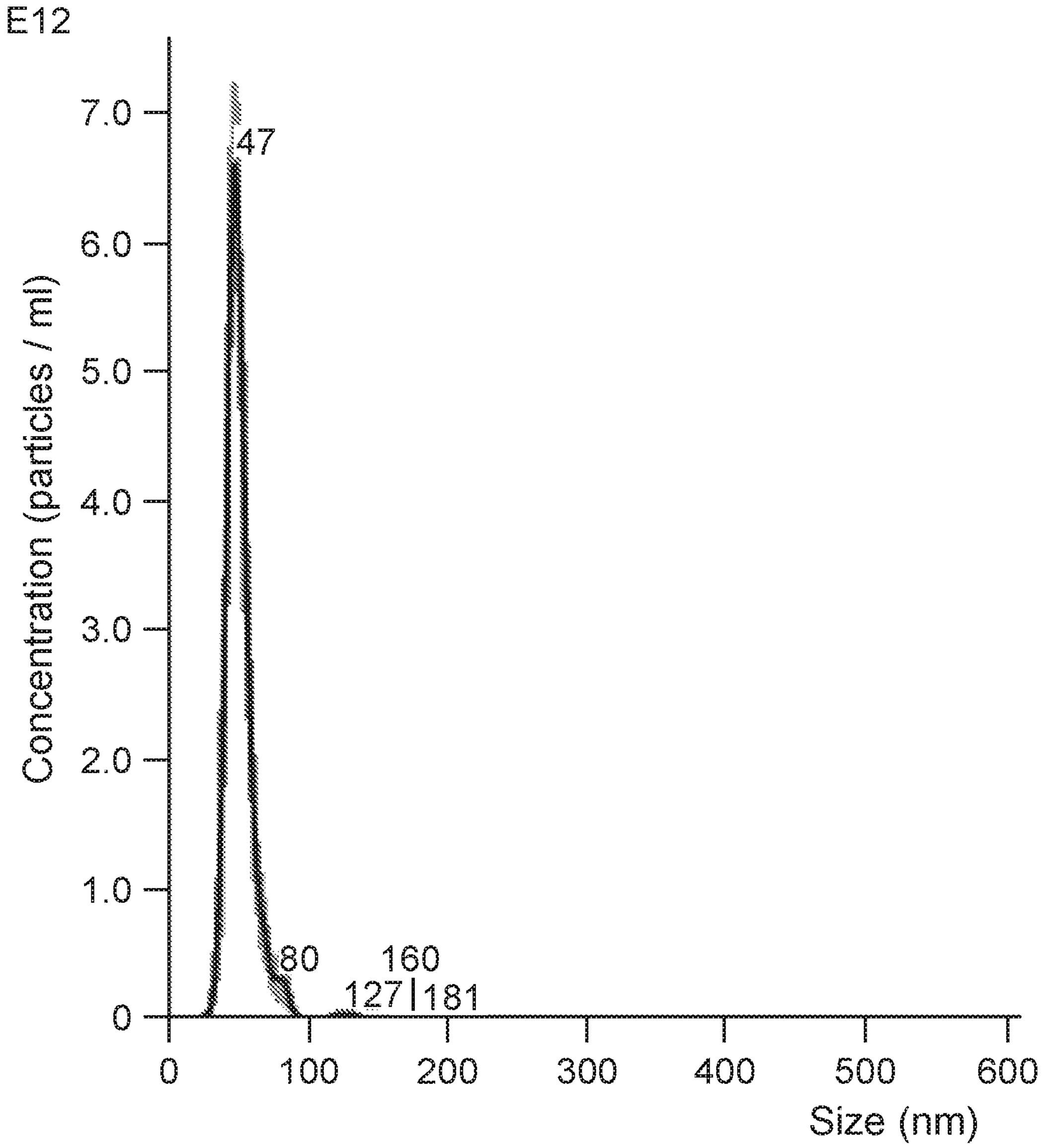
FIG. 15A is a graph graphs demonstrating a standard primary population of LNP characterized by nanoparticle tracking analysis (NTA) in the liquid state (~50 nm).
Figure 15B:
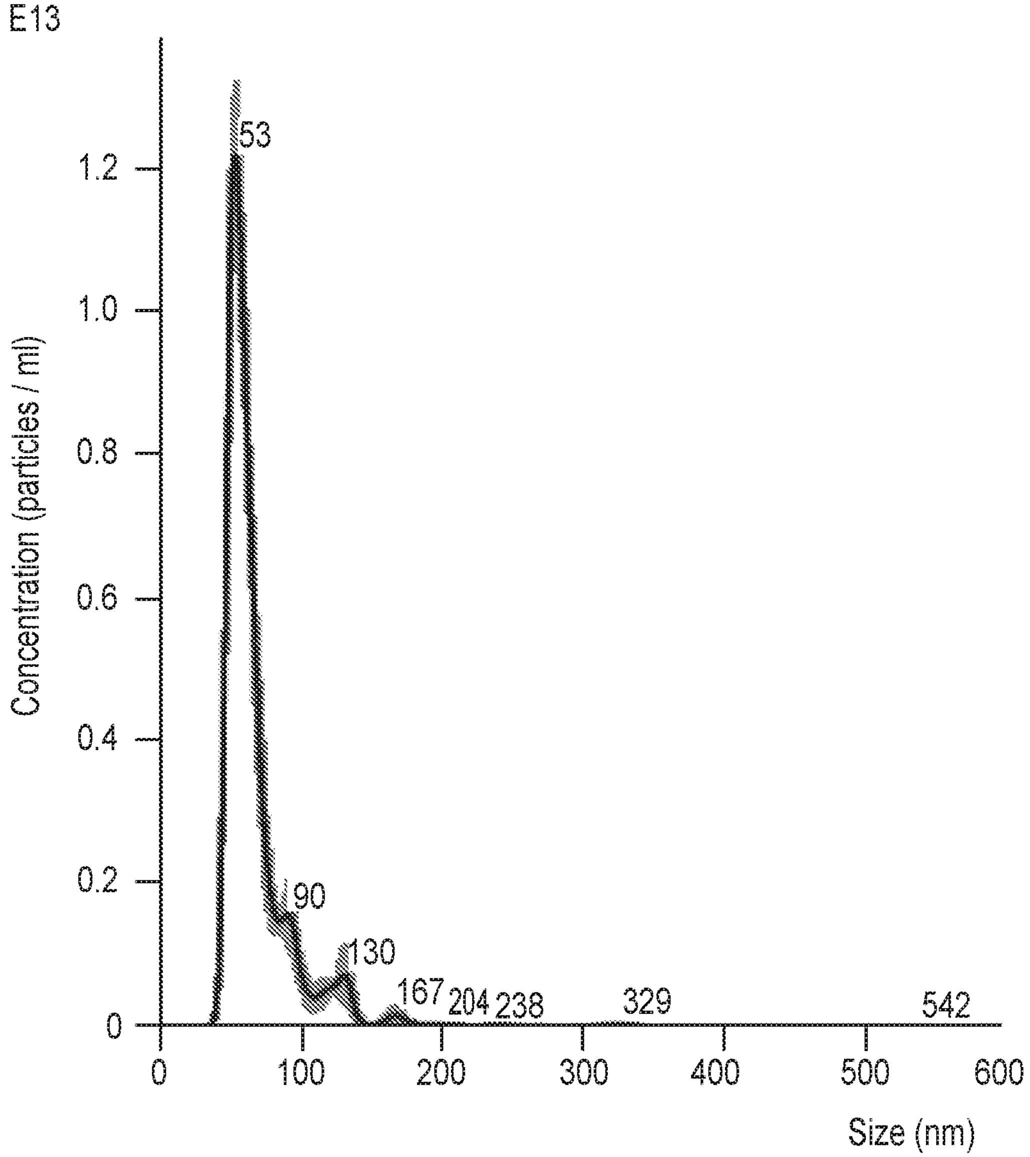
FIG. 15B is a graph demonstrating a conservation of the primary nanoparticle population after subjecting the formulation (Acetate-sucrose) to lyophilization and reconstitution in distilled, deionized water.

FIGS. 15A and 15B are graphs demonstrating a standard primary population of LNP characterized by nanoparticle tracking analysis (NTA) in the liquid state (~50 nm) (15A)

and conservation of the primary nanoparticle population after subjecting the formulation (Acetate-sucrose) to lyophilization and reconstitution in distilled, deionized water (15B).

Figure 16:
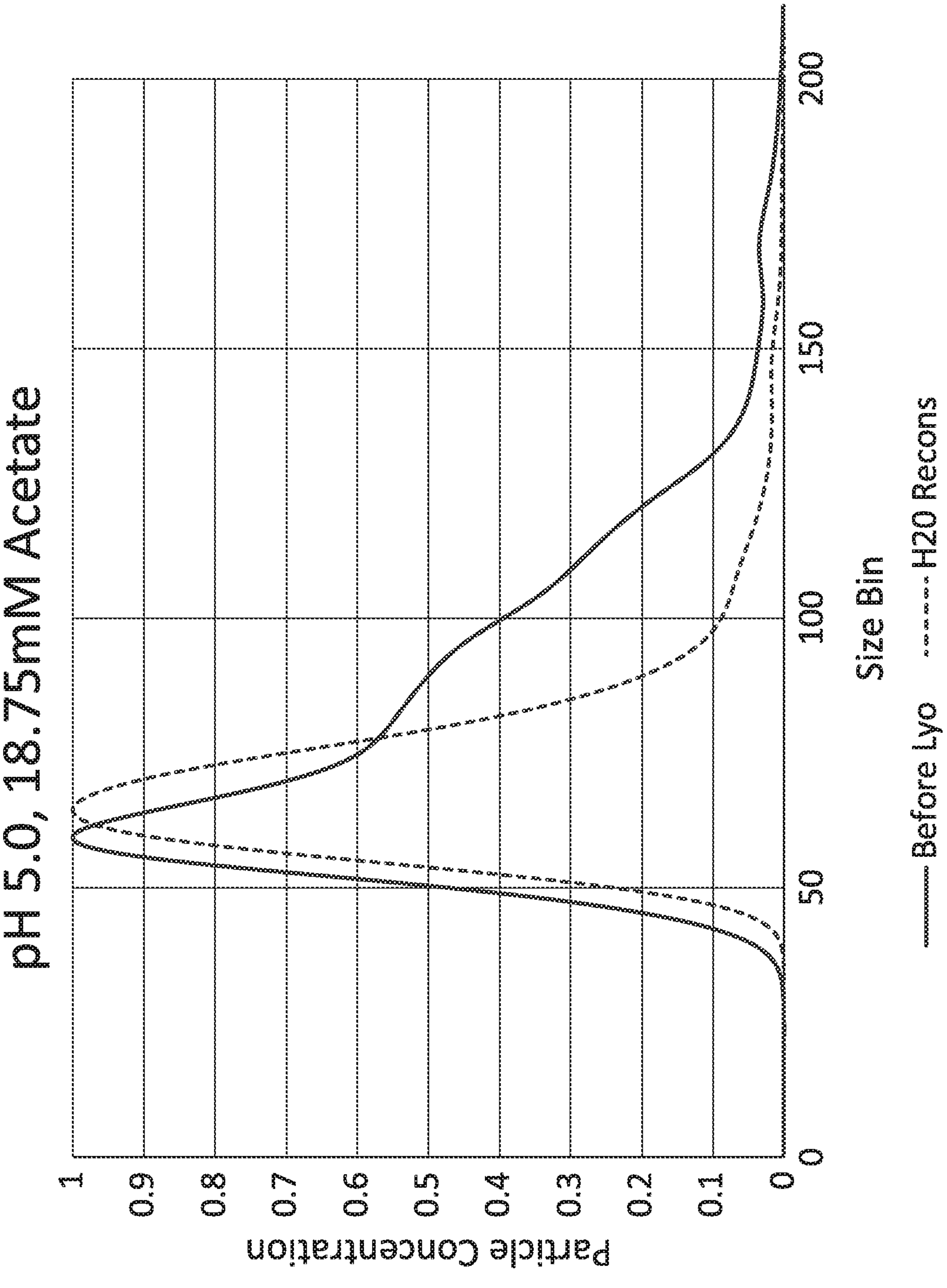
FIG. 16 are graphs demonstrating the overlay of particle distribution for liquid and lyophilized/reconstituted product LNP formulations.

FIG. 16 are graphs demonstrating the overlay of particle distribution for liquid and lyophilized/reconstituted product LNP formulations.

Figure 17:
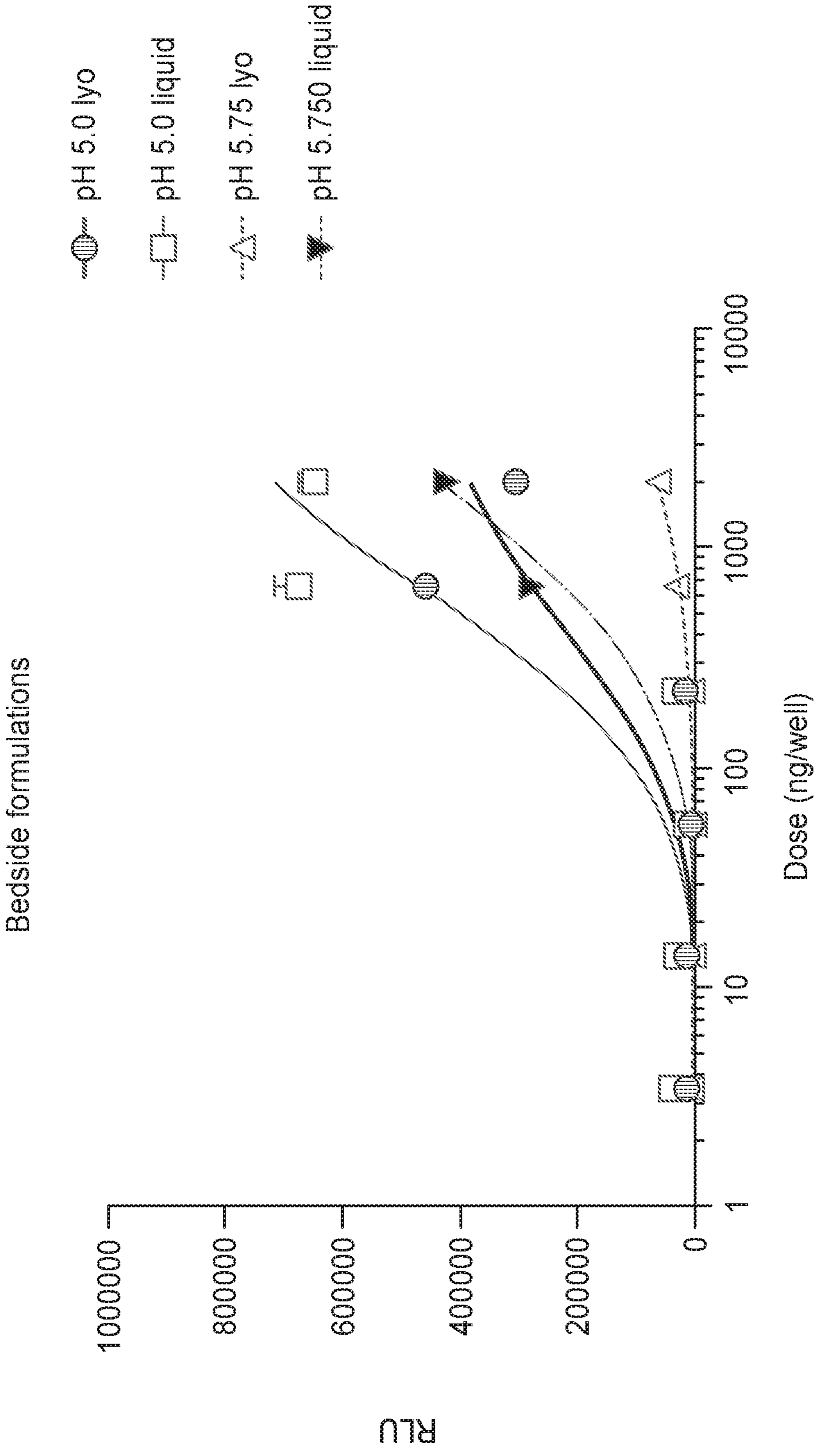
FIG. 17 is a graph demonstrating the increased in vitro expression was observed for pH 5.0 lyophilized formulation compared to pH 5.75.

FIG. 17 is a graph demonstrating the increased in vitro expression was observed for pH 5.0 lyophilized formulation compared to pH 5.75.

Figure 18:
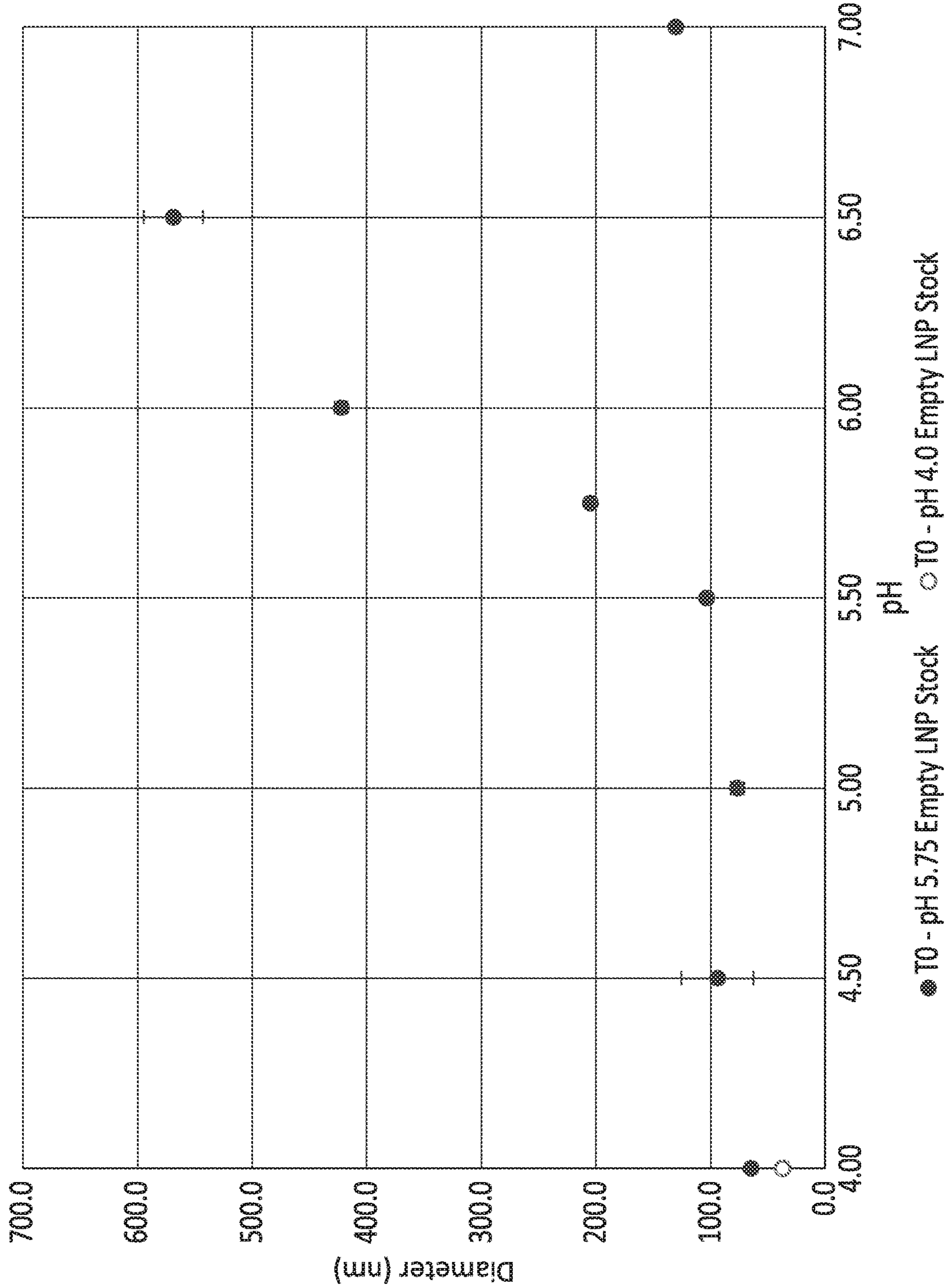
FIG. 18 is a graph demonstrating that an advantageous pH was determined by varying mRNA and LNP solution pH values prior to combination in the field mixing process. Particle size control was advantageously achieved at pH<6.0.

FIG. 18 is a graph demonstrating that an advantageous pH was determined by varying mRNA and LNP solution pH values prior to combination in the field mixing process. Particle size control was advantageously achieved at pH<6.0.

Figure 19:
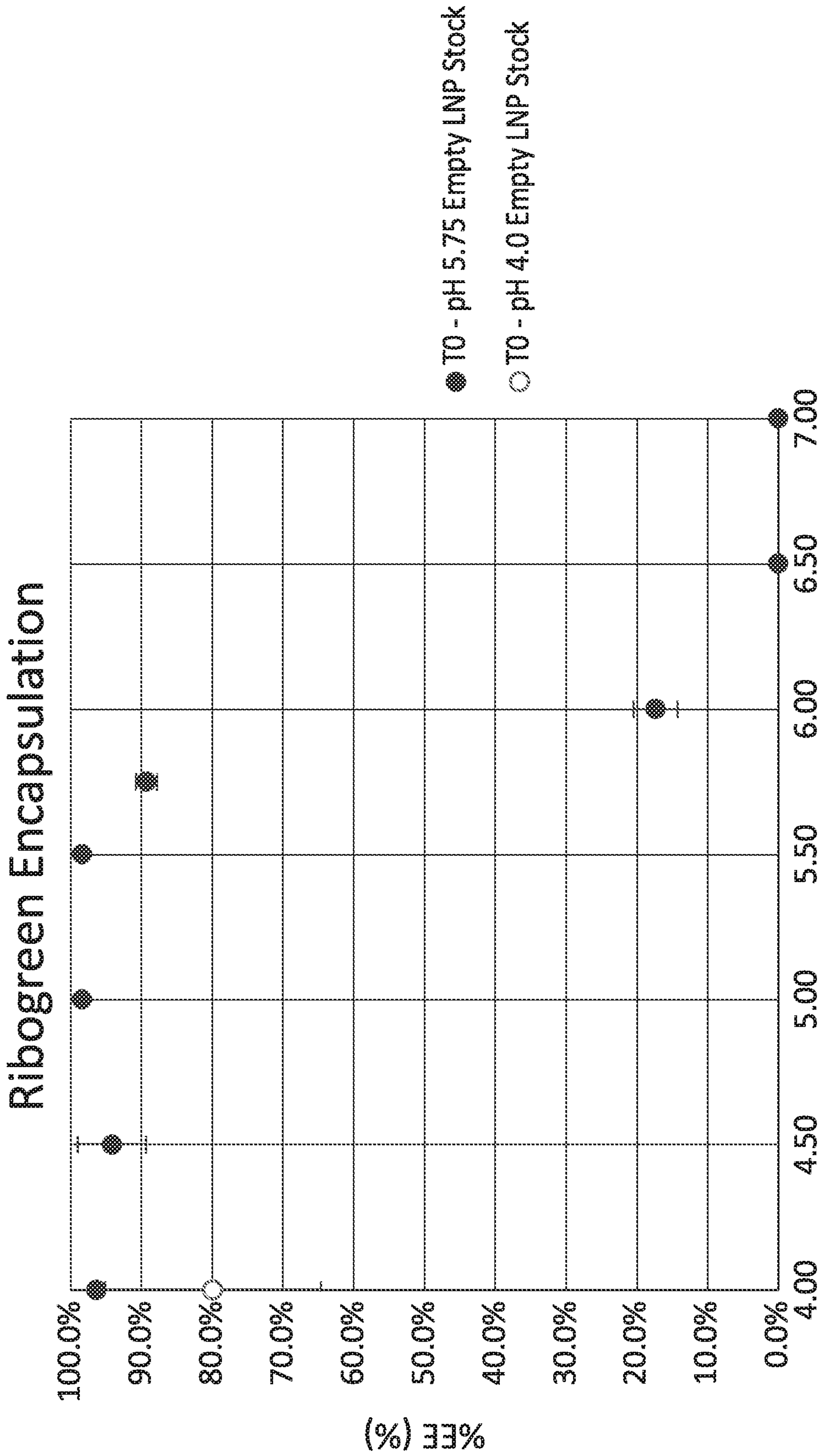
FIG. 19 is a graph demonstrating that advantageous pH was determined by varying mRNA and LNP solution pH values prior to combination in the processes described herein and increased encapsulation was achieved at pH<6.0 (Ribogreen Assay).

FIG. 19 is a graph demonstrating that advantageous pH was determined by varying mRNA and LNP solution pH values prior to combination in the processes described herein and increased encapsulation was achieved at pH<6.0 (Ribogreen Assay).

Figure 20:
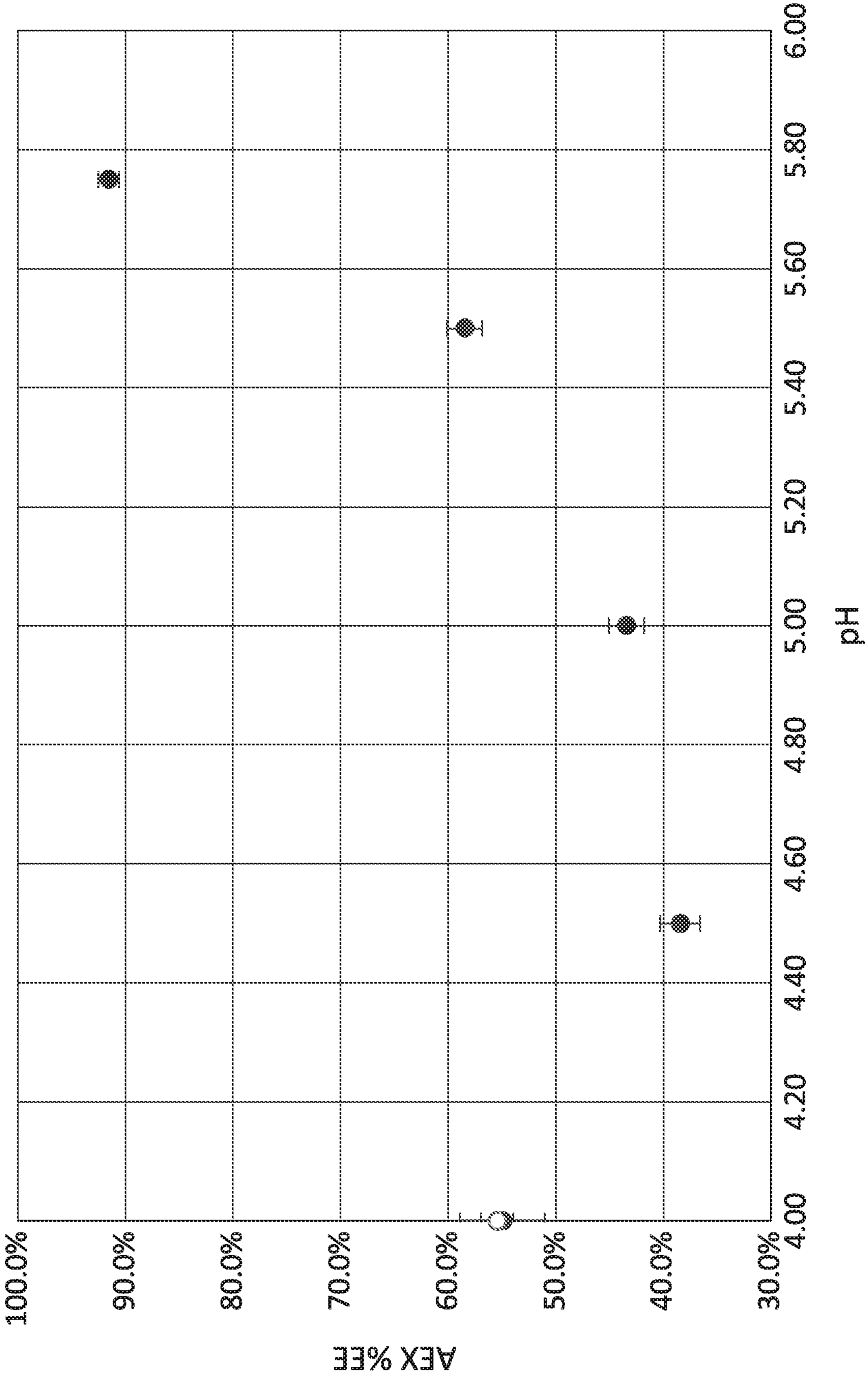
FIG. 20 is a graph demonstrating advantageous pH was determined by varying mRNA and LNP solution pH values prior to combination in the processes described herein and increased encapsulation was achieved at pH<6.0 (AEX Assay).

FIG. 20 is a graph demonstrating advantageous pH was determined by varying mRNA and LNP solution pH values prior to combination in the processes described herein and increased encapsulation was achieved at pH<6.0 (AEX Assay).

Figure 21:
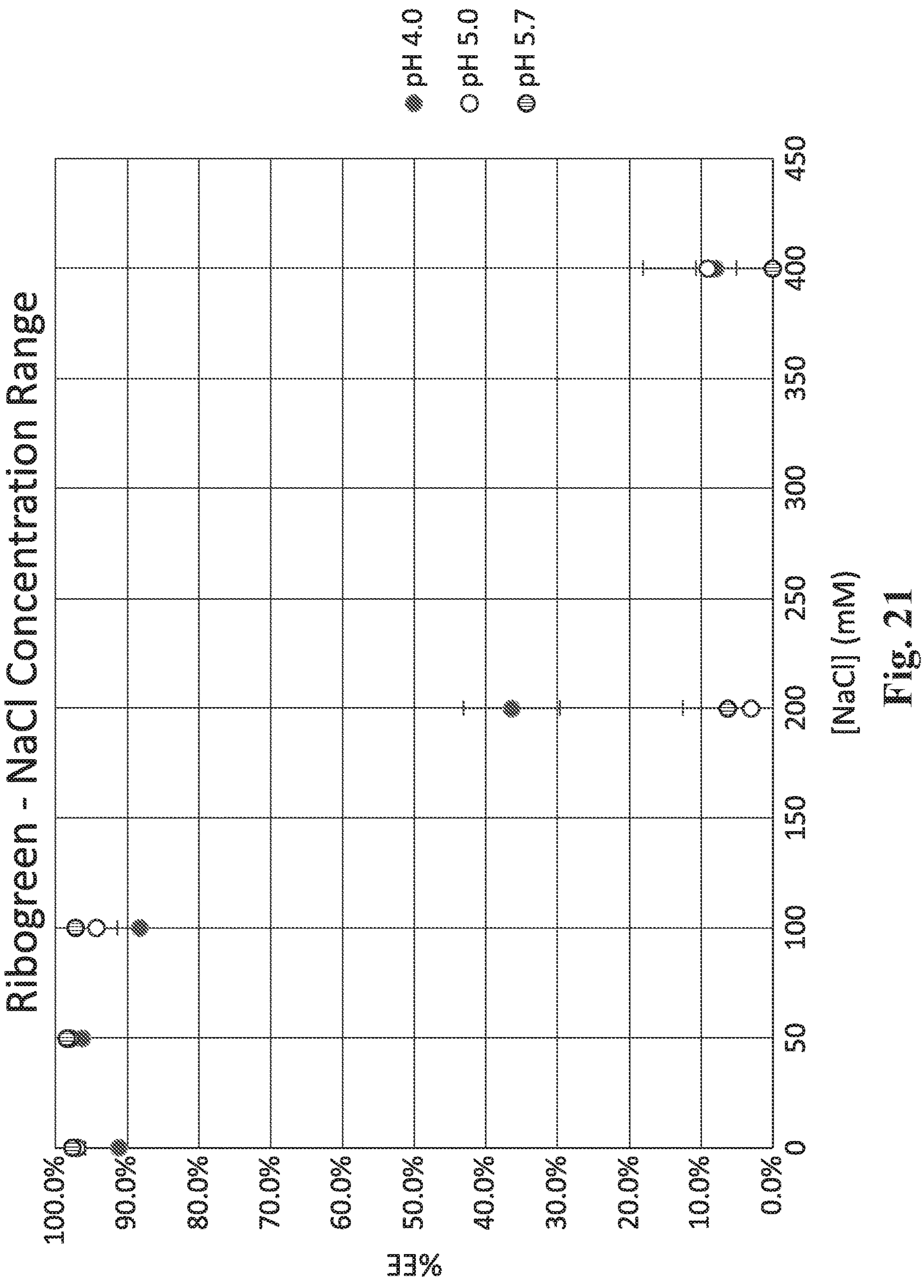
FIG. 21 is a graph demonstrating that ionic strength sensitivity was assessed by varying molar concentration of NaCl within the LNP and mRNA solution together in the processes described herein and advantageous concentrations that favor mRNA encapsulation were <200 mM.

FIG. 21 is a graph demonstrating that ionic strength sensitivity was assessed by varying molar concentration of NaCl within the LNP and mRNA solution together in the processes described herein and advantageous concentrations that favor mRNA encapsulation were <200 mM.

Figure 22:
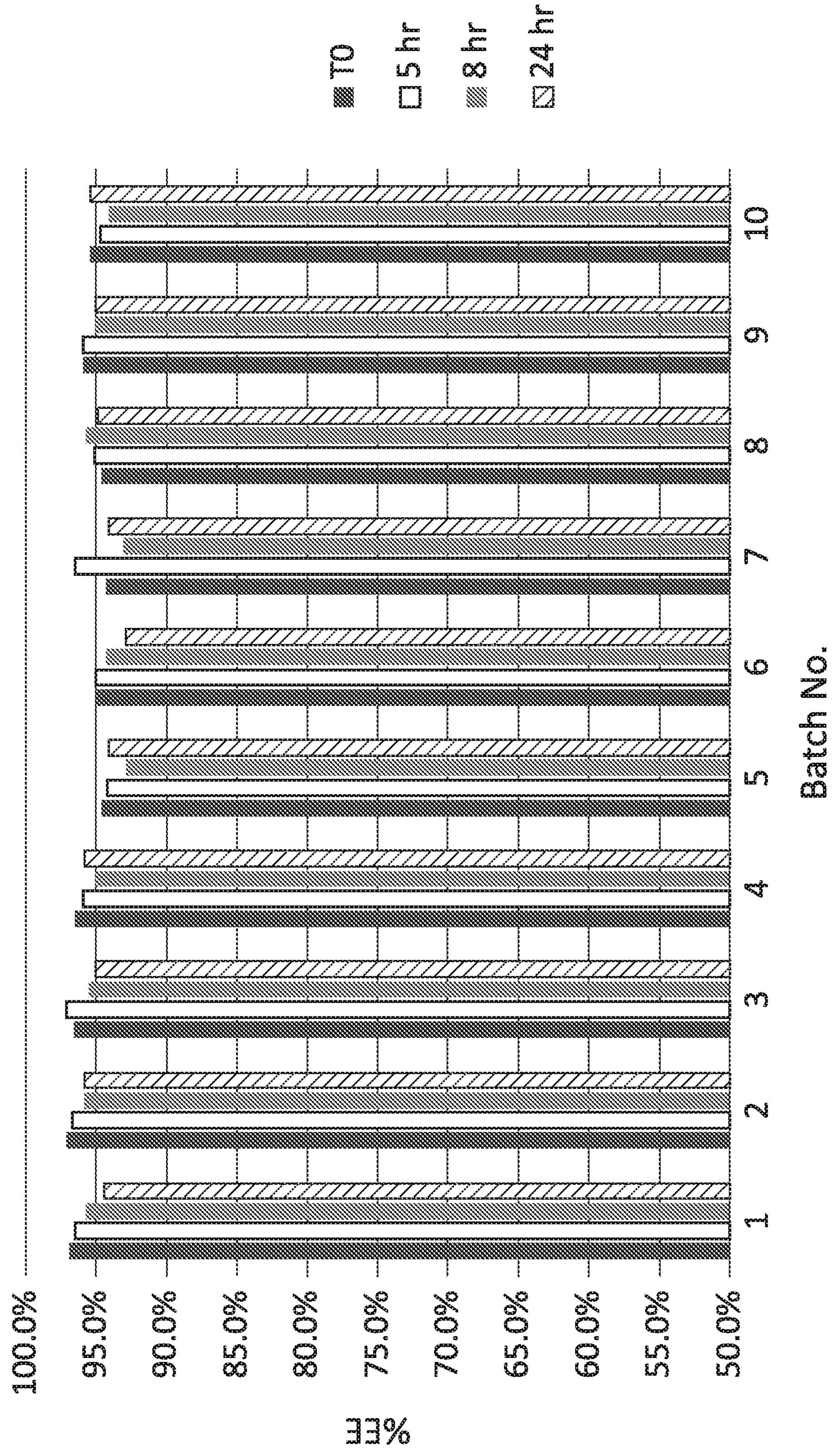
FIG. 22 is a graph demonstrating that low batch-to-batch variability in mRNA encapsulation is observed with the processes described herein and that mRNA-loaded LNPs showed consistent mRNA encapsulation after aging for 24 hr.

FIG. 22 is a graph demonstrating that low batch-to-batch variability in mRNA encapsulation is observed with the processes described herein and that mRNA-loaded LNPs showed consistent mRNA encapsulation after aging for 24 hr.

Figure 23:
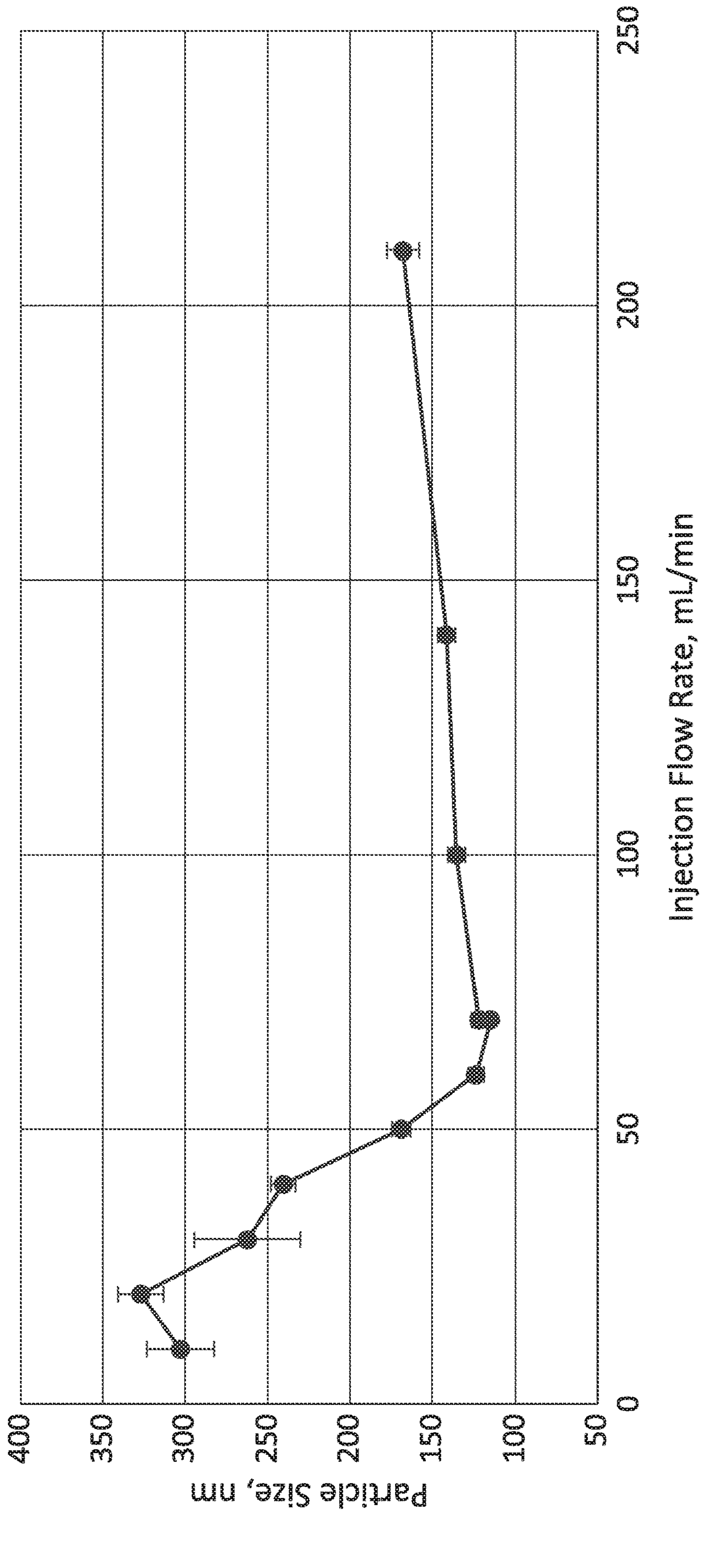
FIG. 23 is a graph demonstrating the impact of injection flow rate on particle size via DLS measurement where a solution of mRNA was directly injected into a vial containing a buffered solution of LNPs and resulting particle diameter was sensitive to injection rate.

FIG. 23 is a graph demonstrating the impact of injection flow rate on particle size via DLS measurement where a solution of mRNA was directly injected into a vial containing a buffered solution of LNPs and resulting particle diameter was sensitive to injection rate.

Figure 24:
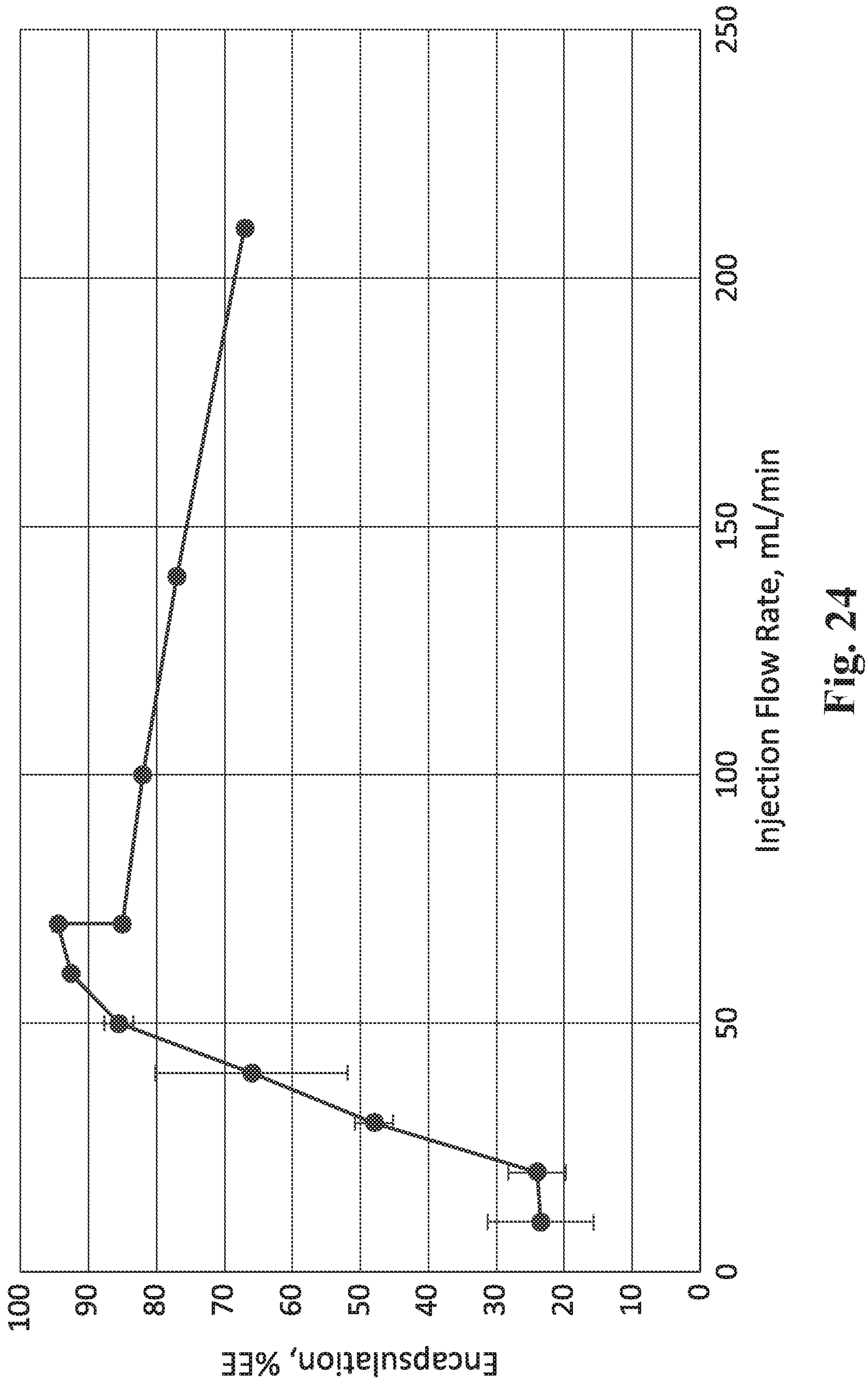
FIG. 24 is a graph demonstrating the impact of injection flow rate on mRNA encapsulation (Ribogreen Assay) where a solution of mRNA was directly injected into a vial containing a buffered solution of LNPs.

FIG. 24 is a graph demonstrating the impact of injection flow rate on mRNA encapsulation (Ribogreen Assay) where a solution of mRNA was directly injected into a vial containing a buffered solution of LNPs.

Figure 25:
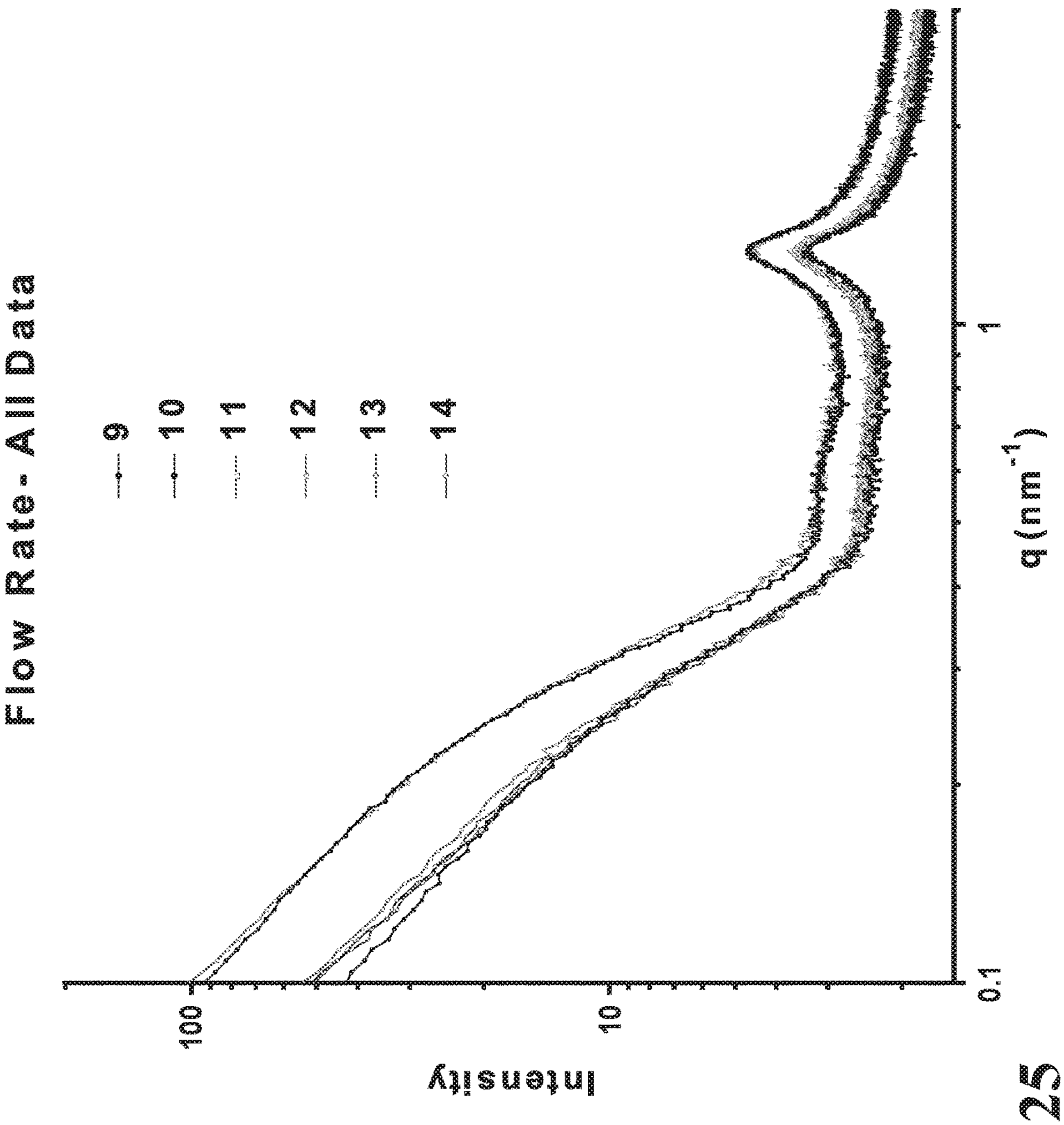
FIG. 25 is a graph demonstrating that mRNA lipid nanoparticle formulations loaded via a process described herein comprised particles showing a high degree of structure, with a pronounced feature at q=1.3 nm−1 (calculated D-spacing ~5 nm) and that comparable structural features were observed with varying flow rate (sample 9-14).

FIG. 25 is a graph demonstrating that mRNA lipid nanoparticle formulations loaded via a process described herein comprised particles showing a high degree of structure, with a pronounced feature at q=1.3 nm−1 (calculated D-spacing ~5 nm) and that comparable structural features were observed with varying flow rate (sample 9-14).

Figure 26:
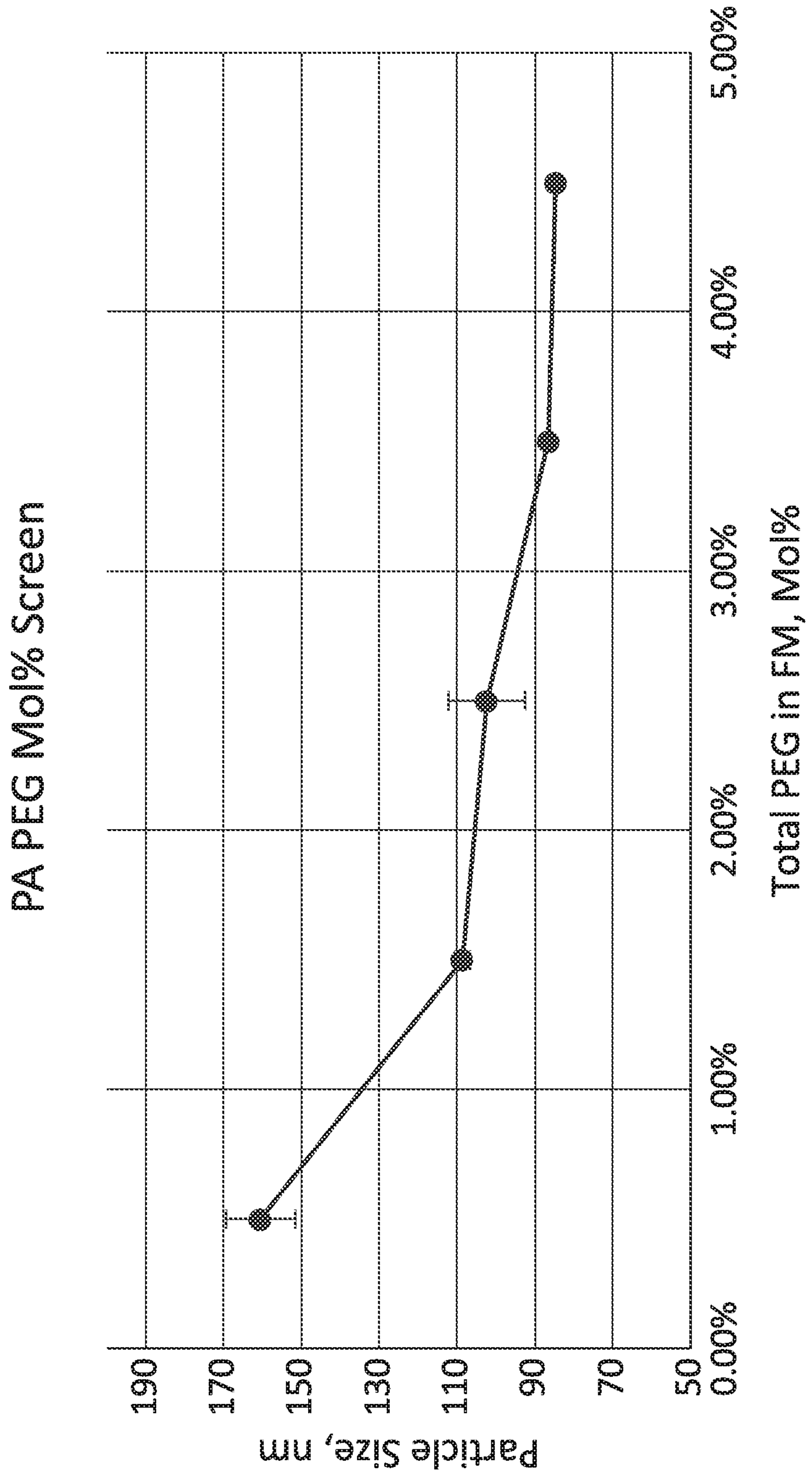
FIG. 26 is a graph demonstrating that the addition of increasing levels of PEG-Lipid conjugate in LNP solution decreased particle size after mixing with mRNA.

FIG. 26 is a graph demonstrating that the addition of increasing levels of PEG-Lipid conjugate in LNP solution decreased particle size after mixing with mRNA.

Figure 27:
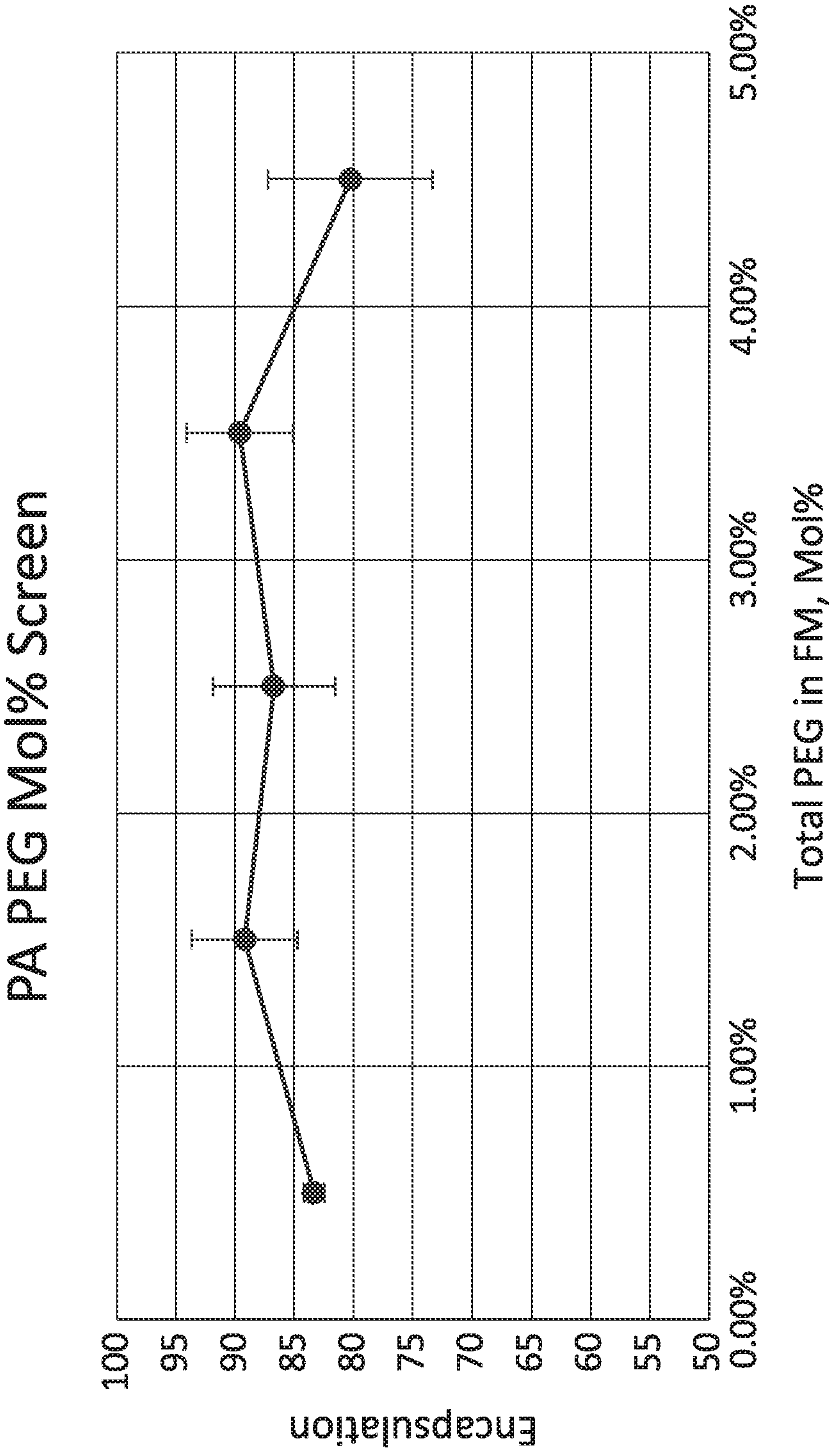
FIG. 27 is a graph demonstrating that the addition of increasing levels of PEG-Lipid conjugate in LNP solution did not affect mRNA encapsulation.

FIG. 27 is a graph demonstrating that the addition of increasing levels of PEG-Lipid conjugate in LNP solution did not affect mRNA encapsulation.

Figure 28:
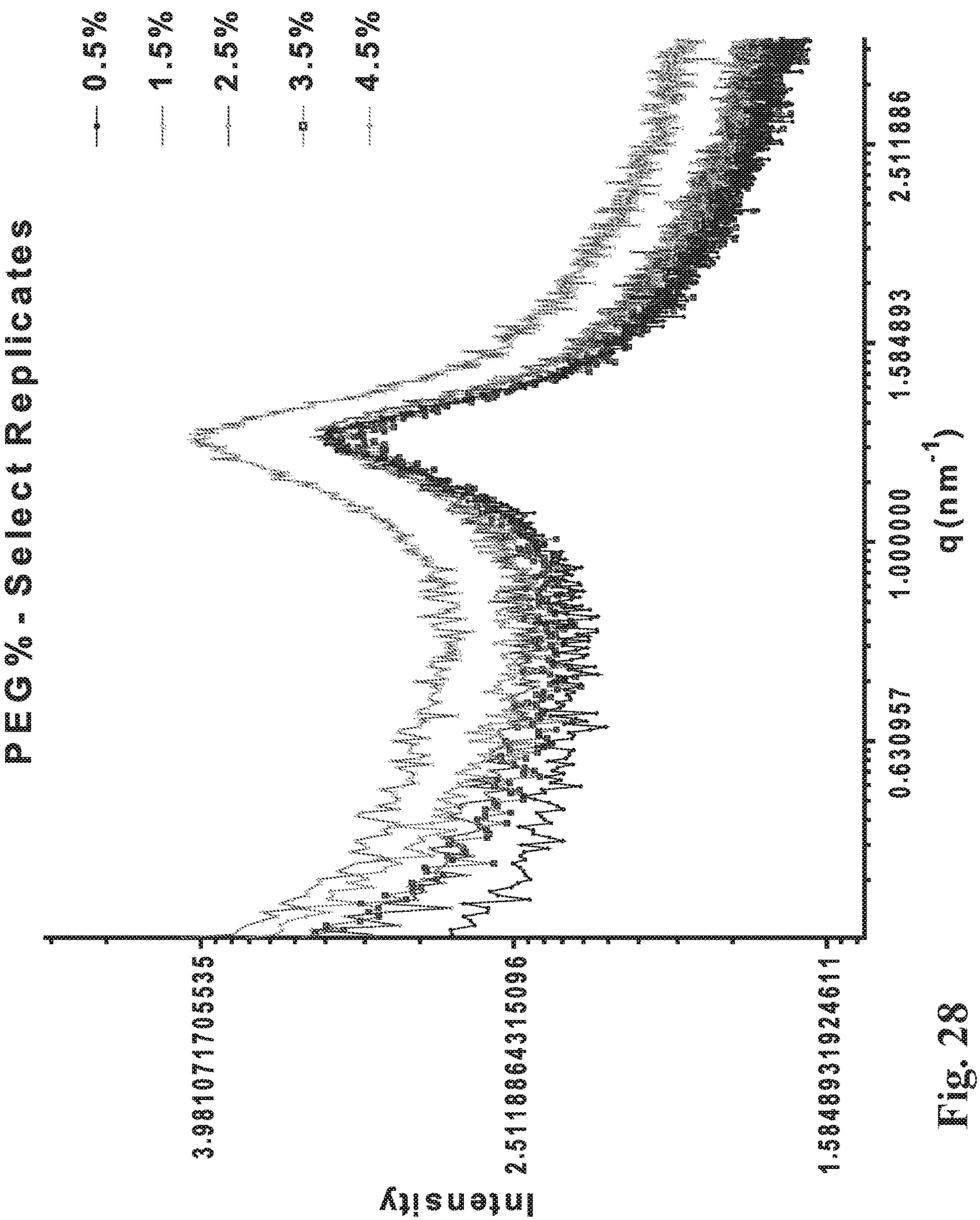
FIG. 28 is a graph demonstrating that mRNA lipid nanoparticle formulations loaded via a process described herein comprised particles showing a high degree of structure, with a pronounced feature at q=1.3 nm−1 (calculated D-spacing ~5 nm) and that comparable structural features were observed with mol % PEG-Lipid included in the mixing step.

FIG. 28 is a graph demonstrating that mRNA lipid nanoparticle formulations loaded via a process described herein comprised particles showing a high degree of structure, with a pronounced feature at q=1.3 nm−1 (calculated D-spacing ~5 nm) and that comparable structural features were observed with mol % PEG-Lipid included in the mixing step.

Figure 29B:
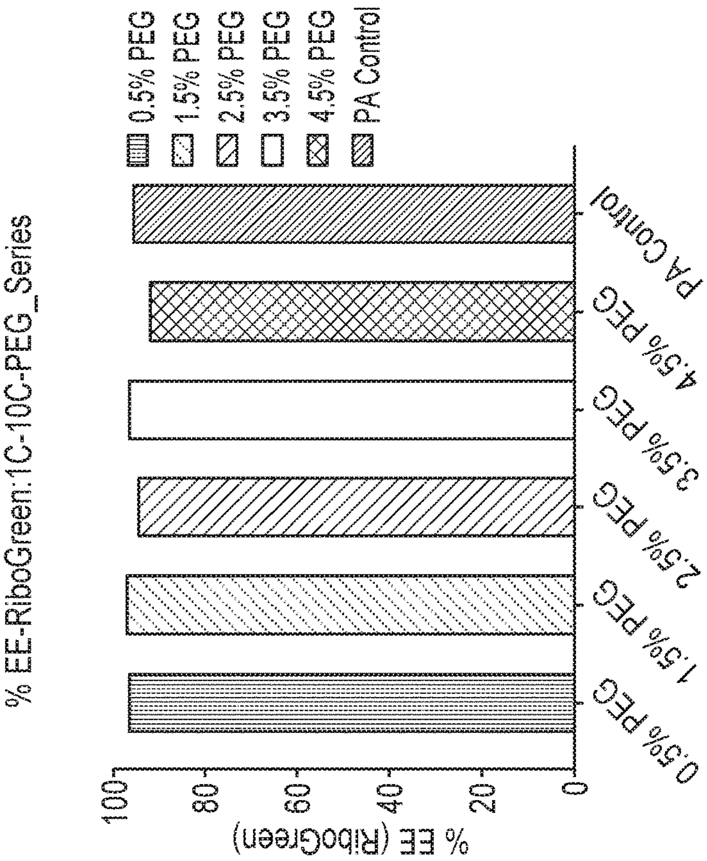
FIG. 29B is a graph demonstrating that the addition of increasing levels of a PEG-Lipid conjugate in LNP solution decreased sensitivity to injection flow rate in mixing processes described herein.
Figure 29A:
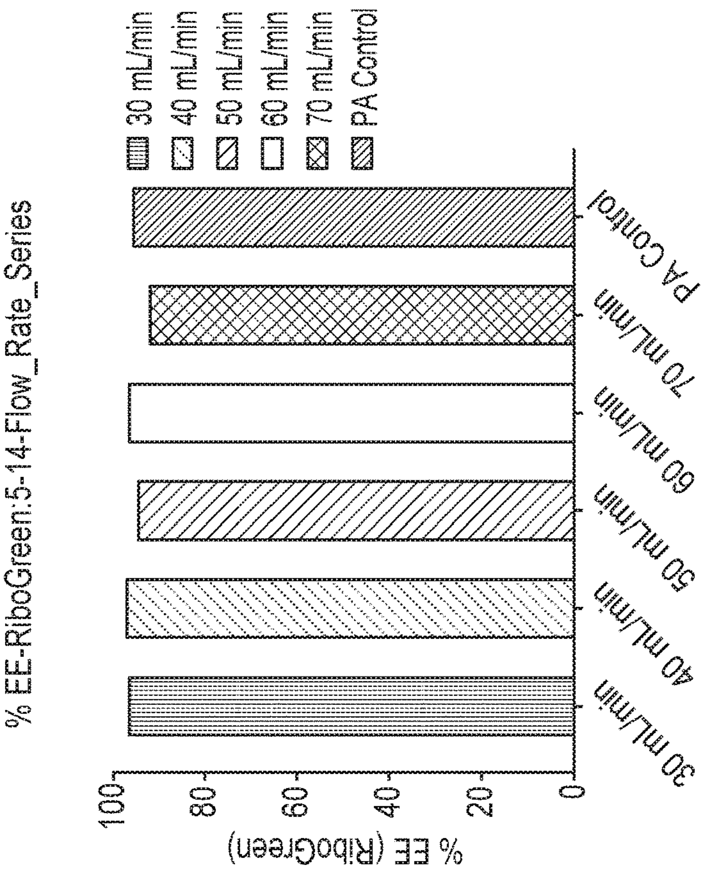
FIG. 29A is a graph demonstrating that the addition of increasing levels of a PEG-Lipid conjugate in LNP solution decreased sensitivity to injection flow rate in mixing processes described herein.

FIG. 29 is a graph demonstrating that the addition of increasing levels of a PEG-Lipid conjugate in LNP solution decreased sensitivity to injection flow rate in mixing processes described herein.

Figure 30:
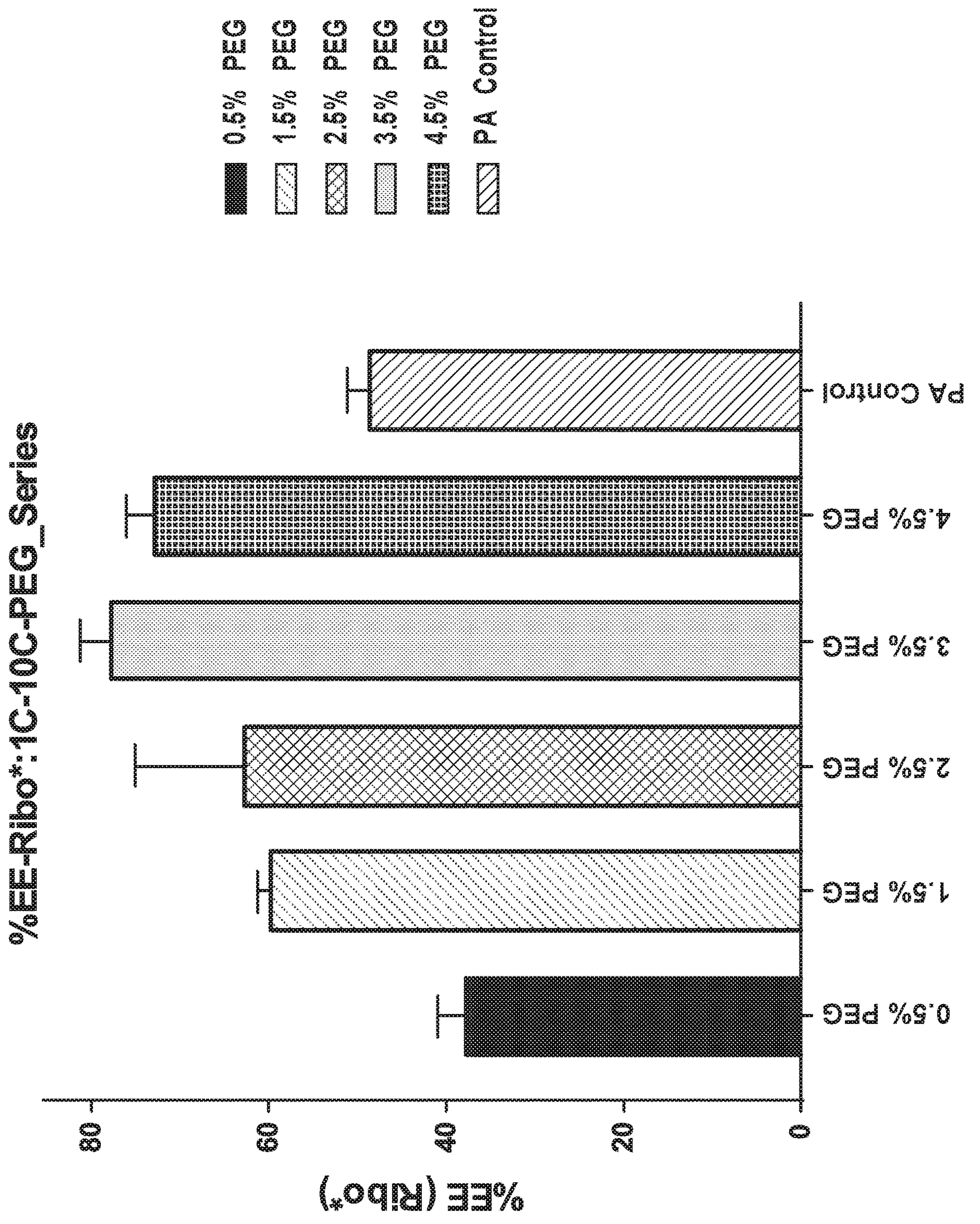
FIG. 30 is a graph demonstrating that the addition of increasing levels of PEG-Lipid conjugate in LNP solution increased encapsulation (Ribostar assay).

FIG. 30 is a graph demonstrating that the addition of increasing levels of PEG-Lipid conjugate in LNP solution increased encapsulation (Ribostar assay).

Figure 31:
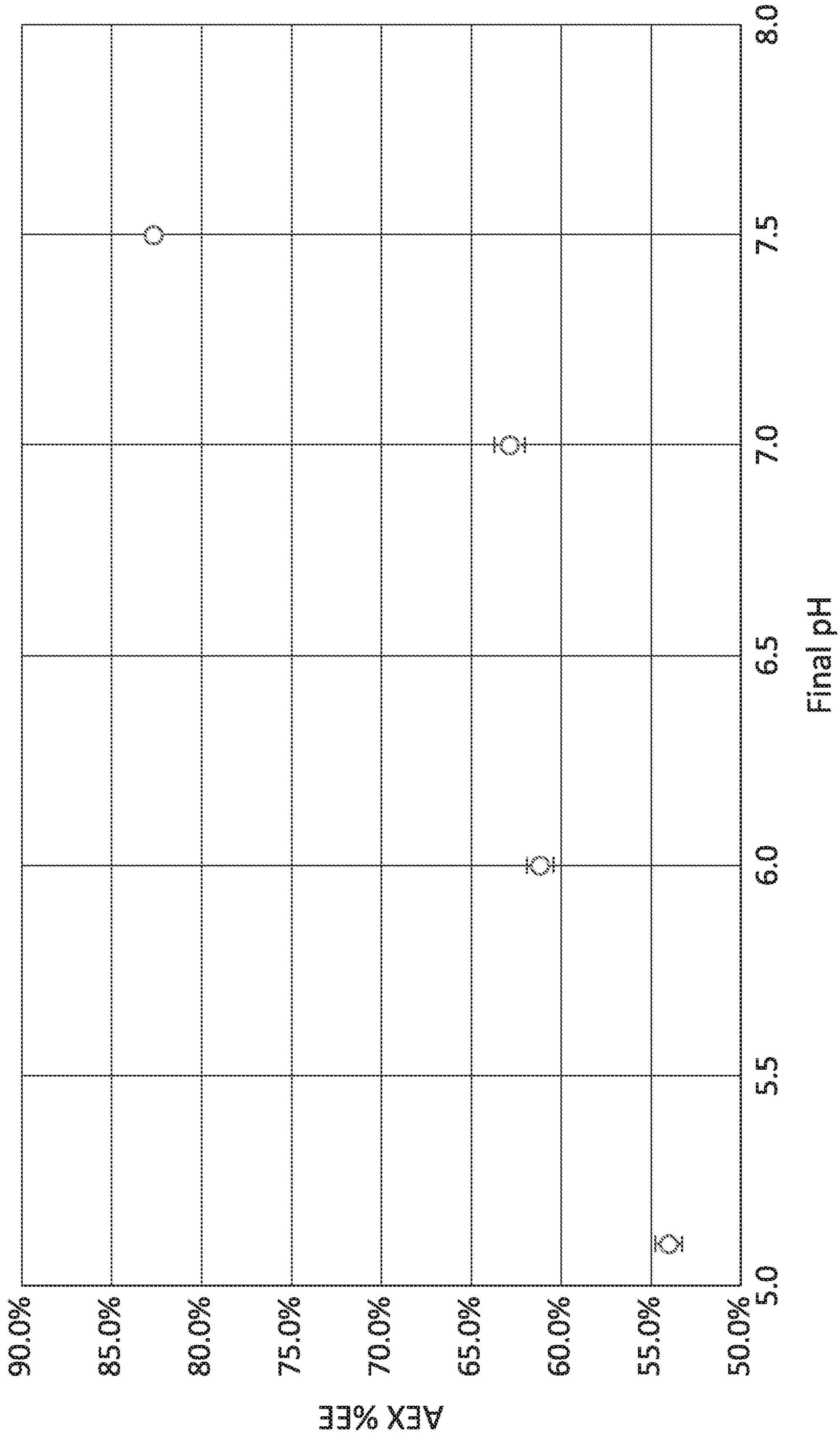
FIG. 31 is a graph demonstrating that the neutralization of mixed product resulted in increased mRNA encapsulation (AEX assay) and neutralization may be achieved through addition of a concentrated sodium phosphate solution to a target pH value.

FIG. 31 is a graph demonstrating that the neutralization of mixed product resulted in increased mRNA encapsulation (AEX assay) and neutralization may be achieved through addition of a concentrated sodium phosphate solution to a target pH value.

Figure 32:
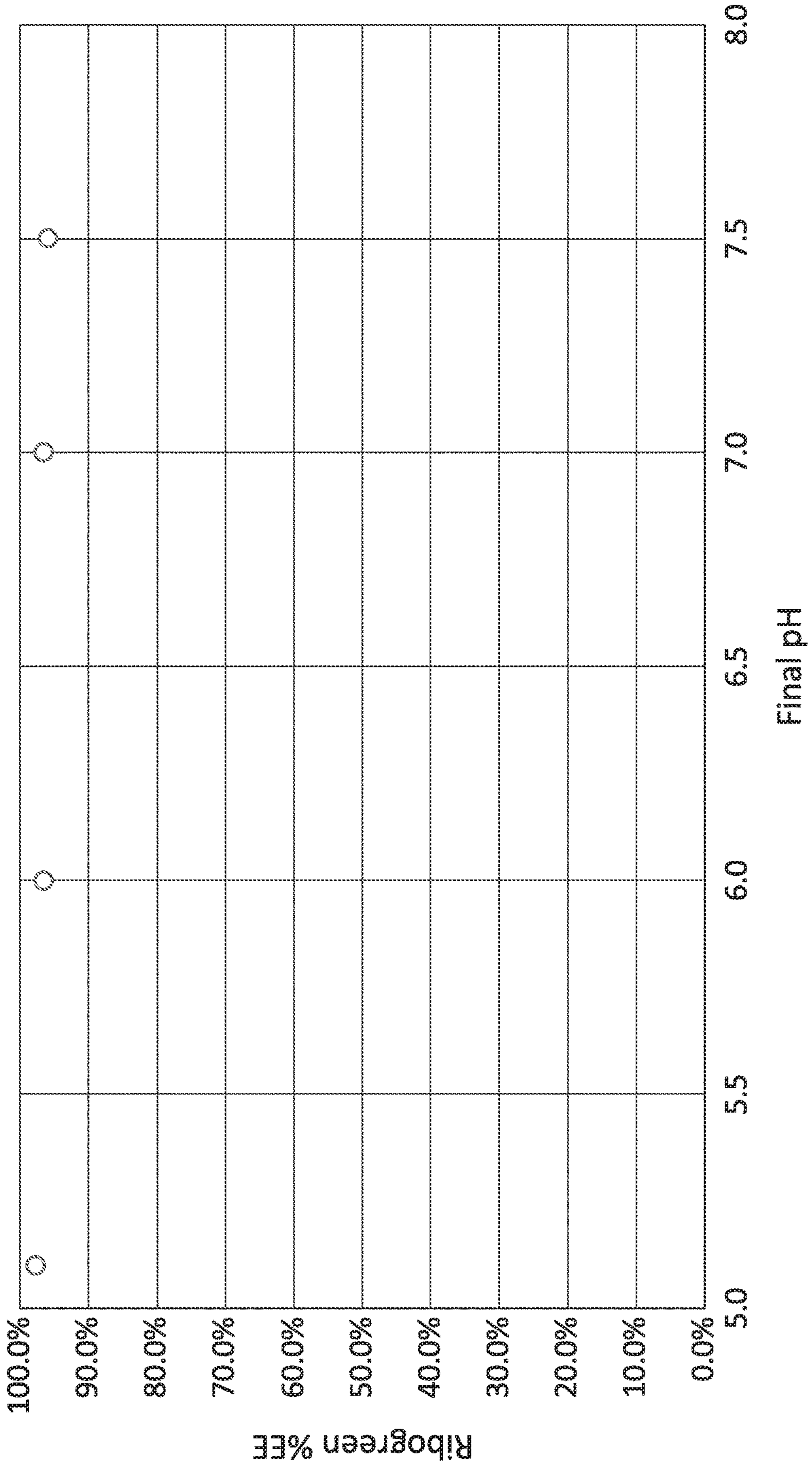
FIG. 32 is a graph demonstrating that a Ribogreen assay was unable to detect sensitivity to pH-neutralization of mixed product and neutralization was achieved through addition of a concentrated sodium phosphate solution to a target pH value.

FIG. 32 is a graph demonstrating that a Ribogreen assay was unable to detect sensitivity to pH-neutralization of mixed product and neutralization was achieved through addition of a concentrated sodium phosphate solution to a target pH value.

Figure 33:
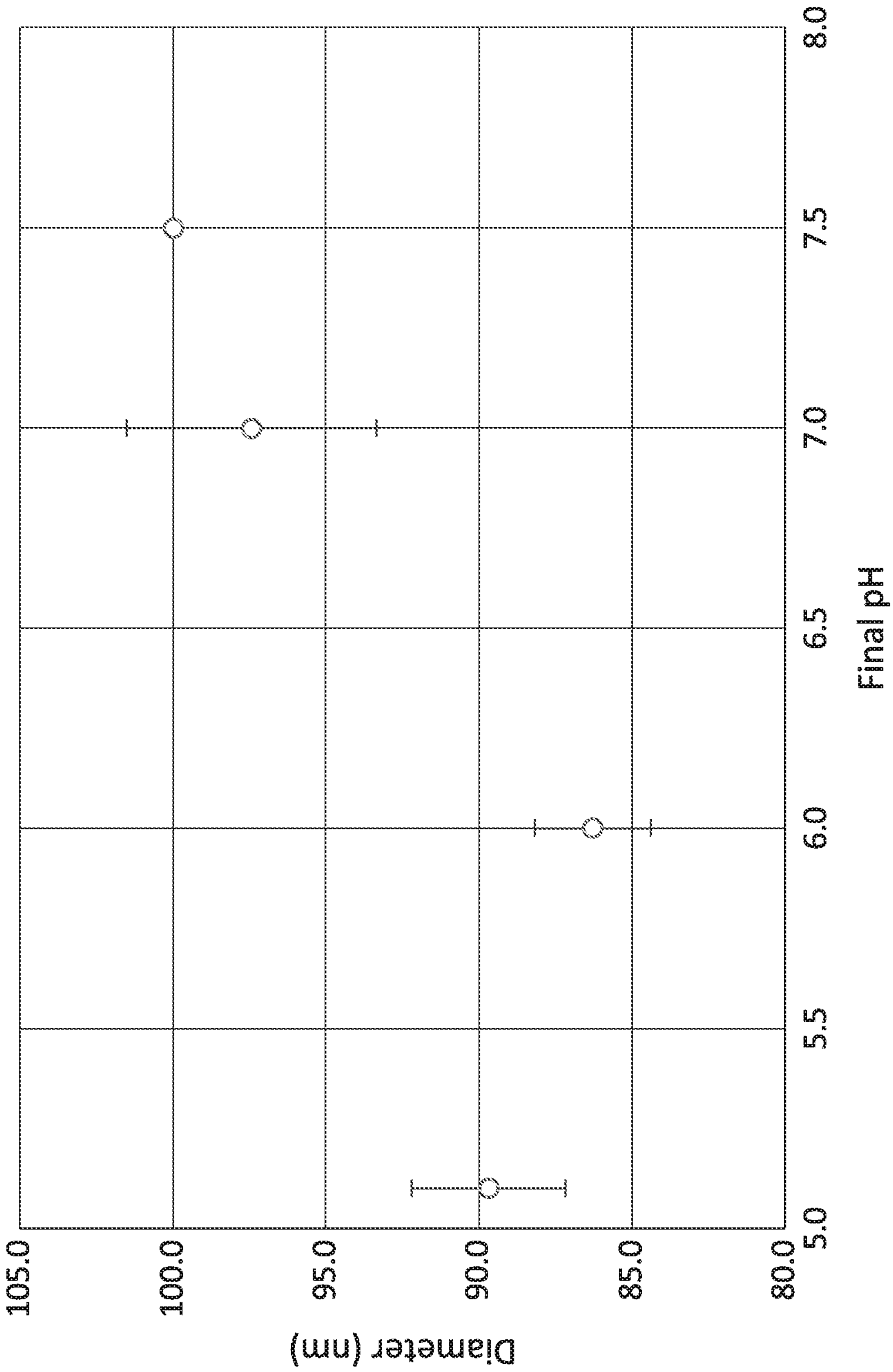
FIG. 33 is a graph demonstrating that the neutralization of mixed product resulted in increased LNP diameter (~10 nm) and neutralization was achieved through addition of a concentrated sodium phosphate solution to a target pH value.

FIG. 33 is a graph demonstrating that the neutralization of mixed product resulted in increased LNP diameter (~10 nm) and neutralization was achieved through addition of a concentrated sodium phosphate solution to a target pH value.

Figure 34:
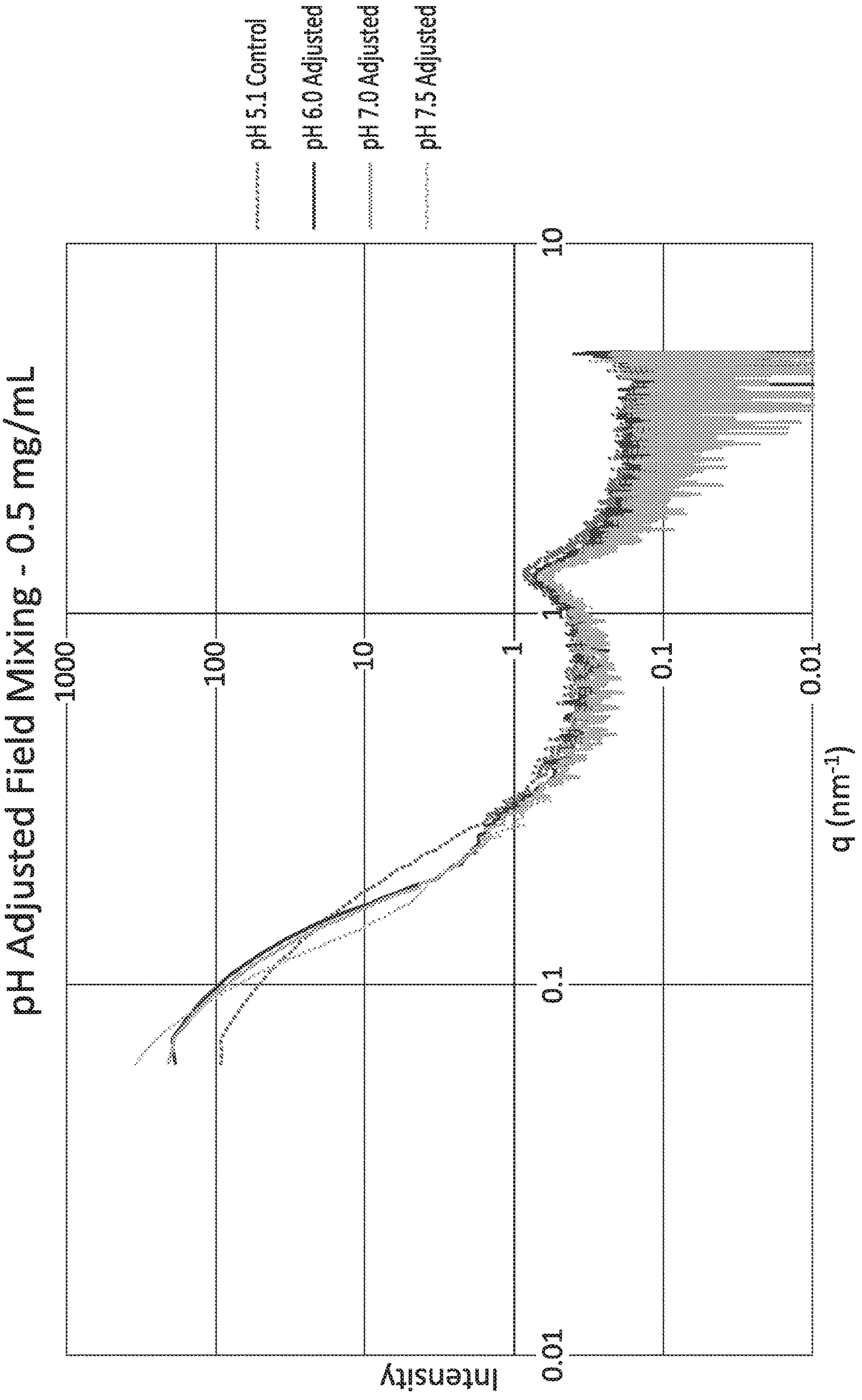
FIG. 34 is a graph demonstrating mRNA lipid nanoparticle formulations loaded via a process described herein comprised particles showing a high degree of structure, with a pronounced feature at q=1.3 $nm^{-1}$ (calculated D-spacing ~5 nm) and a slight decrease in the 1.3 $nm^{-1}$ was observed with neutralization, further the neutralization of the mixed product resulted in the reduction of a structural feature at 0.3 nm−1 (D-spacing ~21 nm).

FIG. 34 is a graph demonstrating mRNA lipid nanoparticle formulations loaded via a process described herein comprised particles showing a high degree of structure, with a pronounced feature at q=1.3 $nm^{-1}$ (calculated D-spacing ~5 nm) and a slight decrease in the 1.3 $nm^{-1}$ was observed with neutralization, further the neutralization of the mixed product resulted in the reduction of a structural feature at 0.3 nm−1 (D-spacing ~21 nm).

Figure 35:
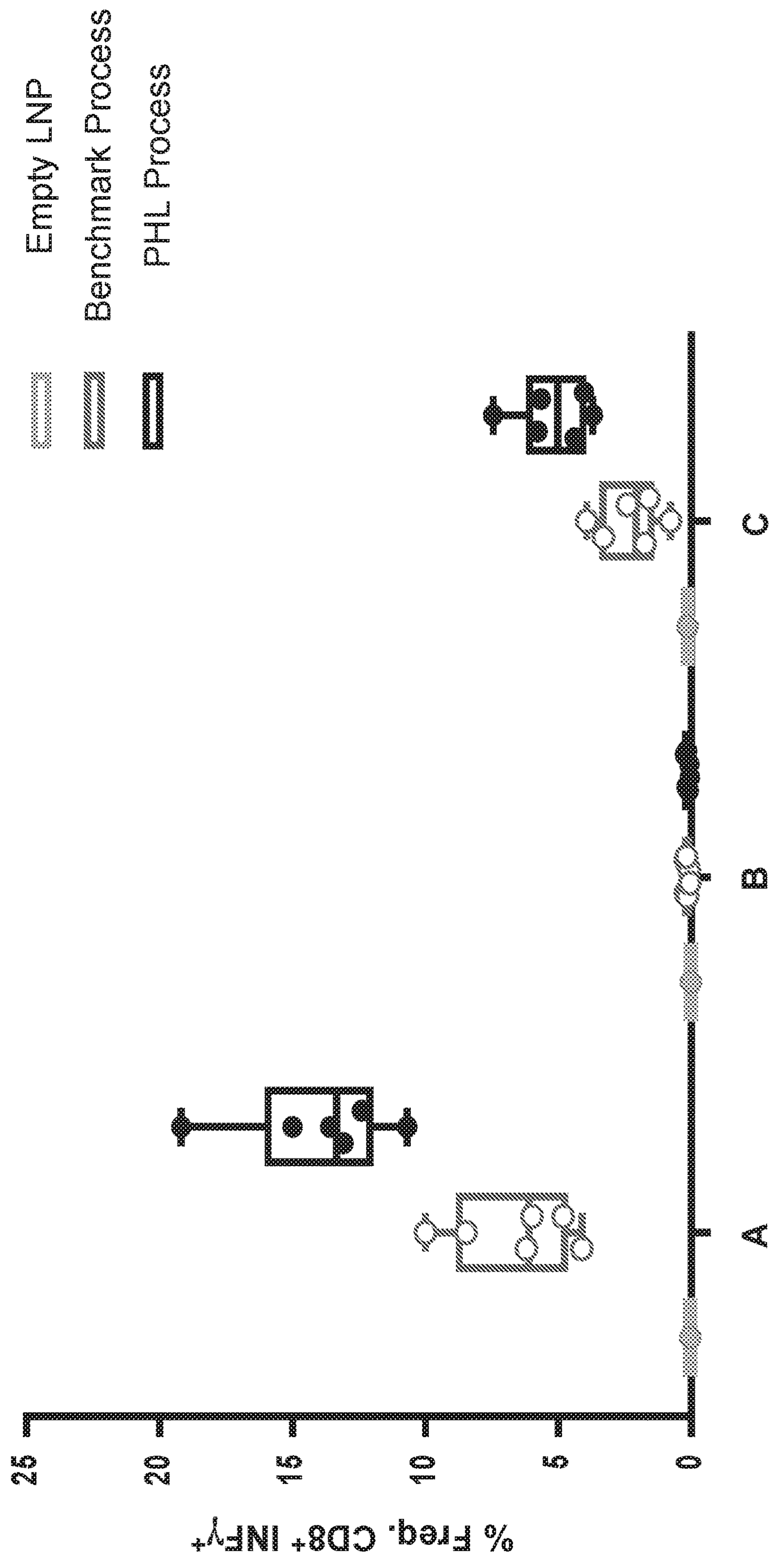
FIG. 35 is a graph demonstrating the increased potency of mixed formulation processes described herein ("PHL Process") relative to control ("Benchmark Process") showing increased antigen-specific T cell responses with mix processes described herein compared to standard process mode.

FIG. 35 is a graph demonstrating the increased potency of mixed formulation processes described herein ("PHL Process") relative to control ("Benchmark Process") showing increased antigen-specific T cell responses with mix processes described herein compared to standard process mode.

EQUIVALENTS

The details of one or more embodiments of the invention are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the invention to the precise form disclosed, but by the claims appended hereto.

The invention claimed is:

1. A method of producing a lipid nanoparticle (LNP) formulation, the method comprising:

mixing a lipid solution comprising an ionizable lipid, a phospholipid, and a structural lipid with an aqueous buffer solution having a pH in a range of about 4.6 to about 5.5, thereby forming a lipid nanoparticle composition comprising a lipid nanoparticle;

storing the lipid nanoparticle composition for at least 1 day, at about 10° C. to 25° C.; and after the storing, adding a nucleic acid solution comprising a nucleic acid to the lipid nanoparticle composition, thereby forming a lipid nanoparticle (LNP) formulation comprising the lipid nanoparticle associated with the nucleic acid.

2. The method of claim 1, wherein before the storing:

the lipid nanoparticle of the lipid nanoparticle composition has an average lipid nanoparticle diameter of less than about 150 nm, less than about 125 nm, less than about 100 nm, less than about 90 nm, less than about 80 nm, less than about 75 nm, less than about 70 nm, less than about 65 nm, less than about 60 nm, less than about 55 nm, less than about 50 nm, less than about 45 nm, less than about 40 nm, less than about 35 nm, or less than about 30 nm; or the lipid nanoparticle of the lipid nanoparticle composition has an average lipid nanoparticle diameter of about 25 nm to about 125 nm, about 30 nm to about 110 nm, about 35 nm to about 100 nm, about 40 nm to about 90 nm, about 45 nm to about 80 nm, or about 50 nm to about 70 nm.

3. The method of claim 1, wherein the lipid nanoparticle composition has a pH that is less than the pKa of the ionizable lipid.

4. The method of claim 1, further comprising processing the lipid nanoparticle formulation.

5. The method of claim 1, wherein the nucleic acid is a ribonucleic acid.

6. The method of claim 1, wherein the nucleic acid is a messenger RNA (mRNA).

7. The method of claim 1, wherein the lipid solution and/or the lipid nanoparticle composition comprises a first organic solvent.

8. The method of claim 7, wherein the first organic solvent is an alcohol.

9. The method of claim 7, wherein the first organic solvent is ethanol.

10. The method of claim 4, wherein the processing comprises at least one step selected from the group consisting of filtering, pH adjusting, buffer exchanging, dialyzing, concentrating, freezing, lyophilizing, or packing.

11. The method of claim 1, wherein the lipid solution, the lipid nanoparticle (LNP) composition, and/or the lipid nanoparticle (LNP) formulation further comprises an encapsulation agent, wherein the encapsulation agent is i) a compound of Formula (EA-I):

(EA-I)

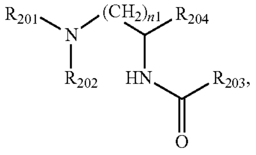

or a salts or isomer thereof, wherein $R_{201}$ and $R_{202}$ are each independently selected from the group consisting of H, $C_1$-$C_6$ alkyl, $C_2$-$C_6$ alkenyl, and $(C{=}NH)N(R_{101})_2$ wherein each $R_{101}$ is independently selected from the group consisting of H, $C_1$-$C_6$ alkyl, and $C_2$-$C_6$ alkenyl;

$R_{203}$ is selected from the group consisting of $C_1$-$C_{20}$ alkyl and $C_2$-$C_{20}$ alkenyl;

$R_{204}$ is selected from the group consisting of H, $C_1$-$C_{20}$ alkyl, $C_2$-$C_{20}$ alkenyl, $C(O)(OC_1$-$C_{20}$ alkyl), $C(O)(OC_2$-$C_{20}$ alkenyl), $C(O)(NHC_1$-$C_{20}$ alkyl), and $C(O)(NHC_2$-$C_{20}$ alkenyl);

n1 is selected from 1, 2, 3, 4, 5, 6, 7, 8, 9, and 10;

ii) a compound of Formula (EA-II):

(EA-II)

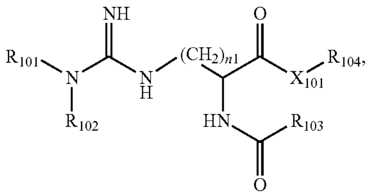

or a salt or isomer thereof, wherein $X_{101}$ is a bond, NH, or O;

$R_{101}$ and $R_{102}$ are each independently selected from the group consisting of H, $C_1$-$C_6$ alkyl, and $C_2$-$C_6$ alkenyl;

$R_{103}$ and $R_{104}$ are each independently selected from the group consisting of $C_1$-$C_{20}$ alkyl and $C_2$-$C_{20}$ alkenyl; and n1 is selected from 1, 2, 3, 4, 5, 6, 7, 8, 9, and 10; or iii)ethyl lauroyl arginate or a salt or isomer thereof.

12. The method of claim 1, wherein the lipid nanoparticle further comprises a PEG lipid.

13. The method of claim 12, wherein the PEG lipid i) is selected from a PEG-modified phosphatidylethanolamine, a PEG-modified phosphatidic acid, a PEG-modified ceramide, a PEG-modified dialkylamine, a PEG-modified diacylglycerol, and a PEG-modified dialkylglycerol;

ii) is a compound of Formula (PL-I):

(PL-I)

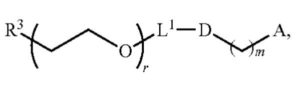

or salts or isomer thereof, wherein:

$R^3$ is —$OR^O$;

$R^O$ is hydrogen, optionally substituted alkyl, or an oxygen protecting group;

r is an integer between 1 and 100, inclusive;

$L^1$ is optionally substituted $C_{1-10}$ alkylene, wherein at least one methylene of the optionally substituted $C_{1-10}$ alkylene is independently replaced with optionally substituted carbocyclylene, optionally substituted heterocyclylene, optionally substituted arylene, optionally substituted heteroarylene, O, $N(R^N)$, S, C(O), $C(O)N(R^N)$, $NR^NC(O)$, C(O)O, OC(O), OC(O)O, $OC(O)N(R^N)$, $NR^NC(O)O$, or $NR^NC(O)N(R^N)$;

D is a moiety obtained by click chemistry or a moiety cleavable under physiological conditions;

m is 0, 1, 2, 3, 4, 5, 6, 7, 8, 9, or 10;

A is of the formula:

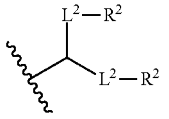 or 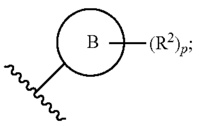

each instance of $L^2$ is independently a bond or optionally substituted $C_{1-6}$ alkylene, wherein one methylene unit of the optionally substituted $C_{1-6}$ alkylene is optionally replaced with O, $N(R^N)$, S, C(O), $C(O)N(R^N)$, $NR^NC(O)$, C(O)O, OC(O), OC(O)O, —$OC(O)N(R^N)$, $NR^NC(O)O$, or $NR^NC(O)N(R^N)$;

each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclylene, optionally substituted heterocyclylene, optionally substituted arylene, optionally substituted heteroarylene, $N(R^N)$, O, S, C(O), $C(O)N(R^N)$, $NR^NC(O)$, $NR^NC(O)N(R^N)$, C(O)O, OC(O), —OC(O)O, $OC(O)N(R^N)$, $NR^NC(O)O$, C(O)S, SC(O), $C(=NR^N)$, $C(=NR^N)N(R^N)$, $NR^NC(=NR^N)$, $NR^NC(=NR^N)N(R^N)$, C(S), $C(S)N(R^N)$, $NR^NC(S)$, $NR^NC(S)N(R^N)$, S(O), OS(O), S(O)O, —OS(O)O, $OS(O)_2$, $S(O)_2O$, $OS(O)_2O$, $N(R^N)S(O)$, $S(O)N(R^N)$, $N(R^N)S(O)N(R^N)$, $OS(O)N(R^N)$, $N(R^N)S(O)O$, $S(O)_2$, $N(R^N)S(O)_2$, $S(O)_2N(R^N)$, $N(R^N)S(O)_2N(R^N)$, $OS(O)_2N(R^N)$, or —$N(R^N)S(O)_2O$;

each instance of $R^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2;

iii) is a compound of Formula (PL-II):

(PL-II)

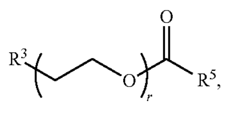

or a salt or isomer thereof, wherein:

$R^3$ is —$OR^O$;

$R^O$ is hydrogen, optionally substituted alkyl or an oxygen protecting group;

r is an integer between 1 and 100;

$R^5$ is optionally substituted $C_{10-40}$ alkyl, optionally substituted $C_{10-40}$ alkenyl, or optionally substituted $C_{10-40}$ alkynyl; and optionally one or more methylene groups of $R^5$ are replaced with optionally substituted carbocyclylene, optionally substituted heterocyclylene, optionally substituted arylene, optionally substituted heteroarylene, $N(R^N)$, O, S, C(O), —$C(O)N(R^N)$, $NR^NC(O)$, $NR^NC(O)N(R^N)$, C(O)O, OC(O), OC(O)O, $OC(O)N(R^N)$, $NR^NC(O)O$, C(O)S, SC(O), $C(=NR^N)$, $C(=NR^N)N(R^N)$, $NR^NC(=NR^N)$, $NR^NC(=NR^N)N(R^N)$, C(S), —$C(S)N(R^N)$, $NR^NC(S)$, $NR^NC(S)N(R^N)$, S(O), OS(O), S(O)O, OS(O)O, $OS(O)_2$, $S(O)_2O$, —$OS(O)_2O$, $N(R^N)S(O)$, $S(O)N(R^N)$, $N(R^N)S(O)N(R^N)$, $OS(O)N(R^N)$, $N(R^N)S(O)O$, $S(O)_2$, —$N(R^N)S(O)_2$, $S(O)_2N(R^N)$, $N(R^N)S(O)_2N(R^N)$, $OS(O)_2N(R^N)$, or $N(R^N)S(O)_2O$; and each instance of $R^N$ is independently hydrogen, optionally substituted alkyl, or a nitrogen protecting group;

iv) is a compound of Formula (PL-III):

(PL-III)

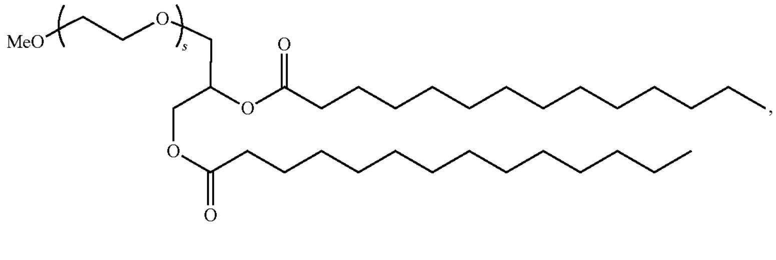, or a salt or isomer thereof, wherein s is an integer between 1 and 100, or v) is (PEG-1)

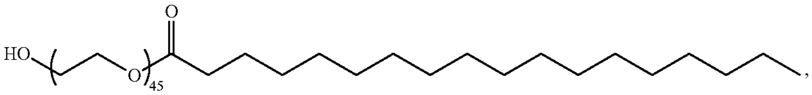

, or (PEG-2)

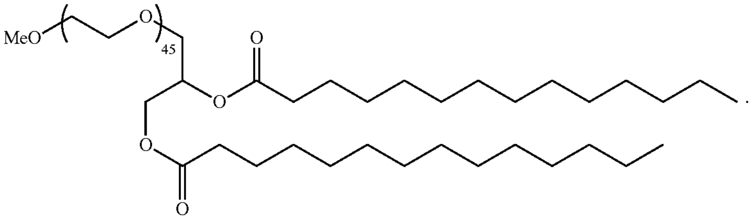

.

—R*YR", —YR", and —R*OR", or $R_2$ and $R_3$, together with the atom to which they are attached, form a heterocycle or carbocycle;

14. The method of claim 1, wherein the structural lipid is selected from cholesterol, fecosterol, sitosterol, ergosterol, campesterol, stigmasterol, brassicasterol, tomatidine, ursolic acid, and alpha-tocopherol.

15. The method of claim 1, wherein the phospholipid is selected from 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), and sphingomyelin.

16. The method of claim 1, wherein the ionizable lipid i) is a compound of Formula (IL-1):

(IL-1)

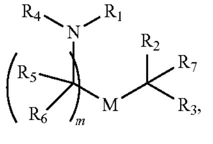

or a salt or isomers thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of hydrogen, a $C_{3-6}$ carbocycle, $—(CH_2)_nQ$, $(CH_2)_nCHQR$, —CHQR, $—CQ(R)_2$, and unsubstituted $C_{1-6}$ alkyl, where Q is selected from a carbocycle, heterocycle, —OR, $—O(CH_2)_nN(R)_2$, —C(O)OR, —OC(O)R, $—CX_3$, $—CX_2H$, $—CXH_2$, —CN, $—N(R)_2$, $—C(O)N(R)_2$, —N(R)C(O)R, $—N(R)S(O)_2R$, $—N(R)C(O)N(R)_2$, $—N(R)C(S)N(R)_2$, $—N(R)R^8$, $N(R)S(O)_2R^8$, $—O(CH_2)_nOR$, $—N(R)C(—NR^9)N(R)_2$, $—N(R)C(=CHR^9)N(R)_2$, $—OC(O)N(R)_2$, —N(R)C(O)OR, —N(OR)C(O)R, $—N(OR)S(O)_2R$, —N(OR)C(O)OR, $—N(OR)C(O)N(R)_2$, $—N(OR)C(S)N(R)_2$, $—N(OR)C(=NR_9)N(R)_2$, $—N(OR)C(—CHR_9)N(R)_2$, $—C(=NR_9)N(R)_2$, $—C(=NR_9)R$, —C(O)N(R) OR, and $—C(R)N(R)_2C(O)OR$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —OC(O)-M"—C(O)O—, —C(O)N(R')—, —N(R')C(O)—, —C(O)—, —C(S)—, —C(S)S—, —SC(S)—, —CH(OH)—, —P(O)(OR')O—, $—S(O)_2—$, —S—S—, an aryl group, and a heteroaryl group, in which M" is a bond, $C_{1-13}$ alkyl or $C_{2-13}$ alkenyl;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, $—S(O)_2R$, $—S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-15}$ alkyl and $C_{3-15}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13; and wherein when $R^4$ is $-(CH_2)_nQ$, $-(CH_2)_nCHQR$, $-CHQR$, or $-CQ(R)_2$, then (i) Q is not $-N(R)_2$ when n is 1, 2, 3, 4 or 5, or (ii) Q is not 5, 6, or 7-membered heterocycloalkyl when n is 1 or 2, or ii) is a compound of Formula (IL-II):

(IL-II)

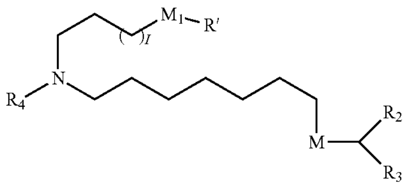

or a salt or isomer thereof, wherein 1 is selected from 1, 2, 3, 4 and 5; M1 is a bond or M'; $R_4$ is hydrogen, unsubstituted $C_{1-3}$ alkyl, or $-(CH_2)_n$ Q, in which n is 2, 3, or 4, and Q is $-OH$, $-NHC(S)N(R)_2$, $-NHC(O)N(R)_2$, $-N(R)C(O)R$, $-N(R)S(O)_2R$, $-N(R)R_8$, $-NHC(=NR_9)N(R)_2$, $-NHC(=CHR_9)N(R)_2$, $-OC(O)N(R)_2$, $-N(R)C(O)OR$, heteroaryl or heterocycloalkyl; M and M' are independently selected from $-C(O)O-$, $-OC(O)-$, $-OC(O)-M''-C(O)O-$, $-C(O)N(R')-$, $-P(O)(OR')O-$, $-S-S-$, an aryl group, and a heteroaryl group; and $R_2$ and $R_3$ are independently selected from the group consisting of H, $C_{1-14}$ alkyl, and $C_{2-14}$ alkenyl; or iii) is a compound of formula (IL-III):

(IL-III)

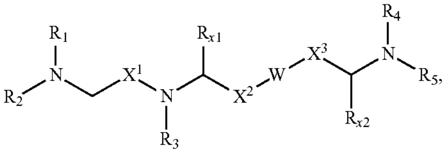

or a salt or isomer thereof, wherein,

W is

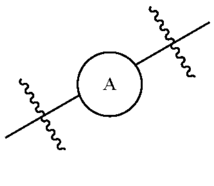

or

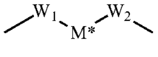, ring A is

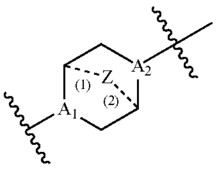

or

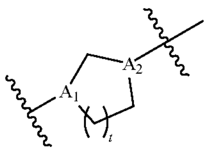;

t is 1 or 2;

$A_1$ and $A_2$ are each independently selected from CH or N;

Z is $CH_2$ or absent wherein when Z is $CH_2$, the dashed lines (1) and (2) each represent a single bond; and when Z is absent, the dashed lines (1) and (2) are both absent;

$R_1$, $R_2$, $R_3$, $R_4$, and $R_5$ are independently selected from the group consisting of $C_{5-20}$ alkyl, $C_{5-20}$ alkenyl, $-R''MR'$, $-R^*YR''$, $-YR''$, and $-R^*OR''$;

$R_{X1}$ and $R_{X2}$ are each independently H or $C_{1-3}$ alkyl;

each M is independently selected from the group consisting of $-C(O)O-$, $-OC(O)-$, $-OC(O)O-$, $-C(O)N(R')-$, $-N(R')C(O)-$, $-C(O)-$, $-C(S)-$, $-C(S)S-$, $-SC(S)-$, $-CH(OH)-$, $-P(O)(OR')O-$, $-S(O)_2-$, $-C(O)S-$, $-SC(O)-$, an aryl group, and a heteroaryl group;

M* is $C_1$-$C_6$ alkyl, $W^1$ and $W^2$ are each independently selected from the group consisting of $-O-$ and $-N(R_6)-$;

each $R_6$ is independently selected from the group consisting of H and $C_{1-5}$ alkyl;

$X^1$, $X^2$, and $X^3$ are independently selected from the group consisting of a bond, $-CH_2-$, $-(CH_2)_2-$, $-CHR-$, $-CHY-$, $-C(O)-$, $-C(O)O-$, $-OC(O)-$, $-(CH_2)_n-C(O)-$, $-C(O)-(CH_2)_n-$, $-(CH_2)_n-C(O)O-$, $-OC(O)-(CH_2)_n-$, $-(CH_2)_n-OC(O)-$, $-C(O)O-(CH_2)_n-$, $-CH(OH)-$, $-C(S)-$, and $-CH(SH)-$;

each Y is independently a $C_{3-6}$ carbocycle;

each R* is independently selected from the group consisting of $C_{1-12}$ alkyl and $C_{2-12}$ alkenyl;

each R is independently selected from the group consisting of $C_{1-3}$ alkyl and a $C_{3-6}$ carbocycle;

each R' is independently selected from the group consisting of $C_{1-12}$ alkyl, $C_{2-12}$ alkenyl, and H;

each R" is independently selected from the group consisting of $C_{3-12}$ alkyl, $C_{3-12}$ alkenyl and $-R^*MR'$; and n is an integer from 1-6;

wherein when ring A is

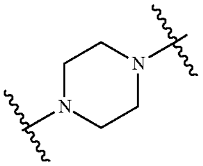, then i) at least one of $X^1$, $X^2$, and $X^3$ is not $-CH_2-$; and/or ii) at least one of $R_1$, $R_2$, $R_3$, $R_4$, and $R_5$ is $-R''MR'$;

iv) is

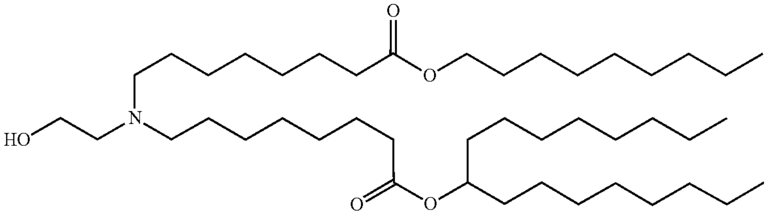
,
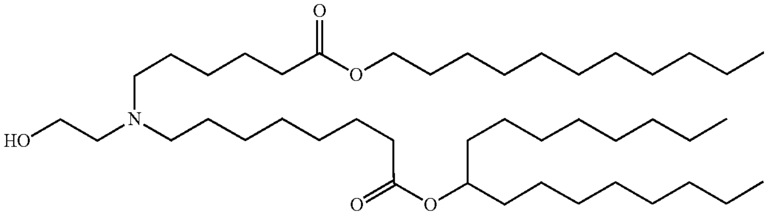
,
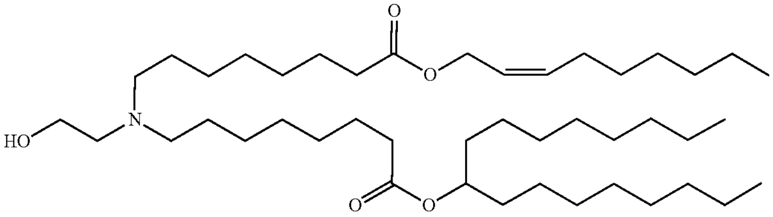
,
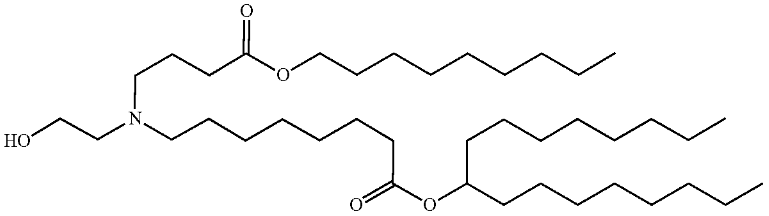
, or
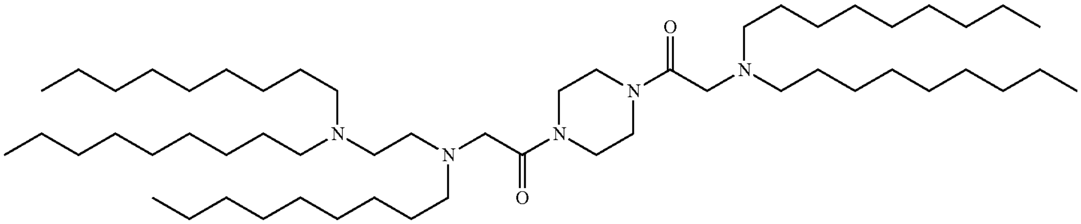
, or a salt or isomer thereof; or v) is selected from 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino) butanoate (DLin-MC3-DMA), 2,2-dilinoleyl-4-(2-dimethylaminoethyl)-[1,3]-dioxolane (DLin-KC2-DMA), 1,2-dioleyloxy-N,N-dimethylaminopropane (DODMA), 2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA), (2R)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2R)), and (2S)—2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2S)).

17. A lipid nanoparticle (LNP) formulation prepared by the method of claim 1.

18. The method of claim 1, wherein during the storing:

i) an average lipid nanoparticle diameter of the lipid nanoparticles in the lipid nanoparticle composition increases by less than about 25% during the storing; and/or ii) a polydispersity index (PDI) of the lipid nanoparticles in the lipid nanoparticle composition increases by less than about 0.25 during the storing.

* * * * *